US007718777B2

(12) United States Patent
Hoogenboom et al.

(10) Patent No.: US 7,718,777 B2
(45) Date of Patent: May 18, 2010

(54) MHC-PEPTIDE COMPLEX BINDING LIGANDS

(75) Inventors: Henricus Renerus Jacobus Mattheus Hoogenboom, Maastricht (NL); Yoram Reiter, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 620 days.

(21) Appl. No.: 11/582,416

(22) Filed: Oct. 18, 2006

(65) Prior Publication Data

US 2007/0196369 A1 Aug. 23, 2007

Related U.S. Application Data

(62) Division of application No. 10/371,942, filed on Feb. 20, 2003, now abandoned.

(60) Provisional application No. 60/358,994, filed on Feb. 20, 2002.

(51) Int. Cl.
| C07K 16/00 | (2006.01) |
| C07K 16/28 | (2006.01) |
| C07K 16/30 | (2006.01) |
| C07K 16/40 | (2006.01) |
| C07K 7/06  | (2006.01) |
| C08H 1/00  | (2006.01) |

(52) U.S. Cl. .............. 530/388.2; 530/388.22; 530/388.26; 530/388.8; 530/388.85

(58) Field of Classification Search .............. None
See application file for complete search history.

(56) References Cited

U.S. PATENT DOCUMENTS

| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 5,591,829 A | 1/1997 | Matsushita |
| 5,695,928 A | 12/1997 | Stewart et al. |
| 5,952,471 A | 9/1999 | Griffiths Lawson |
| 6,054,297 A | 4/2000 | Carter et al. |
| 6,291,160 B1 | 9/2001 | Lerner et al. |
| 6,342,221 B1 | 1/2002 | Thorpe et al. |
| 6,416,738 B1 | 7/2002 | Theodore et al. |
| 6,992,176 B2 | 1/2006 | Reiter et al. |
| 2003/0129191 A1 | 7/2003 | Theodore et al. |
| 2003/0165993 A1 | 9/2003 | Buechler et al. |
| 2003/0223994 A1 | 12/2003 | Hoogenboom et al. |
| 2005/0152912 A1 | 7/2005 | Reiter et al. |
| 2005/0250833 A1 | 11/2005 | Attali et al. |
| 2005/0255101 A1 | 11/2005 | Reiter et al. |
| 2005/0287141 A1 | 12/2005 | Reiter |
| 2006/0083735 A1 | 4/2006 | Reiter et al. |

FOREIGN PATENT DOCUMENTS

| EP | 1178116 | 2/2002 |
| JP | 11-510375 | 9/1999 |
| WO | WO 91/12332 | 8/1991 |
| WO | WO 95/29193 | 11/1995 |
| WO | WO 97/02342 | 1/1997 |
| WO | WO 99/49893 | 10/1999 |
| WO | WO 00/25813 A1 * | 5/2000 |
| WO | WO 01/72768 | 10/2001 |
| WO | WO 01/96401 | 12/2001 |
| WO | WO 03/068201 | 8/2003 |
| WO | WO 03/070752 | 8/2003 |
| WO | WO 2004/084798 | 10/2004 |
| WO | WO 2006/103429 | 10/2006 |

OTHER PUBLICATIONS

Rudikoff et al (Proc Natl Acad Sci USA 1982 vol. 79 p. 1979).*
Ngo et al. "Computational Complexity, Protein Structure Prediction, and the Levinthal Paradox", The Protein Folding Problem and Tertiary Structure Prediction, p. 491-495, 1994.
Reiter et al. "Antibody Engineering for Targeted Therapy of Cancer: Recombinant Fv-Immunotoxins", Current Pharmaceutical Biotechnology, 2: 19-46, 2001.
Aharoni et al. "Immunomodulation of Experimental Allergic Encephalomyelitis by Antibodies to the Antigen-Ia Complex", Nature, 351: 147-150, 1991. Abstract.
Altman et al. "Phenotypic Analysis of Antigen-Specific T Lymphocytes", Science, 274(5284): 94-96, 1996. Abstract.
Andersen et al. "A Recombinant Antibody With the Antigen-Specific, Major Histocompatibility Complex-Restricted Specificity of T Cells", Proc. Natl. Acad. Sci. USA, 93: 1820-1824, 1996.
Anichini et al. "Melanoma Cells and Normal Melanocytes Share Antigens Recognized by HLA-A2-Restricted Cytotoxic T Cell Clones From Melanoma Patients", The Journal of Experimental Medicine, 177: 989-998, 1993.
Arai et al. "Identification of Human Telomerase Reverse Transcriptase-Derived Peptides That Induce HLA-A24-Restricted Antileukemia Cytotoxic T Lymphocytes", Blood, 97(9): 2903-2907, 2001.

(Continued)

*Primary Examiner*—Ram R Shukla
*Assistant Examiner*—Marianne Dibrino

(57) ABSTRACT

Disclosed are protein ligands comprising an immunoglobulin heavy chain variable (VH) domain and an immunoglobulin light chain variable (VL) domain, wherein the proteins bind a complex comprising an MHC and a peptide, do not substantially bind the MHC in the absence of the bound peptide, and do not substantially bind the peptide in the absence of the MHC, and the peptide is a peptide fragment of gp100, MUC1, TAX, or hTERT. Also disclosed are methods of using and identifying such ligands.

2 Claims, 44 Drawing Sheets

OTHER PUBLICATIONS

Bakker et al. "Melanocyte Lineage-Specific Antigen Gp100 Is Recognized by Melanoma-Derived Tumor-Infiltrating Lymphocytes", The Journal of Experimental Medicine, 179: 1005-1009, 1994.

Binyamin et al. "Single-Domain $V_H$ Antibody Fragments From a Phage Display Library", Methods in Molecular Biology, 207: 133-143, 2003.

Boon et al. "Human Tumor Antigens Recognized by T Lymphocytes", The Journal of Experimental Medicine, 183: 725-729, 1996.

Carmon et al. "Novel Breast-Tumor-Associated MUC1-Derived Peptides: Characterization in Db-/-X β2 Microglobulin (β2m) Null Mice Transgenic for a Chimeric HLA-A2.1/Db β2 Microglobulin Single Chain", International Journal of Cancer, 85(3): 391-397, 2000. Abstract.

Chames et al. "Direct Selection of a Human Antibody Fragment Directed Against the Tumor T-Cell Epitope HLA-A1-MAGE-A1 From a Nonimmunized Phage-Fab Library", Proc. Natl. Acad. Sci. USA, 97: 7969-7974, 2000.

Chowdhury et al. "Improving Antibody Affinity by Mimicking Somatic Hypermutation in Vitro", Nature Biotechnology, 17(6): 568-572, 1999. Abstract.

Cohen et al. "Direct Detection and Quantitation of a Distinct T-Cell Epitope Derived From Tumor-Specific Epithelial Cell-Associated Mucin Using Human Recombinant Antibodies Endowed With the Antigen-Specific, Major Histocompatibility Complex-Restricted Specificity of T Cells", Cancer Research, 62: 5835-5844, 2002.

Cohen et al. "Generation of Recombinant Immunotoxins for Specific Targeting of Tumor-Related Peptides Presented by MHC Molecules", Methods in Molecular Biology, 207: 269-282, 2003.

Coulie et al. "A New Gene Coding for a Differentiation Antigen Recognized by Autologous Cytolytic T Lymphocytes on HLA-A2 Melanomas", Journal of Experimental Medicine, 180: 35-42, 1994.

Counter et al. "Telomerase Activity in Normal Leukocytes and in Hematologic Malignancies", Blood, 85(9): 2315-2320, 1995.

Dadaglio et al. "Characterization and Quantitation of Peptide-MHC Complexes Produced from Hen Egg Lysozyme Using a Monoclonal Antibody", Immunity, 6(6): 727-738, 1997. Abstract.

Day et al. "Direct Delivery of Exogenous MHC Class I Molecule-Binding Oligopeptides to the Endoplasmic Reticulum of Viable Cells", Proc. Natl. Acad. Sci. USA, 94: 8064-8069, 1997.

De Haard et al. "A Large Non-Immunized Human Fab Fragment Phage Library That Permits Rapid Isolation and Kinetic Analysis of High Affinity Antibodies", The Journal of Biological Chemistry, 274(26): 218-18230, 1999.

Denkberg et al. "Critical Role for CD8 in Binding of MHC Tetramers to TCR: CD8 Antibodies Block Specific Binding of Human Tumor-Specific MHC-Peptide Tetramers to TCR", The Journal of Immunology, 167: 270-276, 2001.

Denkberg et al. "Direct Visualization of Distinct T Cell Epitopes Derived From A Melanoma Tumor-Associated Antigen by Using Human Recombinant Antibodies With MHC-Restricted T Cell Receptor-Like Specificity", Proc. Natl. Acad. Sci. USA, 99(14): 9421-9426, 2002.

Denkberg et al. "Recombinant Human Single-Chain MHC-Peptide Complexes Made from *E. Coli* by In Vitro Refolding: Functional Single-Chain MHC-Peptide Complexes and Tetramers With Tumor Associated Antigens", European Journal of Immunology, 30(12): 3522-3532, 2000. Abstract.

Derby et al. "High Avidity CTL Exploit Two Complementary Mechanisms to Provide Better Protection Against Viral Infection Than Low-Avidity CTL", The Journal of Immunology, 166: 1690-1697, 2001.

Dudley et al. "T-Cell Clones From Melanoma Patients Immunized Against an Anchor-Modified GP100 Peptide Display Discordant Effector Phenotypes", Cancer Journal, 6(2): 69-77, 2000. Abstract.

Dutoit et al. "Heterogenous T-Cell Response to MAGE-A10[254-262]: High Avidity-Specific Cytolytic T Lymphocytes Show Superior Antitumor Activity", Cancer Research, 61: 5850-5856, 2001.

Kawakami et al. "Identification of a Human Melanoma Antigen Recognized by Tumor-Infiltrating Lymphocytes Associated With in Vivo Tumor Rejection", Proc. Natl. Acad, Sci. USA, 91: 6458-6462, 1994.

Kim et al. "Specific Association of Human Telomerase Activity With Immortal Cells and Cancer", Science, 266(5193): 2011-2015, 1994. Abstract.

Kirkin et al. "Generation of Human-Melanoma-Specific T Lymphocyte Clones Defining Novel Cytolytic Targets With Panels of Newly Established Melanoma Cell Lines", Cancer Immunology and Immunotherapy, 41(2): 71-81, 1995. Abstract.

Krogsgaard et al. "Visualization of Myelin Basic Protein (MBP) T Cell Epitopes in Multiple Sclerosis Lesions Using a Monoclonal Antibody Specific for the Human Histocompatibility Leukocyte Antigen (HLA)-DR2-MBP 85-99 Complex", The Journal of Experimental Medicine, 191(8): 1395-1412, 2000.

Kugler et al. "Regression of Human Metastatic Renal Cell Carcinoma After Vaccination With Tumor Cell-Dendritic Cell Hybrids", Nature Medicine, 6(3): 332-336, 2000. Abstract.

Lee et al. "Characterization of Circulating T Cells Specific for Tumor-Associated Antigens in Melanoma Patients", Nature Medicine, 5(6): 677-685, 1999. Abstract.

Lev et al. "Isolation and Characterization of Human Recombinant Antibosies Endowed With the Antigen-Specific, Major Histocompatibility Complex-Restricted Specificity of T Cells Directed Toward the Widely Expressed Tumor T-Cell Epitopes of the Telomerase Catalytic Subunit", Cancer Research, 62: 3184-3194, 2002.

Lode et al. "Targeted Cytokines for Cancer Immunotherapy", Immunology Research, 21(2-3): 279-288, 2000. Abstract.

McEachern et al. "Telomeres and Their Control", Annual Review of Genetics, 34: 331-358, 2000. Abstract.

Minev et al. "Cytotoxic T Cell Immunity Against Telomerase Reverse Transcriptase in Humans", Proc. Natl. Acad. Sci. USA, 97(9): 4796-4801, 2000.

Murphy et al. "A Novel MHC Class II Epitope Expressed in Thymic Medulla But Not Cortex", Nature, 338: 765-768, 1989. Abstract.

Nakamura et al. "Reversing Time: Origin of Telomerase", Cell, 92: 587-590, 1998.

Niv et al. "Recombinant Single-Chain and Disulfide-Stabilized Fv Immunotoxins for Cancer Therapy", Methods in Molecular Biology, 207: 255-268, 2002.

Offringa et al. "Design and Evaluation of Antigen-Specific Vaccination Strategies Against Cancer", Current Opinion in Immunology, 12(5): 576-582, 2000. Abstract.

Ogg et al. "Quantitation of HIV-1-Specific Cytotoxic T Lymphocytes and Plasma Load of Viral RNA", Science, 279(5359): 2103-2106, 1998. Abstract.

Pastan "Targeted Therapy of Cancer With Recombinant Immunotoxins", Biochimica et Biophysica Acta, 1333: C1-C6, 1997.

Polakova et al. "Antibodies Directed Against the MHC-I Molecule H-2Dd Complexed With an Antigenic Peptide: Similarities to a T Cell Receptor With the Same Specificity", The Journal of Immunology, 165(10): 5703-5712, 2000.

Porgador et al. "Localization, Qunatitation, and in Situ Detection of Specific Peptide-HC Class I Complexes Using a Monoclonal Antibody", Immunity, 6(6): 715-726, 1997. Abstract.

Reay et al. "Determinatin of the Relationship Between T Cell Responsiveness and the Number of MHC-Peptide Complexes Using Specific Monoclonal Antibodies", The Journal of Immunology, 164(11): 5626-5634, 2000.

Reiter et al. "An Antibody Single-Domain Phage Display Library of a Native Heavy Chain Variable Region: Isolation of Functional Single-Domain VH Molecules With a Unique Interface", Journal of Molecular Biology, 290(3): 685-698, 1999. Abstract.

Reiter et al. "Peptide-Specific Killing of Antigen-Presenting Cells by a Recombinant Antibody-Toxin Fusion Protein Targeted to Major Histocompatibility Complex/Peptide Class I Complexes With T Cell Receptor-Like Specificity", Proc. Natl. Acad. Sci. USA, 94: 4631-4636, 1997.

Reiter et al. "Recombinant Immunotoxins in Targeted Cancer Cell Therapy", Advances in Cancer Research, 81: 93-124, 2001. Abstract.

Renkvist et al. "A Listing of Human Tumor Antigens Recognized by T Cells", Cancer Immunology and Immunotherapy, 50: 3-15, 2001.

Restifo et al. "Identification of Human Cancers Deficient in Antigen Processing", The Journal of Experimental Medicine, 177: 265-272, 1993.

Rivoltini et al. "Recognition of Melanoma-Derived Antigens by CTL: Possible Mechanisms Involved in Down-Regulating Anti-Tumor T-Cell Reactivity", Critical Review in Immunology, 18(1-2): 55-63, 1998. Abstract.

Rosenberg "Progress in Human Tumour Immunology and Immunotherapy", Nature, 411: 380-384, 2001. Abstract.

Seliger et al. "Antigen-Processing Machinery Breakdown and Tumor Growth", Immunology Today, 21(9): 455-464, 2000. Abstract.

Shay et al. "Telomerase and Cancer", Human Molecular Genetics, 10(7): 677-685, 2001.

Stanislawski et al. "Circumventing Tolerance to a Human MDM2-Derived Tumor Antigen by TCR Gene Transfer", Nature Immunology, 2(10): 962-970, 2001. Abstract.

Stryhn et al. "Shared Fine Specificity Between T-Cell Receptors and an Antibody Recognizing a Peptide/Major Histocompatibility Class I Complex", Proc. Natl. Acad. Sci. USA, 93: 10338-10342, 1996.

Vonderheide et al. "The Telomerase Catalytic Subunit Is a Widely Expressed Tumor-Associated Antigen Recognized by Cytotoxic T Lymphocytes", Immunity, 10(6): 673-679, 1999. Abstract.

Waterhouse et al. "Combinatorial Infection and In Vivo Recombination: A strategy for Making Large Phage Antibody Repertoires", Nucleic Acids Research, 21(9): 2265-2266, 1993.

Withoff et al. "Bi-Specific Antibody Therapy for the Treatment of Cancer", Current Opinion in Molecular Therapy, 3(1): 53-62, 2001. Abstract.

Wülfing et al. "Correctly Folded T-Cell Receptor Fragments in the Periplasm of *Escherichia Coli*", Journal of Molecular Biology, 242(5): 655-669, 1994. Abstract.

Zhong et al. "Antigen-Unspecific B Cells and Lymphoid Dendritic Cells Both Show Extensive Surface Expression of Processed Antigen-Major Histocompatibility Complex Class II Complexes After Soluble Protein Exposure in Vivo or in Vitro", The Journal of Experimental Medicine, 186(5): 673-682, 1997.

Zhong et al. "Production, Specificity, and Funtionality of Monoclonal Antibodies to Specific Peptide-Major Histocompatibility Complex Class II Complexes Formed by Processing of Exogenous Protein", Proc. Natl. Acad. Sci. USA, 94: 13856-13861, 1997.

International Preliminary Report on Patentability Dated Oct. 10, 2005 From the International Bureau of WIPO Re.: Application No. PCT/IL2004/000275.

Invitation to Pay Additional Fees Dated Feb. 16, 2005 From the Intenational Searching Authority Re.: Application No. PCT/IL2004/000275.

Anikeeva et al. "Soluble HIV-Specific T Cell Receptor: Expression, Purification and Analysis of the Specificity", Journal of Immunological Methods, XP004430548, 277(1-2): 75-86, Jun. 1, 2003.

Chames et al. "TCR-Like Human Antibodies Expressed on Human CTLs Mediate Antibody Affinity-Dependent Cytolytic Activity", The Journal of Immunology, 169: 1110-1118, 2002.

Kfir et al. "Antibody-Mediated Targeting of Human Single-Chain Class I MHC With Covalently Linked Peptides Induces Efficient Killing of Tumor Cells by Tumor or Viral-Specific Cytotoxic T Lymphocytes", Cancer Immunology & Immunotherapy, XP019333169, 54(9): 867-879, Sep. 1, 2005. Abstract.

Noy et al. "T-Cell Receptor-Like Antibodies: Novel Reagents for Clinical Cancer Immunology and Immunotherapy", Future Drugs, XP009067037, 5(3): 523-536, Jun. 1, 2005. Abstract, Table 1.

Andersen et al. "A Recombinant Antibody With the Antigen-Specific, Major Histocompatibility Complex-Restricted Specificity of T Cells", Proc. Natl. Acad. Sci. USA, 93(5): 1820-1824, 1996.

Anton et al. "MHC Class I-Associated Peptides Produced From Endogenous Gene Products With Vastly Different Efficiencies", The Journal of Immunology, 158: 2535-2542, 1997.

Biddison et al. "Tax and M1 Peptide/HLA-A2-Specific Fabs and T Cell Receptors Recognize Nonidentical Structural Features on Peptide/HLA-A2 Complexes", Journal of Immunology, 171(6): 3064-3074, 2003.

Bieganowska et al. "Direct Analysis of Viral-Specific CD8 T Cells With Soluble HLA-A2/Tax11-19 Tetramer Complexes in Patients With Human T-Cell Lymphotropic Virus-Associated Myelopathy", The Journal of Immunology, 162: 1765-1771, 1999.

Bird et al. "Single-Chain Antigen-Binding Proteins", Science, 242: 423-426, 1988.

Boerner et al. "Production of Antigen-Specific Human Monoclonal Antibodies From In-Vitro-Primed Human Splenocytes", The Journal of Immunology, 147(1): 86-95, 1991.

Christinck et al. "Peptide Binding to Class I MHC on Living Cells and Quantitation of Complexes Required for CTL Lysis", Nature, 352: 67-70, 1991.

Chung et al. "Competitive Inhibition In Vivo and Skewing of the T Cell Repertoire of Antigen-Specific CTL Priming by an Anti-Peptide-MHC Monoclonal Antibody", The Journal of Immunology, 167: 699-707, 2001.

Cohen et al. "Direct Phenotypic Analysis of Human MHC Class I Antigen Presentation: Visualization, Quantification, and In Situ Detection of Human Viral Epitopes Using Peptide-Specific, MHC-Restricted Human Recombinant Antibodies", Journal of Immunology, 170(8): 4349-4361, 2003.

Cohen et al. Recombinant Antibodies With MHC-Restricted, Peptide-Specific, T-Cell Receptor-Like Specificity: New Tools to Study Antigen Presentation and TCR-Peptide-MHC Interactions, Journal of Molecular Recognition, 16(5): 324-332, 2003. Abstract.

Cote et al. "Generation of Human Monoclonal Antibodies Reactive With Cellular Antigens", PNAS, 80: 2026-2030, 1983.

Daugherty et al. "Polymerase Chain Reaction Facilities the Cloning, CDR-Grafting, and Rapid Expression of a Murine Monoclonal Antibody Directed Against the CD18 Component of Leukocyte Integrins", Nucleic Acids Research, 19(9): 2471-2476, 1991.

Demotz et al. "The Minimal Number of Class II MHC-Antigen Complexes Needed for T Cell Activation", Science, 249: 1028-1030, 1990.

Engberg et al. "Recombinant Antibodies With the Antigen-Specific, MHC Restricted Specificity of T Cells: Novel Reagents for Basic and Clinical Investigations and Immunotherapy", Immunotechnology, 4(3-4): 273-278, 1999.

Engberg et al. "Recombinent Antibodies With the Antigen-Specific, MHC Restricted Specificity of T Cells: Novel Reagents for Basic and Clinical Investigations and Immunotherapy", Immunotechnology, 4(Nos. 3-4): 273-278, 1999.

Gennaro "Remington's Pharmaceutical Sciences 18th Edition", Mack Printing Co., p. 1579, 1990.

Grassmann et al. "Transformation to Continuous Growth of Primary Human T Lymphocytes by Human T-Cell Leukemia Virus Type I X-Region Genes Tranduced by a Herpesvirus Saimiri Vector", PNAS, 86: 3351-3355, 1989.

Haard et al. "A Large Non-Immunized Human Fab Fragment Phage Library That Permits Rapid Isolation and Kinetic Analysis of High Affinity Antibodies", The Journal of Biological Chemistry, 274(26): 18218-18230, 1999.

Harding et al. "Quantitation of Antigen-Presenting Cell MHC Class II/ Peptide Complexes Necessary for T-Cell Stimulation", Nature, 346: 574-576, 1990.

Harlow et al. "Antibodies, a Laboratory Manual", Cold Spring Harbor Laboratory, USA, p. 287, 1988.

Hoogenboom et al. "By-Passing Immunisation—Human Antibodies From Synthetic Repertoires of Germline VH Gene Segments Rearranged In Vitro", Journal of Molecular Biology, 227: 381-388, 1992.

Jones et al. "Replacing the Complementarity-Determining Regions on a Human Antibody With Those From a Mouse", Nature, 321: 522-525, 1986.

Köhler et al. "Continuous Cultures of Fused Cells Secreting Antibody of Predefined Specificity", Nature, 256: 495-497, 1975.

Kondo et al. "Activity of Immunotoxins Constructed With Modified Pseudomonas Exotoxin A Lacking the Cell Recognition Domain", The Journal of Biological Chemistry, 263(19): 9470-9475, 1988.

Lonberg et al. "Antigen-Specific Human Antibodies From Mice Comprising Four Distinct Genetic Modifications", Nature, 368: 856-859, 1994.

Marks et al. "By-Passing Immunization—Human Antibodies From V-Gene Libraries Displayed on Phage", Journal of Molecular Biology, 222: 581-597, 1991.

Morrison "Success in Specification", Nature, 368: 812-813, 1994.

Neuberger "Generating High-Avidity Human Mabs in Mice", Nature Biotechnology, 14: 396, 1996.

Parkhurst et al. "Improved Induction of Melanoma-Reactive CTL With Peptides From the Melanoma Antigen Gp100 Modified at HLA-A*0201-Binding Residues", The Journal of Immunology, 157: 2539-2548, 1996. Tables II, III.

Pascolo et al. "HLA-A2.1-Restricted Education and Cytolytic Activity of CD8+ T Lymphocyes From β2 Microglobulin (β2m) HLA-A2.1 Monochain Transgenic H-2Db β2m Double Knockout Mice", Journal of Experimental Medicine, 185(12): 2043-2051, 1977.

Patamawenu "Generation of Functional HLA-A2 Molecules Covealently Attached to Antigenic Peptides", B.S. (University of Maryland) Thesis, p. 8-9, 1988. Abstract.

Poiesz et al. "Detection and Isolation of Type C Retrovirus Particles From Fresh and Cultured Lymphocytes of a Patient With Cutaneous T-Cell Lymphoma", PNAS, 77(12): 7415-7419, 1980.

Poljak et al. "Structure and Specificity of Antibody Molecules", Philosophical Transactions of the Royal Society of London, Series B, 272: 43-51, 1975.

Porter "The Hydrolysis of Rabbit γ-Globulin and Antibodies With Crystalline Papain", Biochemical Journal, 73: 119-126, 1959.

Pozzatti et al. "The Human T-Lymphotropic Virus Type I "Tax" Gene Can Cooperate With the "Ras" Oncogene to Induce Neoplastic Transformation of Cells", Molecular and Cellular Biology, 10(1): 413-417, 1990.

Rammensee et al. "MHC Ligands and Peptide Motifs", Molecular Biology Intelligence Unit, Landes Bioscience, p. 235-281, 1997.

Reiter et al. "Peptide-Specific Killing of Antigen-Presenting Cells by a Recombinant Antibody-Toxin Fusion Protein Targeted to Major Histocompatibility Complex/Peptide Class I Complexes With T Cell Receptor-Like Specificity", Proc. Natl. Acad. Sci. USA, 94(9): 4631-4636, 1997. Esp. Abstract.

Riechmann et al. "Reshaping Human Antibodies for Therapy", Nature, 332: 323-327, 1988.

Robert et al. "Antibody-Conjugated MHC Class I Tetramers Can Target Tumor Cells for Specific lysis by T Lumphocytes", European Journal of Immunology, 30: 3165-3170, 2000.

Rosenberg "Insight", Nature, 411: 380-384, 2001.

Rudikoff et al. "Single Amino Acid Substitution Altering Antigen-Binding Specificity", Proceedings of the National Academy of Sciences, USA, 79(6): 1979-1983, 1982.

Saito et al. "In Vivo Selection of T-Cell Receptor Junctional Region Sequences by HLA-A2 Human T-Cell Lymphotropic Virus Type 1 Tax11-19 Peptide Complexes", Journal of Virology, 75(2): 1065-1071, 2001.

Shiono et al. "Spontaneous Production of Anti-IFN-Alpha and Anti-IL-12 Autoantibodies by Thymoma Cells From Myasthenia Gravis Patients Suggests Autoimmunization in the Tumor", International Immunology, 15(8): 903-913, 2003. GenPept AAO4555.

Shriner et al. "Comparison of the Human Immune Response to Conjugate and Polysaccharide Pneumococcal Vaccination Using. a Reconstituted SCID Mouse Model", Vaccine, 24(49-50): 7197-7203, 2006. GenPept ABG38407.

Stedman Definition "Fab Fragment", Stedman's Online Medical Dictionary, 27th Edition. world wide web.stedmans.com.

Stubbs et al. "Influence of Core Fucosylation on the Flexibility of a Biantennary N-Linked Oligosaccharide", Biochemistry, 35: 937-947, 1996.

Verhoeyen et al. "Reshaping Human Antiodies: Grafting an Antilysozyme Activity", Science, 239: 1534-1536, 1988.

Winter et al. "Man-Made Antibodies", Nature, 349: 293-299, 1991.

Yamano et al. "Detection of HTLV-I Tax11-19 Peptide/HLA-A*201 Complexes Are Overexpressed in HAM/TSP Patients", Aids Research and Human Retroviruses, 19(Suppl.): S-38, 2003. Abstract. & 11th International Conference on Human Retrovirology: HTLV and Related Viruses, San Francisco, USA, 2003. Abstract.

Yamano et al. "Increased Expression of Human T Lymphocyte Virus Type I (HTLV-I) Tax11-19 Peptide-Human Histocompatibility Leukocyte Antigen A*201 Complexes on CD4+ CD25+ T Cells Detected by Peptide-Specific, Major Histocompatibility Complex-Restricted Antibodies in Patients With HTLV-I-Associated Neurological Disease", Journal of Experimental Medicine, 199(10): 1367-1377, 2004.

Yoshida et al. "Isolation and Characterization of Retrovirus From Cell Lines of Human Adult T-Cell Leukemia and Its Implication in the Disease", PNAS, 79: 2031-2035, 1982.

* cited by examiner

Nucleotide (top) and amino acid (bottom) sequence of the light chain variable region of antibody clone 1A11

```
1    GACATCCAGTTGACCCAGTCTCCATCCTCCCTGTCTGCATCTGTAGGAGACAGAGTCACC
1     D  I  Q  L  T  Q  S  P  S  S  L  S  A  S  V  G  D  R  V  T

CDR1
61   ATCACTTGCCGGGCAAGTCAGAGCATTAGCACCTATTTAAATTGGTATCAACACAGACCA
21    I  T  C  R  A  S  Q  S  I  S  T  Y  L  N  W  Y  Q  H  R  P

CDR2
121  GGGAAAGCCCCTAAGCTCCTGATCTATTCTGCATCCAGTTTGCAGAGTGGGGTCCCATCA
41    G  K  A  P  K  L  L  I  Y  S  A  S  S  L  Q  S  G  V  P  S

181  AGGTTCAGTGGCAGTGGGTCTGGGACAGATTTCACTCTCACCATCAGCAGTCTCCAACCT
61    R  F  S  G  S  G  S  G  T  D  F  T  L  T  I  S  S  L  Q  P

CDR3
241  GAAGATTTTGCAACCTACTACTGTCAGCAGAGTGACATTATCCCTCTCACTTTCGGCGGA
81    E  D  F  A  T  Y  Y  C  Q  Q  S  D  I  I  P  L  T  F  G  G

301  GGGACCAAGGTGGAGATCAACCGA (SEQ ID NO:7)
101   G  T  K  V  E  I  N  R  (SEQ ID NO:8)
```

FIG. 1A

Nucleotide (top) and amino acid (bottom) sequence of the heavy chain variable region of antibody clone 1A11

```
1    CAGGTACAGCTGCAGCAGTCAGGTCCAGGACTGGTGAAGCCCTCGCAGACCCTCTCACTC
1     Q  V  Q  L  Q  Q  S  G  P  G  L  V  K  P  S  Q  T  L  S  L

CDR1
61   ACCTGCGCCATCTCCGGGGACAGTATCTCTAGTAACAGTGTTGTTTGGAACTGGATCAGG
21    T  C  A  I  S  G  D  S  I  S  S  N  S  V  V  W  N  W  I  R

CDR2
121  CAGTCCCCATCGAGAGGCCTTGAGTGGCTGGGAAGGACATACTATAGGTCCAAGTGGTAT
41    Q  S  P  S  R  G  L  E  W  L  G  R  T  Y  Y  R  S  K  W  Y

181  AATGATTATGCAGTATCTGTGAAAAGTCGAATAACCATCAACCCAGACACATCCAAGAAC
61    N  D  Y  A  V  S  V  K  S  R  I  T  I  N  P  D  T  S  K  N

241  CAGTTCTCCCTGCAACTGAACTCTGTGACTCCCGACGACACGGCTCTCTATTACTGTGCA
81    Q  F  S  L  Q  L  N  S  V  T  P  D  D  T  A  L  Y  Y  C  A

CDR3
301  AGAGCATCATTTGGGACCAGCGGCAAATTCGACGACTGGGGCCAGGGAACCCTGGTCACC
101   R  A  S  F  G  T  S  G  K  F  D  D  W  G  Q  G  T  L  V  T

361  GTCTCAAGC (SEQ ID NO:9)
121   V  S  S  (SEQ ID NO:10)
```

FIG. 1B

Nucleotide (top) and amino acid (bottom) sequence of the light
chain variable region of antibody clone 1A7

```
1    CAGTCTGTCGTGACGCAGCCGCCCTCAGTGTCTGGGGCCCCAGGGCAGAGGGTCACCATC
1     Q  S  V  V  T  Q  P  P  S  V  S  G  A  P  G  Q  R  V  T  I
                                  CDR1
61   TCCTGCACTGGGAGCAGCTCCAACATCGGGGCAGGTTATGATGTACACTGGTACCAGCAG
21    S  C  T  G  S  S  S  N  I  G  A  G  Y  D  V  H  W  Y  Q  Q
                                                CDR2
121  CTTCCAGGAACAGCCCCCAAACTCCTCATCTATGGTAACAGCAATCGGCCCTCAGGGGTC
41    L  P  G  T  A  P  K  L  L  I  Y  G  N  S  N  R  P  S  G  V

181  CCTGACCGATTCTCTGGCTCCAAGTCTGGCACCTCAGCCTCCCTGGCCATCACTGGGCTC
61    P  D  R  F  S  G  S  K  S  G  T  S  A  S  L  A  I  T  G  L
                                               CDR3
241  CAGGCTGAGGATGAGGCTGATTATTACTGCCAGTCCTATGACAGCAGCCTGAGTGCCCTA
81    Q  A  E  D  E  A  D  Y  Y  C  Q  S  Y  D  S  S  L  S  A  L

301  TTCGGCGGAGGGACCAAGCTGACCGTCCTA (SEQ ID NO:11)
101   F  G  G  G  T  K  L  T  V  L  (SEQ ID NO:12)   FIG. 2A
```

Nucleotide (top) and amino acid (bottom) sequence of the heavy
chain variable region of antibody clone 1A7

```
1    CAGGTACAGCTGCAGCAGTCAGGCCCAGGACTGGTGAAGCCTTCGGAGACCCTGTCCCTC
1     Q  V  Q  L  Q  Q  S  G  P  G  L  V  K  P  S  E  T  L  S  L
                                          CDR1
61   ACTTGCACTGTCTCTGGTGGCTCCATCAGAAATTACTACTGGAGCTGGATCCGGCAGCCC
21    T  C  T  V  S  G  G  S  I  R  N  Y  Y  W  S  W  I  R  Q  P
                                                    CDR2
121  CCAGGGAAGGGACTGGAGTGGATTGGGTATATGTATTACAGTGGGGGAGCCAATTACAAC
41    P  G  K  G  L  E  W  I  G  Y  M  Y  Y  S  G  G  A  N  Y  N

181  CCCTCCCTCAACAGTCGAGTCACCATATCACTAGACACGTCCAAGAACCAGTTCTCCCTG
61    P  S  L  N  S  R  V  T  I  S  L  D  T  S  K  N  Q  F  S  L

241  AAACTGACCTCTGTGACCGCTGCGGACACGGCCGTGTATTATTGTGCGAGAATTCCCAAC
81    K  L  T  S  V  T  A  A  D  T  A  V  Y  Y  C  A  R  I  P  N
              CDR3
301  TACTATGATAGAAGTGGTTATTATCCCGGTTACTGGTACTTCGATCTCTGGGGCCGTGGA
101   Y  Y  D  R  S  G  Y  Y  P  G  Y  W  Y  F  D  L  W  G  R  G

361  ACCCTGGTCACCGTCTCAAGC (SEQ ID NO:13)
121   T  L  V  T  V  S  S  (SEQ ID NO:14)   FIG. 2B
```

Nucleotide (top) and amino acid (bottom) sequence of the light chain variable region of antibody clone 1A9

```
1     GATGTTGTGATGACTCAGTCTCCACTCTCCCTGCCCGTCACCCCTGGAGAGCCGGCCTCC
1      D  V  V  M  T  Q  S  P  L  S  L  P  V  T  P  G  E  P  A  S
                                        CDR1
61    ATCTCCTGCAGGTCTAGTCAGAGCCTCCTGCACAGTAATGGATACAAGTATGTGAATTGG
21     I  S  C  R  S  S  Q  S  L  L  H  S  N  G  Y  K  Y  V  N  W
                                                            CDR2
121   TACCTGCAGAAGCCGGGGCAGTCTCCACAGCTCCTGATCTATTTCGGTTCTTATCGGGCC
41     Y  L  Q  K  P  G  Q  S  P  Q  L  L  I  Y  F  G  S  Y  R  A

181   TCCGGGGTCCCTGACAGGTTCAGTGGCAGTGGATCAGGCACAGATTTTACACTGAAAATC
61     S  G  V  P  D  R  F  S  G  S  G  S  G  T  D  F  T  L  K  I
                                                            CDR3
241   AGCAGAGTGGAGGCTGAGGATGTTGGGATTTATTACTGCATGCAAGCTACACACTGGCCG
81     S  R  V  E  A  E  D  V  G  I  Y  Y  C  M  Q  A  T  H  W  P

301   TACACTTTTGGCCAGGGGACCAGGCTGGAGATCAAACGA (SEQ ID NO:15)
101    Y  T  F  G  Q  G  T  R  L  E  I  K  R   (SEQ ID NO:16)
```

FIG. 3A

Nucleotide (top) and amino acid (bottom) sequence of the heavy chain variable region of antibody clone 1A9

```
1     CAGGTGCAGCTGGTGCAGTCTGGGGGAGGCGTGGTCCAGCCTGGGAGGTCCCTGAGACTC
1      Q  V  Q  L  V  Q  S  G  G  G  V  V  Q  P  G  R  S  L  R  L
                                        CDR1
61    TCCTGTGCAGCCTCTGGATTCACCTTCAGTAGCTATGGCATGCACTGGGTCCGCCAGGCT
21     S  C  A  A  S  G  F  T  F  S  S  Y  G  M  H  W  V  R  Q  A
                                                            CDR2
121   CCAGGCAAGGGGCTGGAGTGGGTGGCAGTTATATCATATGATGGAAGTAATAAATACTAT
41     P  G  K  G  L  E  W  V  A  V  I  S  Y  D  G  S  N  K  Y  Y

181   GCAGACTCCGTGAAGGGCCGATTCACCATCTCCAGAGACAATTCCAAGAACACGCTGTAT
61     A  D  S  V  K  G  R  F  T  I  S  R  D  N  S  K  N  T  L  Y

241   CTGCAAATGAACAGCCTGAGAGCCGAGGACACGGCTGTGTATTACTGTGCGAGAGATTAC
81     L  Q  M  N  S  L  R  A  E  D  T  A  V  Y  Y  C  A  R  D  Y
        CDR3
301   TACGGTGACTACGCTTTGCTTGACTACTGGGGCCAGGGCACCCTGGTCACCGTCTCAAGC
101    Y  G  D  Y  A  L  L  D  Y  W  G  Q  G  T  L  V  T  V  S  S
      (SEQ ID NO: 17)
      (SEQ ID NO: 18)
```

FIG. 3B

Nucleotide (top) and amino acid (bottom) sequence of the light chain variable region of antibody clone 1C8

```
1    GACATCCAGTTGACCCAGTCTCCATCCTCCCTGTCTGCATCTGTAGGAGACAGAGTCACC
1     D  I  Q  L  T  Q  S  P  S  S  L  S  A  S  V  G  D  R  V  T
                                    CDR1
61   ATCACTTGCCGGGCAAGTCAGAGCATTAGCACCTATTTAAATTGGTATCAACACAGACCA
21    I  T  C  R  A  S  Q  S  I  S  T  Y  L  N  W  Y  Q  H  R  P
                                           CDR2
121  GGGAAAGCCCCTAAGCTCCTGATCTATTCTGCATCCAGTTTGCAGAGTGGGGTCCCATCA
41    G  K  A  P  K  L  L  I  Y  S  A  S  S  L  Q  S  G  V  P  S

181  AGGTTCAGTGGCAGTGGGTCTGGGACAGATTTCACTCTCACCATCAGCAGTCTCCAACCT
61    R  F  S  G  S  G  S  G  T  D  F  T  L  T  I  S  S  L  Q  P
                                  CDR3
241  GAAGATTTTGCAACCTACTACTGTCAGCAGAGTGACATTATCCCTCTCACTTTCGGCGGA
81    E  D  F  A  T  Y  Y  C  Q  Q  S  D  I  I  P  L  T  F  G  G

301  GGGACCAAGGTGGAGATCAACCGA (SEQ ID NO:19)
101   G  T  K  V  E  I  N  R  (SEQ ID NO:20)
```

FIG. 4A

Nucleotide (top) and amino acid (bottom) sequence of the heavy chain variable region of antibody clone 1C8

```
1    CAGGTACAGCTGCAGCAGTCAGGTCCAGGACTGGTGAAGCCCTCGCAGACCCTCTCACTC
1     Q  V  Q  L  Q  Q  S  G  P  G  L  V  K  P  S  Q  T  L  S  L
                                           CDR1
61   ACCTGCGCCATCTCCGGGGACAGTATCTCTAGTAACAGTGTTGTTTGGAACTGGATCAGG
21    T  C  A  I  S  G  D  S  I  S  S  N  S  V  V  W  N  W  I  R
                                                         CDR2
121  CAGTCCCCATCGAGAGGCCTTGAGTGGCTGGGAAGGACATACTATAGGTCCAAGTGGTAT
41    Q  S  P  S  R  G  L  E  W  L  G  R  T  Y  Y  R  S  K  W  Y

181  AATGATTATGCAGTATCTGTGAAAAGTCGAATAACCATCAACCCAGACACATCCAAGAAC
61    N  D  Y  A  V  S  V  K  S  R  I  T  I  N  P  D  T  S  K  N

241  CAGTTCTCCCTGCAACTGAACTCTGTGACTCCCGACGACACGGCTCTCTATTACTGTGCA
81    Q  F  S  L  Q  L  N  S  V  T  P  D  D  T  A  L  Y  Y  C  A
                         CDR3
301  AGAGCATCATTTGGGACCAGCGGCAAATTCGACGACTGGGGCCAGGGAACCCTGGTCACC
101   R  A  S  F  G  T  S  G  K  F  D  D  W  G  Q  G  T  L  V  T

361  GTCTCAAGC (SEQ ID NO:21)
121   V  S  S  (SEQ ID NO:22)
```

FIG. 4B

Nucleotide (top) and amino acid (bottom) sequence of the light chain variable region of antibody clone 1D7

```
1     GAAACGACACTCACGCAGTCTCCAGGCACCCTGTCTTTGTCTCCAGGAGAGAGAGCCACC
1       E  T  T  L  T  Q  S  P  G  T  L  S  L  S  P  G  E  R  A  T

CDR1
61    CTCTCCTGCAGGGCCAGTCGGTATATTAACGCCAACTTCTTAGCCTGGTACCAGCAGAAA
21      L  S  C  R  A  S  R  Y  I  N  A  N  F  L  A  W  Y  Q  Q  K

CDR2
121   CCTGGCCAGGCTCCCAGGCTCCTCATCTATGATGCATCCACCCGGGCCACTGGCATCCCA
41      P  G  Q  A  P  R  L  L  I  Y  D  A  S  T  R  A  T  G  I  P

181   GACAGGTTCAGTGGCAGTGGGTCTGGGACAGACTTCACTCTCACCATCAGCAGGCTGGAG
61      D  R  F  S  G  S  G  S  G  T  D  F  T  L  T  I  S  R  L  E

CDR3
241   CCTGAAGATTTTGCAGTGTATTACTGTCAGCAGTATGGTAGCTCACCTCGGACGTTCGGC
81      P  E  D  F  A  V  Y  Y  C  Q  Q  Y  G  S  S  P  R  T  F  G

301   CAGGGGACCAAGGTGGAAATCAAACGA  (SEQ ID NO:23)
101     Q  G  T  K  V  E  I  K  R  (SEQ ID NO:24)
```

FIG. 5A

Nucleotide (top) and amino acid (bottom) sequence of the heavy chain variable region of antibody clone 1D7

```
1     CAGGTCCAGCTGGTGCAGTCTGGGGCTGAGGTGAAGAAGCCTGGGTCCTCGGTGAAGGTC
1       Q  V  Q  L  V  Q  S  G  A  E  V  K  K  P  G  S  S  V  K  V

CDR1
61    TCCTGCAAGGCTTCTGGAGGCACCTTCAGCAGCTATGCTATCAGCTGGGTGCGACAGGCC
21      S  C  K  A  S  G  G  T  F  S  S  Y  A  I  S  W  V  R  Q  A

CDR2
121   CCTGGACAAGGGCTTGAGTGGATGGGAGGGATCATCCCTATCTTTGGTACAGCAAACTAC
41      P  G  Q  G  L  E  W  M  G  G  I  I  P  I  F  G  T  A  N  Y

181   GCACAGAAGTTCCAGGGCAGAGTCACGATTACCGCGGACGAATCCACGAGCACAGCCTAC
61      A  Q  K  F  Q  G  R  V  T  I  T  A  D  E  S  T  S  T  A  Y

241   ATGGAGCTGAGCAGCCTGAGATCTGAGGACACGGCCGTGTATTACTGTGCGAGAGATTCC
81      M  E  L  S  S  L  R  S  E  D  T  A  V  Y  Y  C  A  R  D  S

CDR3
301   AGCAGTGGCTGGCTCTATGATGCTTTTGATATCTGGGGCCAAGGGACAATGGTCACCGTC
101     S  S  G  W  L  Y  D  A  F  D  I  W  G  Q  G  T  M  V  T  V

361   TCAAGC  (SEQ ID NO:25)
121     S  S  (SEQ ID NO:26)
```

FIG. 5B

Nucleotide (top) and amino acid (bottom) sequence of the light chain variable region of antibody clone 1G2

```
1    GAAATTGTGCTGACTCAGTCTCCAGACACCCTGTCTTTGTCTCCAGGGGAAAGAGCCACC
1      E   I   V   L   T   Q   S   P   D   T   L   S   L   S   P   G   E   R   A   T
                                                CDR1
61   CTCTCCTGCAGGGCCAGTCAGAGTGTTAGCCACAGCTACTTAGCCTGGTACCAGCAGAAA
21     L   S   C   R   A   S   Q   S   V   S   H   S   Y   L   A   W   Y   Q   Q   K
                                                     CDR2
121  CCTGGCCAGGCTCCCAGGCTCCTCATTTATGATACATCCAGCAGGGCCACTGACATCCCA
41     P   G   Q   A   P   R   L   L   I   Y   D   T   S   S   R   A   T   D   I   P

181  GACAGGTTCAGTGGCAGTGGGTCTGGGACAGACTTCACTCTCACCATCAGCAGATTGGAG
61     D   R   F   S   G   S   G   S   G   T   D   F   T   L   T   I   S   R   L   E
                                                CDR3
241  CCTGAAGATTCTGCAGTGTATTACTGTCAGCAGTATGTTAGCTCACCTCTCACTTTTGGC
81     P   E   D   S   A   V   Y   Y   C   Q   Q   Y   V   S   S   P   L   T   F   G

301  CAGGGGACCAAGCTGGAGATCAAACGA (SEQ ID NO:27)
101    Q   G   T   K   L   E   I   K   R   (SEQ ID NO:28)
```

FIG. 6A

Nucleotide (top) and amino acid (bottom) sequence of the heavy chain variable region of antibody clone 1G2

```
1    CAGGTCCAGCTGGTACAGTCTGGGGGAGGCGTGGTCCAGCCTGGGAGGTCCCTGAGACTC
1      Q   V   Q   L   V   Q   S   G   G   G   V   V   Q   P   G   R   S   L   R   L
                                                CDR1
61   TCCTGTGCAGCCTCTGGATTCACCTTCAGTACCTATGGCTTGCACTGGGTCCGCCAGGCT
21     S   C   A   A   S   G   F   T   F   S   T   Y   G   L   H   W   V   R   Q   A
                                                                    CDR2
121  CCAGGCAAGGGGCTGGAGTGGGTGGCATTTATATCATATGATGGAAGTAATAAATACTAC
41     P   G   K   G   L   E   W   V   A   F   I   S   Y   D   G   S   N   K   Y   Y

181  GCAGACTCCGTGAAGGGCCGATTCACCATCTCCAGAGACAATTCCAAGAACACGCTGTAT
61     A   D   S   V   K   G   R   F   T   I   S   R   D   N   S   K   N   T   L   Y

241  CTGCAAATGAACGGCCTGAGAGCCGAGGACACGGCCGTATATTACTGTGCGAAGACTGTG
81     L   Q   M   N   G   L   R   A   E   D   T   A   V   Y   Y   C   A   K   T   V
                CDR3
301  GGTGTCACGTTTGTCTCGGATGCTTTTGATATATGGGGCCAAGGGACAATGGTCACCGTC
101    G   V   T   F   V   S   D   A   F   D   I   W   G   Q   G   T   M   V   T   V

361  TCAAGC (SEQ ID NO:29)
121    S   S   (SEQ ID NO:30)
```

FIG. 6B

Nucleotide (top) and amino acid (bottom) sequence of the light
chain variable region of antibody clone 2B2

```
1    GATGTTGTGATGACTCAGTCTCCAGGCACCCTGTCTGTGTCTCCGGGGGATAGCGCCACC
1     D  V  V  M  T  Q  S  P  G  T  L  S  V  S  P  G  D  S  A  T
                                      CDR1
61   CTCTCCTGCTGGGCCAGTCAGAGTCTTAGTGACAGCTACGTGTCCTGGTACCAACAGAAG
21    L  S  C  W  A  S  Q  S  L  S  D  S  Y  V  S  W  Y  Q  Q  K
                                         CDR2
121  CCTGGCCAGGCTCCCAGGCTCCTAATACATAGCGCGTCCATCAGGGCCCCTGGCATCCCG
41    P  G  Q  A  P  R  L  L  I  H  S  A  S  I  R  A  P  G  I  P

181  GACAGGTTCAGTGGCAGTGTGTCTGGCACGGAGTTCACTCTGACCATCAGCGGACTGGAG
61    D  R  F  S  G  S  V  S  G  T  E  F  T  L  T  I  S  G  L  E
                                             CDR3
241  CCTGAAGATTTTGCAGTGTATTCCTGTCACCAGTATGGTTTCTTACCTTGGACGTTCGGC
81    P  E  D  F  A  V  Y  S  C  H  Q  Y  G  F  L  P  W  T  F  G

301  CAAGGGACCAAGGTGGAGATCAGACGA  (SEQ ID NO:31)
101   Q  G  T  K  V  E  I  R  R   (SEQ ID NO:32)
```

FIG. 7A

Nucleotide (top) and amino acid (bottom) sequence of the heavy
chain variable region of antibody clone 2B2

```
1    CAGGTCCAGCTGGTACAGTCTGGGGCTGAGGTGAAGAAGCCTGGGGCCTCAGTGAAGGTC
1     Q  V  Q  L  V  Q  S  G  A  E  V  K  K  P  G  A  S  V  K  V
                                            CDR1
61   TCCTGCAAGGCTTCTGGTTACACCTTTACCAGGTATGGTATCAGCTGGGTGCGACAGGCC
21    S  C  K  A  S  G  Y  T  F  T  R  Y  G  I  S  W  V  R  Q  A
                                              CDR2
121  CCTGGACAAGGGCTTGAGTGGATGGGATGGATCAGCTCTTCCAATGGTTACACAAAGTAT
41    P  G  Q  G  L  E  W  M  G  W  I  S  S  S  N  G  Y  T  K  Y

181  GCACAGAATCTCCAGGGCAGACTCACCCTGACCACAGACACATCCACGGGCACAGCCTAC
61    A  Q  N  L  Q  G  R  L  T  L  T  T  D  T  S  T  G  T  A  Y

241  ATGGAACTGAGGAGCCTGAGATCTGAGGACACGGCCCTTTATTACTGTGCGAGATATGAT
81    M  E  L  R  S  L  R  S  E  D  T  A  L  Y  Y  C  A  R  Y  D
         CDR3
301  ATTAGTGGCCTAGATGGTTTTGATATTTGGGGCCAAGGGACAATGGTCACCGTCTCAAGC
101   I  S  G  L  D  G  F  D  I  W  G  Q  G  T  M  V  T  V  S  S
     (SEQ ID NO: 33)
     (SEQ ID NO: 34)
```

FIG. 7B

Nucleotide (top) and amino acid (bottom) sequence of the light chain variable region of antibody clone 2C5

```
1      GAAACGACACTCACGCAGTCTCCAGGCACCCTGTCTTTGTCTCCAGGGGAAAGAGCCACC
1       E  T  T  L  T  Q  S  P  G  T  L  S  L  S  P  G  E  R  A  T

CDR1
61     CTCTCCTGCAGGGCCAGTCAGAGTGTTAGCAGCAACTACTTAGCCTGGTACCAGCAGAAA
21      L  S  C  R  A  S  Q  S  V  S  S  N  Y  L  A  W  Y  Q  Q  K

CDR2
121    CCTGGCCAGGCTCCCAGGCTCCTCATCTATGCTGCTTCCAGCAGGGCCACTGGCATCCCA
41      P  G  Q  A  P  R  L  L  I  Y  A  A  S  R  A  T  G  I  P

181    GACAGGTTCAGTGGCAGTGGGTCTGGGACAGACTTCACTCTCACCATCAGCAGACTGGAG
61      D  R  F  S  G  S  G  S  G  T  D  F  T  L  T  I  S  R  L  E

CDR3
241    CCTGAAGATTTTGCAGTGTATTACTGTCAGCAGTATGGTTCCTCACGCAGTTTTGGCCAG
81      P  E  D  F  A  V  Y  Y  C  Q  Q  Y  G  S  S  R  S  F  G  Q

301    GGGACCAAGCTGGAGATCAAACGA (SEQ ID NO:35)
101     G  T  K  L  E  I  K  R   (SEQ ID NO:36)
```

FIG. 8A

Nucleotide (top) and amino acid (bottom) sequence of the heavy chain variable region of antibody clone 2C5

```
1      CAGGTGCAGCTGCAGGAGTCTGGGGGAGGCCTGGTCAAGCCTGGGGGGTCCCTGAGACTC
1       Q  V  Q  L  Q  E  S  G  G  G  L  V  K  P  G  G  S  L  R  L

CDR1
61     TCCTGTGCAGCCTCTGGATTCACCTTCAGTAGCTATAGCATGAACTGGGTCCGCCAGGCT
21      S  C  A  A  S  G  F  T  F  S  S  Y  S  M  N  W  V  R  Q  A

CDR2
121    CCAGGGAAGGGGCTGGAGTGGGTTTCATACATTAGTAGTAGTGGTAGTACCATATACTAC
41      P  G  K  G  L  E  W  V  S  Y  I  S  S  S  G  S  T  I  Y  Y

181    GCAGACTCTGTGAGGGGCCGATTCACCATCTCCAGAGACAACGCCAAGAACACGCTGTAT
61      A  D  S  V  R  G  R  F  T  I  S  R  D  N  A  K  N  T  L  Y

241    CTCCAAATGAACAGTCTGAGAGCCGAGGACACAGCTGTTTATTACTGTGTAAGAGGTGAT
81      L  Q  M  N  S  L  R  A  E  D  T  A  V  Y  Y  C  V  R  G  D

CDR3
301    CCTTACTTCTACTACTACGGTATGGACATCTGGGGCCAAGGGACCACGGTCACCGTCTCA
101     P  Y  F  Y  Y  Y  G  M  D  I  W  G  Q  G  T  T  V  T  V  S

361    AGC (SEQ ID NO:37)
121     S  (SEQ ID NO:38)
```

FIG. 8B

Nucleotide (top) and amino acid (bottom) sequence of the light
chain variable region of antibody clone 2D1

```
  1       GACATCCAGTTGACCCAGTCTCCATCCTCCCTGTCTGCTTCTGTAGGAGACAGAGTCATC
  1        D  I  Q  L  T  Q  S  P  S  S  L  S  A  S  V  G  D  R  V  I

CDR1
 61       ATCACTTGCCGGGCAACTCAGAGCATTAGCACCCACTTAAATTGGTATCAGCAGAAGCCA
 21        I  T  C  R  A  T  Q  S  I  S  T  H  L  N  W  Y  Q  Q  K  P

CDR2
121       GGGAAAGCCCCTAAGCTCCTGATCTATTCTGCATCCAGTTTACAAAGTGGGGTCCCATCT
 41        G  K  A  P  K  L  L  I  Y  S  A  S  S  L  Q  S  G  V  P  S

181       AGGTTCAGTGGCAGTGGATCTGGGACAGATTTCACTCTCACCATCAGCAGTCTGCAACCT
 61        R  F  S  G  S  G  S  G  T  D  F  T  L  T  I  S  S  L  Q  P

CDR3
241       GAAGATTTTGCAACTTACTACTGTCAACAGAGTTACAGTTCCCCCCCGATCACCTTCGGC
 81        E  D  F  A  T  Y  Y  C  Q  Q  S  Y  S  S  P  P  I  T  F  G

301       CAAGGGACACGACTGGAGATTAAACGA  (SEQ ID NO:39)
101        Q  G  T  R  L  E  I  K  R  (SEQ ID NO:40)
```

FIG. 9A

Nucleotide (top) and amino acid (bottom) sequence of the heavy
chain variable region of antibody clone 2D1

```
  1       CAGGTGCAGCTGCAGGAGTCCGGCCCAGGACTGGTGAAGCCTTCGGAGACCCTGTCCCTC
  1        Q  V  Q  L  Q  E  S  G  P  G  L  V  K  P  S  E  T  L  S  L

CDR1
 61       ACCTGCACTGTCTCTGGTGGCTCCATCAGTAGTAACATGTACTACTGGGGCTGGGTCCGC
 21        T  C  T  V  S  G  G  S  I  S  S  N  M  Y  Y  W  G  W  V  R

CDR2
121       CAGCCCCCAGGGAAGGGGCTGGAGTGGATTGGGAGTATCGATTATAGTGGGAGCACCTAC
 41        Q  P  P  G  K  G  L  E  W  I  G  S  I  D  Y  S  G  S  T  Y

181       TACAATCCGTCCCTCAGGAGTCGAGTCACCATGTCCGTAGACACGTCCAAGAAGCAGTTC
 61        Y  N  P  S  L  R  S  R  V  T  M  S  V  D  T  S  K  K  Q  F

241       TCCCTGAAGATGACCTCTGTGACCGCTGCGGACACGGCCGTGTATTACTGTGCGAGAGAA
 81        S  L  K  M  T  S  V  T  A  A  D  T  A  V  Y  Y  C  A  R  E

CDR3
301       TCCGGGTCCCCATACTACTTTGACTACTGGGGCCAGGGCACCCTGGTCACCGTCTCAAGC
101        S  G  S  P  Y  Y  F  D  Y  W  G  Q  G  T  L  V  T  V  S  S
          (SEQ ID NO: 41)
          (SEQ ID NO: 42)
```

FIG. 9B

Nucleotide (top) and amino acid (bottom) sequence of the light chain variable region of antibody clone 2F1

```
  1    CAGTCTGTGTTGACGCAGCCGCCCTCAGTGTCTGCGGCCCCAGGACAGACAGTCACCATC
  1     Q  S  V  L  T  Q  P  P  S  V  S  A  A  P  G  Q  T  V  T  I

CDR1
 61    TCCTGCTCTGGAAGCAGCTCCAACATTGGGAGGAATTATGTCTCGTGGTTCCAACAAGTC
 21     S  C  S  G  S  S  N  I  G  R  N  Y  V  S  W  F  Q  Q  V

CDR2
121    CCAGGGAGAGCCCCCAAACTCCTCATTTATGACAATAATCAGCGACCGTCAGGGATTCCT
 41     P  G  R  A  P  K  L  L  I  Y  D  N  N  Q  R  P  S  G  I  P

181    GGCCGATTCTCAGCCTCCAAGTCTGACACCTCAGCCACCCTGGACATCACCGGACTCCAG
 61     G  R  F  S  A  S  K  S  D  T  S  A  T  L  D  I  T  G  L  Q

CDR3
241    AGTGGGGACGAGGCCGTTTATTACTGCGGAACATGGGATTCCACCCTGGACCTTTATGTC
 81     S  G  D  E  A  V  Y  Y  C  G  T  W  D  S  T  L  D  L  Y  V

301    TTCGGCGGTGGGACCCATGTCCCCGTCCTA (SEQ ID NO:43)
101     F  G  G  G  T  H  V  P  V  L  (SEQ ID NO:44)
```

FIG. 10A

Nucleotide (top) and amino acid (bottom) sequence of the heavy chain variable region of antibody clone 2F1

```
  1    GAGGTCCAGCTGGTGCAGTCTGGGGCTGAGGTGAAGAAGCCTGGGGCCTCAGTGAAGGTT
  1     E  V  Q  L  V  Q  S  G  A  E  V  K  K  P  G  A  S  V  K  V

CDR1
 61    TCCTGCAAGGCATCTGGATACACCTTCACCAGCTACTATATCCACTGGGTGCGACAGGCC
 21     S  C  K  A  S  G  Y  T  F  T  S  Y  Y  I  H  W  V  R  Q  A

CDR2
121    CCTGGACAAGGTCTTGAGTGGATGGGAGCAATCAACCCGAGTGGTGGTAGCACACCCTAC
 41     P  G  Q  G  L  E  W  M  G  A  I  N  P  S  G  G  S  T  P  Y

181    GCACAGAAGTTCCAGGGCAGAGTCACCATGACCAGGGACACGTCCACGAGCACAGTCTAC
 61     A  Q  K  F  Q  G  R  V  T  M  T  R  D  T  S  T  S  T  V  Y

241    ATGGAGCTGAGCAGCCTGAGATCTGAGGACACGGCCGTGTATTACTGTGCGAGAGATGGG
 81     M  E  L  S  S  L  R  S  E  D  T  A  V  Y  Y  C  A  R  D  G

CDR3
301    ACCTATGGTTCGGGGAGTTATCCCTACTACTACTACTACGGTATGGACGTCTGGGGCCAA
101     T  Y  G  S  G  S  Y  P  Y  Y  Y  Y  Y  G  M  D  V  W  G  Q

361    GGGACCACGGTCACCGTCTCAAGC (SEQ ID NO:45)
121     G  T  T  V  T  V  S  S  (SEQ ID NO:46)
```

FIG. 10B

Nucleotide (top) and amino acid (bottom) sequence of the light chain variable region of antibody clone G2D12

```
1    AATTTTATGCTGACTCAGCCCCACTCTGTGTCGGAGTCTCCGGGAAAGACGGTAACCATC
1     N  F  M  L  T  Q  P  H  S  V  S  E  S  P  G  K  T  V  T  I
                                      CDR1
61   TCCTGCACCGGCAGCGGTGGCAGCATTGACAACAATTATGTCCACTGGTACCAACAGCGC
21    S  C  T  G  S  G  G  S  I  D  N  N  Y  V  H  W  Y  Q  Q  R
                                                              CDR2
121  CCGGGCAGTGCCCCCACCACTGTGATGTTTGAAGATAACCAAAGACCCTCTGGGGTCCCT
41    P  G  S  A  P  T  T  V  M  F  E  D  N  Q  R  P  S  G  V  P

181  GATCGGTTCTCTGGCTCCATTGACAGCTCCTCCAACTCTGCCTCCCTCGTCATCTCTGGA
61    D  R  F  S  G  S  I  D  S  S  S  N  S  A  S  L  V  I  S  G
                                                        CDR3
241  CTGAAGACTGAGGACGAGGGTGACTACTACTGTCAGTCTTCTGATGGAAGTAAAGTGGTC
81    L  K  T  E  D  E  G  D  Y  Y  C  Q  S  S  D  G  S  K  V  V

301  TTCGGCGGAGGGACCAAGCTGACCGTCCTAGGTCAG   (SEQ ID NO:47)
101   F  G  G  G  T  K  L  T  V  L  G  Q   (SEQ ID NO:48)
```

FIG. 11A

Nucleotide (top) and amino acid (bottom) sequence of the heavy chain variable region of antibody clone G2D12

```
1    GAGGTCCAGCTGGTGCAGTCTGGGGGAGGCGTGGTCCAGCCTGGGAGGTCCCTGACACTC
1     E  V  Q  L  V  Q  S  G  G  G  V  V  Q  P  G  R  S  L  T  L
                                              CDR1
61   TCCTGTGCAGCCTCTGGATTCACCTTCAGTAGCTATGGCATGCACTGGGTCCGCCAGGCT
21    S  C  A  A  S  G  F  T  F  S  S  Y  G  M  H  W  V  R  Q  A
                                                           CDR2
121  CCAGGCAAGGGGCTGGAGTGGGTGTCAGTTATATCATATGATGGAAGTAATAAATACTAT
41    P  G  K  G  L  E  W  V  S  V  I  S  Y  D  G  S  N  K  Y  Y

181  GCAGACTCCGTGAAGGGCCGATTCACCATCTCCAGAGACAATTCCAAGAACACGCTGTAT
61    A  D  S  V  K  G  R  F  T  I  S  R  D  N  S  K  N  T  L  Y

241  CTGCAAATGAACAGCCTGAGAACTGAGGACACGGCTGTGTATTACTGTGCGAAAACCCTG
81    L  Q  M  N  S  L  R  T  E  D  T  A  V  Y  Y  C  A  K  T  L
                  CDR3
301  TCCGCGGGGGAGTGGATTGGAGGGGGAGCTTTTGATATCTGGGGCCATGGGACAATGGTC
101   S  A  G  E  W  I  G  G  A  F  D  I  W  G  H  G  T  M  V

361  ACCGTCTCAAGC   (SEQ ID NO:49)
121   T  V  S  S   (SEQ ID NO:50)
```

FIG. 11B

Nucleotide (top) and amino acid (bottom) sequence of the light chain variable region of antibody clone G3F12

```
  1    GAAACGACACTCACGCAGTCTCCAGGCACCCTGTCTTTGTCTCCAGGGGAAAGAGCCACC
  1     E   T   T   L   T   Q   S   P   G   T   L   S   L   S   P   G   E   R   A   T
                                          CDR1
 61    CTCTCCTGCAGGGCCAGTCAGAGTGTTAGCAGCAGCTACTTAGCCTGGTACCAGCAGAAA
 21     L   S   C   R   A   S   Q   S   V   S   S   S   Y   L   A   W   Y   Q   Q   K
                                                                    CDR2
121    CCTGGCCAGGCTCCCAGGCTCCTCATCTATGGTGCATCCAGCAGGGCCACTGGCATCCCA
 41     P   G   Q   A   P   R   L   L   I   Y   G   A   S   S   R   A   T   G   I   P

181    GACAGGTTCAGTGGCAGTGGGTCTGGGACAGACTTCACTCTCACCATCAGCAGACTGGAG
 61     D   R   F   S   G   S   G   S   G   T   D   F   T   L   T   I   S   R   L   E
                                                    CDR3
241    CCTGAAGATTTTGCAGTGTATTACTGTCAGCAGCATGATAGCTCACCACGGACGTTCGGC
 81     P   E   D   F   A   V   Y   Y   C   Q   Q   H   D   S   S   P   R   T   F   G

301    CAAGGGACCAAGGTGGAAATCAAACGA   (SEQ ID NO:51)
101     Q   G   T   K   V   E   I   K   R   (SEQ ID NO:52)
```

FIG. 12A

Nucleotide (top) and amino acid (bottom) sequence of the heavy chain variable region of antibody clone G3F12

```
  1    CAGGTCCAGCTGGTGCAGTCTGGGGGAGGCGTGGTCCAGCCTGGGAGGTCCCTGAGACTC
  1     Q   V   Q   L   V   Q   S   G   G   G   V   V   Q   P   G   R   S   L   R   L
                                          CDR1
 61    TCCTGTGCAGCCTCTGGATTCACCTTCAGTAGTTATGGCATGCACTGGGTCCGCCAGGCT
 21     S   C   A   A   S   G   F   T   F   S   S   Y   G   M   H   W   V   R   Q   A
                                                                             CDR2
121    CCAGGCAAGGGGCTGGAGTGGGTGGCATTTATATCATATGATGGAAGTGATAAGAACTTT
 41     P   G   K   G   L   E   W   V   A   F   I   S   Y   D   G   S   D   K   N   F

181    GCAGACTCCGTGAAGGGCCGATTCACCATCTCCAGAGACAATTCCAAGAACACTCTATAT
 61     A   D   S   V   K   G   R   F   T   I   S   R   D   N   S   K   N   T   L   Y

241    CTGCAAATGAACAGCCTGAGAGCTGAGGACACGGCTGTGTATTACTGTGCGAAAGATTCC
 81     L   Q   M   N   S   L   R   A   E   D   T   A   V   Y   Y   C   A   K   D   S
         CDR3
301    TACTATGATAATAGTGCTTTTCAGGCAGACTGGGGCCAGGGCACCCTGGTCACCGTCTCA
101     Y   Y   D   N   S   A   F   Q   A   D   W   G   Q   G   T   L   V   T   V   S

361    AGC   (SEQ ID NO:53)
121     S    (SEQ ID NO:54)
```

FIG. 12B

Nucleotide (top) and amino acid (bottom) sequence of the light chain variable region of antibody clone G3F3

```
1    AATTTTATGCTGACTCAGCCCCACTCTGTGTCGGAGTCTCCGGGAAAGACGGTAACCATC
1      N  F  M  L  T  Q  P  H  S  V  S  E  S  P  G  K  T  V  T  I
                                    CDR1
61   TCCTGCACCGGCAGCGGTGGCAGCATTGACAACAATTATGTCCACTGGTACCAACAGCGC
21     S  C  T  G  S  G  G  S  I  D  N  N  Y  V  H  W  Y  Q  Q  R
                                                         CDR2
121  CCGGGCAGTGCCCCCACCACTGTGATGTTTGAAGATAACCAAAGACCCTCTGGGGTCCCT
41     P  G  S  A  P  T  T  V  M  F  E  D  N  Q  R  P  S  G  V  P

181  GATCGGTTCTCTGGCTCCATTGACAGCTCCTCCAACTCTGCCTCCCTCGTCATCTCTGGA
61     D  R  F  S  G  S  I  D  S  S  S  N  S  A  S  L  V  I  S  G
                                                   CDR3
241  CTGAAGACTGAGGACGAGGGTGACTACTACTGTCAGTCTTCTGATGGAAGTAAAGTGGTC
81     L  K  T  E  D  E  G  D  Y  Y  C  Q  S  S  D  G  S  K  V  V

301  TTCGGCGGAGGGACCAAGCTGACCGTCCTA (SEQ ID NO:55)
101    F  G  G  G  T  K  L  T  V  L   (SEQ ID NO:56)
```

FIG. 13A

Nucleotide (top) and amino acid (bottom) sequence of the heavy chain variable region of antibody clone G3F3

```
1    GAGGTCCAGCTGGTGCAGTCTGGGGGAGGCGTGGTCCAGCCTGGGAGGTCCCTGACACTC
1      E  V  Q  L  V  Q  S  G  G  G  V  V  Q  P  G  R  S  L  T  L
                                    CDR1
61   TCCTGTGCAGCCTCTGGATTCACCTTCAGTAGCTATGGCATGCACTGGGTCCGCCAGGCT
21     S  C  A  A  S  G  F  T  F  S  S  Y  G  M  H  W  V  R  Q  A
                                                         CDR2
121  CCAGGCAAGGGGCTGGAGTGGGTGTCAGTTATATCATATGATGGAAGTAATAAATACTAT
41     P  G  K  G  L  E  W  V  S  V  I  S  Y  D  G  S  N  K  Y  Y

181  GCAGACTCCGTGAAGGGCCGATTCACCATCTCCAGAGACAATTCCAAGAACACGCTGTAT
61     A  D  S  V  K  G  R  F  T  I  S  R  D  N  S  K  N  T  L  Y

241  CTGCAAATGAACAGCCTGAGAACTGAGGACACGGCTGTGTATTACTGTGCGAAAACCCTG
81     L  Q  M  N  S  L  R  T  E  D  T  A  V  Y  Y  C  A  K  T  L
              CDR3
301  TCCGCGGGGGAGTGGATTGGAGGGGGAGCTTTTGATATCTGGGGCCATGGGACAATGGTC
101    S  A  G  E  W  I  G  G  A  F  D  I  W  G  H  G  T  M  V

361  ACCGTCTCAAGC (SEQ ID NO:57)
121    T  V  S  S  (SEQ ID NO:58)
```

FIG. 13B

Nucleotide (top) and amino acid (bottom) sequence of the light chain variable region of antibody clone G3G4

```
1    GAAACGACACTCACGCAGTCTCCAGGCACCCTGTCTTTGTCTCCAGGGGAAAGAGCCACC
1     E  T  T  L  T  Q  S  P  G  T  L  S  L  S  P  G  E  R  A  T
                        CDR1
61   CTCTCCTGCAGGGCCAGTCAGAGTGTTAGCAGCAGCTACTTAGCCTGGTACCAGCAGAAA
21    L  S  C  R  A  S  Q  S  V  S  S  S  Y  L  A  W  Y  Q  Q  K
                                              CDR2
121  CCTGGCCAGGCTCCCAGGCTCCTCATCTATGGTGCATCCAGCAGGGCCACTGGCATCCCA
41    P  G  Q  A  P  R  L  L  I  Y  G  A  S  S  R  A  T  G  I  P

181  GACAGGTTCAGTGGCAGTGGGTCTGGGACAGACTTCACTCTCACCATCAGCAGACTGGAG
61    D  R  F  S  G  S  G  S  G  T  D  F  T  L  T  I  S  R  L  E
                                        CDR3
241  CCTGAAGATTTTGCAGTGTATTACTGTCAGCAGCATGATAGCTCACCACGGACGTTCGGC
81    P  E  D  F  A  V  Y  Y  C  Q  Q  H  D  S  S  P  R  T  F  G

301  CAAGGGACCAAGGTGGAAATCAAACGA  (SEQ ID NO:59)
101   Q  G  T  K  V  E  I  K  R   (SEQ ID NO:60)
```

FIG. 14A

Nucleotide (top) and amino acid (bottom) sequence of the heavy chain variable region of antibody clone G3G4

```
1    CAGGTCCAGCTGGTGCAGTCTGGGGGAGGCGTGGTCCAGCCTGGGAGGTCCCTGAGACTC
1     Q  V  Q  L  V  Q  S  G  G  G  V  V  Q  P  G  R  S  L  R  L
                                CDR1
61   TCCTGTGCAGCCTCTGGATTCACCTTCAGTAGTTATGGCATGCACTGGGTCCGCCAGGCT
21    S  C  A  A  S  G  F  T  F  S  S  Y  G  M  H  W  V  R  Q  A
                                                    CDR2
121  CCAGGCAAGGGGCTGGAGTGGGTGGCATTTATATCATATGATGGAAGTGATAAGAACTTT
41    P  G  K  G  L  E  W  V  A  F  I  S  Y  D  G  S  D  K  N  F

181  GCAGACTCCGTGAAGGGCCGATTCACCATCTCCAGAGACAATTCCAAGAACACTCTATAT
61    A  D  S  V  K  G  R  F  T  I  S  R  D  N  S  K  N  T  L  Y

241  CTGCAAATGAACAGCCTGAGAGCTGAGGACACGGCTGTGTATTACTGTGCGAAAGATTCC
81    L  Q  M  N  S  L  R  A  E  D  T  A  V  Y  Y  C  A  K  D  S
         CDR3
301  TACTATGATAATAGTGCTTTTCAGGCAGACTGGGGCCAGGGCACCCTGGTCACCGTCTCA
101   Y  Y  D  N  S  A  F  Q  A  D  W  G  Q  G  T  L  V  T  V  S

361  AGC  (SEQ ID NO:61)
121   S   (SEQ ID NO:62)
```

FIG. 14B

Nucleotide (top) and amino acid (bottom) sequence of the light chain variable region of antibody clone M3A1

```
1    GAAACGACACTCACGCAGTCTCCAGGCACCCTGTCTTTGTCTCCAGGGGAAAGAGCCACC
1     E  T  T  L  T  Q  S  P  G  T  L  S  L  S  P  G  E  R  A  T
                                      CDR1
61   CTCTCCTGCAGGGCCAGTCAGAGTGTTAGCAGCAGCTACTTAGCCTGGTACCAGCAGAAA
21    L  S  C  R  A  S  Q  S  V  S  S  S  Y  L  A  W  Y  Q  Q  K
                                               CDR2
121  CCTGGCCAGGCTCCCAGGCTCCTCATCTATGGTGCATCCAGCAGGGCCACTGGCATCCCA
41    P  G  Q  A  P  R  L  L  I  Y  G  A  S  S  R  A  T  G  I  P

181  GACAGGTTCAGTGGCAGTGGGTCTGGGACAGACTTCACTCTCACCATCAGCAGACTGGAG
61    D  R  F  S  G  S  G  S  G  T  D  F  T  L  T  I  S  R  L  E
                                 CDR3
241  CCTGAAGATTTTGCAGTGTATTACTGTCAGCAGTATGGTAGCTCACCTCGAACGTTCGGC
81    P  E  D  F  A  V  Y  Y  C  Q  Q  Y  G  S  S  P  R  T  F  G

301  CAAGGGACCAAGGTGGAAATCAAACGA (SEQ ID NO:63)
101   Q  G  T  K  V  E  I  K  R  (SEQ ID NO:64)
```

FIG. 15A

Nucleotide (top) and amino acid (bottom) sequence of the heavy chain variable region of antibody clone M3A1

```
1    GAGGTCCAGCTGGTGCAGTCTGGGGCTGAGGTGAAGAAGCCTGGGTCCTCGGTGAAGGTC
1     E  V  Q  L  V  Q  S  G  A  E  V  K  K  P  G  S  S  V  K  V
                                            CDR1
61   TCCTGCAAGGCTTCTGGAGGCACCTTCAGCAGCTATGCTATCAGCTGGGTGCGACAGGCC
21    S  C  K  A  S  G  G  T  F  S  S  Y  A  I  S  W  V  R  Q  A
                                                         CDR2
121  CCTGGACAAGGGCTTGAGTGGATGGGAGGGATCATCCCTATCTTTGGTACAGCAAACTAC
41    P  G  Q  G  L  E  W  M  G  G  I  I  P  I  F  G  T  A  N  Y

181  GCACAGAAGTTCCAGGGCAGAGTCACGATTACCGCGGACGAATCCACGAGCACAGCCTAC
61    A  Q  K  F  Q  G  R  V  T  I  T  A  D  E  S  T  S  T  A  Y

241  ATGGAGCTGAGCAGCCTGAGATCTGAGGACACGGCCGTGTATTACTGTGCGAGAGGTCCA
81    M  E  L  S  S  L  R  S  E  D  T  A  V  Y  Y  C  A  R  G  P
              CDR3
301  GAATATTGTATTAATGGTGTATGCTCTCTGGACGTCTGGGGCCAAGGGACCACGGTCACC
101   E  Y  C  I  N  G  V  C  S  L  D  W  G  Q  G  T  T  V  T

361  GTCTCAAGC (SEQ ID NO:65)
121   V  S  S  (SEQ ID NO:66)
```

FIG. 15B

Nucleotide (top) and amino acid (bottom) sequence of the light chain variable region of antibody clone M3B8

```
1      GAAATTGTGATGACACAGTCTCCAGCCACCCTGTCTTTGTCTCCAGGGGAAAGAGCCACC
1        E  I  V  M  T  Q  S  P  A  T  L  S  L  S  P  G  E  R  A  T

CDR1
61     CTCTCCTGCAGGGCCAGTCAGAGTGTTAGCAGCTACTTAGCCTGGTACCAACAGAAACCT
21       L  S  C  R  A  S  Q  S  V  S  S  Y  L  A  W  Y  Q  Q  K  P

CDR2
121    GGCCAGGCTCCCAGGCTCCTCATCTATGATGCATCCAACAGGGCCACTGGCATCCCAGCC
41       G  Q  A  P  R  L  L  I  Y  D  A  S  N  R  A  T  G  I  P  A

181    AGGTTCAGTGGCAGTGGGTCTGGGACAGACTTCACTCTCACCATCAGCAGCCTAGAGCCT
61       R  F  S  G  S  G  S  G  T  D  F  T  L  T  I  S  S  L  E  P

CDR3
241    GAAGATTTTGCAGTGTATTACTGTCACCAATATGGTAGCTCACCTCAAACGTTCGGCCAA
81       E  D  F  A  V  Y  Y  C  H  Q  Y  G  S  S  P  Q  T  F  G  Q

301    GGGACCAAGGTGGAAATCAAACGA (SEQ ID NO:67)
101      G  T  K  V  E  I  K  R  (SEQ ID NO:68)
```

FIG. 16A

Nucleotide (top) and amino acid (bottom) sequence of the heavy chain variable region of antibody clone M3B8

```
1      GAGGTCCAGCTGGTGCAGTCTGGGGCTGAGGTGAAGAAGCCTGGGTCCTCGGTGAAGGTC
1        E  V  Q  L  V  Q  S  G  A  E  V  K  K  P  G  S  S  V  K  V

CDR1
61     TCCTGCAAGGCTTCTGGAGGCACCTTCAGCAGCTATGCTATCAGCTGGGTGCGACAGGCC
21       S  C  K  A  S  G  G  T  F  S  S  Y  A  I  S  W  V  R  Q  A

CDR2
121    CCTGGACAAGGGCTTGAGTGGATGGGAGGGATCATCCCTATCTTTGGTACAGCAAACTAC
41       P  G  Q  G  L  E  W  M  G  G  I  I  P  I  F  G  T  A  N  Y

181    GCACAGAAGTTCCAGGGCAGAGTCACGATTACCGCGGACGAATCCACGAGCACAGCCTAC
61       A  Q  K  F  Q  G  R  V  T  I  T  A  D  E  S  T  S  T  A  Y

241    ATGGAGCTGAGCAGCCTGAGATCTGAGGACACGGCCGTGTATTACTGTGCGGTCCACTAC
81       M  E  L  S  S  L  R  S  E  D  T  A  V  Y  Y  C  A  V  H  Y

CDR3
301    GGTGACTACGTTTTCTCCTCTATGGACGTCTGGGGCCAAGGGACCACGGTCACCGTCTCA
101      G  D  Y  V  F  S  S  M  D  V  W  G  Q  G  T  T  V  T  V  S

361    AGC (SEQ ID NO:69)
121      S  (SEQ ID NO:70)
```

FIG. 16B

Nucleotide (top) and amino acid (bottom) sequence of the light chain variable region of antibody clone T3E3

```
1    GAAATTGTGCTGACTCAGTCTCCAGCCACCCTGTCTTTGTCTCCAGGGGAAAGAGCCACC
1     E  I  V  L  T  Q  S  P  A  T  L  S  L  S  P  G  E  R  A  T
                        CDR1
61   CTCTCCTGCAGGGCCAGTCAGAGTGTTGGCAGCTACTTAGCCTGGTACCAACAGAAGCCT
21    L  S  C  R  A  S  Q  S  V  G  S  Y  L  A  W  Y  Q  Q  K  P
                                           CDR2
121  GGCTAGGCTCCCAGACTCCTCATCTATGATGCATCCCACAGGGCCACTGGCATCCCAGCC
41    G  *  A  P  R  L  L  I  Y  D  A  S  H  R  A  T  G  I  P  A

181  AGGTTCAGTGGCAGTGGGTCTGGGACAGACTTCACTCTCACCATCAGCAGCCTAGAGCCT
61    R  F  S  G  S  G  S  G  T  D  F  T  L  T  I  S  S  L  E  P
                                      CDR3
241  GAAGATTTTGCAGTTTATTACTGTCAGCAGCGTAGCAACTGGCCTCCGATGTACACTTTT
81    E  D  F  A  V  Y  Y  C  Q  Q  R  S  N  W  P  P  M  Y  T  F

301  GGCCAGGGGACCAAGCTGGAGATCAAACGA (SEQ ID NO:71)
101   G  Q  G  T  K  L  E  I  K  R  (SEQ ID NO:72)
```

FIG. 17A

Nucleotide (top) and amino acid (bottom) sequence of the heavy chain variable region of antibody clone T3E3

```
1    GAGGTCCAGCTGGTGCAGTCTGGGGCTGAGGTGAAGAAGCCTGGGTCCTCGGTGAAGGTC
1     E  V  Q  L  V  Q  S  G  A  E  V  K  K  P  G  S  S  V  K  V
                                CDR1
61   TCCTGCAAGGCTTCTGGAGGCACCTTCAGCAGCTATACTATCAGCTGGGTGCGACAGGCC
21    S  C  K  A  S  G  G  T  F  S  S  Y  T  I  S  W  V  R  Q  A
                                                       CDR2
121  CCTGGACAAGGGCTTGAGTGGATGGGAGGGATCATCCCTATCTTTGGTACAGCAAACTAC
41    P  G  Q  G  L  E  W  M  G  G  I  I  P  I  F  G  T  A  N  Y

181  GCACAGAAGTTCCAGGGCAGAGTCACGATTACCGCGGACAAATCCACGAGCACAGCCTAC
61    A  Q  K  F  Q  G  R  V  T  I  T  A  D  K  S  T  S  T  A  Y

241  ATGGAGCTGAGCAGCCTGAGATCTGAGGACACGGCCGTGTATTACTGTGCGGGGGATACG
81    M  E  L  S  S  L  R  S  E  D  T  A  V  Y  Y  C  A  G  D  T
        CDR3
301  GATAGTAGTGGTTATTACGGCGCGGTTGACTACTGGGGCCAGGGCACCCTGGTCACCGTC
101   D  S  S  G  Y  Y  G  A  V  D  Y  W  G  Q  G  T  L  V  T  V

361  TCAAGC (SEQ ID NO:73)
121   S  S  (SEQ ID NO:74)
```

FIG. 17B

Nucleotide (top) and amino acid (bottom) sequence of the light chain variable region of antibody clone T3F1

```
  1      GAAATTGTGCTGACTCAGTCTCCAGCCACCCTGTCTTTGTCTCCAGGGGAAAGAGCCACC
  1       E  I  V  L  T  Q  S  P  A  T  L  S  L  S  P  G  E  R  A  T

CDR1
 61      CTCTCCTGCAGGGCCAGTCAGAGTGTTGGCAGCTACTTAGCCTGGTACCAACAGAAGCCT
 21       L  S  C  R  A  S  Q  S  V  G  S  Y  L  A  W  Y  Q  Q  K  P

CDR2
121      GGCTAGGCTCCCAGACTCCTCATCTATGATGCATCCCACAGGGCCACTGGCATCCCAGCC
 41       G  *  A  P  R  L  L  I  Y  D  A  S  H  R  A  T  G  I  P  A

181      AGGTTCAGTGGCAGTGGGTCTGGGACAGACTTCACTCTCACCATCAGCAGCCTAGAGCCT
 61       R  F  S  G  S  G  S  G  T  D  F  T  L  T  I  S  S  L  E  P

CDR3
241      GAAGATTTTGCAGTTTATTACTGTCAGCAGCGTAGCAACTGGCCTCCGATGTACACTTTT
 81       E  D  F  A  V  Y  Y  C  Q  Q  R  S  N  W  P  P  M  Y  T  F

301      GGCCAGGGGACCAAGCTGGAGATCAAACGA  (SEQ ID NO:75)
101       G  Q  G  T  K  L  E  I  K  R   (SEQ ID NO:76)
```

FIG. 18A

Nucleotide (top) and amino acid (bottom) sequence of the heavy chain variable region of antibody clone T3F1

```
  1      GAGGTCCAGCTGGTGCAGTCTGGGGCTGAGGTGAAGAAGCCTGGGTCCTCGGTGAAGGTC
  1       E  V  Q  L  V  Q  S  G  A  E  V  K  K  P  G  S  S  V  K  V

CDR1
 61      TCCTGCAAGGCTTCTGGAGGCACCTTCAGCAGCTATACTATCAGCTGGGTGCGACAGGCC
 21       S  C  K  A  S  G  G  T  F  S  S  Y  T  I  S  W  V  R  Q  A

CDR2
121      CCTGGACAAGGGCTTGAGTGGATGGGAGGGATCATCCCTATCTTTGGTACAGCAAACTAC
 41       P  G  Q  G  L  E  W  M  G  G  I  I  P  I  F  G  T  A  N  Y

181      GCACAGAAGTTCCAGGGCAGAGTCACGATTACCGCGGACAAATCCACGAGCACAGCCTAC
 61       A  Q  K  F  Q  G  R  V  T  I  T  A  D  K  S  T  S  T  A  Y

241      ATGGAGCTGAGCAGCCTGAGATCTGAGGACACGGCCGTGTATTACTGTGCGGGGGATACG
 81       M  E  L  S  S  L  R  S  E  D  T  A  V  Y  Y  C  A  G  D  T

CDR3
301      GATAGTAGTGGTTATTACGGCGCGGTTGACTACTGGGGCCAGGGCACCCTGGTCACCGTC
101       D  S  S  G  Y  Y  G  A  V  D  Y  W  G  Q  G  T  L  V  T  V

361      TCAAGC  (SEQ ID NO:77)
121       S  S   (SEQ ID NO:78)
```

FIG. 18B

Nucleotide (top) and amino acid (bottom) sequence of the light chain variable region of antibody clone T3F2

```
1      GAAATTGTGCTGACTCAGTCTCCACTCTCCCTGCCCGTCACCCCTGGAGAGCCGGCCTCC
1        E  I  V  L  T  Q  S  P  L  S  L  P  V  T  P  G  E  P  A  S
                                                      CDR1
61     ATCTCCTGCAGGTCTAGTCAGAGCCTCCTGCATAGTAATGGATACAACTATTTGGATTGG
21       I  S  C  R  S  S  Q  S  L  L  H  S  N  G  Y  N  Y  L  D  W
                                                                 CDR2
121    TACCTGCAGAAGCCAGGGCAGTCTCCACAGCTCCTGATCTATTTGGGTTCTAATCGGGCC
41       Y  L  Q  K  P  G  Q  S  P  Q  L  L  I  Y  L  G  S  N  R  A

181    TCCGGGGTCCCTGACAGGTTCAGTGGCAGTGGATCAGGCACAGATTTTACACTGAAAATC
61       S  G  V  P  D  R  F  S  G  S  G  S  G  T  D  F  T  L  K  I
                                                      CDR3
241    AGCAGAGTGGAGGCTGAGGATGTTGGGGTTTATTACTGCATGCAAGCTCTACAAACTCCT
81       S  R  V  E  A  E  D  V  G  V  Y  Y  C  M  Q  A  L  Q  T  P

301    CGGACGTTCGGCCAAGGGACCAAGGTGGAAATCAAACGA  (SEQ ID NO:79)
101      R  T  F  G  Q  G  T  K  V  E  I  K  R   (SEQ ID NO:80)
```

FIG. 19A

Nucleotide (top) and amino acid (bottom) sequence of the heavy chain variable region of antibody clone T3F2

```
1      CAGGTGCAGCTGGTGCAATCTGGGGGAGGCGTGGTCCAGCCTGGGAGGTCCCTGAGACTC
1        Q  V  Q  L  V  Q  S  G  G  G  V  V  Q  P  G  R  S  L  R  L
                                                      CDR1
61     TCCTGTGCAGCCTCTGGATTCACCTTCAGTAGCTATGGCATGCACTGGGTCCGCCAGGCT
21       S  C  A  A  S  G  F  T  F  S  S  Y  G  M  H  W  V  R  Q  A
                                                             CDR2
121    CCAGGCAAGGGGCTGGAGTGGGTGGCAGTTATATCATATGATGGAAGTAATAAATACTAT
41       P  G  K  G  L  E  W  V  A  V  I  S  Y  D  G  S  N  K  Y  Y

181    GCAGACTCCGTGAAGGGCCGATTCACCATCTCCAGAGACAATTCCAAGAACACGCTGTAT
61       A  D  S  V  K  G  R  F  T  I  S  R  D  N  S  K  N  T  L  Y

241    CTGCAAATGAACAGCCTGAGAGCTGAGGACACGGCTGTGTATTACTGTGCGAGAGACTTT
81       L  Q  M  N  S  L  R  A  E  D  T  A  V  Y  Y  C  A  R  D  F
                CDR3
301    GACTACGGTGACTCATACTACTACTACGGTATGGACGTCTGGGGCCAAGGGACCACGGTC
101      D  Y  G  D  S  Y  Y  Y  Y  G  M  D  V  W  G  Q  G  T  T  V

361    ACCGTCTCAAGC  (SEQ ID NO:81)
121      T  V  S  S  (SEQ ID NO:82)
```

FIG. 19B

Nucleotide (top) and amino acid (bottom) sequence of the light chain variable region of antibody clone 4A9

```
1    GACATCCAGATGACCCAGTCTCCTTCCATCCTGTCTGCATCTGTAGGAGACAGAGTCACC
1      D  I  Q  M  T  Q  S  P  S  I  L  S  A  S  V  G  D  R  V  T
                              CDR1
61   ATCACTTGCCGGGCCAGTCAGAGATTTGGTGATTACTTGGCCTGGTATCAGCAGAAGCCA
21     I  T  C  R  A  S  Q  R  F  G  D  Y  L  A  W  Y  Q  Q  K  P
                                             CDR2
121  GGGCAAGCCCCTAAGCTCCTGATCTATGGTGCATCCACTTTGCAGAGTGGGGTCCCATCA
41     G  Q  A  P  K  L  L  I  Y  G  A  S  T  L  Q  S  G  V  P  S

181  AGGTTCAGCGGCAGTGGCTCTGGGACAGAGTTCACTCTCACCATCAGCGGCCTGCAGCCT
61     R  F  S  G  S  G  S  G  T  E  F  T  L  T  I  S  G  L  Q  P
                              CDR3
241  GAAGATTTTGCAACTTACTATTGTCAGCAGGCTAACAGTTTCCCCATCACCTTCGGCAAA
81     E  D  F  A  T  Y  Y  C  Q  Q  A  N  S  F  P  I  T  F  G  K

301  GGGACACGGCTGGACATCAGACGA   (SEQ ID NO:83)
101    G  T  R  L  D  I  R  R   (SEQ ID NO:84)
```

FIG. 20A

Nucleotide (top) and amino acid (bottom) sequence of the heavy chain variable region of antibody clone 4A9

```
1    CAGGTCCAGCTGGTGCAGTCTGGGGCTGAGGTGAAGAAGCCTGGGTCCTCAGTGAAGGTC
1      Q  V  Q  L  V  Q  S  G  A  E  V  K  K  P  G  S  S  V  K  V
                                             CDR1
61   TCCTGCAAGGCTTCTGGAGGCACCTTCAGCAGCTATGCTATCAGCTGGGTGCGACAGGCC
21     S  C  K  A  S  G  G  T  F  S  S  Y  A  I  S  W  V  R  Q  A
                                                         CDR2
121  CCTGGACAAGGGCTTGAGTGGATGGGATGGATCAACGTTGGCAATGGTAACGCAATATAT
41     P  G  Q  G  L  E  W  M  G  W  I  N  V  G  N  G  N  A  I  Y

181  TCACAGAAGTTCCAGGGCAGAGTCACCATTACCAGGGACACATCCGCGACCACAGCCTAC
61     S  Q  K  F  Q  G  R  V  T  I  T  R  D  T  S  A  T  T  A  Y

241  ATGGAACTGAGCAGCCTGAGATCTGAAGACACGGCTGTGTATTACTGTGCGAGAGACGGG
81     M  E  L  S  S  L  R  S  E  D  T  A  V  Y  Y  C  A  R  D  G
         CDR3
301  GAGAGAGCCTGGGACCTTGACTACTGGGGCCAGGGAACCCTGGTCACCGTCTCAAGC

101    E  R  A  W  D  L  D  Y  W  G  Q  G  T  L  V  T  V  S  S
       (SEQ ID NO: 85)
       (SEQ ID NO: 86)
```

FIG. 20B

Nucleotide (top) and amino acid (bottom) sequence of the light chain variable region of antibody clone 4B4

```
1    AATTTTATGCTGACTCAGCCCCACTCTGTGTCGGAGTCTCCGGGGAAGACCGTAACCATC
1      N  F  M  L  T  Q  P  H  S  V  S  E  S  P  G  K  T  V  T  I
                                CDR1
61   TCCTGCACCGGCAGCGGTGGCAGCATTGCCACCAACTATGTGCAGTGGTACCAGCAGCGC
21     S  C  T  G  S  G  G  S  I  A  T  N  Y  V  Q  W  Y  Q  Q  R
                                              CDR2
121  CCGGGCAGTGCCCCCGCCACTGTGATCTATGAGGATGACCAAAGACCCTCTGGGGTCCCT
41     P  G  S  A  P  A  T  V  I  Y  E  D  D  Q  R  P  S  G  V  P

181  GATCGGTTCTCTGGCTCCATCGACAGCTCCTCCAACTCTGCCTCCCTCACCATCTCTGGA
61     D  R  F  S  G  S  I  D  S  S  S  N  S  A  S  L  T  I  S  G
                                        CDR3
241  CTGAAGACTGAGGACGAGGCTGACTACTACTGTCAGTCTTATGATAGCAGCAATCAGGTA
81     L  K  T  E  D  E  A  D  Y  Y  C  Q  S  Y  D  S  S  N  Q  V

301  TTCGGCGGAGGGACCAAGCTGACCGTCCTA  (SEQ ID NO:87)
101    F  G  G  G  T  K  L  T  V  L  (SEQ ID NO:88)
```

FIG. 21A

Nucleotide (top) and amino acid (bottom) sequence of the heavy chain variable region of antibody clone 4B4

```
1    CAGGTGCAGCTACAGCAGTGGGGCGCAGGACTGTTGAAGCCTTCGGAGACCCTGTCCCTC
1      Q  V  Q  L  Q  Q  W  G  A  G  L  L  K  P  S  E  T  L  S  L
                                CDR1
61   ACCTGCGCTGTCTATGGTGGGTCCTTCAGTGGTTACTACTGGAGCTGGATCCGCCAGCCC
21     T  C  A  V  Y  G  G  S  F  S  G  Y  Y  W  S  W  I  R  Q  P
                                              CDR2
121  CCAGGGAAGGGGCTGGAGTGGATTGGGGAAATCAATCATAGTGGAAGCACCAACTACAAC
41     P  G  K  G  L  E  W  I  G  E  I  N  H  S  G  S  T  N  Y  N

181  CCGTCCCTCAAGAGTCGAGTCACCATATCAGTAGACACGTCCAAGAACCAGTTCTCCCTG
61     P  S  L  K  S  R  V  T  I  S  V  D  T  S  K  N  Q  F  S  L

241  AAGCTGAGCTCTGTGACCGCCGCGGACACGGCTGTGTATTACTGTGCGAGGATGGTACGT
81     K  L  S  S  V  T  A  A  D  T  A  V  Y  Y  C  A  R  M  V  R
       CDR3
301  TACTACTACGGTATGGACGTCTGGGGCCAAGGGACCACGGTCACCGTCTCAAGC  (SEQ ID NO:89)
101    Y  Y  Y  G  M  D  V  W  G  Q  G  T  T  V  T  V  S  S  (SEQ ID NO:90)
```

FIG. 21B

Nucleotide (top) and amino acid (bottom) sequence of the light chain variable region of antibody clone 4C2

```
1    TCCTATGTGCTGACTCAGCCACCCTCAGTGTCAGAGGCCCCAGGAAAGACGGCCAGGATT
1      S  Y  V  L  T  Q  P  P  S  V  S  E  A  P  G  K  T  A  R  I
                                CDR1
61   ACCTGTGAGGGCATCACGATTGGAAGGAAGAGTGTGCATTGGTACCAGCAGAAGCCAGGC
21     T  C  E  G  I  T  I  G  R  K  S  V  H  W  Y  Q  Q  K  P  G
                                        CDR2
121  CAGGCCCCTGTGTTGGTCGTCTATGATGATACTGTCCGGCCCTCAGGGGTCCCTGAGCGA
41     Q  A  P  V  L  V  V  Y  D  D  T  V  R  P  S  G  V  P  E  R

181  TTCTCTGGCTCCAACTCTGGGAACACGGCCACCCTGATCATCAGCGGAGTCGAAGCCGGG
61     F  S  G  S  N  S  G  N  T  A  T  L  I  I  S  G  V  E  A  G
                                            CDR3
241  GATGAGGCCGACTATTACTGCCAGGTGTGGGATAGTAGCACTGATCCCCAAGTGGTCTTC
81     D  E  A  D  Y  Y  C  Q  V  W  D  S  S  T  D  P  Q  V  V  F

301  GGCGGAGGGACCAAGGTGACCGTCCTG (SEQ ID NO:91)
101    G  G  G  T  K  V  T  V  L  (SEQ ID NO:92)
```

FIG. 22A

Nucleotide (top) and amino acid (bottom) sequence of the heavy chain variable region of antibody clone 4C2

```
1    CAGGTACAGCTGCAGCAGTCAGGTCCAGGACTGGTGAAGCCCTCGCAGACCCTCTCACTC
1      Q  V  Q  L  Q  Q  S  G  P  G  L  V  K  P  S  Q  T  L  S  L
                                CDR1
61   ACCTGTGCCATCTCCGGGGACAGTGTCTCTAGCAAGAATTCTTCTTGGAACTGGATCAGG
21     T  C  A  I  S  G  D  S  V  S  S  K  N  S  S  W  N  W  I  R
                                                            CDR2
121  CAGTCCCCATCGAGAGGCCTTGAGTGGCTGGGGAGGACATACTACAGGTCCAAGTGGTAT
41     Q  S  P  S  R  G  L  E  W  L  G  R  T  Y  Y  R  S  K  W  Y

181  TATGATTATGCAGTCTCTGTGAAAGGTCGAATAACCTTCACCCCAGACACATCCAAGAAC
61     Y  D  Y  A  V  S  V  K  G  R  I  T  F  T  P  D  T  S  K  N

241  CAGGTCTCCCTGCACCTGAACGCTGTGACTCCCGAGGACACGGCTATGTATTACTGTGTA
81     Q  V  S  L  H  L  N  A  V  T  P  E  D  T  A  M  Y  Y  C  V
              CDR3
301  AGGGGCAGTATTTTTGATGTGTGGGGCCAAGGGACAATGGTCACCGTCTCAAGC (SEQ ID NO:93)
101    R  G  S  I  F  D  V  W  G  Q  G  T  M  V  T  V  S  S  (SEQ ID NO:94)
```

FIG. 22B

Nucleotide (top) and amino acid (bottom) sequence of the light chain variable region of antibody clone 4G9

```
1    GACATCCAGATGACCCAGTCTCCTTCCATCCTGTCTGCATCTGTAGGAGACAGAGTCACC
1     D  I  Q  M  T  Q  S  P  S  I  L  S  A  S  V  G  D  R  V  T
                    CDR1
61   ATCACTTGCCGGGCCAGTCAGAGATTTGGTGATTACTTGGCCTGGTATCAGCAGAAGCCA
21    I  T  C  R  A  S  Q  R  F  G  D  Y  L  A  W  Y  Q  Q  K  P
                                 CDR2
121  GGGCAAGCCCCTAAGCTCCTGATCTATGGTGCATCCACTTTGCAGAGTGGGGTCCCATCA
41    G  Q  A  P  K  L  L  I  Y  G  A  S  T  L  Q  S  G  V  P  S

181  AGGTTCAGCGGCAGTGGCTCTGGGACAGAGTTCACTCTCACCATCAGCGGCCTGCAGCCT
61    R  F  S  G  S  G  S  G  T  E  F  T  L  T  I  S  G  L  Q  P
                                       CDR3
241  GAAGATTTTGCAACTTACTATTGTCAGCAGGCTAACAGTTTCCCCATCACCTTCGGCAAA
81    E  D  F  A  T  Y  Y  C  Q  Q  A  N  S  F  P  I  T  F  G  K

301  GGGACACGGCTGGACATCAGACGA (SEQ ID NO:95)
101   G  T  R  L  D  I  R  R  (SEQ ID NO:96)
```

FIG. 23A

Nucleotide (top) and amino acid (bottom) sequence of the heavy chain variable region of antibody clone 4G9

```
1    CAGGTCCAGCTGGTGCAGTCTGGGGCTGAGGTGAAGAAGCCTGGGTCCTCAGTGAAGGTC
1     Q  V  Q  L  V  Q  S  G  A  E  V  K  K  P  G  S  S  V  K  V
                                      CDR1
61   TCCTGCAAGGCTTCTGGAGGCACCTTCAGCAGCTATGCTATCAGCTGGGTGCGACAGGCC
21    S  C  K  A  S  G  G  T  F  S  S  Y  A  I  S  W  V  R  Q  A
                                                      CDR2
121  CCTGGACAAGGGCTTGAGTGGATGGGATGGATCAACGTTGGCAATGGTAACGCAATATAT
41    P  G  Q  G  L  E  W  M  G  W  I  N  V  G  N  G  N  A  I  Y

181  TCACAGAAGTTCCAGGGCAGAGTCACCATTACCAGGGACACATCCGCGACCACAGCCTAC
61    S  Q  K  F  Q  G  R  V  T  I  T  R  D  T  S  A  T  T  A  Y

241  ATGGAACTGAGCAGCCTGAGATCTGAAGACACGGCTGTGTATTACTGTGCGAGAGACGGG
81    M  E  L  S  S  L  R  S  E  D  T  A  V  Y  Y  C  A  R  D  G
         CDR3
301  GAGAGAGCCTGGGACCTTGACTACTGGGGCCAGGGAACCCTGGTCACCGTCTCAAGC
101   E  R  A  W  D  L  D  Y  W  G  Q  G  T  L  V  T  V  S  S
     (SEQ ID NO: 97)
     (SEQ ID NO: 98)
```

FIG. 23B

Nucleotide (top) and amino acid (bottom) sequence of the light chain variable region of antibody clone 3A12

```
1    GAAACGACACTCACGCAGTCTCCAGGCACCCTGTCTTTGTCTCCAGGGGAAAGAGCCACC
1     E  T  T  L  T  Q  S  P  G  T  L  S  L  S  P  G  E  R  A  T

CDR1
61   CTCTCCTGCAGGGCCAGTCAGAGTGTTAGCAGCAGGTACTTAGCCTGGTACCAGCAGAAA
21    L  S  C  R  A  S  Q  S  V  S  S  R  Y  L  A  W  Y  Q  Q  K

CDR2
121  CCTGGCCAGGCTCCCAGGCTCCTCATCTATGGTGCATCCAGCAGGGCCACTGGCATCCCA
41    P  G  Q  A  P  R  L  L  I  Y  G  A  S  S  R  A  T  G  I  P

181  GACAGGTTCAGTGGCAGTGGGTCTGGGACAGACTTCACTCTCACCATCAGCAGACTGGAG
61    D  R  F  S  G  S  G  S  G  T  D  F  T  L  T  I  S  R  L  E

CDR3
241  CCTGAAGATTTTGCAGTGTATTACTGTCAGCAGTATGGTAGCTCAAACACTTTTGGCCAG
81    P  E  D  F  A  V  Y  Y  C  Q  Q  Y  G  S  S  N  T  F  G  Q

301  GGGACCAAGCTGGAGATCAAACGA (SEQ ID NO:99)
101   G  T  K  L  E  I  K  R   (SEQ ID NO:100)
```

FIG. 24A

Nucleotide (top) and amino acid (bottom) sequence of the heavy chain variable region of antibody clone 3A12

```
1    CAGGTGCAGCTGCAGGAGTCGGGCCCAGGACTGGTGAAGCCTTCGGAGACCCTGTCCCTC
1     Q  V  Q  L  Q  E  S  G  P  G  L  V  K  P  S  E  T  L  S  L

CDR1
61   ACCTGCACTGTCTCTGGTGGCTCCATCAGCAGTAGTAGTTACTACTGGGGCTGGATCCGC
21    T  C  T  V  S  G  G  S  I  S  S  S  S  Y  Y  W  G  W  I  R

CDR2
121  CAGCCCCCAGGGAAGGGGCTGGAGTGGATTGGGAGTATCTATTATAGTGGGAGCACCTAC
41    Q  P  P  G  K  G  L  E  W  I  G  S  I  Y  Y  S  G  S  T  Y

181  TACAACCCGTCCCTCAAGAGTCGAGTCACCATATCCGTAGACACGTCCAAGAACCAGTTC
61    Y  N  P  S  L  K  S  R  V  T  I  S  V  D  T  S  K  N  Q  F

241  TCCCTGAAGCTGAGCTCTGTGACCGCCGCAGACACGGCTGTGTATTACTGTGCGAGATCC
81    S  L  K  L  S  S  V  T  A  A  D  T  A  V  Y  Y  C  A  R  S

CDR3
301  AGGAGTGGGAGCTACCTCAATGATGCTTTTGATATCTGGGGCCAAGGGACAATGGTCACC
101   R  S  G  S  Y  L  N  D  A  F  D  I  W  G  Q  G  T  M  V  T

361  GTCTCAAGC (SEQ ID NO:101)
121   V  S  S   (SEQ ID NO:102)
```

FIG. 24B

Nucleotide (top) and amino acid (bottom) sequence of the light chain variable region of antibody clone 3B1

```
1    GAAACGACACTCACGCAGTCTCCAGGCACCCTGTCTTTGTCTCCAGGGGAAAGAGCCACC
1     E  T  T  L  T  Q  S  P  G  T  L  S  L  S  P  G  E  R  A  T
                                       CDR1
61   CTCTCCTGCAGGGCCAGTCAGAGTGTTAGCAGCAGCTACTTAGCCTGGTACCAGCAGAAA
21    L  S  C  R  A  S  Q  S  V  S  S  S  Y  L  A  W  Y  Q  Q  K
                                                    CDR2
121  CCTGGCCAGGCTCCCAGGCTCCTCATCTATGGTGCATCCAGCAGGGCCACTGGCATCCCA
41    P  G  Q  A  P  R  L  L  I  Y  G  A  S  S  R  A  T  G  I  P

181  GACAGGTTCAGTGGCAGTGGGTCTGGGACAGACTTCACTCTCACCATCAGCAGACTGGAG
61    D  R  F  S  G  S  G  S  G  T  D  F  T  L  T  I  S  R  L  E
                                      CDR3
241  CCTGAAGATTTTGCAGTGTATTACTGTCAGCAGTATGGTAGCTCATCGGGGACGTTCGGC
81    P  E  D  F  A  V  Y  Y  C  Q  Q  Y  G  S  S  S  G  T  F  G

301  CAAGGGACCAAGGTGGAAATCAAACGA (SEQ ID NO:103)
101   Q  G  T  K  V  E  I  K  R  (SEQ ID NO:104)       FIG. 25A
```

Nucleotide (top) and amino acid (bottom) sequence of the heavy chain variable region of antibody clone 3B1

```
1    CAGGTACAGCTGCAGCAGTCAGGGGCTGAGGTGAAGAAGCCTGGGTCCTCGGTGAAGGTC
1     Q  V  Q  L  Q  Q  S  G  A  E  V  K  K  P  G  S  S  V  K  V
                                         CDR1
61   TCCTGCAAGGCTTCTGGAGGCACCTTCAGCAGCTATGCTATCAGCTGGGTGCGACAGGCC
21    S  C  K  A  S  G  G  T  F  S  S  Y  A  I  S  W  V  R  Q  A
                                                         CDR2
121  CCTGGACAAGGGCTTGAGTGGATGGGAAGGATCATCCCTATCCTTGGTATAGCAAACTAC
41    P  G  Q  G  L  E  W  M  G  R  I  I  P  I  L  G  I  A  N  Y

181  GCACAGAAGTTCCAGGGCAGAGTCACGATTACCGCGGACAAATCCACGAGCACAGCCTAC
61    A  Q  K  F  Q  G  R  V  T  I  T  A  D  K  S  T  S  T  A  Y

241  ATGGAGCTGAGCAGCCTGAGATCTGAGGACACGGCCGTGTATTACTGTGCGAGAGGTTTC
81    M  E  L  S  S  L  R  S  E  D  T  A  V  Y  Y  C  A  R  G  F
                CDR3
301  CGTCCGTACTACTACTACGGTATGGACGTCTGGGGCCAAGGGACCACGGTCACCGTCTCA
101   R  P  Y  Y  Y  Y  G  M  D  V  W  G  Q  G  T  T  V  T  V  S

361  AGC (SEQ ID NO:105)
121   S  (SEQ ID NO:106)                              FIG. 25B
```

Nucleotide (top) and amino acid (bottom) sequence of the light chain variable region of antibody clone 3F5

```
1    GAAACGACACTCACGCAGTCTCCAGGCACCCTGTCTTTGTCTCCAGGGGAAAGAGCCACC
1      E  T  T  L  T  Q  S  P  G  T  L  S  L  S  P  G  E  R  A  T

CDR1
61   CTCTCCTGCAGGGCCAGTCAGAGTGTTGGCAGCAACTTAGCCTGGTACCAGCAGAGACCT
21     L  S  C  R  A  S  Q  S  V  G  S  N  L  A  W  Y  Q  Q  R  P

CDR2
121  GGCCAGGCTCCCAGCCTCCTCATCTATGGTGCATCCAGCAGGGCCACTGGCGTCCCAGAC
41     G  Q  A  P  S  L  L  I  Y  G  A  S  S  R  A  T  G  V  P  D

181  AGGTTCAGTGGCAGTGGGTCTGGGACAGACTTCACTCTCACCATCAGCAGACTGGAGCCT
61     R  F  S  G  S  G  S  G  T  D  F  T  L  T  I  S  R  L  E  P

CDR3
241  GAAGATTTTGCTGTATATTACTGTCAGCAGTATGGTGACTCACCTCGCTTGTACACTTTT
81     E  D  F  A  V  Y  Y  C  Q  Q  Y  G  D  S  P  R  L  Y  T  F

301  GGCCAGGGGACCAAGCTGGAGATCAAACGA  (SEQ ID NO:107)
101    G  Q  G  T  K  L  E  I  K  R   (SEQ ID NO:108)
```

FIG. 26A

Nucleotide (top) and amino acid (bottom) sequence of the heavy chain variable region of antibody clone 3F5

```
1    CAGGTGCAGCTACAGCAGTGGGGCGCAGGACTGTTGAAGCCTTCGGAGACCCTGTCCCTC
1      Q  V  Q  L  Q  Q  W  G  A  G  L  L  K  P  S  E  T  L  S  L

CDR1
61   ACCTGCGCTGTCTATGGTGGGTCCTTCAGTGGTTACTACTGGAGCTGGATCCGCCAGCCC
21     T  C  A  V  Y  G  G  S  F  S  G  Y  Y  W  S  W  I  R  Q  P

CDR2
121  CCAGGGAAGGGGCTGGAGTGGATTGGGGAAATCAATCATAGTGGAAGCACCAACTACAAC
41     P  G  K  G  L  E  W  I  G  E  I  N  H  S  G  S  T  N  Y  N

181  CCGTCCCTCAAGAGTCGAGTCACCATATCAGTAGACACGTCCAAGAACCAGTTCTCCCTG
61     P  S  L  K  S  R  V  T  I  S  V  D  T  S  K  N  Q  F  S  L

241  AAGCTGAGCTCTGTGACCGCCGCGGACACGGCTGTGTATTACTGTGCGAGAGTGGCTTAC
81     K  L  S  S  V  T  A  A  D  T  A  V  Y  Y  C  A  R  V  A  Y

CDR3
301  TATGATAGTAGTGGTTATTACCCCTATGATGCTTTTGATATCTGGGGCCAAGGGACAATG
101    Y  D  S  S  G  Y  Y  P  Y  D  A  F  D  I  W  G  Q  G  T  M

361  GTCACCGTCTCAAGC  (SEQ ID NO:109)
121    V  T  V  S  S  (SEQ ID NO:110)
```

FIG. 26B

Nucleotide (top) and amino acid (bottom) sequence of the light chain variable region of antibody clone 3G3.

```
1    GAAACGACACTCACGCAGTCTCCAGGCACCCTGTCTCTGTCTCCAGGGGAAAGAGCCACC
1      E  T  T  L  T  Q  S  P  G  T  L  S  L  S  P  G  E  R  A  T

CDR1
61   CTCTCCTGCAGGGCCAGTCAGAGTGTTAGCAGCAGCTACTTAGCCTGGTACCAGCAGAAA
21     L  S  C  R  A  S  Q  S  V  S  S  S  Y  L  A  W  Y  Q  Q  K

CDR2
121  CCTGGCCAGGCTCCCAGGCTCCTCATCTATGGTGCATCCAGCAGGGCCACTGGCATCCCA
41     P  G  Q  A  P  R  L  L  I  Y  G  A  S  S  R  A  T  G  I  P

181  GACAGGTTCAGTGGCAGTGGGTCTGGGACAGACTTCACTCTCACCATCAGCAGACTGGAG
61     D  R  F  S  G  S  G  S  G  T  D  F  T  L  T  I  S  R  L  E

CDR3
241  CCTGAAGATTTTGCAGTGTATTACTGTCAGCAGTATGGTAGCTCACCGTACACTTTTGGC
81     P  E  D  F  A  V  Y  Y  C  Q  Q  Y  G  S  S  P  Y  T  F  G

301  CAGGGGACCAAGCTGGAGATCAAACGA  (SEQ ID NO:111)
101    Q  G  T  K  L  E  I  K  R  (SEQ ID NO:112)
```

FIG. 27A

Nucleotide (top) and amino acid (bottom) sequence of the heavy chain variable region of antibody clone 3G3

```
1    CAGGTGCAGCTGGTGCAATCTGGGGGAGGCGTGGTCCAGCCTGGGAGGTCCCTGAGACTC
1      Q  V  Q  L  V  Q  S  G  G  G  V  V  Q  P  G  R  S  L  R  L

CDR1
61   TCCTGTGCAGCCTCTGGATTCACCTTCAGTAGCTATGCTATGCACTGGGTCCGCCAGGCT
21     S  C  A  A  S  G  F  T  F  S  S  Y  A  M  H  W  V  R  Q  A

CDR2
121  CCAGGCAAGGGGCTGGAGTGGGTGGCAGTTATATCATATGATGGAAGTAATAAATACTAT
41     P  G  K  G  L  E  W  V  A  V  I  S  Y  D  G  S  N  K  Y  Y

181  GCAGACTCCGTGAAGGGCCGATTCACCATCTCCAGAGACAATTCCAAGAACACGCTGTAT
61     A  D  S  V  K  G  R  F  T  I  S  R  D  N  S  K  N  T  L  Y

241  CTGCAAATGAACAGCCTGAGAGCCGAGGACACGGCCGTGTATTACTGTGCGAGAGAATTA
81     L  Q  M  N  S  L  R  A  E  D  T  A  V  Y  Y  C  A  R  E  L

CDR3
301  CGATTTTTGGAGTGGTCCTCCGATGCTTTTGATATCTGGGGCCAAGGGACAATGGTCACC
101    R  F  L  E  W  S  S  D  A  F  D  I  W  G  Q  G  T  M  V  T

361  GTCTCAAGC   (SEQ ID NO:113)
121    V  S  S  (SEQ ID NO:114)
```

FIG. 27B

Nucleotide (top) and amino acid (bottom) sequence of the light chain variable region of antibody clone 3H2

```
1    GAAACGACACTCACGCAGTCTCCAGGCACCCTGTCTTTGTCTCCAGGGGAAAGAGCCACC
1     E  T  T  L  T  Q  S  P  G  T  L  S  L  S  P  G  E  R  A  T
                                     CDR1
61   CTCTCCTGCAGGGCCAGTCAGAGTGTTAGCAGCAGCTATTTAGCCTGGTACCAGCAGAAA
21    L  S  C  R  A  S  Q  S  V  S  S  S  Y  L  A  W  Y  Q  Q  K
                                              CDR2
121  CCTGGCCAGGCTCCCAGGCTCCTCATCTATGGTGCATCCACCAGGGCCACTGGCGTCCCA
41    P  G  Q  A  P  R  L  L  I  Y  G  A  S  T  R  A  T  G  V  P

181  GACAGGTTCAGTGGCAGTGGGTCTGGGACAGACTTCACTCTCACCATCAGCAGACTGGAG
61    D  R  F  S  G  S  G  S  G  T  D  F  T  L  T  I  S  R  L  E
                                                    CDR3
241  CCTGAAGATTTTGCAGTTTATTACTGTCAACAGTACGGTACCTCACTTACGTGGACGTTC
81    P  E  D  F  A  V  Y  Y  C  Q  Q  Y  G  T  S  L  T  W  T  F

301  GGCCAAGGGACCAAGGTGGAAATCAAACGA (SEQ ID NO:115)
101   G  Q  G  T  K  V  E  I  K  R  (SEQ ID NO:116)
```

FIG. 28A

Nucleotide (top) and amino acid (bottom) sequence of the heavy chain variable region of antibody clone 3H2

```
1    CAGGTGCAGCTGCAGGAGTCGGGCCCAGGACTGGTGAAGCCTTCGGAGACCCTGTCCCTC
1     Q  V  Q  L  Q  E  S  G  P  G  L  V  K  P  S  E  T  L  S  L
                                              CDR1
61   ACCTGCACTGTCTCTGGTGGCTCCATCAGCAGTAGTAGTTACTACTGGGCCTGGATCCGC
21    T  C  T  V  S  G  G  S  I  S  S  S  S  Y  Y  W  A  W  I  R
                                                    CDR2
121  CAGCCCCCAGGGAAGGGGCTGGAGTGGATTGGGGAAATCAATCATAGTGGAAGCACCAAC
41    Q  P  P  G  K  G  L  E  W  I  G  E  I  N  H  S  G  S  T  N

181  TACAACCCGTCCCTCAAGAGTCGAGTCACCATATCAGTAGACACGTCCAAGAACCAGTTC
61    Y  N  P  S  L  K  S  R  V  T  I  S  V  D  T  S  K  N  Q  F

241  TCCCTGAATCTGAACTCTGTGACCGCCGCAGACACGGCTGTGTATTACTGTGCGAGAGTA
81    S  L  N  L  N  S  V  T  A  A  D  T  A  V  Y  Y  C  A  R  V
                         CDR3
301  GTAGCAGCAGCTGGTCACTACTACTACTACTACATGGACGTCTGGGGCAAAGGGACCACG
101   V  A  A  A  G  H  Y  Y  Y  Y  Y  M  D  V  W  G  K  G  T  T

361  GTCACCGTCTCAAGC (SEQ ID NO:117)
121   V  T  V  S  S  (SEQ ID NO:118)
```

FIG. 28B

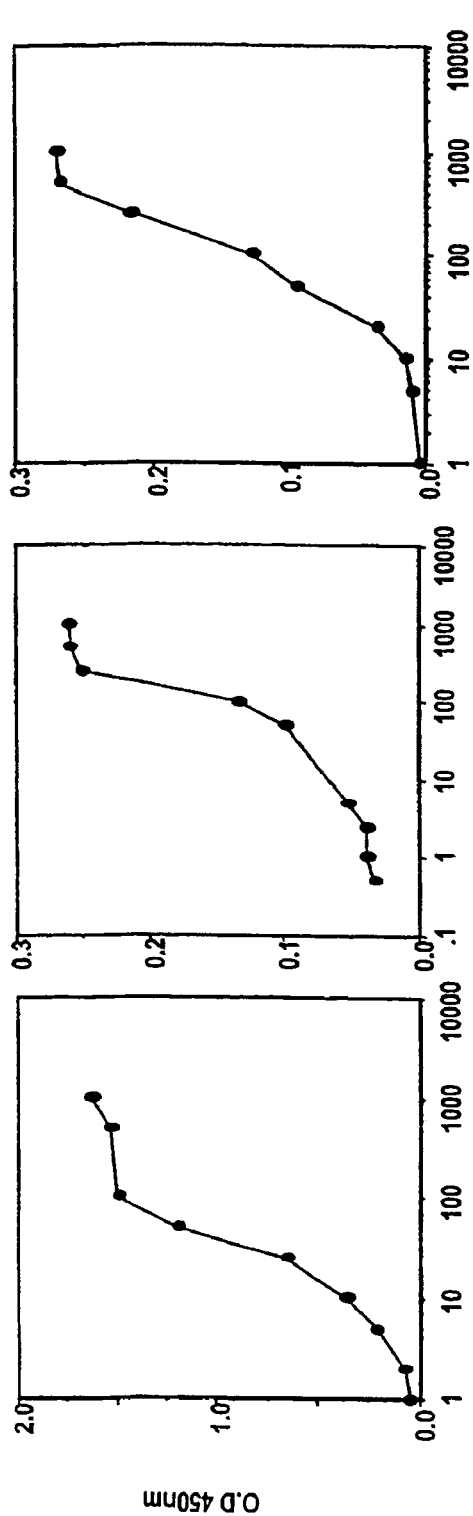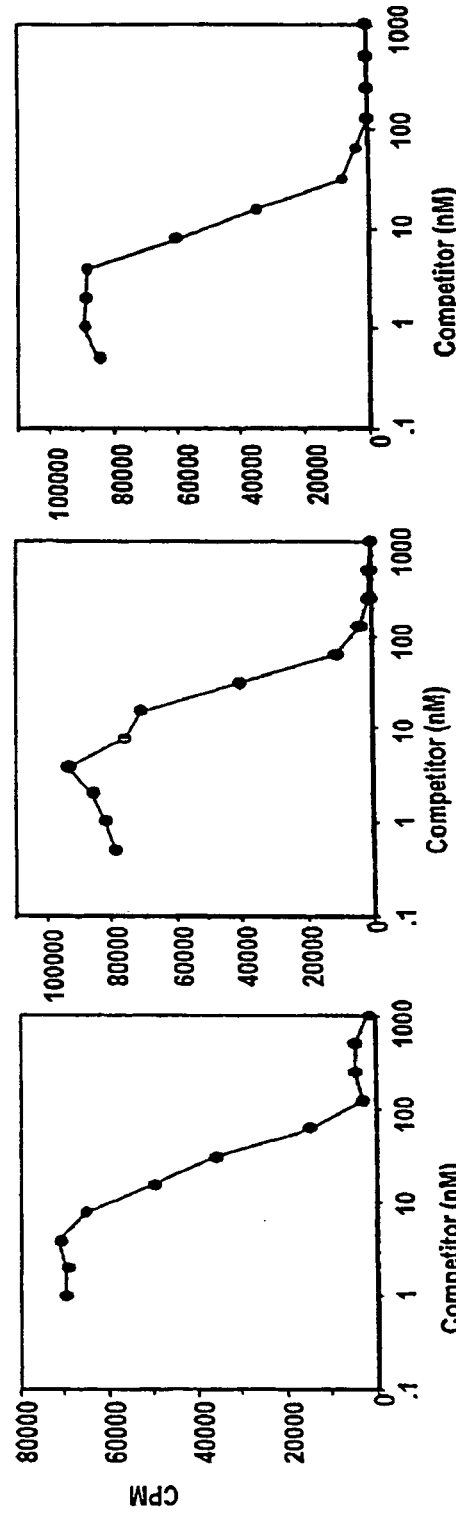
FIG. 32A  FIG. 32B  FIG. 32C
FIG. 32D  FIG. 32E  FIG. 32F

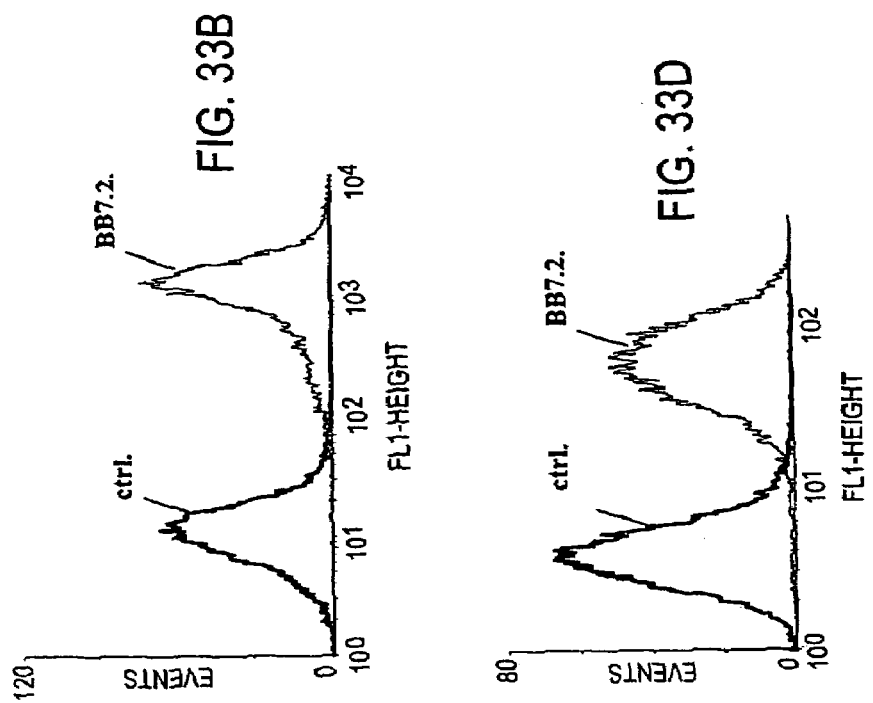
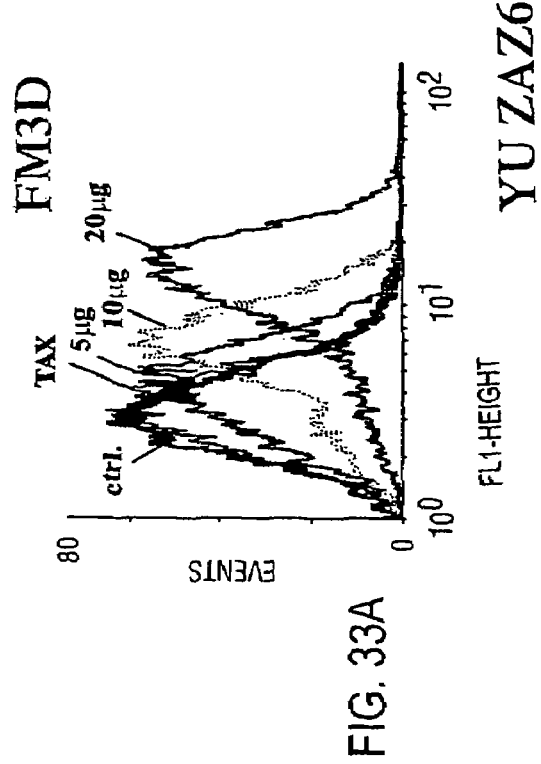
FIG. 33A  FIG. 33B  FIG. 33C  FIG. 33D

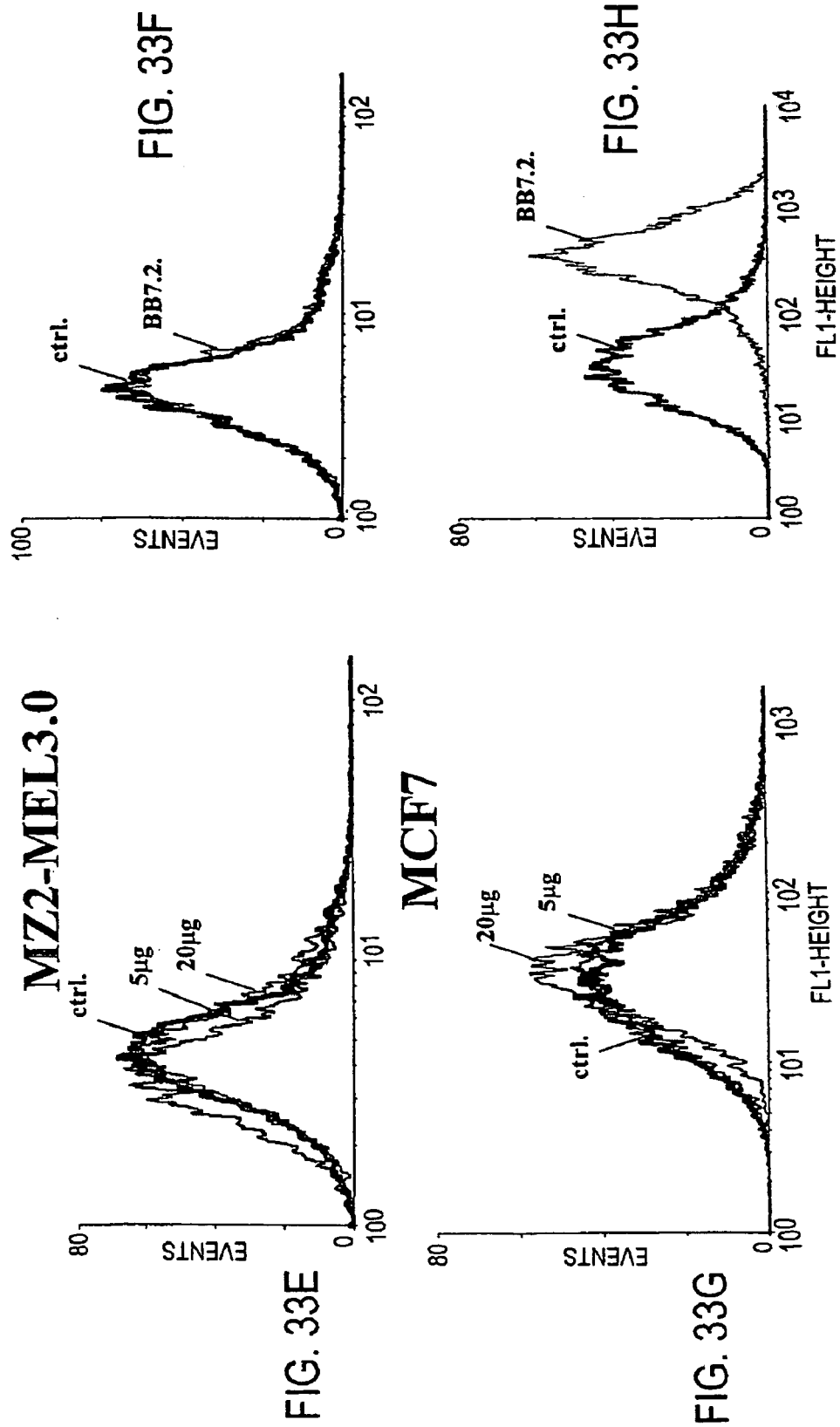

Selection of Recombinant Fab Antibodies with TCR-like Specificity

| Cycle No. | Phage Input | Phage Output | Ration (O/I) | Enrichment | MHC-peptide binders | TCR-like Binders | Finger Pattern |
|---|---|---|---|---|---|---|---|
| A. T540 | | | | | | | |
| 1 | $6 \times 10^{13}$ | $1 \times 10^{7}$ | $2 \times 10^{7}$ | - | | | |
| 2 | $5 \times 10^{12}$ | $1 \times 10^{7}$ | $3 \times 10^{6}$ | - | 23/94 (24%) | 13/94 (14%) | 2 |
| 3 | $1 \times 10^{13}$ | $1 \times 10^{10}$ | $9 \times 10^{4}$ | 1200 | 60/94 (64%) | 41/94 (44%) | 3 |
| B. T865 | | | | | | | |
| 1 | $6 \times 10^{13}$ | $2 \times 10^{7}$ | $3 \times 10^{7}$ | | | | |
| 2 | $8 \times 10^{12}$ | $1 \times 10^{7}$ | $2 \times 10^{6}$ | | 17/94 (18%) | 5/94 (5%) | 3 |
| 3 | $4 \times 10^{12}$ | $6 \times 10^{9}$ | $2 \times 10^{3}$ | 600 | 58/94 (62%) | 21/94 (22%) | 3 |

FIG. 34A

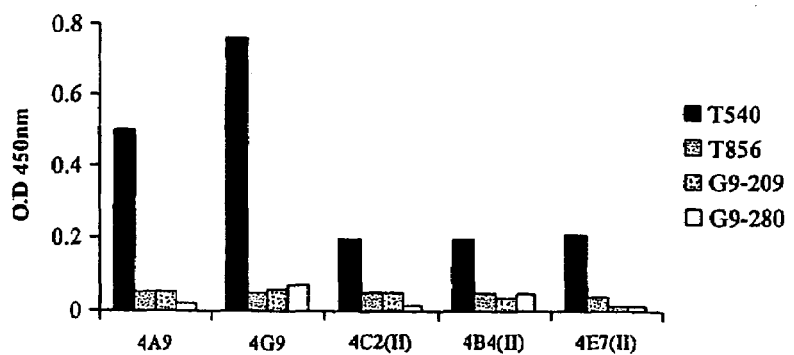

FIG. 34B

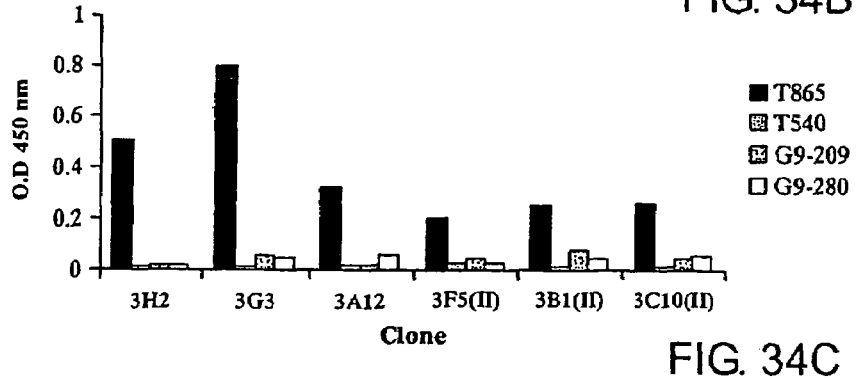

FIG. 34C

Selection of Recombinant Fab Antibodies with TCR-like specificity to MUC1-D6 peptide.

| Panning Cycle | Phage Input | Phage Output | Ratio (O/I) | Enrichment | MHC-peptide binders | TCR-like binders | Finger Pattern |
|---|---|---|---|---|---|---|---|
| 1 | $7.2 \times 10^{12}$ | $5.4 \times 10^5$ | $7.5 \times 10^{-8}$ | - | - | - | - |
| 2 | $5 \times 10^{13}$ | $3 \times 10^7$ | $6 \times 10^{-7}$ | 55 | 46/90 (51%) | 41/90 (45%) | 8 |
| 3 | $4.9 \times 10^{13}$ | $1.7 \times 10^{10}$ | $3.5 \times 10^{-4}$ | 580 | 76/90 (84%) | 72/90 (80%) | 16 |

MHC-PEPTIDE COMPLEX BINDING LIGANDS

RELATED APPLICATIONS

This application is a divisional of pending U.S. patent application Ser. No. 10/371,942 filed on Feb. 20, 2003, which claims the benefit of U.S. Provisional Patent Application No. 60/358,994 filed on Feb. 20, 2002, the contents of which are incorporated herein by reference.

FIELD AND BACKGROUND OF THE INVENTION

In recent years, major advances in tumor immunology have led to an increased understanding of the immune responses against tumors. For example, with respect to melanoma, human melanoma and other tumor cells express antigens that are recognized by cytotoxic T lymphocytes (CTL) derived from cancer patients (Boon and van der Bruggen (1996) *J Exp Med* 183:725-9; Rosenberg (2001) *Nature* 411:380-4; Renkvist and Parmiani (2001) *Cancer Immunol Immunother* 50:3-15). The cascade of molecular recognition events associated with these tumor-associated immune responses involve the expression of specific peptides in complex with MHC class I molecules on the cancer cells. For example, human melanomas express tumor-associated peptides that are presented to the immune system in a complex with class I HLA-A2 molecules (Anichini et al. (1993) *J. Exp. Med.* 177: 989-98; Coulie et al. (1994) *J. Exp. Med.* 180:35-42). Several categories of cancer-associated antigens have been reported as targets for CTLs in vitro and in vivo such as cancer-testis antigens that are expressed in different tumors and in normal testis, melanocyte differentiation antigens, point mutations of normal genes, antigens that are overexpressed in malignant tissues, and viral antigens (Renkvist and Parmiani (2001) *Cancer Immunol Immunother* 50:3-15). Although there is strong experimental evidence demonstrating the presence of these antigens on a variety of tumors, they are apparently unable to elicit a strong enough anti-tumor immune response (Rivoltini et al. (1998) *Crit Rev Immunol* 18:55-63).

Therefore many modern cancer immunotherapy approaches are now designed to induce and enhance T cell reactivity against these tumor antigens. Intensive research on cancer peptides has culminated in many clinical trials involving therapeutic vaccination of cancer patients with antigenic peptides or proteins (Rosenberg (2001) *Nature* 411:380-4; Offringa and Melief (2000) *Curr Opin Immunol* 12:576-82). Moreover, several studies demonstrated that the inability of the patient's immune system to elicit an effective immune response against the tumor is often due to poor antigen presentation (Restifo et al. (1993) *J. Exp. Med.* 177:265-72; Seliger and Ferrone (2000) *Immunol. Today* 21:455-64). Nevertheless, these studies have encouraged the development of new immunotherapeutic strategies that employ vaccination protocols with tumor cells, tumor extracts, RNA-loaded dendritic cells, or tumor cell-dendritic cell hybrid vaccination (Esche (1999) *Curr Opin Mol Ther* 1:72-81; Kugler et al. (2000) *Nat. Med.* 6:332-36). Tumor-specific MHC-peptide complexes present on the surface of tumor cells may also offer a unique and specific target for an antibody-based therapeutic approach. To develop such a strategy, targeting moieties such as recombinant antibodies that will specifically recognize peptide-MHC complexes must be isolated.

The recent advent of MHC-peptide tetramers has provided a new tool for studying antigen-specific T cell populations in health and disease, even when they are very rare, by monitoring tetramer-T cell binding via flow cytometry (Altman et al. (1996) *Science* 274:94-96; Lee et al. (1999) *Nat. Med.* 5:677-85; Ogg et al. (1998) *Science* 279:2103-06). However, to date there are very few tools available to detect, visualize, count, and study antigen (MHC-peptide) presentation. Indeed, several studies demonstrated that the inability of the patient's immune system to elicit an effective immune response against the tumor is often due to poor antigen presentation (Restifo et al. (1993) *J. Exp. Med.* 177:265-72; Seliger and Ferrone (2000) *Immunol. Today* 21:455-64). Antibodies with T cell receptor-like specificity could enable measuring the antigen presentation capabilities of such tumor or antigen presenting cells, for example by direct visualization of the specific MHC-peptide complex on the cell surface. Some attempts to use recombinant soluble T cell receptors for this purpose have largely failed because of their inherent low affinity for their target as well as their instability as recombinant-engineered molecules (Wulfing and Pluckthun (1994) *J Mol Biol* 242:655-69). Therefore, in addition to being used as targeting agents, TCR-like antibodies would serve as a valuable tool to obtain precise information about the presence, expression pattern, and distribution of the target tumor antigen, i.e., the MHC-peptide complex, on the tumor cell surface, on tumor metastases, in lymphoid organs, and on professional antigen-presenting cells.

Antibodies that specifically recognize class I MHC-peptide complexes have been used in murine systems to study antigen presentation, to localize and quantify antigen-presenting cells displaying a T cell epitope, or as a targeting tool in a mouse model (Andersen et al. (1996) *Proc. Natl. Acad. Sci. U.S.A.* 93:1820-24; Porgador (1997) *Immunity* 6:715-26; Day (1997) *Proc Natl Acad Sci USA* 94:8064-9; Zhong (1997) *Proc Natl Acad Sci USA* 1997 94, 13856-61; Zhong (1997) *J Exp Med.* 186, 673-82; Dadaglio (1997) *Immunity* 6, 727-38; Murphy et al. (1989) *Nature* 338:765-8; Aharoni (1991) *Nature.* 351:147-50; Krogsgaard et al. (2000) *J Exp Med.* 191, 1395-412; Reiter and Pastan (1997) *Proc. Natl. Acad. Sci. U.S.A.* 94:4631-36).

SUMMARY OF THE INVENTION

This invention provides, in part, protein ligands that bind to MHC-peptide complexes. The peptide component of a complex can be, e.g., a tumor associated antigen (TAA). As used herein, "TAA" refers to a peptide fragment presented on a MHC molecule, wherein the peptide fragment or the polypeptide that it is processed from is associated with a tumorous or cancerous state. Renkvist and Parmiani (2001) *Cancer Immunol Immunother* 50:3-15 provides a list of exemplary TAAs. A ligand of the invention can specifically bind to a TAA, e.g., a TAA listed in Renkvist (supra).

In a preferred embodiment, the protein ligands are antibodies, or antigen-binding fragments thereof. In another preferred embodiment, the protein ligands are modified scaffold polypeptides (or peptides). In still another preferred embodiment, the protein ligands are cyclic peptides or linear peptides, e.g., of less than 25 amino acids. Whereas many examples described herein refer to antibody ligands or fragments thereof, it is understood, that the invention can be practiced using any protein ligand (e.g., antibody and non-antibody ligand) provided herein.

The anti-(MHC-peptide complex) ligands bind to MHC-peptide complexes with high affinity and specificity for the peptide moiety within the complex, and thus can be used as diagnostic, prophylactic, or therapeutic agents in vivo and in vitro. Preferably the ligands specifically bind to the MHC-peptide complex with a partial or complete peptide-specificity.

"MHC" is a major histocompatibility complex (MHC) protein that includes at least two subunits. The identity of the subunits depends on the class of MHC molecule. For example, a Class I MHC includes a α subunit and β2-microglobulin. In another example, a Class II MHC includes a α subunit and a β subunit.

"MHC-peptide complex" is complex that includes at least an MHC and a peptide. The peptide is bound in the peptide binding groove of the MHC. The peptide can be added exogenously, or can be assembled into the complex within a cell, e.g., in a TAP2 dependent process. For example, the peptide can be produced by the processing of an antigen by the proteasome.

As used herein, "specific binding" refers to the property of the antibody: (1) to bind to MHC-peptide complex with an affinity of at least $1 \times 10^7$ $M^{-1}$, and (2) to preferentially bind to MHC-peptide complex, with an affinity that is at least two-fold, 50-fold, 100-fold, or greater than its affinity for binding to a non-specific antigen (e.g., BSA, casein) other than a MHC-peptide complex.

In one aspect, the invention features a protein that includes: an immunoglobulin heavy chain variable (VH) domain and an immunoglobulin light chain variable (VL) domain. The protein binds a complex comprising an MHC and a peptide, does not substantially bind the MHC in the absence of the bound peptide, and does not substantially bind the peptide in the absence of the MHC. The term "does not substantially bind" means that the binding affinity is less than 2% of the binding affinity of the protein for complex. Typically, the protein is isolated. The peptide can be a peptide fragment of gp100, MUC1, TAX, or hTERT, e.g., a peptide fragment listed in Table 1.

In one embodiment, the protein includes a label or signaling entity, e.g., a label or signaling entity described herein, or at least a component of a label or signaling entity. In another embodiment, the protein includes a cytotoxin or at least a component of a cytotoxin. In still another embodiment, the protein is attached to an insoluble support, e.g., a solid support. For example, the solid support can be a surface of a multi-well container or a planar array.

In one embodiment, the protein is attached to a cell. For example, the protein can include a transmembrane domain that is inserted to the plasma membrane of the cell. The cell can be, e.g., an immune cell, e.g., a T cell, a cytotoxic T lymphocyte (CTL).

The VH and VL domains of the protein can be components of the same polypeptide chain or of different polypeptide chains. In a particular embodiment, the different polypeptide chains are attached by a disulfide bond.

The protein can include an effector domain, e.g., an Fc domain or a non-immunoglobulin effector domain, e.g., a synthetic peptide that specifically binds to a target. In another implementation, the effector domain includes an antigen binding domain (e.g., specific for a target other than an MHC-peptide complex or for a different epitope of an MHC-peptide complex), e.g., an scFv antigen binding domain.

The association constant for binding of the protein to the complex can be at least $10^7$ $M^{-1}$, $10^8$ $M^{-1}$, $10^9$ $M^{-1}$, or $10^{10}$ $M^{-1}$. In one embodiment, the protein binds to the complex if the peptide fragment is in the complex, but not if a non-overlapping peptide fragment that differs by at least 3 amino acids from the peptide fragment is in the complex.

The invention also provides a pharmaceutical composition that includes the protein, and a pharmaceutical carrier. For example, the protein can include a cytotoxin or a label (e.g., an imaging component).

In another aspect, the invention features an isolated protein that binds a complex comprising an MHC and a peptide, and the bound epitope of the complex includes a moiety of the peptide and a moiety of the MHC. The peptide can be a peptide fragment of gp100, MUC1, TAX, or hTERT. The peptide can be a peptide fragment of gp100, MUC1, TAX, or hTERT, e.g., a peptide fragment listed in Table 1. In one embodiment, the protein includes at least one immunoglobulin variable domain, e.g., two immunoglobulin variable domains, e.g., an immunoglobulin heavy chain variable domain and an immunoglobulin light chain variable domain. In another embodiment, the protein includes a synthetic peptide, e.g., a synthetic peptide that independently binds the complex.

In one embodiment, the protein includes a label or signaling entity, e.g., a label or signaling entity described herein, or at least a component of a label or signaling entity. In another embodiment, the protein includes a cytotoxin or at least a component of a cytotoxin. In still another embodiment, the protein is attached to an insoluble support, e.g., a solid support. For example, the solid support can be a surface of a multi-well container or a planar array.

In one embodiment, the protein is attached to a cell. For example, the protein can include a transmembrane domain that is inserted to the plasma membrane of the cell. The cell can be, e.g., an immune cell, e.g., a T cell, a cytotoxic T lymphocyte (CTL).

The VH and VL domains of the protein can be components of the same polypeptide chain or of different polypeptide chains. In a particular embodiment, the different polypeptide chains are attached by a disulfide bond.

The protein can include an effector domain, e.g., an Fc domain or a non-immunoglobulin effector domain, e.g., a synthetic peptide that specifically binds to a target. In another implementation, the effector domain includes an antigen binding domain (e.g., specific for a target other than an MHC-peptide complex or for a different epitope of an MHC-peptide complex), e.g., an scFv antigen binding domain.

The association constant for binding of the protein to the complex can be at least $10^7$ $M^{-1}$, $10^8$ $M^{-1}$, $10^9$ $M^{-1}$, or $10^{10}$ $M^{-1}$. In one embodiment, the protein binds to the complex if the peptide fragment is in the complex, but not if a non-overlapping peptide fragment that differs by at least 3 amino acids from the peptide fragment is in the complex.

The invention also provides a pharmaceutical composition that includes the protein, and a pharmaceutical carrier. For example, the protein can include a cytotoxin or a label (e.g., an imaging component).

In yet another aspect, the invention features a cytotoxic entity that includes a moiety that (1) binds a complex that includes an MHC and a peptide, does not substantially bind the MHC in the absence of the bound peptide, and does not substantially bind the peptide in the absence of the MHC and/or (2) binds an epitope of the MHC-peptide complex that includes a moiety of the peptide and a moiety of the MHC.

In one embodiment, the component of the moiety that binds the complex includes an immunoglobulin variable domain. In another embodiment, the complex binding moiety includes a modified scaffold domain (e.g., a non-immunoglobulin scaffold domain), a disulfide loop, or linear peptide.

The cytotoxic entity can include, for example, a radionucleoside or a polypeptide (e.g., peptide) toxin, or at least a component thereof. In another example, the cytotoxic entity includes a heterologous immune cell.

The association constant for binding of the cytotoxic entity to the complex can be at least $10^7$ M$^{-1}$, $10^8$ M$^{-1}$, $10^9$ M$^{-1}$, or $10^{10}$ M$^{-1}$. The peptide of the complex can be, e.g., a peptide fragment of gp100, MUC1, TAX, or hTERT, e.g., a fragment listed in Table 1. The invention also provides a pharmaceutical composition that includes the cytotoxic entity and a pharmaceutical carrier.

In another aspect, the invention features a cytotoxic T cell that includes one or more nucleic acids for expressing a heterologous protein that (1) binds a complex that includes an MHC and a peptide, does not substantially bind the MHC in the absence of the bound peptide, and does not substantially bind the peptide in the absence of the MHC and/or (2) binds an epitope of the MHC-peptide complex that includes a moiety of the peptide and a moiety of the MHC. The protein can include one or more polypeptide chains. Multiple chains can be encoded by a single nucleic acid, e.g., by different segments of the single nucleic acid, or by a plurality of nucleic acids. The protein functions to bind the cell to the MHC complex.

In one embodiment, the heterologous protein includes an immunoglobulin variable domain that binds the complex, independently or in cooperation with other factors. In another embodiment, the heterologous protein includes a modified scaffold domain (e.g., a non-immunoglobulin scaffold domain), a disulfide loop, or linear peptide, that binds the complex, independently or in cooperation with other factors.

In one embodiment, the heterologous protein includes a cell surface attachment signal that anchors the protein on a surface of the cell. For example, the attachment signal can include a transmembrane domain, a glyco-phosphotidyl-inositol anchor signal, or another cell surface attachment sequence.

The cytotoxic T cell can have a cytotoxic activity that is specific for a cell that displays the MHC and peptide components of the complex on its cell surface.

The association constant for binding of the cytotoxic T cell to the complex can be at least $10^7$ M$^{-1}$, $10^8$ M$^{-1}$, $10^9$ M$^{-1}$, or $10^{10}$ M$^{-1}$. The peptide of the complex can be, e.g., a peptide fragment of gp100, MUC1, TAX, or hTERT, e.g., a fragment listed in Table 1. The invention also provides a pharmaceutical composition that includes the cytotoxic T cell and a pharmaceutical carrier.

In another aspect, the invention features an isolated nucleic acid that includes a segment that encodes an immunoglobulin variable domain such that a protein that includes the immunoglobulin variable domain and a second immunoglobulin variable domain: (1) binds a complex that includes an MHC and a peptide, does not substantially bind the MHC in the absence of the bound peptide, and does not substantially bind the peptide in the absence of the MHC and/or (2) binds an epitope of the MHC-peptide complex that includes a moiety of the peptide and a moiety of the MHC. The peptide can be, e.g., a peptide fragment of gp100, MUC1, TAX, or hTERT.

The nucleic acid can include a second segment that encodes the second immunoglobulin variable domain, e.g., as a polypeptide region of the same polypeptide chain as the first immunoglobulin variable domain or as a second polypeptide chain.

In one embodiment, the nucleic acid includes a region that encodes a label or signaling entity, e.g., a label or signaling entity described herein, or at least a component of a label or signaling entity. In another embodiment, the nucleic acid includes region that encodes a cytotoxin or at least a component of a cytotoxin.

In one embodiment, the nucleic acid includes a region that encodes a cell surface attachment signal operably linked to the binding immunoglobulin variable domain. The protein encoded by the nucleic acid is attached to a cell. For example, the cell attachment signal can include a transmembrane domain that is inserted to the plasma membrane of the cell.

In another embodiment, the nucleic acid includes a region that encodes an effector domain, e.g., an Fc domain or a non-immunoglobulin effector domain, e.g., a synthetic peptide that specifically binds to a target. The effector domain is translationally fused, or otherwise operably linked to the immunoglobulin variable domain. In another implementation, the effector domain includes an antigen binding domain (e.g., specific for a target other than an MHC-peptide complex or for a different epitope of an MHC-peptide complex), e.g., an scFv antigen binding domain.

In yet another aspect, the invention features a host cell that includes heterologous nucleic acid sequences that encode a protein comprising an immunoglobulin heavy chain variable domain and an immunoglobulin light chain variable domain. The protein binds to an MHC-peptide complex if the peptide present in the complex. The peptide can be a peptide fragment of gp100, MUC1, TAX, or hTERT, e.g., a fragment listed in Table 1. The host cell can be a mammalian cell, e.g., an immune cell, or a non-mammalian cell, e.g., another eukaryotic cell such as a yeast cell or a prokaryotic cell. The nucleic acid can encode a protein or protein variant described herein.

In another aspect, the invention features a transgenic animal whose genome includes heterologous nucleic acid sequences that encode a protein comprising an immunoglobulin heavy chain variable domain and an immunoglobulin light chain variable domain, wherein the protein binds to an MHC-peptide complex if the peptide present in the complex. The peptide can be a peptide fragment of gp100, MUC1, TAX, or hTERT, e.g., a fragment listed in Table 1.

In one embodiment, the heterologous nucleic acid sequences include a region that encodes a label or signaling entity, e.g., a label or signaling entity described herein, or at least a component of a label or signaling entity. In another embodiment, the nucleic acid includes a region that encodes a cytotoxin or at least a component of a cytotoxin.

In one embodiment, the heterologous nucleic acid sequences includes a region that encodes a cell surface attachment signal operably linked to one or more of the immunoglobulin variable domains. The protein encoded by the heterologous nucleic acid sequences is attached to a cell. For example, the cell attachment signal can include a transmembrane domain that is inserted to the plasma membrane of the cell.

In another embodiment, the heterologous nucleic acid sequences include a region that encodes an effector domain, e.g., an Fc domain or a non-immunoglobulin effector domain, e.g., a synthetic peptide that specifically binds to a target. The effector domain is translationally fused, or otherwise operably linked to the immunoglobulin variable domain. In another implementation, the effector domain includes an antigen binding domain (e.g., specific for a target other than an MHC-peptide complex or for a different epitope of an MHC-peptide complex), e.g., an scFv antigen binding domain.

In one embodiment, the heterologous nucleic acid sequences are operably linked to a regulatory element, e.g., an element which directs tissue or cell specific expression, e.g., expression in immune cells, e.g., cytotoxic immune cells.

The invention also features a kit that includes a nucleic acid, a protein, a cell, or transgenic animal described herein and instructions for use of the protein to treat, prevent, or detect a disorder, e.g., a neoplastic disorder.

In one aspect, the invention features a method that includes providing a protein library that comprises a plurality of proteins, e.g., each protein comprising a immunoglobulin variable domain that includes a CDR sequence from a subject with a preselected MHC allele; optionally selecting an MHC complex known to be the same allele as the preselected allele; contacting the library to an MHC-peptide complex, wherein the MHC component of the complex is the same allele as the given MHC allele; and isolating a member of the library that binds the complex and specifically recognizes the peptide in the complex. The CDR sequence from the subject can be a germline CDR sequence or a somatic mutant thereof. For example, the CDR sequences of the subject are isolated from nucleic acid encoding affinity matured immunoglobulin domains.

In one embodiment, the isolated member binds the complex with an affinity of 100 nM, 50 nM, 10 nM or less. In another embodiment, a plurality of members (e.g., at least two, five, ten, 20, or 50) of the library are isolated, and each member of the plurality binds the complex and specifically recognizes the peptide in the complex, the binding of the complex having an affinity of 100 nM, 50 nM or less.

In one embodiment, the library includes a first plurality of at least $10^3$, $10^4$, $10^6$, $10^8$, or $10^{10}$ proteins, e.g., between $10^4$ and $10^{12}$ proteins. In an embodiment, each protein of the first plurality is a single chain antibody or a Fab fragment. The library can include a second plurality of protein, e.g., proteins that differ from the first plurality.

In an embodiment, each protein of the library is attached to an array.

In another embodiment, the protein library is a display library. For example, each protein is displayed on a replicable genetic package, e.g., a viral particle or a cell. In another example, the protein is directly attached to a nucleic acid that encodes it, or its complement.

In one embodiment, the library further includes a second plurality of proteins. Each protein of the second plurality includes an immunoglobulin variable domain that includes a CDR from a second subject with the preselected MHC allele. In another embodiment, each protein of the second plurality includes an immunoglobulin variable domain that includes a CDR from a second subject with an MHC allele, other than the preselected MHC allele.

In one embodiment, the MHC-peptide complex is a single-chain MHC-peptide complex. For example, the method can further include expressing the single-chain MHC-peptide complex in a prokaryotic or eukaryotic cell.

In an embodiment, the MHC component of the complex is tagged, e.g., biotinylated (e.g., via a birA tag). The tag can be bound to a support, e.g., a magnetic particle, an array, or other support, e.g., a solid or semi-porous support.

In an embodiment, the MHC-peptide complex is attached to the surface of a cell. The MHC-peptide complex can be assembled within the cell and the peptide can be processed by a cellular proteasome. The protein from which the peptide is derived can be overexpressed.

In an embodiment, the MHC-peptide complex is assembled in vitro. The complex can be attached to a support, e.g., a magnetic particle, an array, or other support, e.g., a solid or semi-porous support.

In an embodiment, the peptide component of the complex is a peptide fragment of MUC1, hTERT, TAX, or gp100, e.g., a fragment listed in Table 1 or a peptide fragment described in Renkvist et al. (supra).

In another embodiment, the MHC-peptide complex is attached to a cell surface, e.g., a living cell surface. The library is contacted to the cell. The cell can present a plurality of MHC-peptide complexes. The cell can be loaded with the peptide, e.g., exogenous peptide, the cell can overexpress a protein that includes the peptide, and so forth.

The isolated protein can be formulated as a pharmaceutical composition. The composition can be administered to a subject, e.g., a test subject, or a subject identified as having a disorder, e.g., a neoplastic or autoimmune disorder.

The formulating can include attaching a toxic entity or label to the isolated protein. The invention also provides proteins identified by the method and pharmaceutical compositions that include the identified protein.

In another aspect, the invention features a method that includes: contacting members of a protein library to a single-chain MHC-peptide complex; and isolating one or more members that (1) bind to the single-chain MHC-peptide complex, does not substantially bind the MHC in the absence of the peptide, and does not substantially bind the peptide in the absence of the MHC and/or (2) bind to an epitope that includes the MHC component of the complex and that includes the peptide component of the complex.

In one embodiment, the isolated member binds the complex with an affinity of 100 nM, 50 nM, 10 nM or less. In another embodiment, a plurality of members (e.g., at least two, five, ten, 20, or 50) of the library are isolated, and each member of the plurality binds the complex and specifically recognizes the peptide in the complex, the binding of the complex having an affinity of 100 nM, 50 nM or less.

In one embodiment, the library includes a first plurality of at least $10^3$, $10^4$, $10^6$, $10^8$, or $10^{10}$ proteins, e.g., between $10^4$ and $10^{12}$ proteins. The library can include a second plurality of protein, e.g., proteins that differ from the first plurality.

In one embodiment, each protein of the first plurality is a modified scaffold domain protein (e.g., an immunoglobulin scaffold domain, a non-immunoglobulin scaffold domain, such as a domain of less than 70 or 50 amino acids). Each protein of the first plurality can include a synthetic peptide. In another embodiment, each protein of the first plurality is a single chain antibody or a Fab fragment.

In an embodiment, each protein of the library is attached to an array.

In another embodiment, the protein library is a display library. For example, each protein is displayed on a replicable genetic package, e.g., a viral particle or a cell. In another example, the protein is directly attached to a nucleic acid that encodes it, or its complement.

The isolated protein can be formulated as a pharmaceutical composition. The composition can be administered to a subject, e.g., a test subject, or a subject identified as having a disorder, e.g., a neoplastic or autoimmune disorder.

The formulating can include attaching a toxic entity or label to the isolated protein. The invention also provides proteins identified by the method and pharmaceutical compositions that include the identified protein.

In still another aspect, the invention features a method that includes: contacting a protein library to a first mixture of MHC-peptide complexes; isolating a plurality of members of the library, wherein each isolated member of the plurality displaying an antigen binding domain that binds to an MHC- and the epitope recognized by the antigen binding domain comprising a moiety of the MHC and a moiety of the peptide; and identifying members of the plurality that do not substantially bind to a second mixture of MHC-peptide complexes. The first and/or second mixture can include complexes having different MHC alleles and/or different peptides. In one example, the first and/or second mixture includes a cell that presents a plurality of different MHC-peptide complexes. In another example, the first and/or second mixture includes complexes isolated from one or more cells or displayed on one or more cells.

The peptide component of the each complex in the first and/or second mixture can be a peptide that is endogenously processed by the cell. The first mixture can include complexes from one or more indicated cells, and the second mixture can include complexes from one or more normal cells.

The method can further including, after the identifying, purifying MHC-peptide complexes with one of the identified members. The purified complexes can be characterized, e.g., to identify the peptide component of the purified MHC-peptide complexes (e.g., by mass spectroscopy) and/or the MHC allele.

For example, the indicated cells can be cancer cells, or cells of individual with an immune disorder. The first and/or second mixture can include a cell, e.g., a living cell, a mammalian cell, and/or a cancer cell. The cell can have TAP1 or TAP2 activity. The cell can be attached to a magnetic particle.

In one embodiment, the identified member binds to a complex of the first mixture with an affinity of 100 nM, 50 nM, 10 nM or less. In another embodiment, a plurality of members (e.g., at least two, five, ten, 20, or 50) of the library are isolated, and each member of the plurality binds the complex and specifically recognizes the peptide in the complex, the binding of the complex having an affinity of 100 nM, 50 nM or less.

In one embodiment, the MHC component of the complex can be a class I MHC. In another embodiment, the MHC component of the complex can be a class II MHC. The MHC allele can be, e.g., any of the HLA-allotypes described in Schreuder et al., The HLA Dictionary 2001: a summary of HLA-A, -B, -C, -DRB1/3/4/5, -DQB1 alleles and their association with serologically defined HLA-A, -B, -C, -DR and -DQ antigens. *Human Immunology* 2001: 62: 826-849. For example, the allele is A*0201. In one embodiment, the library includes a first plurality of at least $10^3$, $10^4$, $10^6$, $10^8$, or $10^{10}$ proteins, e.g., between $10^4$ and $10^{12}$ proteins. The library can include a second plurality of protein, e.g., proteins that differ from the first plurality.

In one embodiment, each protein of the first plurality is a modified scaffold domain protein (e.g., an immunoglobulin scaffold domain, a non-immunoglobulin scaffold domain, such as a domain of less than 70 or 50 amino acids). Each protein of the first plurality can include a synthetic peptide. In another embodiment, each protein of the first plurality is a single chain antibody or a Fab fragment.

In an embodiment, each protein of the library is attached to an array.

In another embodiment, the protein library is a display library. For example, each protein is displayed on a replicable genetic package, e.g., a viral particle or a cell. In another example, the protein is directly attached to a nucleic acid that encodes it, or its complement.

The identified protein can be formulated as a pharmaceutical composition. The composition can be administered to a subject, e.g., a test subject, or a subject identified as having a disorder, e.g., a neoplastic or autoimmune disorder.

The formulating can include attaching a toxic entity or label to the identified protein. The invention also provides proteins identified by the method and pharmaceutical compositions that include the identified protein.

In another aspect, the invention features a collection that includes a plurality of proteins. Each protein of the plurality: (1) binds a complex comprising an MHC and a peptide, does not substantially bind the MHC in the absence of the bound peptide, and does not substantially bind the peptide in the absence of the MHC and/or (2) binds to an epitope that includes a component of an MHC and a component of the peptide. The peptide of the bound complex can differ for each protein of the plurality, or can be the same for each or at least some proteins of the plurality. The MHC of the bound complex can be the same allele for each protein of the plurality or a different allele for each protein of the plurality. The plurality can include at least 2, 10, or 20 proteins.

The peptide bound by at least some of the proteins of the plurality can be a peptide of a cancer-specific antigen. The peptide can be a peptide described in Renkvist et al. (supra) and/or a peptide from a viral antigen, MUC1, TAX, gp100, or hTERT, e.g., a peptide in Table 1.

Each protein of the plurality can be attached to a support (e.g., an array), a display package, or a cell.

The invention also provides a method that includes providing a collection of proteins as described above, contacting a cell to each protein of the collection; and determining if the cell is bound by a protein of the collection. A related method includes eluting peptides from surfaces of cells; binding the peptides to an MHC protein to form complexes; determining if one or more proteins of the collection binds to one of the complexes.

In another aspect, the invention features a method that includes: providing a first nucleic acid segment encoding a heavy chain variable region and a second nucleic acid segment encoding a light chain variable region, wherein the heavy chain variable region and the light chain variable region form an antigen binding protein that binds an MHC-target peptide complex if the target peptide is present; introducing said first and second nucleic acid segments into a cytotoxic cell; and maintaining the cytotoxic cell under conditions that allow expression and assembly of said antigen-binding protein.

The introducing can include providing a virus that includes the first and second nucleic acid segments and infecting the cytotoxic cell with the virus. The introducing can be effected in vivo (e.g., in a subject animal) or ex vivo. The method can further include, after the introducing, administering the cytotoxic cell to a subject, e.g., a test animal, a patient, or a subject identified for a disorder, e.g., a neoplastic or autoimmune disorder.

In another aspect, the invention features a method of ablating or killing a target cell that displays a peptide on a surface MHC molecule. The method includes: contacting the target cell with a protein described herein, the protein specifically recognizing the displayed peptide on the surface MHC molecule of the target cell, and ablating or killing the target cell. For example, the target cell is a cancer cell.

The protein can include a cytotoxic agent. The protein can be attached to an effector cell, e.g., prior to contacting the protein to the target cell, during or after contacting the protein to the target cell.

In still another aspect, the invention features a method of treating or preventing a cancerous disorder in a subject. The method includes administering to the subject a cytotoxic entity or cytotoxic cell described herein in an amount effective to treat or prevent the disorder.

In another aspect, the invention features a method for in vivo imaging a subject. The method includes: administering to a subject a protein described herein, wherein the protein further comprises a label that can be in vivo imaged, and detecting distribution of the protein in the subject.

In still another aspect, the invention features a method for detecting an MHC-peptide complex in a sample. The method includes contacting the sample with a protein described herein; and detecting binding of the protein and the sample, wherein detection of binding indicates presence of the MHC-peptide complex in the sample.

The sample can include cells. The method can further include sorting the cells bound by the protein from cells not bound by the protein. For example, the protein is fluorescently labeled and the sorting comprises fluorescently activated cell sorted. In another example, the protein is attached to an insoluble support, e.g., a column matrix or a magnetic particle.

In another aspect, the invention features a method that includes: providing a first nucleic acid segment encoding a heavy chain variable region and a second nucleic acid segment encoding a light chain variable region, wherein the heavy chain variable region and the light chain variable region form an antigen binding protein that binds an MHC-target peptide complex if the target peptide is present; introducing said first and second nucleic acid segments into a host cell; and maintaining the host cell under conditions that allow expression and assembly of said antigen-binding protein. The target peptide can be a peptide fragment of gp100, MUC1, TAX, or hTERT, e.g., a peptide listed in Table 1.

The first and second nucleic acid segments can be segments of the same nucleic acid or of different nucleic acids. In one embodiment, the first and second nucleic acid segments are in frame and are translated as a single polypeptide. The nucleic acid can include a third segment that encodes a linker is located between the first and second nucleic acid segments. In another embodiment, the first and second nucleic acid segments are translated as separate polypeptide chains. The separate polypeptide chains can be covalently bond by a non-peptide bond.

The antigen binding protein can be soluble and secreted, or attached to a surface of the host cell. In the latter case, for example, the antigen binding protein can include a polypeptide that includes a transmembrane domain inserted into the host cell membrane, and optionally a cytoplasmic domain, e.g., a T cell receptor cytoplasmic domain.

The host cell can be a bacterial cell or a eukaryotic cell, e.g., a yeast, insect, plant, or mammalian cell (e.g., a human, rodent, dairy mammal cell). For example, the mammalian cell is a COS cell, or a T cell.

The introducing can occur in vitro or in vivo. The maintaining can occur in vitro or in vivo in a subject, e.g., the host cell is a cell of the subject, cell of a blood relative of an individual for treatment (e.g., shares a grandparent), a cell of a subject having the same MHC alleles as the individual for treatment.

In an embodiment, the T cell mediates a cytotoxic activity against a cell that includes a cell-surface MHC-peptide complex in which the cell-surface peptide is the target peptide. For example, the T cell is mediates a cytotoxic activity against a cancer cell.

The antigen binding protein can include a purification tag. The method can further include purifying the antigen binding protein from media surrounding the cell, and/or from a lysate or membranes of the cell. The method can further include modifying the purified protein. The method can further include contacting the host cell to a cell that includes a cell-surface MHC-peptide complex in which the cell-surface peptide is the target peptide.

In still another aspect, the invention features a method that includes: providing a host cell that expresses a first nucleic acid segment encoding a heavy chain variable region and a second nucleic acid segment encoding a light chain variable region, wherein the expressed heavy chain variable region and the expressed light chain variable region assemble as an antigen binding protein that binds an epitope of a MHC-peptide complex, wherein the epitope includes a moiety of the MHC and a moiety of the peptide, and the peptide is a fragment of hTERT, MUC1, TAX or gp100; and harvesting the antigen-binding protein from the host cell. For example, the host cell is a cell of a transgenic animal, e.g., a mammal. The host cell can be a fibroblast, a mammary cell, an immune cell. In an embodiment, the antigen-binding protein further includes a purification tag. The method can further include purifying the harvested antigen-binding protein to at least 50, 70, 80, 90, 95, or 99% purity.

Further, the invention provides anti-(MHC-peptide complex) antibodies, antibody fragments, and pharmaceutical compositions thereof, as well as nucleic acids, recombinant expression vectors and host cells for making such antibodies and fragments. Methods of using the antibodies of the invention to detect a MHC-peptide complex, or to ablate or kill a cell that presents a particular MHC-peptide complex either in vitro or in vivo, are also encompassed by the invention. For example, the peptide is a cancer associated antigen.

The protein ligands of the invention interact with, e.g., bind to a MHC-peptide complex, preferably a human MHC-peptide complex, with high affinity and specificity. Preferably, the protein ligand does not substantially bind the MHC in the absence of the bound peptide, and does not substantially bind the peptide in the absence of the MHC. The epitope bound by the protein ligand can include, e.g., a moiety of the MHC and a moiety of the bound peptide. The bound peptide can be a TAA.

For example, the protein ligand binds to a human MHC-peptide complex with an affinity constant of at least $10^7$ $M^{-1}$, preferably, at least $10^8$ $M^{-1}$, $10^9$ $M^{-1}$, or $10^{10}$ $M^{-1}$. In one embodiment, the anti-(MHC-peptide complex) ligand binds all or part of the epitope of an antibody described herein, e.g., an anti-(gp100 peptide-MHC complex) antibody (such as: 1A11, 1A7, 1A9, 1C8, 1D7, 1G2, 2B2, 2C5, 2D1, 2F1, G2D12, G3F12, G3F3, or G3G4), an anti-(hTERT peptide-MHC complex) antibody (such as: 4A9, 4B4, 4C2, 4G9, 3A12, 3B1, 3F5, 3G3, or 3H2), an anti-(MUC1 peptide MHC complex) antibody (such as: M3A1 or M3B8), or an anti-(TAX peptide MHC complex) antibody (such as: T3E3, T3F1, or T3F2) (e.g., in which TAX is derived from HTLV-1). The anti-(MHC-peptide complex) ligand can inhibit, e.g., competitively inhibit, the binding of an antibody described herein, e.g., an anti-(gp100 peptide-MHC complex) antibody (such as: 1A11, 1A7, 1A9, 1C8, 1D7, 1G2, 2B2, 2C5, 2D1, 2F1, G2D12, G3F12, G3F3, or G3G4), an anti-(hTERT peptide-MHC complex) antibody (such as: 4A9, 4B4, 4C2, 4G9, 3A12, 3B1, 3F5, 3G3, or 3H2), an anti-(MUC1 peptide MHC complex) antibody (such as: M3A1 or M3B8), or an anti (TAX peptide MHC complex) antibody (such as: T3E3, T3F1, or T3F2). An anti-(MHC-peptide complex) ligand may bind to an epitope, e.g., a conformational or a linear epitope, which epitope when bound prevents binding of an antibody described herein, e.g., an anti-(gp100 peptide-MHC complex) antibody (such as: 1A11, 1A7, 1A9, 1C8, 1D7, 1G2, 2B2, 2C5, 2D1, 2F1, G2D12, G3F12, G3F3, or G3G4), an anti-(hTERT peptide-MHC complex) antibody (such as: 4A9, 4B4, 4C2, 4G9, 3A12, 3B1, 3F5, 3G3, or 3H2), an anti-(MUC1 peptide MHC complex) antibody (such as: M3A1 or M3B8), or an anti(TAX peptide MHC complex) antibody (such as: T3E3, T3F1, or T3F2). The epitope can be in close proximity spatially or functionally-associated, e.g., an overlapping or adjacent epitope in linear sequence or conformationally to the one recognized by an antibody described above or elsewhere herein. Preferably, the epitope includes a moiety from the peptide, e.g., from a peptide fragment of gp100, MUC1, or hTERT.

MHC-peptide complexes that include a TAA can identify a cancer cell. The antibodies of the invention bind to the cell surface of these cells, and in particular, to the cell surface of the living cells. Preferably, the protein ligands of the present invention are also internalized with the MHC-peptide complex, which permits the intracellular delivery of an agent conjugated to the antibody, e.g., a cytotoxic or a labeling agent. Accordingly, the protein ligands of the invention can be used to target living normal, benign hyperplastic, and cancerous cells that display on their surfaces TAA in an MHC-peptide complex.

In a preferred embodiment, the protein ligand is an antibody. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The term "antibody" includes intact immunoglobulins of types IgA, IgG, IgE, IgD, IgM (as well as subtypes thereof), wherein the light chains of the immunoglobulin may be of types kappa or lambda.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to a MHC-peptide complex (e.g., a human MHC-peptide complex, e.g., a complex wherein the peptide is a TAA). Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The antibody is preferably monospecific, e.g., a recombinant antibody, a monoclonal antibody, or antigen-binding fragment thereof. The term "monospecific antibody" refers to an antibody that displays a single binding specificity and affinity for a particular target, e.g., epitope, regardless of method of identification or synthesis. This term includes a "monoclonal antibody" or "monoclonal antibody composition," which as used herein refer to a preparation of antibodies or fragments thereof of single molecular composition. The term also includes a "recombinant antibody" which is described below.

The anti-(MHC-peptide complex) antibodies can be full-length (e.g., an IgG (e.g., an IgG1, IgG2, IgG3, IgG4), IgM, IgA (e.g., IgA1, IgA2), IgD, and IgE, but preferably an IgG) or can include only an antigen-binding fragment (e.g., a Fab, F(ab')$_2$ or scFv fragment). The antibody, or antigen-binding fragment thereof, can include two heavy chain immunoglobulins and two light chain immunoglobulins, or can be a single chain antibody. The antibodies can, optionally, include a constant region chosen from a kappa, lambda, alpha, gamma, delta, epsilon or a mu constant region gene. A preferred anti-(MHC-peptide complex) antibody includes a heavy and light chain constant region substantially from a human antibody, e.g., a human IgG1 constant region or a portion thereof. As used herein, "isotype" refers to the antibody class (e.g., IgM or IgG1) that is encoded by heavy chain constant region genes.

In a preferred embodiment, the antibody (or fragment thereof) is a recombinant or modified anti-(MHC-peptide complex) antibody, e.g., a chimeric, a humanized, a deimmunized, or an in vitro generated antibody. The term "recombinant" or "modified" human antibody, as used herein, is intended to include all antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include humanized, CDR grafted, chimeric, deimmunized, in vitro generated antibodies, and may optionally include constant regions derived from human germline immunoglobulin sequences. In other embodiments, the anti-(MHC-peptide complex) antibody is a human antibody.

Also within the scope of the invention are antibodies, or antigen-binding fragments thereof, which bind overlapping epitopes, adjacent epitopes, and/or substantially identical epitopes (e.g., identical epitopes) of antibodies disclosed herein, e.g., an anti-(gp100 peptide-MHC complex) antibody (such as: 1A11, 1A7, 1A9, 1C8, 1D7, 1G2, 2B2, 2C5, 2D1, 2F1, G2D12, G3F12, G3F3, or G3G4), an anti-(hTERT peptide-MHC complex) antibody (such as: 4A9, 4B4, 4C2, 4G9, 3A12, 3B1, 3F5, 3G3, or 3H2), an anti-(MUC1 peptide MHC complex) antibody (such as: M3A1 or M3B8), or an anti (TAX peptide MHC complex) antibody (such as: T3E3, T3F1, or T3F2).

Also within the scope of the invention are antibodies, or antigen-binding fragments thereof, which competitively inhibit or compete with the binding of the anti-(MHC-peptide complex) antibodies disclosed herein to MHC-peptide complexes, e.g., antibodies which competitively inhibit or compete with the binding of monospecific antibodies, e.g., an anti-(gp100 peptide-MHC complex) antibody (such as: 1A11, 1A7, 1A9, 1C8, 1D7, 1G2, 2B2, 2C5, 2D1, 2F1, G2D12, G3F12, G3F3, or G3G4), an anti-(hTERT peptide-MHC complex) antibody (such as: 4A9, 4B4, 4C2, 4G9, 3A12, 3B1, 3F5, 3G3, or 3H2), an anti-(MUC1 peptide MHC complex) antibody (such as: M3A1 or M3B8), or an anti (TAX peptide MHC complex) antibody (such as: T3E3, T3F1, or T3F2).

Any combination of anti-(MHC-peptide complex) antibodies is within the scope of the invention, e.g., two or more antibodies that bind to different regions of MHC-peptide complex, e.g., antibodies that bind to two different epitopes on the MHC-peptide complex, e.g., a bispecific antibody.

In one embodiment, the anti-(MHC-peptide complex) antibody, or antigen-binding fragment thereof, includes at least one light or heavy chain immunoglobulin (or preferably, at least one light chain immunoglobulin and at least one heavy chain immunoglobulin). Preferably, each immunoglobulin includes a light or a heavy chain variable region having at least one, two and, preferably, three complementarity determining regions (CDR's) substantially identical to a CDR from an anti-(MHC-peptide complex) light or heavy chain variable region, respectively, i.e., from a variable region of one of an anti-(gp100 peptide-MHC complex) antibody (such as: 1A11, 1A7, 1A9, 1C8, 1D7, 1G2, 2B2, 2C5, 2D1, 2F1, G2D12, G3F12, G3F3, or G3G4), an anti-(hTERT peptide-MHC complex) antibody (such as: 4A9, 4B4, 4C2, 4G9, 3A12, 3B1, 3F5, 3G3, 4E7, 3C10, or 3H2), an anti-(MUC1 peptide MHC complex) antibody (such as: M3A1, M3C8, M2B1, or M3B8), or an anti(TAX peptide MHC complex) antibody (such as: T3E3, T3F1, or T3F2).

In a preferred embodiment, the antibody (or fragment thereof) includes at least one, two and preferably three CDR's from the light or heavy chain variable region of antibodies listed in FIGS. 1 to 28 having an amino acid sequence chosen from the sequences in FIGS. 1A to 28A (light chain CDR's, i.e., FIGS. 1A, 2A, 3A, . . . 38A), or FIGS. 1B to 28B (heavy chain CDR's, i.e., FIGS. 1B, 2B, 3B, . . . 38B), or a sequence substantially identical thereto. The SEQ ID NO's correspond to heavy and light CDR1, CDR2, or CDR3 of an antibody also listed in Table 2 to 5. In other embodiments, the antibody (or fragment thereof) can have at least one, two and preferably three CDR's from the light or heavy chain variable region of an antibody listed in FIGS. 1 to 28 or listed above. In one preferred embodiment, the antibody, or antigen-binding fragment thereof, includes all six CDR's from the human anti-(MHC-peptide complex) antibody, e.g., an antibody listed in FIGS. 1 to 28. In those embodiments, the CDR's have the amino acid sequences in FIGS. 1A to 28A (light chain CDR's, i.e., FIGS. 1A, 2A, 3A, . . . 38A), or FIGS. 1B to 28B (heavy chain CDR's, i.e., FIGS. 1B, 2B, 3B, . . . 38B). In one embodiment, the antibody heavy and light chain amino acid sequences are related (e.g., substantially identical to or variants of) respective heavy and light chain amino acid sequences of an antibody described herein.

In another preferred embodiment, the antibody (or fragment thereof) includes at least one, two and preferably three CDR's from the light or heavy chain variable region of an antibody listed in FIGS. 1 to 28 having an amino acid sequence that differs by no more than 3, 2.5, 2, 1.5, 1, or 0.5 substitutions, insertions or deletions for every 10 amino acids relative to the amino acid sequences in FIGS. 1A to 28A (light chain CDR's, i.e., FIGS. 1A, 2A, 3A, . . . 38A), or FIGS. 1B to 28B (heavy chain CDR's, i.e., FIGS. 1B, 2B, 3B, . . . 38B). Further, the antibody, or antigen-binding fragment thereof, can include six CDR's, each of which differs by no more than 3, 2.5, 2, 1.5, 1, or 0.5 substitutions, insertions or deletions for every 10 amino acids relative to the corresponding CDRs of the human anti-(MHC-peptide complex) antibody, e.g., an antibody list in FIGS. 1 to 28.

In another embodiment, the light or heavy chain immunoglobulin of the anti-(MHC-peptide complex) antibody, or antigen-binding fragment thereof, can further include a light or a heavy chain variable framework that has no more than 3, 2.5, 2, 1.5, or 1, 0.5 substitutions, insertions or deletions for every 10 amino acids in FR1, FR2, FR3, or FR4 relative to the corresponding frameworks of an antibody listed in FIGS. 1 to 28. In a preferred embodiment, the light or heavy chain immunoglobulin of the anti-(MHC-peptide complex) antibody, or antigen-binding fragment thereof, further includes a light or a heavy chain variable framework, e.g., FR1, FR2, FR3, or FR4, that is identical to a framework of an antibody listed in FIGS. 1 to 28.

In one embodiment, the light or the heavy chain variable framework can be chosen from: (a) a light or heavy chain variable framework including at least 80%, 90%, 95%, or preferably 100% of the amino acid residues from a human light or heavy chain variable framework, e.g., a light or heavy chain variable framework residue from a human mature antibody or a human germline sequence, or a consensus sequence; (b) a light or heavy chain variable framework including from 20% to 80%, 40% to 80%, or 60% to 90% of the amino acid residues from a human light or heavy chain variable framework, e.g., a light or heavy chain variable framework residue from a human mature antibody or a human germline sequence, or a consensus sequence; (c) a non-human framework (e.g., a rodent framework); or (d) a non-human framework that has been modified, e.g., to remove antigenic or cytotoxic determinants, e.g., deimmunized, or partially humanized.

In one embodiment, the heavy or light chain framework includes an amino acid sequence, which is at least 80%, 85%, 90%, 95%, 97%, 98%, 99% or higher identical to a sequence listed in FIGS. 1 to 28 (A and B); or which differs at least 1 or 5 but less than 40, 30, 20, or 10 residues from, the amino acid sequence listed in FIGS. 1 to 28 (A and B).

Preferred anti-(MHC-peptide complex) antibodies include at least one, preferably two, light and at least one, preferably two, heavy chain variable regions having the amino acid sequence shown in FIGS. 1 to 28 (A and B), the heavy and light chain combination being a combination shown.

In other embodiments, the light or heavy chain variable framework of the anti-(MHC-peptide complex) antibody, or antigen-binding fragment thereof, includes at least one, two, three, four, five, six, seven, eight, nine, ten, fifteen, sixteen, or seventeen amino acid residues from a human light or heavy chain variable framework, e.g., a light or heavy chain variable framework residue from a human mature antibody, a human germline sequence, or a consensus sequence. In one embodiment, the amino acid residue from the human light chain variable framework is the same as the residue found at the same position in a human germline. Preferably, the amino acid residue from the human light chain variable framework is the most common residue in the human germline at the same position.

An anti-(MHC-peptide complex) ligand described herein can be used alone, e.g., can be administered to a subject or used in vitro in non-derivatized or unconjugated forms. In other embodiments, the anti-(MHC-peptide complex) ligand can be derivatized, modified or linked to another functional molecule, e.g., another peptide, protein, isotope, cell, or insoluble support (e.g., a bead, a matrix, or a planar support such as an array). For example, the anti-(MHC-peptide complex) ligand can be functionally linked (e.g., by chemical coupling, genetic fusion, non-covalent association or otherwise) to one or more other molecular entities, such as an antibody (e.g., if the ligand is an antibody to form a bispecific or a multispecific antibody), a toxin, a radioisotope, a therapeutic (e.g., a cytotoxic or cytostatic) agent or moiety, among others. For example, the anti-(MHC-peptide complex) ligand can be coupled to a radioactive ion (e.g., an $\alpha$-, $\gamma$-, or $\beta$-emitter), e.g., iodine ($^{131}$I or $^{125}$I), yttrium ($^{90}$Y), lutetium ($^{177}$Lu), actinium ($^{225}$Ac), rhenium ($^{186}$Re), or bismuth ($^{212}$ or $^{213}$Bi).

In another aspect, the invention provides, compositions, e.g., pharmaceutical compositions, which include a pharmaceutically acceptable carrier, excipient or stabilizer, and at least one of the anti-(MHC-peptide complex) ligands (e.g., antibodies or fragments thereof) described herein. Preferably, the anti-(MHC-peptide complex) ligand does not substantially bind the MHC in the absence of the peptide, and does not substantially bind the peptide in the absence of the MHC. In one embodiment, the compositions, e.g., the pharmaceutical compositions, comprise a combination of two or more of the aforesaid anti-(MHC-peptide complex) ligands.

In another aspect, the invention features a kit that includes an anti-(MHC-peptide complex) antibody (or fragment thereof), e.g., an anti-(MHC-peptide complex) antibody (or fragment thereof) as described herein, for use alone or in combination with other therapeutic modalities, e.g., a cytotoxic or labeling agent, e.g., a cytotoxic or labeling agent as described herein, along with instructions on how to use the anti-(MHC-peptide complex) antibody or the combination of such agents to treat, prevent or detect cancerous lesions. Preferably, the antibody does not substantially bind the MHC in the absence of the peptide, and does not substantially bind the peptide in the absence of the MHC.

The invention also features nucleic acid sequences that encode a heavy and light chain immunoglobulin or immunoglobulin fragment described herein. For example, the invention features, a first and second nucleic acid encoding a heavy and light chain variable region, respectively, of a anti-(MHC-peptide complex) antibody molecule as described herein. In another aspect, the invention features host cells and vectors containing the nucleic acids of the invention.

In another aspect, the invention features, a method of producing a anti-(MHC-peptide complex) antibody, or antigen-binding fragment thereof. The method includes: providing a first nucleic acid encoding a heavy chain variable region, e.g., a heavy chain variable region as described herein; providing a second nucleic acid encoding a light chain variable region, e.g., a light chain variable region as described herein; and expressing said first and second nucleic acids in a host cell under conditions that allow assembly of said light and heavy chain variable regions to form an antigen binding protein. The first and second nucleic acids can be linked or unlinked, e.g., expressed on the same or different vector, respectively.

The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell. For example, nucleic acids encoding the antibodies described herein can be expressed in a transgenic animal. In one embodiment, the nucleic acids are placed under the control of a tissue-specific promoter (e.g., a mammary specific promoter) and the antibody is produced in the transgenic animal. For example, the antibody molecule is secreted into the milk of the transgenic animal, such as a transgenic cow, pig, horse, sheep, goat or rodent.

The invention also features a method of treating, e.g., ablating or killing, a cell, e.g., a normal, benign or hyperplastic cell (e.g., a cell found in pulmonary, breast, renal, urothelial, colonic, prostatic, or hepatic cancer and/or metastasis). Methods of the invention include contacting the cell with a anti-(MHC-peptide complex) ligand, in an amount sufficient to treat, e.g., ablate or kill, the cell. The ligand can include another entity, e.g., a cytotoxic entity. The anti-(MHC-peptide complex) ligand can also be displayed on a cell surface, e.g., the surface of cytotoxic T lymphocytes that have been transfected with the genes encoding the ligand fused to a membrane anchor, thereby programming these T cells with the ligand's specificity. Methods of the invention can be used, for example, to treat or prevent a disorder, e.g., a cancerous (e.g., a malignant or metastatic disorder), or non-cancerous disorder (e.g., a benign or hyperplastic disorder) by administering to a subject a anti-(MHC-peptide complex) ligand in an amount effective to treat or prevent such disorder.

The subject method can be used on cells in culture, e.g. in vitro or ex vivo. For example, cancerous or metastatic cells (e.g., pulmonary, breast, renal, urothelial, colonic, prostatic, or hepatic cancer or metastatic cells) can be cultured in vitro in culture medium and the contacting step can be effected by adding the anti-(MHC-peptide complex) ligand to the culture medium. The method can be performed on cells (e.g., cancerous or metastatic cells) present in a subject, as part of an in vivo (e.g., therapeutic or prophylactic) protocol. For in vivo embodiments, the contacting step is effected in a subject and includes administering the anti-(MHC-peptide complex) ligand to the subject under conditions effective to permit both binding of the ligand to the cell, and the treating, e.g., the killing or ablating of the cell.

The method of the invention can be used to treat or prevent cancerous disorders, e.g., including but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, as well as adenocarcinomas which include malignancies such as most colon cancers, rectal cancer, renal-cell carcinoma, liver cancer, non-small cell carcinoma of the lung, cancer of the small intestine and cancer of the esophagus. Metastatic lesions of the aforementioned cancers can also be treated or prevented using the methods and compositions of the invention.

The subject can be a mammal, e.g., a primate, preferably a higher primate, e.g., a human (e.g., a patient having, or at risk of, a disorder described herein, e.g., cancer).

The anti-(MHC-peptide complex) antibody or fragment thereof, e.g., an anti-(MHC-peptide complex) antibody or fragment thereof as described herein, can be administered to the subject systemically (e.g., orally, parenterally, subcutaneously, intravenously, intramuscularly, intraperitoneally, intranasally, transdermally, or by inhalation), topically, or by application to mucous membranes, such as the nose, throat and bronchial tubes.

The methods of the invention can further include the step of monitoring the subject, e.g., for a reduction in one or more of: a reduction in tumor size; reduction in cancer markers, e.g., levels of cancer specific antigen (i.e., TAAs) or levels of a cancer-specific MHC-peptide complex; reduction in the appearance of new lesions, e.g., in a bone scan; a reduction in the appearance of new disease-related symptoms; or decreased or stabilization of size of soft tissue mass; or any parameter related to improvement in clinical outcome. The subject can be monitored in one or more of the following periods: prior to beginning of treatment; during the treatment; or after one or more elements of the treatment have been administered. Monitoring can be used to evaluate the need for further treatment with the same anti-(MHC-peptide complex) ligand or for additional treatment with additional agents. Generally, a decrease in one or more of the parameters described above is indicative of the improved condition of the subject.

The anti-(MHC-peptide complex) ligand can be used alone in unconjugated form to thereby ablate or kill cells that present a TAA. For example, if the ligand is an antibody, the ablation or killing can be mediated by an antibody-dependent cell killing mechanisms such as complement-mediated cell lysis and/or effector cell-mediated cell killing. In other embodiments, the anti-(MHC-peptide complex) ligand can be bound to a substance, e.g., a cytotoxic agent or moiety, effective to kill or ablate the cells. For example, the anti-(MHC-peptide complex) ligand can be coupled to a radioactive ion (e.g., an $\alpha$-, $\gamma$-, or $\beta$-emitter), e.g., iodine ($^{131}$I or $^{125}$I), yttrium ($^{90}$Y), lutetium ($^{177}$Lu), actinium ($^{225}$Ac), or bismuth ($^{213}$Bi). The methods and compositions of the invention can be used in combination with other therapeutic modalities. In one embodiment, the methods of the invention include administering to the subject a anti-(MHC-peptide complex) ligand, e.g., a anti-(MHC-peptide complex) antibody or fragment thereof, in combination with a cytotoxic agent, in an amount effective to treat or prevent said disorder. The ligand and the cytotoxic agent can be administered simultaneously or sequentially. In other embodiments, the methods and compositions of the invention are used in combination with surgical and/or radiation procedures.

In another aspect, the invention features methods for detecting the presence of a particular MHC-peptide complex, in a sample, in vitro (e.g., a biological sample, a tissue biopsy, e.g., a cancerous lesion). The subject method can be used to evaluate, e.g., diagnose or stage a disorder described herein, e.g., a cancerous disorder. The method includes: (i) contacting the sample (and optionally, a reference, e.g., control, sample) with an anti-(MHC-peptide complex) ligand, as described herein, under conditions that allow interaction of the anti-(MHC-peptide complex) ligand and the MHC-peptide complex protein to occur; and (ii) detecting formation of a complex between the anti-(MHC-peptide complex) ligand, and the sample (and optionally, the reference, e.g., control, sample). Formation of the complex is indicative of the presence of MHC-peptide complex protein, and can indicate the suitability or need for a treatment described herein. E.g., a statistically significant change in the formation of the complex in the sample relative to the reference sample, e.g., the control sample, is indicative of the presence of MHC-peptide complex in the sample In yet another aspect, the invention provides a method for detecting the presence of a particular MHC-peptide complex in vivo (e.g., in vivo imaging in a subject). The subject method can be used to evaluate, e.g., diagnose, localize, or stage a disorder described herein, e.g., a cancerous disorder. The method includes: (i) administering to a subject (and optionally a control subject) an anti-(MHC-peptide complex) ligand (e.g., an antibody or antigen binding fragment thereof), under conditions that allow interaction of the anti-(MHC-peptide complex) ligand and the MHC-peptide complex protein to occur; and (ii) detecting formation of a complex between the ligand and MHC-peptide complex, wherein a statistically significant change in the formation of the complex in the subject relative to the reference, e.g., the control subject or subject's baseline, is indicative of the presence of the particular MHC-peptide complex.

In other embodiments, a method of diagnosing or staging, a disorder as described herein (e.g., a cancerous disorder), is provided. The method includes: (i) identifying a subject having, or at risk of having, the disorder; (ii) obtaining a sample of a tissue or cell affected with the disorder; (iii) contacting said sample or a control sample with an anti-(MHC-peptide complex) ligand, under conditions that allow interaction of the ligand and the MHC-peptide complex to occur, and (iv) detecting the interaction. Preferably, the anti-(MHC-peptide complex) ligand does not substantially bind the MHC in the absence of the bound peptide, and does not substantially bind the peptide in the absence of the MHC. For example, the peptide can be a TAA. A statistically significant increase in the formation of the complex between the ligand with respect to a reference sample, e.g., a control sample, is indicative of the disorder or the stage of the disorder.

Preferably, the anti-(MHC-peptide complex) ligand used in the in vivo and in vitro diagnostic methods is directly or indirectly labeled with a detectable substance to facilitate detection of the bound or unbound binding agent. Suitable detectable substances include various enzymes, prosthetic groups, fluorescent materials, luminescent materials and radioactive materials. In one embodiment, the anti-(MHC-peptide complex) ligand is coupled to a radioactive ion. In another embodiment, the ligand is labeled with an NMR contrast agent.

The invention also provides polypeptides and nucleic acids that encompass a range of amino acid and nucleic acid sequences. The term "polypeptide" refers to a linear polymer of two or more amino acid residues linked with peptide bonds, and the term "peptide" is used herein to refer to short polypeptides that have fewer than about 30 amino acids.

Plasmids encoding proteins described herein may be deposited with American Type Culture Collection (ATCC), 10801 University Boulevard, Manassas, Va. 20110-2209 under the terms of the Budapest Treaty on the International Recognition of the Deposit of Microorganisms for the Purposes of Patent Procedure.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of a protein is at least 10% pure. In a preferred embodiment, the preparation of the protein has less than about 30%, 20%, 10% and more preferably 5% (by dry weight), of another protein (also referred to herein as a "contaminating protein"), or of chemical precursors. When the protein or biologically active portion thereof is recombinantly produced, it is also preferably substantially free of culture medium and/or contaminating cellular contents (e.g., endogenous proteins of the recombinant cell), i.e., the other material represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

As used herein, a "naturally-occurring" nucleic acid molecule refers to an RNA or DNA molecule having a nucleotide sequence that occurs in Nature. For example a naturally occurring nucleic acid molecule can encode a natural protein. Likewise, a "naturally-occurring" protein refers to a protein having an amino acid sequence that occurs in Nature.

A "heterologous" sequence refers to a sequence which is introduced into a cell or into the context of a nucleic acid by artifice. A heterologous sequence may be a copy of an endogenous gene, but, for example, inserted into an exogenous plasmid or into a chromosomal site at a position other than its endogenous position.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

Sequences similar or homologous (e.g., at least about 85% sequence identity) to the sequences disclosed herein are also part of this application. In some embodiment, the sequence identity can be about 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG® software package (available from Accelrys, San Diego Calif.), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG® software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

As used herein, the term "homologous" is synonymous with "similarity" and means that a sequence of interest differs from a reference sequence by the presence of one or more amino acid substitutions (although modest amino acid insertions or deletions) may also be present. Presently preferred means of calculating degrees of homology or similarity to a reference sequence are through the use of BLAST algorithms (available from the National Center of Biotechnology Information (NCBI), National Institutes of Health, Bethesda Md.), in each case, using the algorithm default or recommended parameters for determining significance of calculated sequence relatedness. The percent identity between two amino acid or nucleotide sequences can also be determined using the algorithm of E. Meyers and W. Miller ((1989) *CABIOS,* 4:11-17 which has been incorporated into the ALIGN program (version 2.0), using a PAM120 weight residue table, a gap length penalty of 12 and a gap penalty of 4.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65°

C. Very high stringency conditions (4) are the preferred conditions and the ones that should be used unless otherwise specified.

It is understood that the binding agent polypeptides of the invention may have additional conservative or non-essential amino acid substitutions, which do not have a substantial effect on the polypeptide functions. Whether or not a particular substitution will be tolerated, i.e., will not adversely affect desired biological properties, such as binding activity can be determined as described in Bowie, et al. (1990) *Science* 247: 1306-1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of the binding agent, e.g., the antibody, without abolishing or more preferably, without substantially altering a biological activity, whereas an "essential" amino acid residue results in such a change.

Other features and advantages of the instant invention will become more apparent from the following detailed description and claims.

DESCRIPTION OF THE DRAWINGS

FIGS. 1A and 1B list the coding nucleic acid and predicted amino acid sequence of the light chain and heavy chain variable region of antibody 1A11, respectively.

FIGS. 2A and 2B list the coding nucleic acid and predicted amino acid sequence of the light chain and heavy chain variable region of antibody 1A7, respectively.

FIGS. 3A and 3B list the coding nucleic acid and predicted amino acid sequence of the light chain and heavy chain variable region of antibody 1A9, respectively.

FIGS. 4A and 4B list the coding nucleic acid and predicted amino acid sequence of the light chain and heavy chain variable region of antibody 1C8, respectively.

FIGS. 5A and 5B list the coding nucleic acid and predicted amino acid sequence of the light chain and heavy chain variable region of antibody 1D7, respectively.

FIGS. 6A and 6B list the coding nucleic acid and predicted amino acid sequence of the light chain and heavy chain variable region of antibody 1G2, respectively.

FIGS. 7A and 7B list the coding nucleic acid and predicted amino acid sequence of the light chain and heavy chain variable region of antibody 2B2, respectively.

FIGS. 8A and 8B list the coding nucleic acid and predicted amino acid sequence of the light chain and heavy chain variable region of antibody 2C5, respectively.

FIGS. 9A and 9B list the coding nucleic acid and predicted amino acid sequence of the light chain and heavy chain variable region of antibody 2D1, respectively.

FIGS. 10A and 10B list the coding nucleic acid and predicted amino acid sequence of the light chain and heavy chain variable region of antibody 2F1, respectively.

FIGS. 11A and 11B list the coding nucleic acid and predicted amino acid sequence of the light chain and heavy chain variable region of antibody G2D12, respectively.

FIGS. 12A and 12B list the coding nucleic acid and predicted amino acid sequence of the light chain and heavy chain variable region of antibody G3F12, respectively.

FIGS. 13A and 13B list the coding nucleic acid and predicted amino acid sequence of the light chain and heavy chain variable region of antibody G3F3, respectively.

FIGS. 14A and 14B list the coding nucleic acid and predicted amino acid sequence of the light chain and heavy chain variable region of antibody G3G4, respectively.

FIGS. 15A and 15B list the coding nucleic acid and predicted amino acid sequence of the light chain and heavy chain variable region of antibody M3A1, respectively.

FIGS. 16A and 16B list the coding nucleic acid and predicted amino acid sequence of the light chain and heavy chain variable region of antibody M3B8, respectively.

FIGS. 17A and 17B list the coding nucleic acid and predicted amino acid sequence of the light chain and heavy chain variable region of antibody T3E3, respectively.

FIGS. 18A and 18B list the coding nucleic acid and predicted amino acid sequence of the light chain and heavy chain variable region of antibody T3F1, respectively.

FIGS. 19A and 19B list the coding nucleic acid and predicted amino acid sequence of the light chain and heavy chain variable region of antibody T3F2, respectively.

FIGS. 20A and 20B list the coding nucleic acid and predicted amino acid sequence of the light chain and heavy chain variable region of antibody 4A9, respectively.

FIGS. 21A and 21B list the coding nucleic acid and predicted amino acid sequence of the light chain and heavy chain variable region of antibody 4B4, respectively.

FIGS. 22A and 22B list the coding nucleic acid and predicted amino acid sequence of the light chain and heavy chain variable region of antibody 4C2, respectively.

FIGS. 23A and 23B list the coding nucleic acid and predicted amino acid sequence of the light chain and heavy chain variable region of antibody 4G9, respectively.

FIGS. 24A and 24B list the coding nucleic acid and predicted amino acid sequence of the light chain and heavy chain variable region of antibody 3A12, respectively.

FIGS. 25A and 25B list the coding nucleic acid and predicted amino acid sequence of the light chain and heavy chain variable region of antibody 3B1, respectively.

FIGS. 26A and 26B list the coding nucleic acid and predicted amino acid sequence of the light chain and heavy chain variable region of antibody 3F5, respectively.

FIGS. 27A and 27B list the coding nucleic acid and predicted amino acid sequence of the light chain and heavy chain variable region of antibody 3G3, respectively.

FIGS. 28A and 28B list the coding nucleic acid and predicted amino acid sequence of the light chain and heavy chain variable region of antibody 3H2, respectively.

FIGS. 32A-32F. Binding characteristics of three TCR-like Fabs. (A-C) Titration ELISA of purified soluble Fab antibodies G2D12 (A), 1A9 (B), and 2F1 (C) directed to scHLA-A2 containing the G9-154, G9-209, and G9-280 peptides, respectively. Wells were coated with the corresponding MHC-peptide complexes as described M&M. (D-F) Competitive binding analysis of the ability of purified Fab G2D12 (D), 1A9 (E), and 2F1 (F) directed against scHLA-A2-peptide complexes containing the G9-154, G9-209, and G9-280 gp100-derived peptides, respectively to inhibit the binding of $^{125}$I-labeled G2D12, 1A9 or 2F1 to the corresponding HLA-A2-peptide complex. The apparent binding affinity of the recombinant Fab was determined as the concentration of competitor (soluble purified Fab) required for 50% inhibition of the binding of the $^{125}$I-labeled tracer.

FIGS. 33A-33H Detection of MHC-peptide complexes on the surface of tumor cells. Melanoma FM3D (A) and YU ZAZ6 (C) which express HLA-A2 (B and D) as determined by reactivity with MAb BB7.2 were stained with 5, 10, and 20 μg of Fab G2D12 specific for the melanoma gp100-derived G9-154 epitope or with a Fab TCR-like antibody specific for the viral epitope TAX. Detection of binding was with FITC-labeled anti-human Fab. The melanoma HLA-A2-MZ2-MEL3.0 cells were not stained with G2D12 (E) or BB7.2 (F) (indication for HLA-A2$^-$). MCF7 HLA-A2+ breast carcinoma cells were stained with BB7.2 (H) but neither with Fab G2D12 or the TAX-specific Fab (G). Control cells are cells incubated with the secondary FITC-labeled antibody.

FIGS. 34A-34C. Frequency (A) and specificity (B,C) of recombinant Fab antibodies selected on telomerase-derived HLA-A2-restricted peptides. ELISA with phage particles was performed on immobilized scHLA-A2/peptide complexes as described in Materials and Methods. (A) Summary of panning against hTERT T cell epitopes T540 and T865 in complex with scHLA-A2. (B) Phage ELISA of clones selected against scHLA-A2/T540 complex. (clones 4C2(II), 4B4(II) and 4E7(II) are from the second round of panning and clones 4A9 and 4G9 are from the third round). (C) Phage ELISA of clones selected against scHLA-A2/T865. ((clones 3F5(II), 3B1(II) and 3C10(II) are from the second round of panning and clones 3H2, 3G3, and 3A12 are from the third round)

DETAILED DESCRIPTION

Figure 29A:
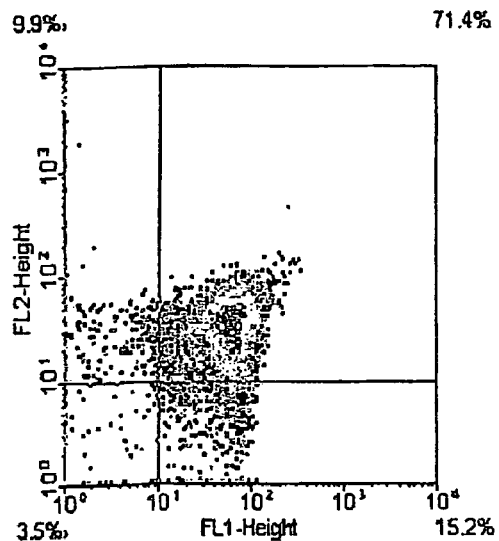
FIGS. 29A-29D. Functional characterization of recombinant scHLA-A2-peptide complexes. (A-D) Functional analysis of scHLA-A2/gp100-derived complexes showing the ability of tetramers to stain a CTL clone, R6C12, specific for the gp100-derived peptide G9-209 in complex with HLA-A2 (A). Staining of more than 70% of the cell population is observed in comparison with control tetramers containing the G9-280 gp100-derived peptide (B) and TAX-derived peptide (C) that did not stain the CTLs. The cells were double-stained with PE-labeled tetramers (y-axis) and FITC-labeled anti-CD8 antibody (x-axis). In (D) the histogram overlay of tetramer staining in A-C is shown to demonstrate the specificity pattern of the recombinant HLA-A2-peptide complexes.

The invention provides, in part, methods of identifying proteins that bind to MHC-peptide complexes and specifically recognize the peptide component of the complex. In some embodiments, the identified protein is an antibody. In other embodiments, the identified protein is a protein other than an antibody and/or other than a T-cell receptor. The identified protein may also be, for example, a small peptide (e.g., a cyclic or linear peptide of between 7 and 25 amino acids), a polypeptide (e.g., a polypeptide of at least 20 amino acids), or a multi-chain protein (e.g., including at least two peptides or polypeptides). For example, the protein can be, e.g., a small peptide or modified protein scaffold. The invention also provides a variety of methods of using such proteins, e.g., for research, diagnostic, therapeutic, and prophylactic applications.

The identified proteins that recognize these MHC-peptide complexes can discriminate between different peptide sequences bound in the complex. In some embodiments, the identified proteins also are specific or at least partially specific for the allele of the MHC component of the complex.

The invention also provides particular antibodies that bind to particular MHC-peptide complexes.

MHC-Peptide Complexes

MHC-peptide complexes include two components: the peptide component and the MHC component. The peptide component is bound in an extended conformation in the groove of the MHC component. The peptide component is typically of less than 30 amino acids.

The MHC component is a major-histocompatibility complex. There are two principal classes of MHC complexes: Class I and Class II. Each complex includes a heterodimer of two polypeptide chains.

Class I complexes are formed from an α polypeptide and β2-microglobulin. The α polypeptide is a transmembrane protein with three extracellular globular domains, α1, α2, and α3. Each α chain is non-covalently associated with a small extracellular protein, β2-microglobulin. The α chain is also highly polymorphic. Class I molecules are present on the surfaces of almost all nucleated cells.

The three-dimensional crystal structure of the Class I complex with peptide bound has been described, e.g., in Bjorkman et al. (1987) Nature 329:506-512. Peptides of about eight to ten amino acids are bound in an extended conformation in the peptide binding site.

Class II molecules are formed from two chains, α and β. Both chains include a transmembrane domain, an immunoglobulin domain, and an amino-terminal peptide binding domain. The peptide binding domain of both chains is polymorphic. Class II molecules are present on the surfaces of a restricted number of antigen-presenting cells, such as B lymphocytes and macrophages.

The three-dimensional crystal structure of the Class II complex with peptide bound has been described, e.g., in Fremont et al. (1998) Immunity 8:305-17. The peptide binding site of Class II molecules resembles that of the Class I molecules. However, it can bind longer (e.g., 15 to 24 amino acids) and more heterogeneous peptides.

The peptide component is the product of intracellular processing of an antigen. The TAP pathway insures that MHC complexes that are secreted to the cell surface include a peptide component from a processed antigen. Thus, processed antigens are displayed on the surface of the cell, indicating to the immune system if any intracellular contents are foreign or aberrant.

T cells include T cell receptors that specifically recognize MHC-peptide complexes. Each T cell receptor has its own specificity for an MHC-presented peptide. An engaged T cell receptor activates the T cell, in the case of cytotoxic T lymphocytes (CTLs) to kill the cell presenting the recognized antigenic peptide.

MHC Complexes and Cancer.

Tumor cells can be identified by antigens that are differentially expressed in tumor cells relative to non-tumor cells. Some of these antigens are processed by the proteasome into peptide fragments that are assembled with an MHC molecule and displayed on the surface of the cell as a complex with the MHC. These antigens, termed "tumor-associated antigens" or TAAs present epitopes that can be specifically recognized by T-cells. Renkvist et al. (2001) Cancer Immunol Immunother 50:3-15 tabulate many known T-cell defined epitopes. The methods described here can be used to identify protein ligands that specifically recognize these T-cell defined epitopes, e.g., immunoglobulins that specifically recognize the peptide component of the epitope when bound to an MHC molecule.

In therapeutic applications, tumor-specific T-cell defined epitopes distinguish a tumor cell from surrounding normal cells. Accordingly, a protein ligand that specifically recognizes one of these epitopes can specifically deliver a cytotoxic activity to the tumor cell but not to normal cells, particularly, surrounding normal cells. In diagnostic and research applications, recognition of the tumor-specific T-cell defined epitopes by a protein ligand identifies that a tumor cell is present.

In some instances, natural T cell mediated reactivity against tumors has been observed (Boon and van der Bruggen (1996) J Exp Med 183:725-9; Rosenberg (2001) Nature 411: 380-4; Renkvist et al. (2001) Cancer Immunol Immunother 50:3-15). Hence, it is desirable to devise T-cell mediated cancer therapies. In particular, protein ligands that specifically recognize particular peptide-MHC complexes are used to direct T cell cytotoxicity against cancer cells. (See also, "T-Cell Reprogramming," below).

MHC Complexes and Pathogens

MHC complexes also present peptide fragments from antigens of pathogens, particularly intracellular pathogens, e.g., viruses, intracellular bacteria, and other organisms. Thus, MHC proteins provide a natural defense against pathogens that attempt to avoid immune surveillance by spending, in some cases, substantial portions of their life cycle within an infected cell. Further, in many cases, the pathogens can remain latent within the cell for extended times.

A protein ligand that specifically recognizes a peptide derived from a pathogen when presented on an MHC protein can be used in therapeutic and diagnostic modes. As described for applications for cancer cells, the protein ligand can be used to deliver a cytotoxin to kill the infected cell. In addition, the protein ligand can be used for in vivo imaging to locate infected cells within a subject and in vitro to assay a sample for an infected cell or for a processed peptide that originated from the pathogen.

Identification of MHC-Peptide Binding Proteins

The invention provides methods for identifying protein ligands that bind to MHC-peptide complexes. The methods can be used to identify protein ligands that bind only if the particular peptide is present in the complex, and not if the particular peptide is absent or if another, non-overlapping or unrelated peptide is present. In many cases, the identified proteins are at least partially specific. An exemplary identified protein may bind to MHC-peptide complex if the particular peptide is present, and also bind if a related peptide that has two substitutions relative to the particular peptide is present.

The identified protein may be a small peptide (e.g., a peptide of between 7 and 20 amino acids), a polypeptide (e.g., a polypeptide of at least 20 amino acids), or a multi-chain protein (e.g., including at least two peptides or polypeptides).

The inventors unexpectedly discovered numerous human Fab fragments that bind to MHC-peptide complexes from a display library prepared from mRNA of B-cells expressing immunoglobulin genes that predominantly have with no or few mutations with respect to germline (see "EXAMPLES" below). Among other features, these discoveries indicate the use of a single-chain MHC complex for peptide presentation during screening and the use of a display library constructed from an unimmunized subject, particularly a subject having the same MHC allele as the MHC-peptide complex that is the target.

The methods include: providing a library (e.g., an expression library, e.g., a display library) and screening the library to identify a member whose polypeptide component binds to an MHC-peptide complex.

The screening can be performed in a number of ways.

In one embodiment, a bacterially prepared MHC class I α polypeptide and β2-microglobulin are purified, e.g., from bacterial inclusion bodies. These proteins are denatured and refolded in vitro in the presence of the peptide component of the MHC-peptide complex. Further α chain and the β2 microglobulin can be covalently linked, e.g., by an approximately 15 amino acid linker, e.g., as described in Denkberg and Reiter (2000) *Eur. J. Immunol.* 30:3522-32. One of the chains, e.g., the α chain, can include a purification handle such as the BirA sequence that is biotinylated or the hexa-histidine tag. This purified complex can be panned against the display library to identify members of the library the bind the MHC-peptide complex.

Bacterial purification and refolding improve the homogeneity of the MHC-peptide complex. The particular peptide of interest which is incorporated in vitro into the complex does not have to compete with a large number of cellular peptides for binding to the MHC complex and, e.g., results in a homogenous target for binding the display library against.

In another embodiment, cells of interest (e.g., cancer cells or infected cells) are attached to a support, and a display library is contacted to the cells. Members of the library that bind to the cells are isolated and characterized. For example, the cells can be isolated from a patient or prepared using a laboratory model for a disease.

In still another embodiment, tissue culture cells that are deficient in TAP2 activity are used. For example, RMAS-HHD cells can be used. The cells are transfected with a nucleic acid that expresses an MHC protein having an allele of interest. The transfected cells are loaded with a peptide of interest. Then, the display library is contacted to the cell to identify display library members that specifically bind to the cells. In another embodiment, a gene encoding the polypeptide of interest is co-transfected into a cell and expressed therein. The cell naturally processes the polypeptide and displays processed peptides in the MHC-Class I context.

The methods include: providing a library and screening the library to identify a member that encodes a protein that binds to the MHC-peptide complex. Preferably, the protein does not substantially bind the MHC in the absence of the bound peptide, and does not substantially bind the peptide in the absence of the MHC. The peptide can be, e.g., a TAA. The screening can be performed in a number of ways. For example, the library can be a display library.

The MHC component of the complex can be tagged and recombinantly expressed. The recombinant MHC is reconstituted with the peptide, e.g., that is produced synthetically. The MHC-peptide complex is attached to a support, e.g., to paramagnetic beads or other magnetically responsive particle.

The MHC complex can also be expressed on the surface of a cell. The display library can be screened to identify members that specifically bind to the cell, e.g., only if the MHC complex displays the peptide of interest.

Display Libraries

A display library is used to identify proteins that bind to the MHC-peptide complex and recognize the peptide moiety of the complex. A display library is a collection of entities; each entity includes an accessible varied protein component and a recoverable component that encodes or identifies the varied protein component. The protein component can be of any length, e.g. from three amino acids to over 300 amino acids. In a selection, the varied protein component of each member of the library is probed with the MHC-peptide complex and if the varied protein component binds to the MHC-peptide complex, the display library member is identified, typically by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the varied protein component and purification of the polypeptide component for detailed characterization.

A variety of formats can be used for display libraries. Examples include the following.

Phage Display. One format utilizes viruses, particularly bacteriophages. This format is termed "phage display." The varied protein component is typically covalently linked to a bacteriophage coat protein. The linkage results form translation of a nucleic acid encoding the varied protein component fused to the coat protein. The linkage can include a flexible peptide linker, a protease site, or an amino acid incorporated as a result of suppression of a stop codon. Phage display is described, for example, in Ladner et al., U.S. Pat. No. 5,223, 409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352: 624-628; Gram et al. (1992) *PNAS* 89:3576-3580; Garrard et al. (1991) *Bio/Technology* 9:1373-1377; Rebar et al. (1996) *Methods Enzymol.* 267:129-49; Hoogenboom et al. (1991) *Nuc Acid Res* 19:4133-4137; and Barbas et al. (1991) *PNAS* 88:7978-7982.

Phage display systems have been developed for filamentous phage (phage fl, fd, and M13) as well as other bacteriophage (e.g. T7 bacteriophage and lambdoid phages; see, e.g., Santini (1998) *J. Mol. Biol.* 282:125-135; Rosenberg et al. (1996) *Innovations* 6:1-6; Houshm et al. (1999) *Anal Biochem* 268:363-370). The filamentous phage display systems typically use fusions to a minor coat protein, such as gene III protein, and gene VIII protein, a major coat protein, but fusions to other coat proteins such as gene VI protein, gene VII protein, gene IX protein, or domains thereof can also be used (see, e.g., WO 00/71694). In a preferred embodiment, the fusion is to a domain of the gene III protein, e.g., the anchor domain or "stump," (see, e.g., U.S. Pat. No. 5,658,727 for a description of the gene III protein anchor domain).

The valency of the varied protein component can also be controlled. Cloning of the sequence encoding the varied protein component into the complete phage genome results in multivariant display since all replicates of the gene III protein are fused to the varied protein component. For reduced valency, a phagemid system can be utilized. In this system, the nucleic acid encoding the varied protein component fused to gene III is provided on a plasmid, typically of length less than 700 nucleotides. The plasmid includes a phage origin of replication so that the plasmid is incorporated into bacteriophage particles when bacterial cells bearing the plasmid are infected with helper phage, e.g. M13K01. The helper phage provides an intact copy of gene III and other phage genes required for phage replication and assembly. The helper phage has a defective origin such that the helper phage genome is not efficiently incorporated into phage particles relative to the plasmid that has a wild type origin.

Bacteriophage displaying the varied protein component can be grown and harvested using standard phage preparatory methods, e.g. PEG precipitation from growth media.

After selection of individual display phages, the nucleic acid encoding the selected varied protein components, by infecting cells using the selected phages. Individual colonies or plaques can be picked, the nucleic acid isolated and sequenced.

Cell-based Display. In still another format the library is a cell-display library. Proteins are displayed on the surface of a cell, e.g., a eukaryotic or prokaryotic cell. Exemplary prokaryotic cells include *E. coli* cells, *B. subtilis* cells, spores (see, e.g., Lu et al. (1995) *Biotechnology* 13:366). Exemplary eukaryotic cells include yeast (e.g., *Saccharomyces cerevisiae, Schizosaccharomyces pombe, Hanseula,* or *Pichia pastoris*). Yeast surface display is described, e.g., in Boder and Wittrup (1997) *Nat. Biotechnol.* 15:553-557. U.S. Provisional Patent Application Ser. No. 60/326,320, filed Oct. 1, 2001, describes a yeast display system that can be used to display immunoglobulin proteins such as Fab fragments.

In one embodiment, nucleic acid encoding immunoglobulin variable domains are cloned into a vector for yeast display. The cloning joins the nucleic acid encoding at least one of the variable domains with nucleic acid encoding a fragments of a yeast cell surface protein, e.g., Flo1, a-agglutinin, α-agglutinin, or fragments derived thereof e.g. Aga2p, Aga1p. A domain of these proteins can anchor the polypeptide encoded by the diversified nucleic acid sequence by a GPI-anchor (e.g. a-agglutinin, α-agglutinin, or fragments derived thereof e.g. Aga2p, Aga1p), by a transmembrane domain (e.g., Flo1). The vector can be configured to express two polypeptide chains on the cell surface such that one of the chains is linked to the yeast cell surface protein. For example, the two chains can be immunoglobulin chains.

Ribosome Display. RNA and the polypeptide encoded by the RNA can be physically associated by stabilizing ribosomes that are translating the RNA and have the nascent polypeptide still attached. Typically, high divalent $Mg^{2+}$ concentrations and low temperature are used. See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30. and Schaffitzel et al. (1999) *J Immunol Methods.* 231(1-2):119-35.

Peptide-Nucleic Acid Fusions. Another format utilizes peptide-nucleic acid fusions. Polypeptide-nucleic acid fusions can be generated by the in vitro translation of mRNA that include a covalently attached puromycin group, e.g., as described in Roberts and Szostak (1997) *Proc. Natl. Acad. Sci. USA* 94:12297-12302, and U.S. Pat. No. 6,207,446. The mRNA can then be reverse transcribed into DNA and crosslinked to the polypeptide.

Other Display Formats. Yet another display format is a non-biological display in which the varied protein component is attached to a non-nucleic acid tag that identifies the polypeptide. For example, the tag can be a chemical tag attached to a bead that displays the polypeptide or a radiofrequency tag (see, e.g., U.S. Pat. No. 5,874,214).

Scaffolds. Criteria for evaluating a scaffolding domain can include: (1) amino acid sequence, (2) sequences of several homologous domains, (3) 3-dimensional structure, and/or (4) stability data over a range of pH, temperature, salinity, organic solvent, oxidant concentration. In one embodiment, the scaffolding domain is a small, stable protein domains, e.g., a protein of less than 100, 70, 50, 40 or 30 amino acids. The domain may include one or more disulfide bonds or may chelate a metal, e.g., zinc.

Scaffolds for display can include: antibodies (e.g., Fab fragments, single chain Fv molecules (scFV), single domain antibodies, camelid antibodies, and camelized antibodies); T-cell receptors; MHC proteins themselves; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains).

Examples of small scaffolding domains include: Kunitz domains (58 amino acids, 3 disulfide bonds), *Cucurbida maxima* trypsin inhibitor domains (31 amino acids, 3 disulfide bonds), domains related to guanylin (14 amino acids, 2 disulfide bonds), domains related to heat-stable enterotoxin IA from gram negative bacteria (18 amino acids, 3 disulfide bonds), EGF domains (50 amino acids, 3 disulfide bonds), kringle domains (60 amino acids, 3 disulfide bonds), fungal carbohydrate-binding domains (35 amino acids, 2 disulfide bonds), endothelin domains (18 amino acids, 2 disulfide bonds), and Streptococcal G IgG-binding domain (35 amino acids, no disulfide bonds).

Examples of small intracellular scaffolding domains include SH2, SH3, and EVH domains. Generally, any modular domain, intracellular or extracellular, can be used.

The scaffold domain can include a synthetic peptide. A "synthetic peptide" is an artificial peptide of 30 amino acids or less. The synthetic peptide can include one or more disulfide bonds. Other synthetic peptides, so-called "linear peptides," are devoid of cysteines. Synthetic peptides may have little or no structure in solution (e.g., unstructured), heterogeneous structures (e.g., alternative conformations or "loosely structured), or a singular native structure (e.g., cooperatively folded). Some synthetic peptides adopt a particular structure when bound to a target molecule. Some exemplary synthetic peptides are so-called "cyclic peptides" that have one disulfide bond, and a loop of about 4 to 12 non-cysteine residues, e.g., a sequence of Xaa-Xaa-Xaa-Cys-(Xaa)$_n$-Cys-Xaa-Xaa-Xaa.

where Xaa is any non-cysteine amino acid, and n is an integer between 4 and 12. The selection of amino acids can be varied at each position, e.g., to a mixture of 18 or fewer amino acids. U.S. Pat. No. 5,223,409 also describes a variety of other disulfide bonded peptides and polypeptides that can function as scaffolds.

Another useful type of scaffolding domain is the immunoglobulin (Ig) domain. Methods using immunoglobulin domains for display are described below (see, e.g., "Antibody Display Libraries").

Display technology can also be used to obtain ligands, e.g., antibody ligands, particular epitopes of a target. This can be done, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target.

Iterative Selection. In one preferred embodiment, display library technology is used in an iterative mode. A first display library is used to identify one or more ligands for a target. These identified ligands are then varied using a mutagenesis method to form a second display library. Higher affinity ligands are then selected from the second library, e.g., by using higher stringency or more competitive binding and washing conditions.

In some implementations, the mutagenesis is targeted to regions known or likely to be at the binding interface. If, for example, the identified ligands are antibodies, then mutagenesis can be directed to the CDR regions of the heavy or light chains as described herein. Further, mutagenesis can be directed to framework regions near or adjacent to the CDRs. In the case of antibodies, mutagenesis can also be limited to one or a few of the CDRs, e.g., to make precise step-wise improvements. Likewise, if the identified ligands are enzymes, mutagenesis can be directed to the active site and vicinity.

Some exemplary mutagenesis techniques include: error-prone PCR (Leung et al. (1989) *Technique* 1:11-15), recombination, DNA shuffling using random cleavage (Stemmer (1994) *Nature* 389-391; termed "nucleic acid shuffling"), RACHITT™ (Coco et al. (2001) *Nature Biotech.* 19:354), site-directed mutagenesis (Zooler et al. (1987) *Nucl Acids Res* 10:6487-6504), cassette mutagenesis (Reidhaar-Olson (1991) *Methods Enzymol.* 208:564-586) and incorporation of degenerate oligonucleotides (Griffiths et al. (1994) *EMBO J* 13:3245).

In one example of iterative selection, the methods described herein are used to first identify a protein ligand from a display library that binds a MHC-peptide complex with at least a minimal binding specificity for the varied protein component or a minimal activity, e.g., an equilibrium dissociation constant for binding of greater than 1 nM, 10 nM, or 100 nM. The nucleic acid sequence encoding the initial identified protein ligand are used as a template nucleic acid for the introduction of variations, e.g., to identify a second protein ligand that has enhanced properties (e.g., binding affinity, kinetics, or stability) relative to the initial protein ligand.

Off-Rate Selection. Since a slow dissociation rate can be predictive of high affinity, particularly with respect to interactions between polypeptides and their targets, the methods described herein can be used to isolate ligands with a desired kinetic dissociation rate (i.e., reduced) for a binding interaction to a target.

To select for slow dissociating ligands from a display library, the library is contacted to an immobilized target. The immobilized target is then washed with a first solution that removes non-specifically or weakly bound biomolecules. Then the immobilized target is eluted with a second solution that includes a saturation amount of free target, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting or Screening for Specificity. The display library screening methods described herein can include a selection or screening process that discards display library members that bind to a non-target molecule. Examples of non-target molecules include: (i) a TAA peptide that is not bound to an MHC; (ii) a MHC which is not bound by a peptide; (iii) a MHC which is bound by a peptide that differs from the peptide of interest; and (iv) a MHC which is bound by the peptide of interest, but has a different allele from the MHC of interest.

In one implementation, a so-called "negative selection" step is used to discriminate between the target MHC-peptide complex and related non-target molecule and a related, but distinct non-target molecules. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target MHC-peptide complex.

In another implementation, a screening step is used. After display library members are isolated for binding to the target MHC-peptide complex, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target. The non-target and target binding data can be compared (e.g., using a computer and software) to identify library members that specifically bind to the target MHC-peptide complex.

Diversity

Display libraries include variation at one or more positions in the displayed polypeptide. The variation at a given position can be synthetic or natural. For some libraries, both synthetic and natural diversity are included.

Synthetic Diversity. Libraries can include regions of diverse nucleic acid sequence that originate from artificially synthesized sequences. Typically, these are formed from degenerate oligonucleotide populations that include a distribution of nucleotides at each given position. The inclusion of a given sequence is random with respect to the distribution. One example of a degenerate source of synthetic diversity is an oligonucleotide that includes NNN wherein N is any of the four nucleotides in equal proportion.

Synthetic diversity can also be more constrained, e.g., to limit the number of codons in a nucleic acid sequence at a given trinucleotide to a distribution that is smaller than NNN. For example, such a distribution can be constructed using less than four nucleotides at some positions of the codon. In addition, trinucleotide addition technology can be used to further constrain the distribution.

So-called "trinucleotide addition technology" is described, e.g., in Wells et al. (1985) Gene 34:315-323, U.S. Pat. Nos. 4,760,025 and 5,869,644. Oligonucleotides are synthesized on a solid phase support, one codon (i.e., trinucleotide) at a time. The support includes many functional groups for synthesis such that many oligonucleotides are synthesized in parallel. The support is first exposed to a solution containing a mixture of the set of codons for the first position. The unit is protected so additional units are not added. The solution containing the first mixture is washed away and the solid support is deprotected so a second mixture containing a set of codons for a second position can be added to the attached first unit. The process is iterated to sequentially assemble multiple codons. Trinucleotide addition technology enables the synthesis of a nucleic acid that at a given position can encoded a number of amino acids. The frequency of these amino acids can be regulated by the proportion of codons in the mixture. Further the choice of amino acids at the given position is not restricted to quadrants of the codon table as is the case if mixtures of single nucleotides are added during the synthesis.

Natural Diversity. Libraries can include regions of diverse nucleic acid sequence that originate (or are synthesized based on) from different naturally-occurring sequences. An example of natural diversity that can be included in a display library is the sequence diversity present in immune cells (see also below). Nucleic acids are prepared from these immune cells and are manipulated into a format for polypeptide display. Another example of naturally diversity is the diversity of sequences among different species of organisms. For example, diverse nucleic acid sequences can be amplified from environmental samples, such as soil, and used to construct a display library.

Antibody Display Libraries

In one embodiment, the display library presents a diverse pool of polypeptides, each of which includes an immunoglobulin domain, e.g., an immunoglobulin variable domain. Display libraries are particular useful, for example for identifying human or "humanized" antibodies that recognize human antigens. Such antibodies can be used as therapeutics to treat human disorders such as cancer. Since the constant and framework regions of the antibody are human, these therapeutic antibodies may avoid themselves being recognized and targeted as antigens. The constant regions are also optimized to recruit effector functions of the human immune system. The in vitro display selection process surmounts the inability of a normal human immune system to generate antibodies against self-antigens.

A typical antibody display library displays a polypeptide that includes a VH domain and a VL domain. An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 Ann. Rev Immunol. 6:381-405). The display library can display the antibody as a Fab fragment (e.g., using two polypeptide chains) or a single chain Fv (e.g., using a single polypeptide chain). Other formats can also be used.

As in the case of the Fab and other formats, the displayed antibody can include a constant region as part of a light or heavy chain. In one embodiment, each chain includes one constant region, e.g., as in the case of a Fab. In other embodiments, additional constant regions are displayed.

Antibody libraries can be constructed by a number of processes (see, e.g., WO 00/70023). Further, elements of each process can be combined with those of other processes. The processes can be used such that variation is introduced into a single immunoglobulin domain (e.g., VH or VL) or into multiple immunoglobulin domains (e.g., VH and VL). The variation can be introduced into an immunoglobulin variable domain, e.g., in the region of one or more of CDR1, CDR2, CDR3, FR1, FR2, FR3, and FR4, referring to such regions of either and both of heavy and light chain variable domains. In one embodiment, variation is introduced into all three CDRs of a given variable domain. In another preferred embodiment, the variation is introduced into CDR1 and CDR2, e.g., of a heavy chain variable domain. Any combination is feasible. In one process, antibody libraries are constructed by inserting diverse oligonucleotides that encode CDRs into the corresponding regions of the nucleic acid. The oligonucleotides can be synthesized using monomeric nucleotides or trinucleotides. For example, Knappik et al. (2000) J. Mol. Biol. 296: 57-86 describes a method for constructing CDR encoding oligonucleotides using trinucleotide synthesis and a template with engineered restriction sites for accepting the oligonucleotides.

In another process, an animal, e.g., a rodent, is immunized with the MHC-peptide complex that includes a specific peptide or with a cell that presents a specific peptide on its surface bound to the MHC. The cell can have a particular allele of the MHC protein. The animal is optionally boosted with the antigen to further stimulate the response. Then spleen cells are isolated from the animal, and nucleic acid encoding VH and/or VL domains is amplified and cloned for expression in the display library. Of course, a display library may not need to be screened to obtain nucleic acids that encode antibodies specific for the target in this case.

In yet another process, antibody libraries are constructed from nucleic acid amplified from naïve germline immunoglobulin genes. The amplified nucleic acid includes nucleic acid encoding the VH and/or VL domain. Sources of immunoglobulin-encoding nucleic acids are described below. Amplification can include PCR, e.g., with primers that anneal to the conserved constant region, or another amplification method.

Nucleic acid encoding immunoglobulin domains can be obtained from the immune cells of, e.g., a human, a primate, mouse, rabbit, camel, or rodent. In one example, the cells are selected for a particular property. B cells at various stages of maturity can be selected. In another example, the B cells are naïve.

In one embodiment, fluorescent-activated cell sorting (FACS) is used to sort B cells that express surface-bound IgM, IgD, or IgG molecules. Further, B cells expressing different isotypes of IgG can be isolated. In another preferred embodiment, the B or T cell is cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin or pokeweed mitogen.

In still another embodiment, the cells are isolated from a subject that has an immunological disorder, e.g., systemic lupus erythematosus (SLE), rheumatoid arthritis, vasculitis, Sjogren syndrome, systemic sclerosis, or anti-phospholipid syndrome. The subject can be a human, or an animal, e.g., an animal model for the human disease, or an animal having an analogous disorder. In yet another embodiment, the cells are isolated from a transgenic non-human animal that includes a human immunoglobulin locus.

In one preferred embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al. (2001) *J Immunol.* 166:2228). In another embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g. by degrading uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g., de Haard et al. (1999) *J. Biol. Chem* 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In another embodiment, poly-dT primers may be used (and may be preferred for the heavy-chain genes).

A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity.

The variable domain-encoding gene is then amplified, e.g., using one or more rounds. If multiple rounds are used, nested primers can be used for increased fidelity. The amplified nucleic acid is then cloned into a display library vector.

Any method for amplifying nucleic acid sequences may be used for amplification. Methods that maximize, and do not bias, diversity are preferred. A variety of techniques can be used for nucleic acid amplification. The polymerase chain reaction (PCR; U.S. Pat. Nos. 4,683,195 and 4,683,202, Saiki, et al. (1985) *Science* 230, 1350-1354) utilizes cycles of varying temperature to drive rounds of nucleic acid synthesis. Transcription-based methods utilize RNA synthesis by RNA polymerases to amplify nucleic acid (U.S. Pat. No. 6,066, 457; U.S. Pat. No. 6,132,997; U.S. Pat. No. 5,716,785; Sarkar et. al., *Science* (1989) 244: 331-34; Stofler et al., *Science* (1988) 239: 491). NASBA (U.S. Pat. Nos. 5,130,238; 5,409, 818; and 5,554,517) utilizes cycles of transcription, reverse-transcription, and RnaseH-based degradation to amplify a DNA sample. Still other amplification methods include rolling circle amplification (RCA; U.S. Pat. Nos. 5,854,033 and 6,143,495) and strand displacement amplification (SDA; U.S. Pat. Nos. 5,455,166 and 5,624,825).

Secondary Screening Methods

After selecting candidate display library members that bind to a target, each candidate display library member can be further analyzed, e.g., to further characterize its binding properties for the MHC-peptide complex. Each candidate display library member can be subjected to one or more secondary screening assays. For example, the assays can determine relative binding to different MHC-peptide complexes, e.g., to assess specificity for the peptide moiety and/or the MHC allele. The assay can be for a binding property, a catalytic property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

Exemplary assays for binding properties include the following.

ELISA. Polypeptides encoded by a display library can also be screened for a binding property using an ELISA assay. For example, each polypeptide is contacted to a microtitre plate whose bottom surface has been coated with the target, e.g., a limiting amount of the target. The plate is washed with buffer to remove non-specifically bound polypeptides. Then the amount of the polypeptide bound to the plate is determined by probing the plate with an antibody that can recognize the polypeptide, e.g., a tag or constant portion of the polypeptide. The antibody is linked to an enzyme such as alkaline phosphatase, which produces a calorimetric product when appropriate substrates are provided. The polypeptide can be purified from cells or assayed in a display library format, e.g., as a fusion to a filamentous bacteriophage coat. In another version of the ELISA assay, each polypeptide of a library is used to coat a different well of a microtitre plate. The ELISA then proceeds using a constant target molecule to query each well.

Homogeneous Binding Assays. The binding interaction of candidate polypeptide with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means well known in the art (e.g., using a fluorimeter). By titrating the amount of the first or second binding molecule, a binding curve can be generated to estimate the equilibrium binding constant.

Another example of a homogenous assay is ALPHAS-CREEN™ (Packard Bioscience, Meriden Conn.). ALPHAS-CREEN™ uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding.

The homogenous assays can be performed while the candidate polypeptide is attached to the display library vehicle, e.g., a bacteriophage.

Surface Plasmon Resonance (SPR). The binding interaction of a molecule isolated from a display library and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a biomolecule to a target. Such data can be used to compare different biomolecules. For example, proteins encoded by nucleic acid selected from a display library can be compared to identify individual proteins that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by crystallography or NMR). As a result, an understanding of the physical interaction between the protein and its target can be formulated and used to guide other design processes.

Protein Arrays. Polypeptides identified from the display library can be immobilized on a solid support, for example, on a bead or an array. For a protein array, each of the polypeptides is immobilized at a unique address on a support. Typically, the address is a two-dimensional address. Protein arrays are described below (see, e.g., Diagnostics).

Cellular Assays. Candidate polypeptides (e.g., previously identified by a display library or otherwise) can be screened for biological or other functional activity, e.g., using a cellular assay. For example, in the case of an antibody that binds to the MHC-peptide complex, the activity may be cell- or complement-mediated cytotoxicity toward a cell that present the peptide on a surface MHC group. An antibody can be expressed in a mammalian cell, harvested, and then tested for cell- or complement-mediated cytotoxicity.

The Cr-release assay, for example, can be used to assay cell-mediated cytotoxicity. Peripheral blood lymphocytes (PBL) are prepared as effector cells, while target cells that express the targeted MHC-peptide complex are loaded with $^{51}Cr$. The target cells are washed and then seeded into a flat bottom microtitre plate. PBL (50 T1) are added to the target cells in combination with the ligand (e.g., a known anti-(MHC-peptide complex) ligand or a candidate ligand). Maximum release is determined by the addition of TWEEN-20 to target cells, whereas minimal release is determined in the absence of PBLs. After overnight incubation, $^{51}Cr$ released into the supernatant is counted in a K scintillation counter.

In another embodiment, the library of cells is in the form of a cellular array. The cellular array can likewise be screened for any appropriate detectable activity.

Ligand Production

Standard recombinant nucleic acid methods can be used to express a protein ligand that binds to a MHC-peptide complex and recognizes the peptide moiety. Generally, a nucleic acid sequence encoding the protein ligand is cloned into a nucleic acid expression vector. Of course, if the protein includes multiple polypeptide chains, each chain must be cloned into an expression vector, e.g., the same or different vectors, that are expressed in the same or different cells. If the protein is sufficiently small, i.e., the protein is a peptide of less than 50 amino acids, the protein can be synthesized using automated organic synthetic methods. Methods for producing antibodies are also provided below.

The expression vector for expressing the protein ligand can include, in addition to the segment encoding the protein ligand or fragment thereof, regulatory sequences, including for example, a promoter, operably linked to the nucleic acid(s) of interest. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, and pRIT5 (Pharmacia). Eukaryotic: pWLneo, pSV2cat, pOG44, PXTI, pSG (Stratagene) pSVK3, pBPV, pMSG, and pSVL (Pharmacia). One preferred class of preferred libraries is the display library, which is described below.

Methods well known to those skilled in the art can be used to construct vectors containing a polynucleotide of the invention and appropriate transcriptional/translational control signals. These methods include in vitro recombinant DNA techniques, synthetic techniques and in vivo recombination/genetic recombination. See, for example, the techniques described in Sambrook & Russell, *Molecular Cloning: A Laboratory Manual*, 3$^{rd}$ Edition, Cold Spring Harbor Laboratory, N.Y. (2001) and Ausubel et al., Current Protocols in Molecular Biology (Greene Publishing Associates and Wiley Interscience, N.Y. (1989). Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda P, and trc. Eukaryotic promoters include CMV immediate early, HSV thymidine kinase, early and late SV40, LTRs from retrovirus, mouse metallothionein-I, and various art-known tissue specific promoters.

Generally, recombinant expression vectors will include origins of replication and selectable markers permitting transformation of the host cell, e.g., the ampicillin resistance gene of *E. coli* and *S. cerevisiae* auxotrophic markers (such as URA3, LEU2, HIS3, and TRP1 genes), and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The polynucleotide of the invention is assembled in appropriate phase with translation initiation and termination sequences, and preferably, a leader sequence capable of directing secretion of translated protein into the periplasmic space or extracellular medium. Optionally, a nucleic acid of the invention can encode a fusion protein including an N-terminal identification peptide imparting desired characteristics, e.g., stabilization or simplified purification of expressed recombinant product. Useful expression-vectors for bacteria are constructed by inserting a polynucleotide of the invention together with suitable translation initiation and termination signals, optionally in operable reading phase with a functional promoter. The vector will comprise one or more phenotypic selectable markers and an origin of replication to ensure maintenance of the vector and to, if desirable, provide amplification within the host. Suitable prokaryotic hosts for transformation include $E.\ coli$, $Bacillus\ subtilis$, $Salmonella\ typhimurium$ and various species within the genera $Pseudomonas$, $Streptomyces$, and $Staphylococcus$, although others may also be employed as a matter of choice.

As a representative but nonlimiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega, Madison, Wis., USA).

The present invention further provides host cells containing the vectors of the present invention, wherein the nucleic acid has been introduced into the host cell using known transformation, transfection or infection methods. For example, the host cells can include members of a library or a nucleic acid encoding components of a anti-(MHC-peptide complex) ligand. The host cell can be a eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected, for example, by calcium phosphate transfection, DEAE, dextran mediated transfection, or electroporation (Davis, L. et al., Basic Methods in Molecular Biology (1986)).

Any host/vector system can be used to identify one or more of the target elements of the present invention. These include, but are not limited to, eukaryotic hosts such as HeLa cells, CV-1 cell, COS cells, and Sf9 cells, as well as prokaryotic host such as $E.\ coli$ and $B.\ subtilis$. The most preferred cells are those which do not normally express the particular reporter polypeptide or protein or which expresses the reporter polypeptide or protein at low natural level.

The host of the present invention may also be a yeast or other fungi. In yeast, a number of vectors containing constitutive or inducible promoters may be used. For a review see, Current Protocols in Molecular Biology, Vol. 2, Ed. Ausubel et al., Greene Publish. Assoc. & Wiley Interscience, Ch. 13 (1988); Grant et al., Expression and Secretion Vectors for Yeast, in Methods in Enzymology, Ed. Wu & Grossman, Acad. Press, N.Y. 153:516-544 (1987); Glover, DNA Cloning, Vol. II, IRL Press, Wash., D.C., Ch. 3 (1986); Bitter, Heterologous Gene Expression in Yeast, in Methods in Enzymology, Eds. Berger & Kimmel, Acad. Press, N.Y. 152:673-684 (1987); and The Molecular Biology of the Yeast $Saccharomyces$, Eds. Strathern et al., Cold Spring Harbor Press, Vols. I and 11 (1982).

The host of the invention may also be a prokaryotic cell such as $E.\ coli$, other enterobacteriaceae such as $Serratia\ marescans$, bacilli, various pseudomonads, or other prokaryotes which can be transformed, transfected, infected.

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell.

Introduction of the recombinant construct into the host cell can be effected by calcium phosphate transfection, DEAE, dextran mediated transfection, or electroporation (Davis, L. et al., Basic Methods in Molecular Biology (1986)). The host cells containing one of polynucleotides of the invention, can be used in conventional manners to produce the gene product encoded by the isolated fragment (in the case of an ORF).

Any host/vector system can be used to express one or more of the anti-(MHC-peptide complex) ligands. These include, but are not limited to, eukaryotic hosts such as HeLa cells, CV-1 cell, COS cells, and Sf9 cells, as well as prokaryotic host such as $E.\ coli$ and $B.\ subtilis$. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein.

Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors will comprise an origin of replication, a suitable promoter and also any necessary ribosome-binding sites, polyadenylation site, splice donor and acceptor sites, transcriptional termination sequences, and 5' flanking nontranscribed sequences.

DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. In some embodiments, the template nucleic acid also encodes a polypeptide tag, e.g., penta- or hexa-histidine. The recombinant polypeptides can then be purified using affinity chromatography.

Microbial cells employed in expression of proteins can be disrupted by any convenient method, including freeze-thaw cycling, sonication, mechanical disruption, or use of cell lysing agents. A number of types of cells may act as suitable host cells for expression of the protein. Scopes (1994) *Protein Purification: Principles and Practice*, New York:Springer-Verlag provides a number of general methods for purifying recombinant (and non-recombinant) proteins. The method include, e.g., ion-exchange chromatography, size-exclusion chromatography, affinity chromatography, selective precipitation, dialysis, and hydrophobic interaction chromatography. These methods can be adapted for devising a purification strategy for the anti-MHC-peptide complex protein ligand.

Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods. In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods.

Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

Antibody Production. Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be shuffled into a bacterial cell that cannot suppress a stop codon. In this case, the Fab is not fused to the gene III protein and is secreted into the media.

Antibodies can also be produced in eukaryotic cells. In one embodiment, the antibodies (e.g., scFv's) are expressed in a yeast cell such as *Pichia* (see, e.g., Powers et al. (2001) *J Immunol Methods.* 251:123-35), *Hanseula*, or *Saccharomyces*.

In one preferred embodiment, antibodies are produced in mammalian cells. Preferred mammalian host cells for expressing the clone antibodies or antigen-binding fragments thereof include Chinese Hamster Ovary (CHO cells) (including dhfr– CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

In an exemplary system for recombinant expression of an antibody, or antigen-binding portion thereof, of the invention, a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcγ receptors and complement C1q (Burton and Woof (1992) *Adv. Immunol.* 51:1-84; Jefferis et al. (1998) *Immunol. Rev.* 163:59-76). In a preferred embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Pharmaceutical Compositions

In another aspect, the present invention provides compositions, e.g., pharmaceutically acceptable compositions, which include an anti-(MHC-peptide complex) ligand, e.g., an antibody molecule, other polypeptide or peptide identified as binding to a MHC-peptide complex, or described herein, formulated together with a pharmaceutically acceptable carrier. As used herein, "pharmaceutical compositions" encompass labeled ligands for in vivo imaging as well as therapeutic compositions.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., protein ligand may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for administration of humans with antibodies. The preferred mode of administration is parenteral (e.g., intravenous, subcutaneous, intraperitoneal, intramuscular). In a preferred embodiment, the anti-(MHC-peptide complex) ligand is administered by intravenous infusion or injection. In another preferred embodiment, the anti-(MHC-peptide complex) ligand is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Pharmaceutical compositions typically must be sterile and stable under the conditions of manufacture and storage. A pharmaceutical composition can also be tested to insure it meets regulatory and industry standards for administration. For example, endotoxin levels in the preparation can be tested using the *Limulus amebocyte* lysate assay (e.g., using the kit from Bio Whittaker lot # 7L3790, sensitivity 0.125 EU/mL) according to the USP 24/NF 19 methods. Sterility of pharmaceutical compositions can be determined using thioglycollate medium according to the USP 24/NF 19 methods. For example, the preparation is used to inoculate the thioglycollate medium and incubated at 35° C. for 14 or more days. The medium is inspected periodically to detect growth of a microorganism.

The composition can be formulated as a solution, microemulsion, dispersion, liposome, or other ordered structure suitable to high drug concentration. Sterile injectable solutions can be prepared by incorporating the active compound (i.e., the ligand) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The anti-(MHC-peptide complex) protein ligands of the present invention can be administered by a variety of methods known in the art, although for many applications, the preferred route/mode of administration is intravenous injection or infusion. For example, for therapeutic applications, the anti-(MHC-peptide complex) ligand can be administered by intravenous infusion at a rate of less than 30, 20, 10, 5, or 1 mg/min to reach a dose of about 1 to 100 mg/m$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978.

In certain embodiments, the ligand may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Of course, many other such implants, delivery systems, and modules are also known.

In certain embodiments, the compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody of the invention is 0.1-20 mg/kg, more preferably 1-10 mg/kg. The anti-(MHC-peptide complex) antibody can be administered by intravenous infusion at a rate of less than 30, 20, 10, 5, or 1 mg/min to reach a dose of about 1 to 100 mg/m² or about 5 to 30 mg/m². For ligands smaller in molecular weight than an antibody, appropriate amounts can be proportionally less. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an anti-(MHC-peptide complex) ligand of the invention. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein ligand to elicit a desired response in the individual. A therapeutically effective amount is also one in which any toxic or detrimental effects of the composition is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention are kits comprising the protein ligand that binds to a MHC-peptide complex and instructions for use, e.g., treatment, prophylactic, or diagnostic use. In one embodiment, the instructions for diagnostic applications include the use of the anti-(MHC-peptide complex) ligand (e.g., antibody or antigen-binding fragment thereof, or other polypeptide or peptide) to detect a MHC-peptide complex, in vitro, e.g., in a sample, e.g., a biopsy or cells from a patient having a cancer or neoplastic disorder, or in vivo. In another embodiment, the instructions for therapeutic applications include suggested dosages and/or modes of administration in a patient with a cancer or neoplastic disorder. The kit can further contain a least one additional reagent, such as a diagnostic or therapeutic agent, e.g., a diagnostic or therapeutic agent as described herein, and/or one or more additional anti-(MHC-peptide complex) ligands, formulated as appropriate, in one or more separate pharmaceutical preparations.

Treatments

Protein ligands that bind to a MHC-peptide complex and/or identified by the method described herein have therapeutic and prophylactic utilities. For example, these ligands independently or as part of a therapeutic entity can be administered to cells in culture, e.g. in vitro or ex vivo, or in a subject, e.g., in vivo, to treat, prevent, and/or diagnose a variety of disorders, such as cancers. In another example, the ligands are expressed on cells, e.g., cytotoxic cells. The ligand expressing cells are used to treat, prevent, and/or diagnose a disorder.

As used herein, the term "treat" or "treatment" is defined as the application or administration of an anti-(MHC-peptide complex) antibody, alone or in combination with, a second agent to a subject, e.g., a patient, or application or administration of the agent to an isolated tissue or cell, e.g., cell line, from a subject, e.g., a patient, who has a disorder (e.g., a disorder as described herein), a symptom of a disorder or a predisposition toward a disorder, with the purpose to cure, heal, alleviate, relieve, alter, remedy, ameliorate, improve or affect the disorder, the symptoms of the disorder or the predisposition toward the disorder. Treating a cell refers to the inhibition, ablation, killing of a cell in vitro or in vivo, or otherwise reducing capacity of a cell, e.g., an aberrant cell, to mediate a disorder, e.g., a disorder as described herein (e.g., a cancerous disorder). In one embodiment, "treating a cell" refers to a reduction in the activity and/or proliferation of a cell, e.g., a hyperproliferative cell. Such reduction does not necessarily indicate a total elimination of the cell, but a reduction, e.g., a statistically significant reduction, in the activity or the number of the cell. The application or administration of an anti-(MHC-peptide complex) antibody can be in the form of a soluble compound, e.g., antibody alone or antibody conjugate, or on the surface of the cell, e.g., an effector cell. In some implementations, a nucleic acid encoding the anti-(MHC-peptide complex) antibody is administered.

As used herein, an amount of an anti-(MHC-peptide complex) ligand effective to treat a disorder, or a "therapeutically effective amount" refers to an amount of the ligand which is effective, upon single or multiple dose administration to a subject, in treating a cell, e.g., a cancer cell (e.g., a cell that presents a TAA in association with a MHC), or in prolonging curing, alleviating, relieving or improving a subject with a disorder as described herein beyond that expected in the absence of such treatment. As used herein, "inhibiting the growth" of the neoplasm refers to slowing, interrupting, arresting or stopping its growth and metastases and does not necessarily indicate a total elimination of the neoplastic growth.

As used herein, an amount of an anti-(MHC-peptide complex) ligand effective to prevent a disorder, or a "a prophylactically effective amount" of the ligand refers to an amount of an anti-(MHC-peptide complex) ligand, e.g., an anti-(MHC-peptide complex) antibody described herein, which is effective, upon single- or multiple-dose administration to the subject, in preventing or delaying the occurrence of the onset or recurrence of a disorder, e.g., a cancer.

The terms "induce," "inhibit," "potentiate," "elevate," "increase," "decrease" or the like, e.g., which denote quantitative differences between two states, refer to a difference, e.g., a statistically significant difference, between the two states. For example, "an amount effective to inhibit the proliferation of the hyperproliferative cells that present a TAA" means that the rate of growth of the cells will be different, e.g., statistically significantly different, from the untreated cells. In a preferred embodiment, the TAA is hTERT, MUC1, TAX, or gp100.

As used herein, the term "subject" is intended to include human and non-human animals. Preferred human animals include a human patient having a disorder characterized by abnormal cell proliferation or cell differentiation. The term "non-human animals" of the invention includes all vertebrates, e.g., non-mammals (such as chickens, amphibians, reptiles) and mammals, such as non-human primates, sheep, dog, cow, pig, etc.

In one embodiment, the subject is a human subject. Alternatively, the subject can be a mammal that includes a cell that presents a TAA-like antigen on an MHC to form a complex with which a ligand of the invention cross-reacts. A protein ligand of the invention can be administered to a human subject for therapeutic purposes (discussed further below). Moreover, an anti-(MHC-peptide complex) ligand can be administered to a non-human mammal for veterinary purposes or as an animal model of human disease. Regarding the latter, such animal models may be useful for evaluating the therapeutic efficacy of the ligand (e.g., testing of dosages and time courses of administration).

In one embodiment, the invention provides a method of treating (e.g., ablating or killing) a cell (e.g., a non-cancerous cell, e.g., a normal, benign or hyperplastic cell, or a cancerous cell, e.g., a malignant cell, e.g., cell found in a solid tumor, a soft tissue tumor, or a metastatic lesion (e.g., a cell found in renal, urothelial, colonic, rectal, pulmonary, breast or hepatic, cancers and/or metastasis). Methods of the invention include the steps of contacting the cell with an anti-(MHC-peptide complex) ligand, e.g., an anti-(MHC-peptide complex) antibody described herein, in an amount sufficient to treat, e.g., ablate or kill, the cell.

The subject method can be used on cells in culture, e.g. in vitro or ex vivo. For example, cancerous or metastatic cells (e.g., renal, urothelial, colon, rectal, lung, breast, ovarian, prostatic, or liver cancerous or metastatic cells) can be cultured in vitro in culture medium and the contacting step can be effected by adding the anti-(MHC-peptide complex) ligand to the culture medium. The method can be performed on cells (e.g., cancerous or metastatic cells) present in a subject, as part of an in vivo (e.g., therapeutic or prophylactic) protocol. For in vivo embodiments, the contacting step is effected in a subject and includes administering the anti-(MHC-peptide complex) ligand to the subject under conditions effective to permit both binding of the ligand to the cell and the treating, e.g., the killing or ablating of the cell.

The method can be used to treat a cancer. As used herein, the terms "cancer", "hyperproliferative", "malignant", and "neoplastic" are used interchangeably, and refer to those cells an abnormal state or condition characterized by rapid proliferation or neoplasm. The terms include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be benign, premalignant or malignant.

Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, prostate, ovary as well as adenocarcinomas which include malignancies such as most colon cancers, rectal cancer, renal-cell carcinoma, liver cancer, non-small cell carcinoma of the lung, cancer of the small intestine and so forth. Metastatic lesions of the aforementioned cancers can also be treated or prevented using the methods and compositions of the invention.

The subject method can be useful in treating malignancies of the various organ systems, such as those affecting lung, breast, lymphoid, gastrointestinal (e.g., colon), and genitourinary tract, prostate, ovary, pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. Exemplary solid tumors that can be treated include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of mesenchymal derivation.

The subject method can also be used to inhibit the proliferation of hyperplastic/neoplastic cells of hematopoietic origin, e.g., arising from myeloid, lymphoid or erythroid lineages, or precursor cells thereof. For instance, the present invention contemplates the treatment of various myeloid disorders including, but not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97). Lymphoid malignancies which may be treated by the subject method include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated by the treatment method of the present invention include, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

Methods of administering anti-(MHC-peptide complex) ligands are described in "Pharmaceutical Compositions". Suitable dosages of the molecules used will depend on the age and weight of the subject and the particular drug used. The ligands can be used as competitive agents to inhibit, reduce an undesirable interaction, e.g., between a natural or pathological agent and a MHC-peptide complex, e.g., a MHC-peptide complex wherein the peptide is a TAA such as hTERT, MUC1, TAX, or gp100.

In one embodiment, the anti-(MHC-peptide complex) ligands are used to kill or ablate cancerous cells and normal, benign hyperplastic, and cancerous cells in vivo. The ligands can be used by themselves or conjugated to an agent, e.g., a cytotoxic drug, radioisotope. This method includes: administering the ligand alone or attached to a cytotoxic drug, to a subject requiring such treatment.

The terms "cytotoxic agent" and "cytostatic agent" and "anti-tumor agent" are used interchangeably herein and refer to agents that have the property of inhibiting the growth or proliferation (e.g., a cytostatic agent), or inducing the killing, of hyperproliferative cells, e.g., an aberrant cancer cell. In cancer therapeutic embodiment, the term "cytotoxic agent" is used interchangeably with the terms "anti-cancer" or "anti-tumor" to mean an agent, which inhibits the development or progression of a neoplasm, particularly a solid tumor, a soft tissue tumor, or a metastatic lesion.

Nonlimiting examples of anti-cancer agents include, e.g., antimicrotubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5-fluorouracil (5-FU), methotrexate, 6-mercaptopurine, 6-thioguanine, fludarabine phosphate, cytarabine/Ara-C, trimetrexate, gemcitabine, acivicin, alanosine, pyrazofurin, N-Phosphoracetyl-L-Asparate=PALA, pentostatin, 5-azacitidine, 5-Aza 2'-deoxycytidine, ara-A, cladribine, 5-fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl) propionanilide.

Since the anti-(MHC-peptide complex) ligands that are specific for a TAA recognize cancerous cells that present the TAA, any such cells to which the ligands bind are destroyed. Alternatively, the ligands bind to cells in the vicinity of the cancerous cells and kill them, thus indirectly attacking the cancerous cells which may rely on surrounding cells for nutrients, growth signals and so forth. Thus, the anti-(MHC-peptide complex) ligands (e.g., modified with a cytotoxin) can selectively kill or ablate cells in cancerous tissue (including the cancerous cells themselves).

The ligands may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters, as described herein.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. Procedures for preparing enzymatically active polypeptides of the immunotoxins are described in WO84/03508 and WO85/03508, which are hereby incorporated by reference, and in the appended Examples below. Examples of cytotoxic moieties that can be conjugated to the antibodies include adriamycin, chlorambucil, daunomycin, methotrexate, neocarzinostatin, and platinum.

In the case of polypeptide toxins, recombinant nucleic acid techniques can be used to construct a nucleic acid that encodes the ligand (or a polypeptide component thereof) and the cytotoxin (or a polypeptide component thereof) as translational fusions. The recombinant nucleic acid is then expressed, e.g., in cells and the encoded fusion polypeptide isolated.

Procedures for conjugating protein ligands (e.g., antibodies) with the cytotoxic agents have been previously described. Procedures for conjugating chlorambucil with antibodies are described by Flechner (1973) *European Journal of Cancer*, 9:741-745; Ghose et al. (1972) *British Medical Journal*, 3:495-499; and Szekerke, et al. (1972) *Neoplasma*, 19:211-215, which are hereby incorporated by reference. Procedures for conjugating daunomycin and adriamycin to antibodies are described by Hurwitz, E. et al. (1975) *Cancer Research*, 35:1175-1181 and Arnon et al. (1982) *Cancer Surveys*, 1:429-449, which are hereby incorporated by reference. Procedures for preparing antibody-ricin conjugates are described in U.S. Pat. No. 4,414,148 and by Osawa, T., et al. (1982) *Cancer Surveys*, 1:373-388 and the references cited therein. Coupling procedures as also described in EP 86309516.2.

To kill or ablate normal, benign hyperplastic, or cancerous cells, a first protein ligand is conjugated with a prodrug which is activated only when in close proximity with a prodrug activator. The prodrug activator is conjugated with a second protein ligand, preferably one which binds to a non-competing site on the target molecule. Whether two protein ligands bind to competing or non-competing binding sites can be determined by conventional competitive binding assays. Drug-prodrug pairs suitable for use in the practice of the present invention are described in Blakely et al., (1996) *Cancer Research*, 56:3287-3292.

Alternatively, the anti-(MHC-peptide complex) ligand can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303-316 (Academic Press 1985). Other suitable radioisotopes include α-emitters, such as $^{212}$Bi, $^{213}$Bi, and $^{211}$At, and β-emitters, such as $^{186}$Re and $^{90}$Y. Moreover, Lu$^{117}$ may also be used as both an imaging and cytotoxic agent.

Radioimmunotherapy (RIT) using antibodies labeled with $^{131}$I, $^{90}$Y, and $^{177}$Lu is under intense clinical investigation. There are significant differences in the physical characteristics of these three nuclides and as a result, the choice of radionuclide is very critical in order to deliver maximum radiation dose to the tumor. The higher beta energy particles of $^{90}$Y may be good for bulky tumors. The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the tumor residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers. (Mulligan T et al. (1995) *Clin Cancer Res*. 1: 1447-1454; Meredith R F, et al. (1996) *J Nucl Med* 37:1491-1496; Alvarez R D, et al. (1997) *Gynecologic Oncology* 65: 94-101).

In one embodiment, the anti-(MHC-peptide complex) ligands can be used directly in vivo to eliminate antigen-expressing cells via natural complement-dependent cytotoxicity (CDC) or antibody-dependent cellular cytotoxicity (ADCC). The protein ligands of the invention, can include complement binding effector domain, such as the Fc portions from IgG1, -2, or -3 or corresponding portions of IgM which bind complement. In one embodiment, a population of target cells is ex vivo treated with a binding agent of the invention and appropriate effector cells. The treatment can be supplemented by the addition of complement or serum containing complement. Further, phagocytosis of target cells coated with a protein ligand of the invention can be improved by binding of complement proteins. In another embodiment target, cells coated with the protein ligand which includes a complement binding effector domain are lysed by complement.

In another embodiment, the anti-(MHC-peptide complex) ligands are used to block recognition of the particular MHC-peptide complex by other effectors, e.g., the endogenous immune system. For this implementation, the "blocking" ligand may be an antibody that lacks an effector domain, e.g., a Fab. For example, the MHC-peptide complex may be on the surface of a glial cell or a Langerhans cell. Autoimmune diseases such as multiple sclerosis and diabetes have been implicated with endogenous immune system attacks on these cells. The anti-(MHC-peptide complex) ligands that block recognition of MHC-peptides specific for these cell types can be provided, e.g., systemically or locally. For example, the blocking ligands may be expressed by exogenous or endogenous cells that are in the same tissue, or are the very same cells.

In a related example, the blocking ligands include a signal sequence that causes retention of the blocking ligand in a cell, e.g., in the cell secretory pathway. For example, the KDEL sequence, which causes endoplasmic reticulum retention, can be appended to a polypeptide component of the blocking ligand (e.g., one of the chains, in the case of an antibody).

Also encompassed by the present invention is a method of killing or ablating which involves using the anti-(MHC-peptide complex) ligand for prophylaxis. For example, these materials can be used to prevent or delay development or progression of cancers.

Use of the therapeutic methods of the present invention to treat cancers has a number of benefits. In implementations where the protein ligands specifically recognize the varied protein component of the MHC-peptide complex, other tissue is spared and high levels of the agent are delivered directly to the site where therapy is required. Treatment in accordance with the present invention can be effectively monitored with clinical parameters. Alternatively, these parameters can be used to indicate when such treatment should be employed.

Anti-(MHC-peptide complex) ligands of the invention can be administered in combination with one or more of the existing modalities for treating cancers, including, but not limited to: surgery; radiation therapy, and chemotherapy.

T-Cell Reprogramming

T cells can be reprogrammed to target cells that display particular peptides on their MHC molecules. A protein that specifically recognizes the MHC-peptide complex can be isolated using a method described herein. Nucleic acid encoding the polypeptide chain or chains that form the protein is introduced into a T cell and then expressed.

In one embodiment, the nucleic acid encoding the anti-(MHC-peptide) ligand is functionally fused to a membrane anchor such that the ligand is expressed on the surface of the host cell. The anti-(MHC-peptide) ligand can be an antibody or fragment thereof. In one embodiment the nucleic acid encodes a Fab fragments, and one of the two chains of the fragment are membrane anchored. In another embodiment, both chains of the fragment are membrane anchored.

In one embodiment, if the isolated protein includes an antigen-binding domain, the nucleic acids encoding the variable domains of the antigen binding domain are joined in frame such that the fusion nucleic acid encodes a single-chain antibody domain. The use of a single chain construct insures that the two variable domains associate when expressed in a heterologous cell and that an excess of one of the two domains is not produced.

In another embodiment, a nucleic acid is constructed that encodes both variable domains, but as separate polypeptides, e.g., by using a promoter for each coding nucleic acid, a divergent promoter, or a poly-cistronic cassette.

The nucleic acid is then introduced into the T cell, typically a human T lymphocyte, e.g., a self-A2.1 restricted T lymphocyte. For example, the nucleic acid can be introduced into the cells of a population of human T cells, e.g. from donors or patients with a proportion of T cells that express the allotype of interest. The nucleic acid can be introduced using a retroviral vector. For example, the nucleic acid can be cloned into a retroviral vector (e.g., as described in Willemsen et al. (2000) *Gene Ther.* 7:1369 and Stanislawski et al. (2001) *Nature Immunol.* 2:962).

The nucleic acid can be introduced into a retroviral packaging line, e.g., 293T cells by transfection, e.g., using calcium phosphate precipitation. In one embodiment, the nucleic acid is transferred to T lymphocytes in culture. For example, the transfected 293T cells are cocultured with PBMCs activated with an antibody to CD3 and treated with IL-2. During the coculturing, retroviruses produced by the 293 cells infect the PBMC cells. The function of infected T cells can be tested, e.g., using the Cr-release assay in the presence of a target cell that presents the MHC-peptide to which the ligand is directed. The T cells can be also introduced into a subject.

In a related example, the recipient human T lymphocytes can be obtained from a subject, e.g., a patient, for which treatment is required (i.e., the T lymphocyte is an autologous cell). After introduction of the vector, the modified T lymphocyte can be reintroduced into the subject. Of course, T lymphocytes for such therapy can be obtained from other sources. For example, the recipient T lymphocyte can also be obtained from a relative of the subject or other individual with similar genetic composition, e.g., to minimize adverse immunological reactions.

Diagnostic Uses

Protein ligands that bind to a MHC-peptide complex and identified by the methods described herein have in vitro and in vivo diagnostic, therapeutic and prophylactic utilities.

In one aspect, the present invention provides a diagnostic method for detecting the presence of a MHC-peptide complex that presents a particular peptide, in vitro (e.g., a biological sample, such as tissue, biopsy, e.g., a cancerous tissue) or in vivo (e.g., in vivo imaging in a subject).

The method includes: (i) contacting a sample with anti-(MHC-peptide complex) ligand; and (ii) detecting formation of a complex between the anti-(MHC-peptide complex) ligand and the sample. The method can also include contacting a reference sample (e.g., a control sample) with the ligand, and determining the extent of formation of the complex between the ligand and the sample relative to the same for the reference sample. A change, e.g., a statistically significant change, in the formation of the complex in the sample or subject relative to the control sample or subject can be indicative of the presentation of a particular peptide (e.g., a TAA) on an MHC in the sample.

Another method includes: (i) administering the anti-(MHC-peptide complex) ligand to a subject; and (iii) detecting formation of a complex between the anti-(MHC-peptide complex) ligand, and the subject. The detecting can include determining location or time of formation of the complex.

The anti-(MHC-peptide complex) ligand can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the anti-(MHC-peptide complex) ligand and a MHC-peptide complex can be detected by measuring or visualizing either the ligand bound to the MHC-peptide complex or unbound ligand. Conventional detection assays can be used, e.g., an enzyme-linked immunosorbent assays (ELISA), a radioimmunoassay (RIA) or tissue immunohistochemistry. Further to labeling the anti-(MHC-peptide complex) ligand, the presence of a MHC-peptide complex can be assayed in a sample by a competition immunoassay utilizing standards labeled with a detectable substance and an unlabeled anti-(MHC-peptide complex) ligand.

Fluorophore and chromophore labeled protein ligands can be prepared. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer (1968) *Science,* 162:526 and Brand, L. et al. (1972) *Annual Review of Biochemistry,* 41:843-868. The protein ligands can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the protein ligand can be used to detect the presence or localization of the MHC-peptide complex in a sample, e.g., using fluorescent microscopy (such as confocal or deconvolution microscopy).

Histological Analysis. Immunohistochemistry can be performed using the protein ligands described herein. For example, in the case of an antibody, the antibody can be synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation.

Of course, the antibody (or other polypeptide or peptide) can be unlabeled at the time of binding. After binding and washing, the antibody is labeled in order to render it detectable.

Protein Arrays. The anti-(MHC-peptide complex) ligand can also be immobilized on a protein array. The protein array can be used as a diagnostic tool, e.g., to screen medical samples (such as isolated cells, blood, sera, biopsies, and the like). Of course, the protein array can also include other ligands, e.g., that bind to an MHC-peptide complex or to other target molecules, such as other cancer-specific antigens.

Methods of producing polypeptide arrays are described, e.g., in De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the protein ligands can be grown on a filter in an arrayed format. Polypeptide production is induced, and the expressed polypeptides are immobilized to the filter at the location of the cell. At least some of the antibodies, for example, can recognize different MHC-peptide complexes.

A protein array can be contacted with a labeled target to determine the extent of binding of the target to each immobilized polypeptide ligand. If the target is unlabeled, a sandwich method can be used, e.g., using a labeled probed, to detect binding of the unlabeled target.

Information about the extent of binding at each address of the array can be stored as a profile, e.g., in a computer database. The protein array can be used to identify MHC-peptide complexes that are represented in the sample (e.g., presented on one or more cells in the sample).

FACS. (Fluorescent Activated Cell Sorting). The anti-(MHC-peptide complex) ligand can be used to label cells, e.g., cells in a sample (e.g., a patient sample). The ligand is also attached (or attachable) to a fluorescent compound. The cells can then be sorted using fluorescent activated cell sorted (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the ligand from those cells not bound by the ligand. The separated cells can be cultured and/or characterized.

In vivo Imaging. In still another embodiment, the invention provides a method for detecting the presence of cancerous tissues in vivo that are presenting TAAs on MHC molecules. The method includes (i) administering to a subject (e.g., a patient having a cancer or neoplastic disorder) an anti-(MHC-peptide complex) ligand, conjugated to a detectable marker; (ii) exposing the subject to a means for detecting said detectable marker to the tissues or cells that are presenting the TAA. The protein ligand does not substantially bind the MHC in the absence of the peptide, and does not substantially bind the peptide in the absence of the MHC. For example, the subject is imaged, e.g., by NMR or other tomographic means.

Examples of labels useful for diagnostic imaging in accordance with the present invention include radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed. The protein ligand can be labeled with such reagents using known techniques. For example, see Wensel and Meares (1983) *Radioimmunoimaging and Radioimmunotherapy*, Elsevier, N.Y. for techniques relating to the radiolabeling of antibodies and D. Colcher et al. (1986) *Meth. Enzymol.* 121: 802-816.

A radiolabeled ligand of this invention can also be used for in vitro diagnostic tests. The specific activity of a isotopically-labeled ligand depends upon the half-life, the isotopic purity of the radioactive label, and how the label is incorporated into the antibody.

Procedures for labeling polypeptides with the radioactive isotopes (such as $^{14}$C, $^{3}$H, $^{35}$S, $^{125}$I, $^{32}$P, $^{131}$I) are generally known. For example, tritium labeling procedures are described in U.S. Pat. No. 4,302,438. Iodinating, tritium labeling, and $^{35}$S labeling procedures, e.g., as adapted for murine monoclonal antibodies, are described, e.g., by Goding, J. W. (*Monoclonal antibodies: principles and practice: production and application of monoclonal antibodies in cell biology, biochemistry, and immunology* 2nd ed. London; Orlando: Academic Press, 1986. pp 124-126). Other procedures for iodinating polypeptides, such as antibodies, are described by Hunter and Greenwood (1962) *Nature* 144:945, David et al. (1974) *Biochemistry* 13:1014-1021, and U.S. Pat. Nos. 3,867,517 and 4,376,110. Radiolabeling elements which are useful in imaging include $^{123}$I, $^{131}$I, $^{111}$In, and $^{99m}$Tc, for example. Procedures for iodinating antibodies are described by Greenwood, F. et al. (1963) *Biochem. J.* 89:114-123; Marchalonis, J. (1969) *Biochem. J.* 113:299-305; and Morrison, M. et al. (1971) *Immunochemistry* 289-297. Procedures for $^{99m}$Tc-labeling are described by Rhodes, B. et al. in Burchiel, S. et al. (eds.), *Tumor Imaging: The Radioimmunochemical Detection of Cancer*, New York: Masson 111-123 (1982). Procedures suitable for $^{111}$In-labeling antibodies are described by Hnatowich, D. J. et al. (1983) *J. Immul. Methods*, 65:147-157, Hnatowich, D. et al. (1984) *J. Applied Radiation*, 35:554-557, and Buckley, R. G. et al. (1984) *F.E.B.S.* 166:202-204.

In the case of a radiolabeled ligand, the ligand is administered to the patient, is localized to the tumor bearing the antigen with which the ligand reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 μm to about 10 nM in diameter. Particles can have ferromagnetic, antiferromagnetic or superparamagnetic properties. Particles can include, e.g., magnetite ($Fe_3O_4$), $\gamma$-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as SEPHAROSE™, dextran, dextrin, starch and the like.

The anti-(MHC-peptide complex) ligands can also be labeled with an indicating group containing of the NMR-active $^{19}$F atom, or a plurality of such atoms inasmuch as (i) substantially all of naturally abundant fluorine atoms are the $^{19}$F isotope and, thus, substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett (1982) *Scientific American*, 246:78-88 to locate and image cancerous tissues.

Also within the scope of the invention are kits comprising the protein ligand that binds to a MHC-peptide complex and instructions for diagnostic use, e.g., the use of the anti-(MHC-peptide complex) ligand (e.g., antibody or antigen-binding fragment thereof, or other polypeptide or peptide) to detect MHC-peptide complex, in vitro, e.g., in a sample, e.g., a biopsy or cells from a patient having a cancer or neoplastic disorder, or in vivo, e.g., by imaging a subject. The kit can further contain a least one additional reagent, such as a label or additional diagnostic agent. For in vivo use the ligand can be formulated as a pharmaceutical composition.

Mass Spectroscopy

In another exemplary application, the protein ligands that specifically bind to an MHC-peptide complex are used to isolate cells that have such complexes on their surface or protein complexes released from cells. Peptides in the complexes are analyzed by mass spectroscopy.

The cells can be isolated by FACS or by binding to a support to which the protein ligand is attached (or becomes attached). After isolation, peptides can be eluted from the surface of the cells and analyzed by mass spectroscopy, e.g., MALDI mass spectroscopy. The molecular weight of the eluted peptides can be used to profile the cell, and e.g., to verify that identity of the peptides displayed by complex to which the ligand is directed, and to identify other peptides displayed by other MHC complexes on the surface.

Protein complexes can be purified by affinity chromatography using the peptide ligands and similarly analyzed. Flad et al. (1998) *Cancer Res* 58:5803-11 describe use of MALDI to identify peptides presented by HLA-Class I proteins.

Anti-(MHC-Peptide Complex) Ligands

Table 1 lists exemplary peptides that are displayed by cancer cells as an MHC complex. Protein ligands can be identified which specifically bind to these peptides when they are displayed on an MHC.

TABLE 1

| Protein | Fragment Name | Amino acid Sequence | SEQ ID NO |
|---------|---------------|---------------------|-----------|
| gp100 | G9-209 | (IMDQVPFSV) | SEQ ID NO: 1 |
| gp100 | G9-280 | (YLEPGPVTV) | SEQ ID NO: 2 |
| gp100 | G9-154 | (KTWGQYWQV) | SEQ ID NO: 3 |
| MUC1 | D6 | (LLLTVLTVV) | SEQ ID NO: 4 |
| TAX | | (LLFGYPVYV) | SEQ ID NO: 121 |
| hTERT | T540 | (ILAKFLHWL) | SEQ ID NO: 5 |
| hTERT | T865 | (RLVDDFLLV) | SEQ ID NO: 6 |

See, also Renkvist et al. (2001) *Cancer Immunol Immunother* 50:3-15 for a list of additional peptide-MHC complexes for which protein ligands can be identified.

Table 2 lists antibodies that bind to an MHC-peptide complex wherein the peptide component is a peptide fragment of gp100.

TABLE 2

| Antibody Name | MHC-Bound Peptide Recognized | Nucleic acid Sequence SEQ ID NO: | | Amino acid sequence SEQ ID NO: | |
|---|---|---|---|---|---|
| | | light chain | heavy chain | light chain | heavy chain |
| 1A11 | G9-209 | 7 | 9 | 8 | 10 |
| 1A7 | G9-209 | 11 | 13 | 12 | 14 |
| 1A9 | G9-209 | 15 | 17 | 16 | 18 |
| 1C8 | G9-209 | 19 | 21 | 20 | 22 |
| 1D7 | G9-209 | 23 | 25 | 24 | 26 |
| 1G2 | G9-209 | 27 | 29 | 28 | 30 |
| 2B2 | G9-208 | 31 | 33 | 32 | 34 |
| 2C5 | G9-208 | 35 | 37 | 36 | 38 |
| 2D1 | G9-208 | 39 | 41 | 40 | 42 |
| 2F1 | G9-208 | 43 | 45 | 44 | 46 |
| G2D12 | G9-154 | 47 | 49 | 48 | 50 |
| G3F12 | G9-154 | 51 | 53 | 52 | 54 |
| G3F3 | G9-154 | 55 | 57 | 56 | 58 |
| G3G4 | G9-154 | 59 | 61 | 60 | 62 |

Table 3 lists antibodies that bind to an MHC-peptide complex wherein the peptide component is a peptide fragment of hTERT.

TABLE 3

| Antibody Name | MHC-Bound Peptide Recognized | Nucleic acid Sequence SEQ ID NO: | | Amino acid sequence SEQ ID NO: | |
|---|---|---|---|---|---|
| | | light chain | heavy chain | light chain | heavy chain |
| 4A9 | T540 | 83 | 85 | 84 | 86 |
| 4B4 | T540 | 87 | 89 | 88 | 90 |
| 4C2 | T540 | 91 | 93 | 92 | 94 |
| 4G9 | T540 | 95 | 97 | 96 | 98 |

TABLE 3-continued

| Antibody Name | MHC-Bound Peptide Recognized | Nucleic acid Sequence SEQ ID NO: light chain | Nucleic acid Sequence SEQ ID NO: heavy chain | Amino acid sequence SEQ ID NO: light chain | Amino acid sequence SEQ ID NO: heavy chain |
|---|---|---|---|---|---|
| 3A12 | T865 | 99 | 101 | 100 | 102 |
| 3B1 | T865 | 103 | 105 | 104 | 106 |
| 3F5 | T865 | 107 | 109 | 108 | 110 |
| 3G3 | T865 | 111 | 113 | 112 | 114 |
| 3H2 | T865 | 115 | 117 | 116 | 118 |

Table 4 lists antibodies that bind to an MHC-peptide complex wherein the peptide component is a peptide fragment of MUC-1.

TABLE 4

| Antibody Name | MHC-Bound Peptide Recognized | Nucleic acid Sequence SEQ ID NO: light chain | Nucleic acid Sequence SEQ ID NO: heavy chain | Amino acid sequence SEQ ID NO: light chain | Amino acid sequence SEQ ID NO: heavy chain |
|---|---|---|---|---|---|
| M3A1 | MUC-1 D6 | 63 | 65 | 64 | 66 |
| M3B8 | MUC1-D6 | 67 | 69 | 68 | 70 |

Table 5 lists antibodies that bind to an MHC-peptide complex wherein the peptide component is a peptide fragment of TAX.

TABLE 5

| Antibody Name | MHC-Bound Peptide Recognized | Nucleic acid Sequence SEQ ID NO: light chain | Nucleic acid Sequence SEQ ID NO: heavy chain | Amino acid sequence SEQ ID NO: light chain | Amino acid sequence SEQ ID NO: heavy chain |
|---|---|---|---|---|---|
| T3E3 | TAX | 71 | 73 | 72 | 74 |
| T3F1 | TAX | 75 | 77 | 76 | 78 |
| T3F2 | TAX | 79 | 81 | 80 | 82 |

HLA Classes and Alleles

The following are exemplary HLA alleles: A; B; Cw; DMA; DMB; DOA; DPA1; DPB1; DQA1; DQB1; DRA; DRB1; DRB3; DRB4; DRB5; DRB6; DRB7; E; G; MICA; TAP1; TAP2. See also *Human Mutation* 11:1-3, 1998.

The following invention is further illustrated by the following examples, which should not be construed as further limiting. The contents of all references, pending patent applications and published patents, cited throughout this application are hereby expressly incorporated by reference.

EXAMPLE 1

Methods for Selection and Screening 1.1 Production of Biotinylated scMHC/Peptide Complexes scMHC/peptide complexes were produced by in vitro refolding of inclusion bodies produced in *E. coli* as described (Denkberg and Reiter (2000) *Eur. J Immunol.* 30:3522-32). Briefly, a single chain β2 microglobulin-HLA/A2 (scMHC) construct, in which the β2m and HLA-A2 genes are connected to each other by a flexible peptide linker, was designed to contain the BirA recognition sequence for site-specific biotinylation at the C-terminus (scMHC-BirA). This construct is expressed in *E. coli* and upon induction with IPTG, intracellular inclusion bodies that contain large amounts of the recombinant protein accumulate. Inclusion bodies are purified, reduced and subsequently refolded in a redox-shuffling buffer system (0.1M Tris, 0.5M Arginine, 0.09 mM Oxidized Glutathione, pH 8.0) in the presence of a 5-10 molar excess of the antigenic peptides. Correctly folded MHC/peptide complexes were isolated and purified by anion exchange Q-SEPHAROSE™ chromatography (Pharmacia). Filtration using CENTRICON™ 30 units (CENTRICON™) was used to exchange the elusion buffer with Tris-HCl (10 mM, pH 8.0) and concentrate the scMHC-peptide complex to 1 mg/ml for specific biotinylation using the BirA enzyme (Avidity, Denver, Colo.) as previously described (Altman et al. (1996) *Science* 274:94-96; Denkberg and Reiter (2000) *Eur. J. Immunol.* 30:3522-32). Excess biotin was removed from biotinylated complexes using a G-25 desalting column. The homogeneity and purity of the scMHC-peptide complexes was analyzed by various biochemical means including SDS-PAGE, Size exclusion chromatography, and ELISA assays as described previously (Denkberg and Reiter (2000) *Eur. J Immunol.* 30:3522-32). The biological function of the scMHC-peptide complexes was determined by the ability of tetramers to stain CTL lines and clones in a peptide-specific manner. The generation of the scMHC-peptide tetramers and CTL staining procedures have been previously described in detail (Denkberg and Reiter (2000) *Eur. J Immunol.* 30:3522-32; Denkberg and Reiter (2001) *J Immunol* 167, 270-6).

1.2 Selection of Phage-Antibodies on Biotinylated Complexes

A large human Fab library containing $3.7 \times 10^{10}$ different Fab clones was used for the selection (de Haard et al. (1999) *J Biol Chem.* 274:18218-30). Phages ($10^{13}$) were first preincubated for 1 hr at room temperature in PBS containing 2% nonfat dry milk with streptavidin-coated paramagnetic beads (200 μl; Dynal, Oslo) to deplete streptavidin binders. Streptavidin-coated paramagnetic beads (200 ml; Dynal, Oslo) were also incubated in PBS+2% milk for 1 hr at room temperature. The remaining phages were subsequently incubated for 1 hr with decreasing amounts of biotinylated scMHC-peptide complexes (500 nM for the first round and 100 nM for the following rounds). Streptavidin magnetic beads were added, and the mixture was incubated for 15 min with continuous rotation. A magnetic force was applied to pull down phages bound to biotinylated complexes. After 10 washes of the streptavidin-bound complexes with PBS/0.1% TWEEN and 2 washes with PBS, bound phages were eluted by incubation for 5 min with 1 ml of Triethylamine (TEA) (100 mM). The elution mixture was neutralized by the addition of 100 μl of Tris-HCl (1M, pH 7.4) and used to infect *E. coli* TG1 cells (OD600=0.5) for 30 min at 37° C. Bacteria were grown overnight at 30° C. on 2YT plates containing 100 μg/ml Ampicillin (2YT/A/G) and 2% glucose.

Colonies were collected from the plates in 2YT/A/G and diluted 1:100 in 50 ml of medium. Cells were grown to O.D600 nm=0.5 and M13KO7 helper phage ($5 \times 10^{11}$ cfu) was added to 5 ml of the culture. After incubation at 37° C. for 30 min, the cells were centrifuged, resuspended in 25 ml of 2YT/Ampicillin (100 μg/ml)/Kanamycin (50 μg/ml) and grown overnight at 30° C. Phages were collected from culture supernatants and purified for the next round of panning by PEG precipitation. The diversity of the selected antibodies was determined by DNA fingerprinting. The Fab DNA of different clones was PCR-amplified using the primers pUC-reverse (5'-AGCGGATAACAATTTCACACAGG-3'; SEQ ID NO:119) and fd-tet-seq24 (5'-TTTGTCGTCTTTCCA-GACGTTAGT-3'; SEQ ID NO:120). The resulting PCR fragments were digested with BstNI (New England Biolabs, MA USA) (2 hr, 37° C.) and analyzed by agarose gel electrophoresis.

1.3 Expression and Purification of Soluble Recombinant Fab Antibodies

Soluble Fabs were purified from the periplasmic fraction of BL21 cells using the hexa-histidine tag fused to the CH1 domain of the Fabs. We have produced and analyzed 2-4 Fab clones for each complex, which were selected according to their specificity pattern assayed by ELISA with phage and soluble Fab fragments. An overnight starter culture of Fab specific clones was grown at 30° C. Cells were diluted 1:100 into 500 ml of 2YT/A/G, grown to OD600 nm=0.8-1.0 and induced to express the recombinant Fab antibody by the addition of 1 mM IPTG for 4 hr at 30° C. The cells were centrifuged and the pellet was resuspended in 5 ml of a B-PER solution (Pierce) to release periplasmic contents. After 30 min of rotated incubation at RT, the solution was centrifuged (15000 rpm, 15 min) and the supernatant was incubated with 0.5 ml of pre-washed TALON beads suspension (Clontech) for 45 min at RT. The solution was applied onto a Biorad disposable column, and after sedimentation the beads were washed three times with 10 ml of PBS/0.1% TWEEN-20 (pH 8.0). The bound Fabs were eluted using 0.5 ml of 100 mM Imidazole in PBS. The eluted Fabs were dialyzed twice against PBS (overnight, 4° C.) to remove residual imidazole. The homogeneity and purity of the purified Fabs was determined by analysis on non-reduced and reduced SDS-PAGE.

1.4 ELISA with Phage Clones and Purified Fab Antibodies

The binding specificity of individual phage clones and soluble Fab fragments was determined by ELISA using biotinylated scMHC-peptide complexes. ELISA plates (Falcon) were coated overnight with BSA-biotin (1 μg/well). After having been washed, the plates were incubated (1 hr, RT) with streptavidin (1 μg/well), washed extensively and further incubated (1 hr, RT) with 0.5 μg of MHC/peptide complexes. Plates were blocked for 30 min at RT with PBS/2% and subsequently were incubated for 1 hr at RT with phage clones (~$10^9$ phages/well) or various concentrations of soluble purified Fab, and after washing, with 1:1000 HRP-conjugated/anti-myc antibody. Detection was performed using TMB reagent (Sigma).

1.5 Flow Cytometry

The B cell line RMAS-HHD, which is transfected with a single-chain β2M-HLA-A2 gene (Pascolo et al. (1997) *J Exp Med.* 185, 2043-51), EBV-transformed B-lymphoblast JY cells or tumor cells as indicated were used to determine the reactivity of the recombinant Fab antibodies with cell surface-expressed HLA-A2/peptide complexes. About $10^6$ RMAS-HHD cells were washed twice with serum-free RPMI and incubated overnight at 26° C. in medium containing 100 μM of the peptide. JY cells were loaded with peptide (100 μM) at 37° C. The APCs were subsequently incubated at 37° C. for 2-3 hours to stabilize cell surface expression of MHC-peptide complexes. The cells were incubated for 60-90 min at 4° C. with recombinant Fab antibodies (10-100 μg/ml) in 100 μl. After three washes the cells were incubated with FITC-labeled anti-human Fab (Jackson). After a final wash, the cells were resuspended in ice-cold PBS.

Adherent tumor cells were harvested by trypsinization and resuspended in cold RPMI.

All subsequent washes and incubations were performed in ice-cold PBS as described above for RMAS-HHD peptide-loaded cells. Analysis of the cells was performed by a FACStar flow cytometer (Becton Dickinson) and the results were analyzed with the WinMDI program (Trotter J., see also the online resource provided by the FACS facility at Scripps, La Jolla Calif.).

1.6 Competition Binding Assays

Flexible ELISA plates were coated with BSA-biotin and scMHC-peptide complexes (10 μg in 100 μl) were immobilized as described. The binding of soluble purified Fabs was performed by competitive binding analysis examining the ability of purified Fab to inhibit the binding of [$^{125}$I]-Fab to the specific immobilized scMHC-peptide complex. The recombinant Fab antibodies were labeled with [$^{125}$I] using the Bolton-Hunter reagent. The labeled Fab was added to wells as a tracer (3-5×$10^5$ CPM/well) in the presence of increasing concentrations of the cold Fab fragments as a competitor. Next, the binding assays were performed at RT for 1 hr in PBS. Finally, the plates were washed extensively (5 times) with PBS and the bound radioactivity was determined in a gamma counter. The apparent affinity of the Fabs was determined by extrapolating the concentration of competitor necessary to achieve 50% inhibition of [$^{125}$I]-labeled Fab binding to the immobilized scMHC-peptide complex. Non-specific binding was determined by the addition of a 20-40-fold excess of unlabeled Fab.

EXAMPLE 2

GP100-HLA-A2 Antibodies

Here, for the first time, we have isolated a panel of high affinity human recombinant Fab antibodies endowed with the antigen-specific, MHC-restricted specificity of T cells. These antibodies recognize three common HLA-A2-restricted epitopes of the human melanoma differentiation antigen gp100. HLA-A2 is the most frequent human MHC allele that displays many cancer-associated peptides. The antibodies were isolated from a large non-immune repertoire of phage antibody library selected on recombinant-engineered single-chain MHC-peptide complexes displaying a distinct gp100-derived epitope.

We show that this panel of antibodies recognizes HLA-A2 molecules only when displaying the specific peptide against which they were selected; they do not bind HLA-A2 molecules complexed with other gp100-derived epitopes or with other HLA-A2-restricted control peptides. Hence, they exhibit a TCR-like restriction. Moreover, these antibodies have been used to directly visualize the specific HLA-A2/gp100 epitopes on antigen-presenting cells as well as on the surface of melanoma tumor cells by flow cytometry.

Results:

Recombinant Single-Chain MHC-peptide Complexes with Three Melanoma-Derived gp100, HLA-A2-Restricted Peptides.

Figure 29B:
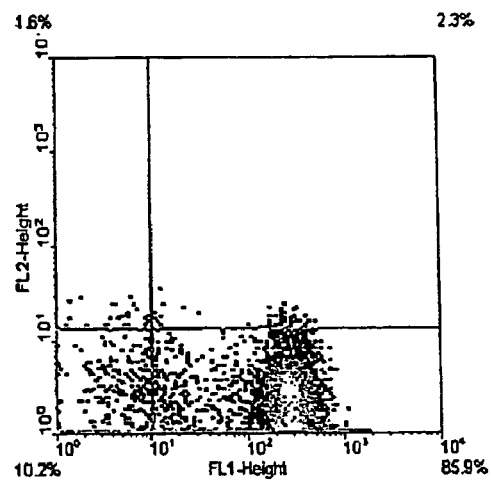
Figure 29C:
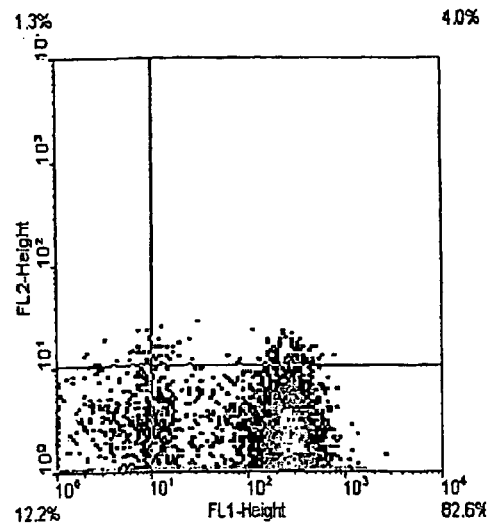
Figure 29D:
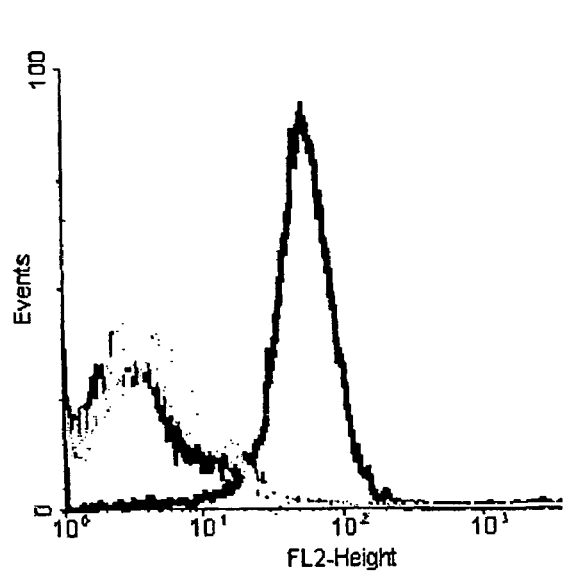

Gp100 is a melanocyte lineage-specific membrane glycoprotein consisting of 661 amino acids that is expressed in most melanoma cells. This protein is recognized by many HLA-A2-restricted melanoma reactive tumor infiltrating lymphocytes (TILs) that have been isolated from melanoma patients (Kawakami et al. (1994) *Proc. Natl. Acad. Sci. U.S.A.* 91:6458-62; Bakker et al. (1994) *J. Exp. Med.* 179:1005-09). Five T cell epitopes have been identified in gp100; three of them are common immunogenic epitopes recognized by CTLs derived from different patients (Kawakami et al. (1995) *J Immunol.* 154:3961-68; Cox et al. (1994) *Science* 264:716-19): G9209 (IMDQVPFSV; SEQ ID NO:1), G9280 (YLEPGPVTV; SEQ ID NO:2), and G9154 (KTWGQYWQV; SEQ ID NO:3). Recombinant MHC-peptide complexes that display the three gp100-derived epitopes were generated by using a single-chain MHC (scMHC) construct that was previously described (Denkberg and Reiter (2000) *Eur. J Immunol.* 30:3522-32; Denkberg and Reiter (2001) *J Immunol* 167, 270-6). In this construct, the extracellular domains of HLA-A2 are connected into a single-chain molecule with β-2 microglobulin using a 15-amino-acid flexible linker. The scMHC-peptide complexes were produced by in vitro refolding of inclusion bodies, from bacterial cultures transformed with the scMHC construct, in the presence of each of the three gp100-derived peptides. Soluble recombinant scMHC-peptide complexes were obtained from refolding solutions using a purification protocol employing ion-exchange and size-exclusion chromatography. The refolded gp100-derived peptide-MHC complexes were very pure, homogeneous and in monomeric form as shown by analysis on SDS-PAGE and size-exclusion chromatography. Recombinant scMHC-peptide complexes generated by this strategy have been previously characterized in detail for their biochemical, biophysical, and biological properties and were found to be functional (Denkberg and Reiter (2000) *Eur. J Immunol.* 30:3522-32; Denkberg and Reiter (2001) *J Immunol* 167, 270-6). To demonstrate that the refolded gp100-derived MHC-peptide complexes are functional, we tested their ability to stain a gp100-derived G9209-specific CTL clone (Dudley and Rosenberg (2000) *Cancer J.* 6:69-77). To this end, we generated scMHC-G9209 tetramers as described previously (Denkberg and Reiter (2000) *Eur. J Immunol.* 30:3522-32). To date, this is a well-established strategy for overcoming the low affinity of the MHC-peptide-TCR interactions (Altman et al. (1996) *Science* 274:94-96; Lee et al. (1999) *Nat. Med.* 5:677-85; Ogg et al. (1998) *Science* 279:2103-06). The scMHC-G9209 tetramers could specifically stain the G9209-restricted CTL clone R6C12 (FIG. 29A). However, a G9280 epitope-containing tetramer did not bind to these cells (FIG. 29B) nor to tetramers containing the HTLV-1-derived, HLA-A2-restricted epitope TAX34 (FIG. 29C). The scMHC-G9209 tetramers could also activate the R6C12 CTLs, as demonstrated by secretion of interferon-γ. These results suggest that the recombinant scMHC complexes are functional and retain the conformation of the native MHC-peptide complex.

Selection of Recombinant Antibodies with TCR-Like Specificity to Three Common T Cell Epitopes of the Melanoma Antigen gp100

To enable efficient selection scMHC-peptide complexes were biotinylated using a BirA sequence tag that was engineered at the C-terminus of the HLA-A2 gene for site-specific biotinylation as previously described (Altman et al. (1996) *Science* 274:94-96; Denkberg and Reiter (2000) *Eur. J Immunol.* 30:3522-32). A large naive repertoire of $3.7 \times 10^{10}$ human recombinant Fab fragments (de Haard et al. (1999) *J Biol Chem.* 274:18218-30) was incubated first with streptavidin-coated beads to avoid the selection of anti-streptavidin antibodies. A magnetic field was applied to precipitate the beads, and the supernatant containing the library depleted of streptavidin binders was used for the subsequent panning in solution on soluble recombinant scMHC-peptide complexes containing each of the three gp100-derived T cell epitopes. After incubation of the library with soluble complexes, binding phages were collected using streptavidin-coated magnetic beads followed by elution with triethylamine. A 1000 to-2500-fold enrichment in phage titer was observed after three rounds of panning using each of the three different gp100-derived peptide-MHC complexes (Table 1).

Figure 30A:
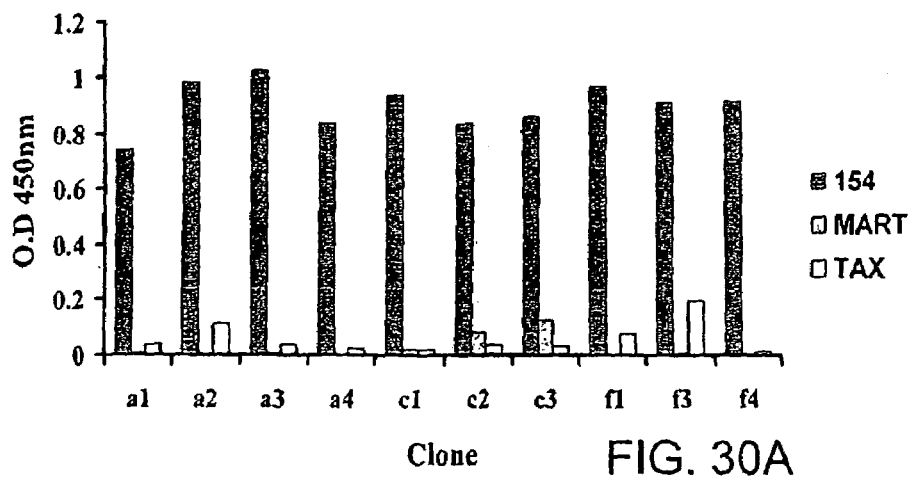
FIGS. 30A-30C. Specificity analysis of phage clones selected on gp100-derived HLA-A2-restricted peptides. Phage clones ($10^8$ phage particles/well) derived mainly from the third round of selection on gp100-derived peptides G9-154 (A), G9-209 (B), and G9-280 (C) were tested for binding specificity on the various immobilized scHLA-A2/ peptide complexes as indicated. Clones 1G2(II) and 2D1(II) are from the second round of panning. Shown is the specific reactivity of phage clones with the MHC-peptide complex to which they were selected for but not with control MHC-peptide complexes containing either a different gp100-derived epitope or other control HLA-A2-restricted peptides.
Figure 30B:
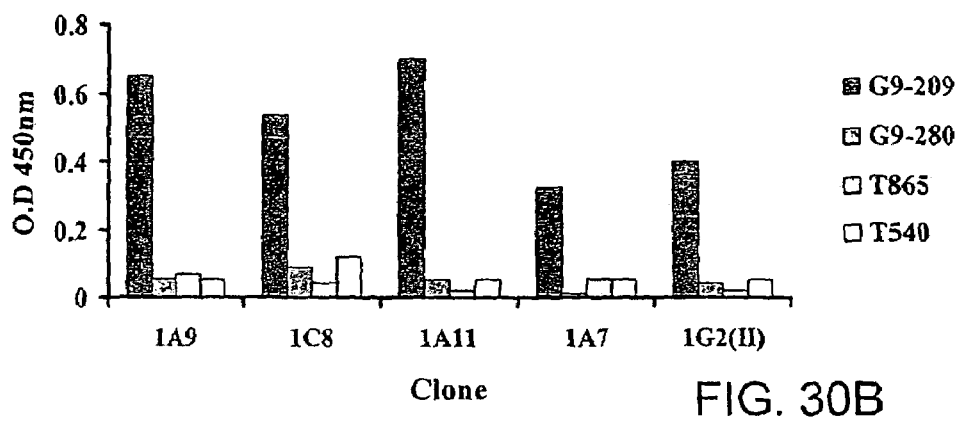
Figure 30C:
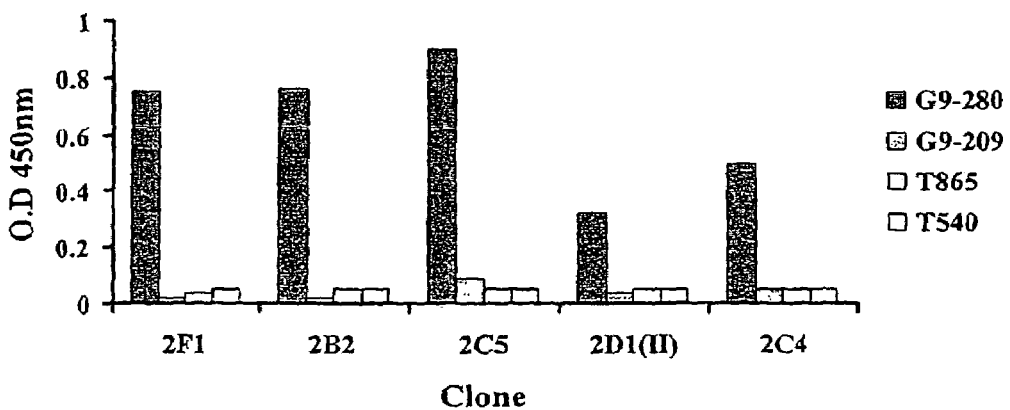

An ELISA with phage particles was performed to determine phage specificity on biotinylated recombinant scMHC-peptide complexes immobilized to BSA-biotin-streptavidin-coated immunoplates. The BSA-biotin-streptavidin spacer enables the correct folding of the complexes, which can be distorted by direct binding to plastic. About 70-90% of randomly selected phages from the third round of panning on each complex reacted with the corresponding MHC-peptide complex (Table 1). The precise specificity of the selected phage antibodies was determined by a differential ELISA on wells coated with scMHC HLA-A2 complexes containing either the specific gp100-derived peptide or control HLA-A2-restricted peptides including the two other gp100-derived epitopes (FIGS. 30A-30C). The diversity pattern of the selected specific clones was assessed by DNA fingerprinting analysis. Two types of Fab phage clones were observed following these specificity assays. One type bound to the HLA-A2/peptide complex without peptide specificity and the second bound to the HLA-A2 complex with a peptide specific manner (termed in Table 1 as TCR-like binders). We assayed these specific clones and revealed the following specificity results: for the G9154 epitope, 24 clones out of 90 analyzed (27%) reacted specifically with the HLA-A2-G9154 complex but not with complexes containing the gp100-derived peptides G9280, G9209, nor with HTLV-1 TAX or melanoma MART1-containing scMHC complexes (Table 1 and FIG. 30A as a representative analysis of 10 TCR-like Fab clones). Diversity analysis of these clones identified 10 different patterns. Thus, several different antibodies with TCR-like specificity were selected. For the G9209 epitope, 20 clones out of the 94 analyzed (21%) reacted specifically with the HLA-A2-G9209 complex but not with control complexes (Table 1 and FIG. 30B analyzing 5 clones). These positive clones yielded 4 different fingerprint patterns. Finally, the panning on HLA-A2 complexes containing the G9280 epitope resulted in 15/94 specific peptide-restricted clones (16%) (Table 1 and FIG. 30C analyzing 5 clones), which exhibited 3 different fingerprint patterns. Most interesting is the unexpected high frequency of idiocratic TCR-like binders that represent 16-27% of the phage clones binding to the MHC-peptide complex (Table 1).

For all three HLA-A2-gp100 peptide complexes screened, we isolated several of such Fab antibodies displaying TCR-like binding pattern, and in all 3 cases, one particular clone dominated the population after 3 rounds of selection (at a frequency of 30-50%).

Characterization of Recombinant Soluble Fab Antibodies with TCR-Like Specificity We have selected 2-4 Fab clones for each HLA-A2-gp100-derived complex that exhibited the most specific peptide-dependent and TCR-like binding pattern as analyzed by the phage ELISA assays presented above. These Fab fragments that bind specifically to each of the three gp100-derived HLA-A2-peptide complexes were produced in a soluble form in *E. coli* TG1 or BL21 cells and were purified by IMAC as described in materials and methods. Yields were approximately 0.5-2 mg of pure material from 1 liter of bacterial culture. SDS-PAGE analysis revealed a homogenous and pure population of Fabs with the predicted molecular size.

Figure 31A:
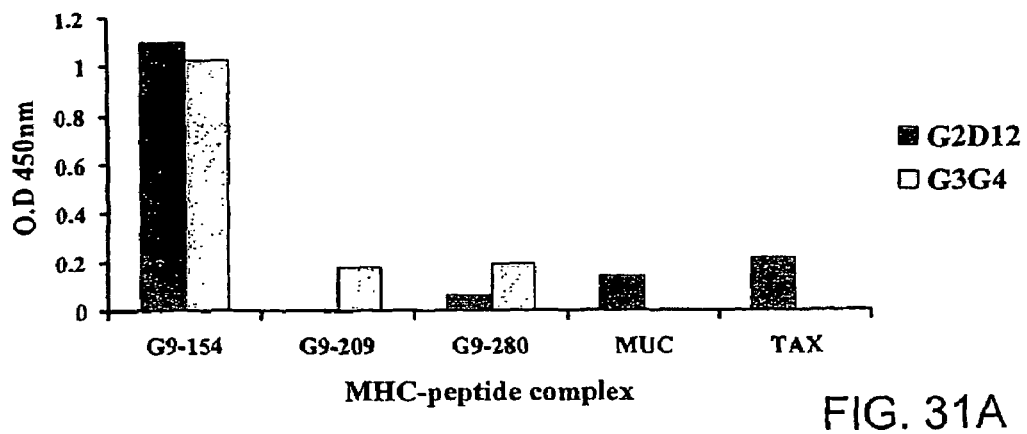
FIGS. 31A-31D. Binding in ELISA of soluble purified Fabs to recombinant scHLA-A2-peptide complexes. Binding of soluble purified Fab clones specific for the gp100-derived epitopes G9-154 (A), G9-209 (B), and G9-280 (C) to immobilized scHLA-A2/peptide complexes as indicated. Shown are the specificities of several Fab clones to the gp100-derived epitopes to which they were selected for but not to the indicated control MHC-peptide complexes containing other gp100 and telomerase-derived HLA-A2-restricted epitopes. (D) The ELISA binding specificity results were confirmed in competition experiments, in which excess specific and control soluble scMHC-peptide complexes were present in solution and competed for binding to the immobilized complex. Competition was observed with the specific soluble MHC-peptide complex but not with control complexes. An example for this type of assay is shown in FIG. 31D, in which soluble G9280 containing HLA-A2 but not G9154/HLA-A2 complexes in solution competed and inhibited the binding of Fab 2F1 to the immobilized G9280/HLA-A2 complexes.

The binding specificity of these purified Fab fragments was determined by ELISA assays on biotinylated MHC-peptide complexes immobilized to wells through BSA-biotin-streptavidin. The correct folding of the bound complexes and their stability during the binding assays were determined by their ability to react with the conformational specific monoclonal antibody W6/32 which binds HLA complexes only when folded correctly and when it contains peptide. When we used soluble purified Fabs, these ELISA assays revealed a very specific recognition pattern (FIGS. 31A-31D). Two Fab clones, G2D12 and G3G4, selected to bind the G9154 HLA-A2 complex, bound only to the specific complex but not to complexes displaying the G9209 or G9280 peptides nor to HLA-A2 complexes containing a MUC1-derived peptide (Carmon et al. (2000) *Int J Cancer.* 85:391-7) or the HTLV-1-derived TAX peptide (FIG. 31A).

Figure 31B:
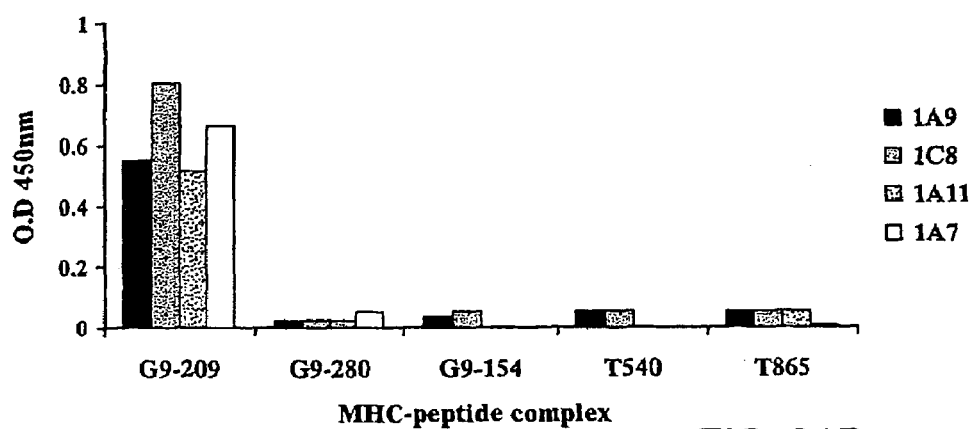
Figure 31C:
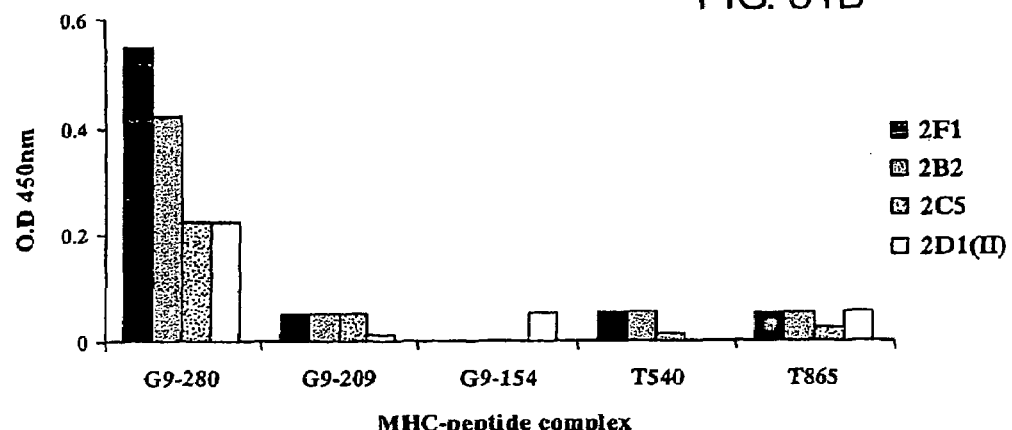

Fab clones specific for the G9209 HLA-A2 complex recognized only this complex, but not the two other gp100-derived peptides in the same context, nor two telomerase-derived HLA-A2 complexes (FIG. 31B). Finally, the HLA-A2-G9280-specific Fab clones recognized only their G9280-derived complexes and no other MHC-peptide complexes (FIG. 31C). The Fab antibodies did not recognize any of 5-7 other HLA-A2-peptide complexes, the peptide alone, empty HLA-A2 molecules (which are difficult to produce because they are unstable in the absence of a peptide), neither strepta-vidin or other protein antigens. Thus, these antigen-specific Fab fragments exhibit binding characteristics and the fine specificity of a TCR-like molecule.

Figure 31D:
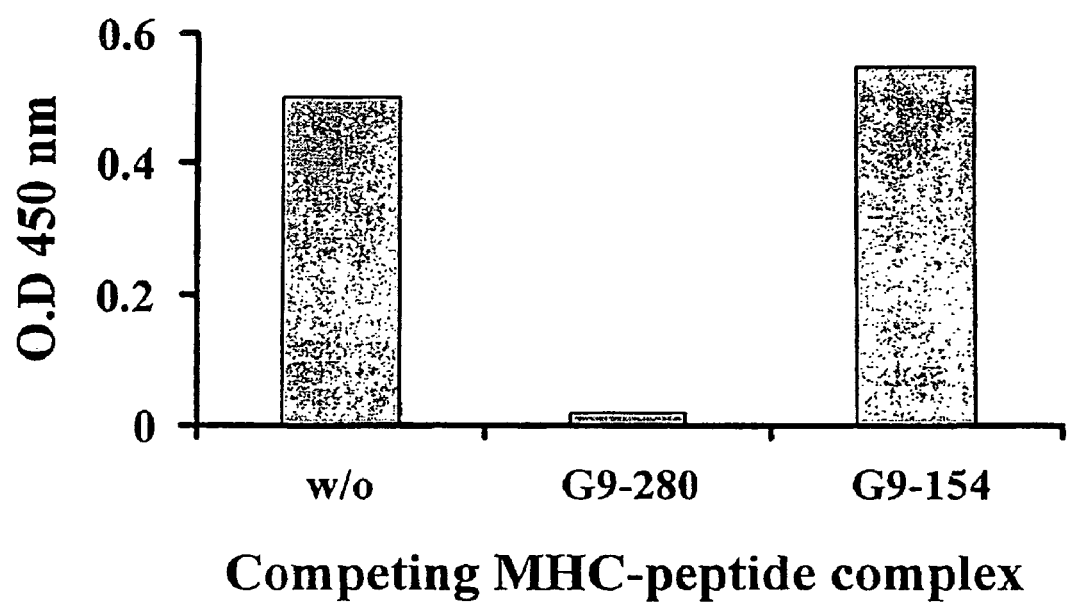

The ELISA binding specificity results were confirmed in competition experiments, in which excess specific and control soluble scMHC-peptide complexes were present in solution and competed for binding to the immobilized complex. Competition was observed with the specific soluble MHC-peptide complex but not with control complexes. An example for this type of assay is shown in FIG. 31D, in which soluble G9280-containing HLA-A2 but not G9154/HLA-A2 complexes in solution competed and inhibited the binding of Fab 2F1 to the immobilized G9280/HLA-A2 complexes.

Next, the affinity binding properties of the TCR-like soluble Fabs were determined using a saturation ELISA assay in which biotinylated complexes were bound to BSA-biotin-streptavidin-coated plates to which increasing amounts of Fab antibody were added. The binding of three specific Fabs to the corresponding gp100-derived HLA-A2-peptide complexes was dose-dependent and saturable (FIGS. 32A-32C). Extrapolating the 50% binding signal revealed that these antibodies possess high affinity with a binding affinity in the nanomolar range. To determine the apparent binding affinity of the TCR-like Fab fragments to their cognate MHC-peptide complex, we performed a competition binding assay in which binding of $^{125}$I-labeled Fab competed with increasing concentrations of unlabeled Fab fragment. The apparent binding affinity of three Fabs, each of them specific for one of the three gp100-derived T cell epitopes was measured to be 15 to-30 nM (FIGS. 32D-32F). These results underscore our success in isolating high affinity Fab antibodies with TCR-like specificity from a large non-immune phage-displayed repertoire of antibodies.

Binding of Fab Antibodies to APCs Displaying the gp100-Derived Epitopes

To demonstrate that the isolated soluble Fab antibodies can bind the specific MHC-peptide complex not only in its recombinant soluble form but also in the native form as expressed on the cell surface, we utilized two APC systems. The first consists of the murine TAP2-deficient RMA-S cells transfected with the human HLA-A2 gene in a single-chain format (Pascolo et al. (1997) *J Exp Med.* 185, 2043-51) (HLA-A2.1/Db-β2m single chain) (RMA-S-HHD cells). gp100-derived or control peptides were loaded on the RMA-S-HHD cells and the ability of the selected Fab antibodies to bind to peptide-loaded cells monitored by FACS. Peptide-induced MHC stabilization of the TAP2 mutant RMA-S-HHD cells was determined by analyzing the reactivity of anti HLA-A2 MAb BB7.2 with-peptide loaded and unloaded cells using FACS. Fab G2D12, which recognized the G9154-containing HLA-A2 complex, reacted only with RMA-S-HHD cells loaded with the G9154 peptide but not with cells loaded with the G9280 peptide or control cells not loaded with peptide. Similarly the G9209-HLA-A2-specific Fab antibody 1A9 recognized RMA-S-HHD cells loaded with G9209 peptide but not at all cells loaded with G9154 peptide. Similar results were observed in FACS analysis of the G9280-specific Fab antibody 2F1. The Fab antibodies were analyzed on RMAS-HHD cells loaded with 5 different control HLA-A2-restricted peptides including cross-reaction studies among the gp100-derived peptides and similar specificity results were observed. Moreover, RMAS-HHD cells loaded with the G9154 epitope reacted only with Fab G2D12 directed toward the G9154-containing complex but not with Fabs 1A9 and 2F1 recognizing HLA-A2 in complex with the G9209 or G9280 epitopes respectively.

The second type of APCs tested were EBV-transformed B lymphoblast JY cells, which express HLA-A2, and were incubated with the gp100-derived or control peptides. These cells are TAP+, and consequently, displaying the exogenous peptide is facilitated by peptide exchange. Using this strategy, we obtained a mixture of exogenously and endogenously derived peptides presented on HLA-A2 that are displayed on the cell surface. In testing the HLA-A2/gp100-specific antibodies 1A9, 2F1, and G2D12, we found intensive staining of JY cells loaded with the specific gp100-derived peptide to which they were selected but no binding was observed when other gp100 or control peptides were used. Control antibodies recognizing a telomerase-derived peptide in complex with scHLA-A2 did not bind to the gp100-derived peptide-loaded JY cells. Furthermore, no binding was observed when these antibodies were incubated with an HLA-A2– EBV B cell line loaded with the gp100 or control peptides.

These results show that the Fab antibodies exhibit TCR-like fine specificity and can specifically recognize their corresponding native HLA-A2 complexes in situ on the surface of cells.

Binding of gp100-Specific TCR-Like Fab Antibodies to Melanoma Cells

To explore whether these TCR-like Fab antibodies would bind endogenously derived MHC-peptide complexes and therefore may eventually be used to visualize these complexes on the surface of tumor cells, we performed flow cytometry analysis on HLA-A2+ melanoma tumor cell lines (FIGS. 33A-33H). These cells represent the normal situation in which MHC-peptide complexes are expected to be present at a much lower density on the cell surface compared with the peptide-loaded RMA-S-HHD or JY cells used above. The G9154-specific Fab antibody G2D12 reacted very intensely in a dose dependent manner with the HLA-A2+ gp100+ melanoma FM3D (FIGS. 33A and 33B) and YU ZAZ6 cells (FIGS. 33C and 33D), but not with the HLA-A2– melanoma MZ2-MEL3.0 cells (FIGS. 33E and 33F) or the HLA-A2+ breast carcinoma tumor cell line MCF7 (FIGS. 33G and 33H). Anti-HLA-A2 MAb BB7.2 was used to confirm HLA type expression (in addition to genomic PCR using HLA-A2-specific primers). A control Fab antibody specific for the HTLV-1-derived HLA-A2-TAX complex did not bind to either cell line (FIGS. 33A, 33C, 33E, and 33G). These results demonstrate that, although in a monovalent form, the high affinity of the Fab antibodies enables efficient detection and visualization of MHC-peptide complexes on the surface of tumor cells. Hence, these TCR-like antibodies can bind to cells that express the specific MHC-peptide complex at a density most likely to be found on gp100-expressing tumor cells, antigen-presenting cells, dendritic and other lymphoid cells involved in tumor antigen presentation to the immune system. Fab antibodies 1A9 and 2F1 specific to the G9209 or G9280 gp100-derived epitopes, respectively, also reacted with FM3D cells but with a lower intensity. This may reflect differential expression of gp100-derived epitopes known as the antigenic variation phenomenon. Indeed, FM3D cells were shown to express high levels of the G9154 epitope in comparison with the two other epitopes as revealed by their relative sensitivity to CTLs specific to the different gp100-derived epitopes in killing assays (Kirkin et al. (1995) *Cancer Immunol. Immunother.* 41:71-81).

Discussion

In this study we have demonstrated the ability to select from a large non-immune repertoire of human Fab fragments a panel of antibodies directed to several T cell epitopes within a single cancer antigen, the melanoma associated antigen gp100.

These antibodies exhibit a very specific and special binding pattern, they can bind with a peptide-specific manner to HLA-A2 complexes. Hence, these are recombinant antibodies with T cell antigen receptor-like specificity. In contrast to the inherent low affinity of TCRs, these molecules display the high affinity binding characteristics of antibodies, while retaining TCR specificity. We have shown by direct ELISA assays and flow cytometry studies that the Fab antibodies selected against the three common immunogenic T cell epitopes of gp100 bind only to the specific HLA-A2 complex and not to control complexes generated with the other two gp100-derived epitopes nor to other HLA-A2-peptide complexes. Most importantly, these recombinant antibodies specifically recognize native gp100-derived MHC-peptide complexes on the surface of cells, including binding to melanoma tumor cells. In this way, they serve as an example of soluble high affinity recombinant TCR-like antibodies capable of binding and detecting specific MHC-peptide complexes on the surface of tumor cells. Interestingly, we were able to isolate a repertoire of several antibodies against each of the gp100-derived epitopes. They exhibit a very specific recognition pattern toward each of the three T cell epitopes even though they are encoded within a single cancer antigen. Until now antibodies with TCR-like specificity have been generated against murine MHC-peptide complexes employing various strategies of immunizations (Andersen et al. (1996) *Proc. Natl. Acad. Sci. U.S.A.* 93:1820-24; Porgador (1997) *Immunity* 6:715-26; Dadaglio (1997) *Immunity* 6, 727-38; Murphy et al. (1989) *Nature* 338:765-8; Aharoni (1991) *Nature.* 351:147-50). Recently the same Fab library was used to select for HLA-A1-MAGE-A1-specific binding antibodies (Chames and Hoogenboom (2000) *Proc. Natl. Acad. Sci. U.S.A.* 97:7969-74). One specific clone, G8, was selected which exhibited TCR-like specificity but revealed a relatively low affinity of 250 nM. Most strikingly, here we selected several different TCR-like antibodies against each MHC-peptide complex screened, whereas all previous successful experiments reported the ability to isolate only a single antibody clone (Andersen et al. (1996) *Proc. Natl. Acad. Sci. U.S.A.* 93:1820-24; Porgador (1997) *Immunity* 6:715-26; Chames and Hoogenboom (2000) *Proc. Natl. Acad. Sci. U.S.A.* 97:7969-74). We also selected an immune phage library constructed from HLA-A2 transgenic mice immunized with the gp100-derived G9209-containing HLA-A2 complex. In contrast to our ability to isolate several antibodies against each MHC-peptide complex using the large non-immune Fab library, we could only isolate a single antibody clone from the murine immunized library, which exhibited TCR-like fine specificity.

The fact that high-affinity antibodies with such unique fine specificity were readily obtained in this study, and that they were in some cases nanomolar affinity, underscores the power of the display technology for this application, as well as add proof to the quality of the human non-immune antibody library used in the selections. The observation that 20-30% of the MHC-peptide binding antibodies had the fine specificity of a TCR-like molecule is nevertheless surprising, especially since they were selected from a non-immune repertoire considered not to be biased towards such specificity. More recently we have been able to isolate from the same phage library recombinant Fab's against a large variety of MHC-peptide complexes containing other cancer-associated or viral HLA-A2-restricted peptides, indicating that this behavior is not gp100 or peptide related.

The unexpected high frequency of these antibodies and our ability to isolate several different antibodies directed to either complex is even more surprising in view of previous reports, in which the use of immunized or naive phage libraries resulted in only a single antibody clone (Andersen et al. (1996) *Proc. Natl. Acad. Sci. U.S.A.* 93:1820-24; Porgador (1997) *Immunity* 6:715-26; Chames and Hoogenboom (2000) *Proc. Natl. Acad. Sci. U.S.A.* 97:7969-74).

It would have been possible that one particular antibody family or antibody V-gene segment would have an intrinsic propensity to bind HLA-A2 molecules, and that the high frequency could be explained by a high abundance of such antibodies in the non-immune library. However, the sequences of the selected clones are derived from many different antibody families and germline segments, without any biases visible in the CDRs either. The high frequency and high affinities for some of the antibodies isolated here, suggest that these molecules may well be present at a high frequency in the antibody repertoires from the B-cell donors of the phage library, but an in vivo role for such antibodies remains unclear.

Whatever eventually the reason for this high frequency of antibodies to MHC-peptides may be, it appears that this phage-based approach can be successfully applied to isolate recombinant antibodies with TCR-like specificity to a large variety of MHC-peptide complexes. Thus, it may now become possible to dissect the role of antigens in various pathological conditions such as cancer, viral infections and autoimmune disease, not only at the level of the T-cell using MHC-tetramers, but also at the level of the APC and diseased cell, using antibodies of the type described in this paper.

Recombinant antibodies with TCR-like specificity, such as have been selected and characterized in this study, represent a valuable new tool in molecular immunology for several major fields of research: (1) for studying antigen presentation in cancer, (2) for developing new immunotherapy targeting molecules, and (3) for studying structure-function relationships in TCR-peptide-MHC interactions. We have shown that these antibodies can be used to detect and visualize the presence of specific T cell epitopes (MHC-peptide complexes) by standard methods of flow cytometry. With appropriate conservation of the MHC-peptide complexes during fixation, the antibodies can be used to detect such complexes by immunohistochemistry opening the door for widespread use in pathology. Indeed, preliminary experiments demonstrate that these Fabs stain a fixed melanoma cell line by immunohistochemistry. As such, they are useful for the study and analysis of antigen presentation on tumor cells by determining the expression of specific tumor-related MHC-peptide complexes on the surface of tumor cells, metastasis, antigen-presenting cells, and lymphoid cells. Such antibodies are also particularly useful for determining the alterations in MHC-peptide complex expression on antigen-presenting cells before, during, and after vaccination protocols with peptides, APCs loaded with tumor cell extracts, or dendritic-tumor cell hybrid vaccinations (Offringa and Melief (2000) *Curr Opin Immunol* 12:576-82; Esche (1999) *Curr Opin Mol Ther* 1:72-81; Kugler et al. (2000) *Nat. Med.* 6:332-36).

The molecules described here are the first examples of high affinity human antibodies directed against the most frequent HLA haplotype, HLA-A2, complexed with cancer peptides. These very specific molecules, which recognize a very specific human tumor antigen, can be used as targeting moieties in various antibody-based immunotherapeutic approaches. This includes the use of these antibodies as recombinant immunotoxins (Pastan (1997) *Biochim Biophys Acta.* 1333, $C_{1-6}$), fusions with cytokine molecules (Lode and Reisfeld (2000) *Immunol Res.* 21:279-88); bi-specific antibody therapy (Withoff (2001) *Curr Opin Mol Ther.* 3:53-62) or immuno-gene therapy (Willemsen et al. (2000) *Gene Ther.* 7:1369).

Another interesting aspect for the use of these TCR-like Fab antibodies is for structure-function studies of MHC-peptide-TCR interactions. By mutating particular residues in the specific peptide and testing the influence of these mutations on the binding of the Fab antibodies and peptide-specific T cell clones it may be possible to obtain important data on structure-function relationship and the different nature of recognition between the TCR-like Fabs and the native TCR. The fact that we have selected so many different antibody sequences binding the same fine-specificity is very interesting for structural studies. Structural models of these antibodies will enable identification common structural features or features also found in TCRs. Crystallization and structure determination of the TCR-like Fab's in complex with the MHC-peptide ligand will be an important goal which would also enable to study the structural differences in molecular recognition by antibodies versus TCRs.

The most important question with respect to immunodiagnostic and -therapeutic applications of TCR-like Fabs relates to the low density and turnover of the specific epitope on the target cell surface. With regard to the density and targeted killing of cells we have previously shown in a murine model, that to achieve efficient killing with a TCR-like immunotoxin molecule a density of several thousand MHC-peptide complexes is required for selective elimination of APCs (Reiter and Pastan (1997) *Proc. Natl. Acad. Sci. U.S.A.* 94:4631-36).

It remains to be determined what the density of the gp100-derived complexes on the cancer cells tested is. The fact that in FACS clear shifts can be seen, indicates that the level of display is detectable using the compositions and methods described herein. The other important issue to consider is the fine-specificity of the antibody. The antibodies characterized in this study were specific for their particular peptide in the HLA-A2 context, in two tests, ELISA and flow cytometry, with a panel of less then 10 other unrelated peptides tested as controls. It is clear from structural studies with MHC-peptide specific antibodies, that related peptides with one or a few mutations in the peptide may also be recognized. Additional methods, such as site-directed mutagenesis and re-selection techniques, can be used to fine tune the specificity of the antibodies, if this is deemed necessary. For example, specificity tuning may be required for certain applications, e.g., in the context of a true natural repertoire of peptides displayed in the MHC on the surface of cells. For other applications, fine tuning may not be necessary to determine the relative levels of the peptide-MHC complex investigated.

Further proof for the specificity of the TCR-like Fab antibodies isolated in this study was obtained in a T cell stimulation/inhibition assay, in which the G9209-specific Fab 1A9 was able to inhibit the release of cytokines (interferon γ and IL-2) from G9209-specific CTL, R6C12, while a control G9280-specific Fab did not inhibit peptide-specific CTL stimulation.

To improve the sensitivity and targeting capabilities of these TCR-like antibody molecules, two antibody engineering approaches can be employed: one increases the affinity of the parental antibodies by affinity maturation strategies without altering their TCR-like fine specificity (Chowdhury and Pastan (1999) *Nat Biotechnol.* 17:568-72) and the second increases the avidity of these recombinant monovalent molecules by making them multi-valent. Combining these strategies may well result in improved second-generation antibody molecules that will be sensitive enough and specific for immunotherapeutic approaches as well as for studying the interaction of tumor cells and the human immune system.

Our study strikingly shows the power of the phage display approach and its ability to select especially fine specificities from a repertoire containing a myriad of different antibodies.

The advent in recent years of the application of tetrameric arrays of class I MHC-peptide complexes now enables us to detect and study rare populations of antigen-specific T cells (Altman et al. (1996) *Science* 274:94-96). Our approach produces antibody molecules that enable phenotypic analysis of antigen (MHC-peptide) presentation, the other side of the coin to MHC-peptide-TCR interactions. Combining these two new approaches will significantly enhance our ability to understand immune responses in health as well as under various pathological conditions such as cancer, viral infections, and also when applied to class II MHC molecules, autoimmune diseases. The effectiveness and feasibility of this approach, as presented in this study, makes it realistic to generate in a generic form antibodies directed towards a large variety of specific MHC-peptide complexes.

EXAMPLE 3

Telomerase-HLA-A2 Antibodies

The recent characterization of MHC-displayed tumor-associated antigens that recognize effector cells of the immune system has created new perspectives for cancer therapy. Antibodies that recognize these tumor associated MHC-peptide complexes with the same specificity as the T-cell antigen receptor will therefore be valuable tools for immunotherapy as well as for the studying antigen presentation in human cancers. Most tumor-associated antigens are expressed in only one or a few tumor types; however, recently specific T-cell epitopes derived from the telomerase catalytic subunit (hTERT) that are widely expressed in many cancers were identified and shown to be recognized by CTLs derived from cancer patients. We selected a large non-immune repertoire of phage Fab antibodies on recombinant human class I HLA-A2 complexes displaying two distinct antigenic T-cell epitopes derived from hTERT. We isolated a surprisingly large panel of high affinity human recombinant Fab antibodies that exhibited peptide-specific, MHC-restricted binding characteristics of T cells. The analyzed Fab's not only recognize the cognate MHC-peptide complex in a recombinant soluble form, but also the native complex as displayed on the surface of antigen-presenting cells and hTERT-expressing tumor cells. These findings demonstrate for the first time the ability to transform the unique fine specificity but low intrinsic affinity of TCRs on T cells into high affinity soluble antibody molecules endowed with a T-cell antigen receptor-like specificity. These molecules may prove to be very important and widely applicable for monitoring the expression of specific MHC-peptide complexes on the surface of tumor and immune cells, for structure-function studies of TCR-peptide-MHC interactions, as well as for developing new targeting agents for immunotherapy.

The design and development of strategies to augment active, specific immunotherapies in patients with a malignant disease has been greatly influenced by and benefited from the progress made in better understanding the mechanisms that lead to an immune response. This is due mainly to the progress made in the availability of well-characterized tumor associated antigens (TAAs) and to the advent of methodology developed to monitor immune responses (Boon and van der Bruggen (1996) *J Exp Med* 183:725-9; Rosenberg (2001) *Nature* 411:380-4; Renkvist and Parmiani (2001) *Cancer Immunol Immunother* 50:3-15; Altman et al. (1996) *Science* 274:94-96; Lee et al. (1999) *Nat. Med.* 5:677-85). Consequently, anti-tumor immune responses can now be correlated with clinical responses in patients immunized with well-defined TAAs. Especially with melanoma, it is now well established that human melanoma cells and other types of tumor cells express antigens that are recognized by cytotoxic T lymphocytes (CTLs) derived from cancer patients (Boon and van der Bruggen (1996) *J Exp Med* 183:725-9; Rosenberg (2001) *Nature* 411:380-4; Renkvist and Parmiani (2001) *Cancer Immunol Immunother* 50:3-15). Exciting clinical trials are therefore now in progress to target these TAAs using various strategies such as vaccination with the cancer peptides or dendritic cells and adoptive cell therapy in order to generate more effective anti-tumor immune responses in cancer patients (Offringa and Melief (2000) *Curr Opin Immunol* 12:576-82; Esche (1999) *Curr Opin Mol Ther* 1:72-81; Kugler et al. (2000) *Nat. Med* 6:332-36). The presence of tumor-specific MHC-peptide complexes on the surface of tumor cells may also represent a unique and specific target for an antibody-based therapeutic approach. To develop such a strategy, new targeting moieties must be isolated such as recombinant antibodies that will recognize specific peptide-MHC complexes. In addition to being used as targeting agents, such antibodies would serve as a valuable tool for obtaining precise information about the presence, expression pattern, and distribution of the target tumor antigen, i.e., the MHC-peptide complex, on the tumor's cell surface, on tumor metastases, in lymphoid organs, and on professional antigen-presenting cells. Such unique antibodies with T-cell receptor-like specificity will for the first time, enable measurement of the antigen presentation capabilities of tumor cells by direct visualization of the specific MHC-peptide complex on the tumor cell surface. Attempts to use soluble T-cell receptors for this purpose have proven difficult because of the inherent low affinity for their target and their instability as recombinant-engineered molecules (Wulfing and Pluckthun (1994) *J Mol Biol* 242:655-69).

In this study we attempted to isolate human recombinant antibodies directed to T-cell epitopes derived from the telomerase catalytic subunit (hTERT). Interestingly, the ribonucleoprotein telomerase is expressed by more than 85% of human cancers. Telomerase maintains the telomeric ends of linear chromosomes, protecting them from degradation and end-to-end fusion (McEachern, et al. (2000) *Annu Rev Genet* 34:331-58; Nakamura and Cech (1998) *Cell* 92:587-90; Shay, et al. (2001) *Hum Mol Genet* 10:677-85; Kim, et al. (1994) *Science* 266:2011-5; Prowse and Greider (1995) *Proc Natl Acad Sci USA* 92:4818-22). Most human cells do not express telomerase and lose telomeric DNA with each cell division (Meyerson, et al. (1997) *Cell* 90:785-95; Nakamura, et al. (1997) *Science* 277:955-9). In contrast, most human tumors exhibit strong telomerase activity and maintain the length of their telomeres (Counter, et al. (1992) *Embo J* 11:1921-9; Counter, et al. (1994) *Proc Natl Acad Sci USA* 91:2900-4; Harley, et al. (1994) *Cold Spring Harb Symp Quant Biol* 59:307-15). Recent studies have demonstrated that peptides derived from the telomerase catalytic subunit can be naturally processed by tumor cells; they are presented in an HLA-A2-restricted manner and serve as a target for antigen-specific CTLs (Vonderheide, et al. (1999) *Immunity* 10:673-9; Minev, et al. (2000) *Proc Natl Acad Sci USA* 97:4796-801). Cytotoxicity was achieved against target cells from a wide variety of tumors including carcinoma, sarcoma, melanoma, leukemia, and lymphoma (Vonderheide, et al. (1999) *Immunity* 10:673-9; Minev, et al. (2000) *Proc Natl Acad Sci USA* 97:4796-801; Counter, et al. (1995) *Blood* 85:2315-20; Arai, et al. (2001) *Blood* 97:2903-7). These findings, together with the identification of telomerase activity in the vast majority of human cancers, suggest that hTERT represents the most widely expressed TAA described so far. Therefore, we have screened a large non-immune phage antibody library (de Haard et al. (1999) *J Biol Chem.* 274:18218-30) on recombinant-engineered single-chain MHC-peptide complexes displaying two distinct hTERT-derived epitopes.

We have isolated and describe the isolation of a panel of human antibodies with antigen-specific, MHC-restricted specificity of T cells binding with high affinity HLA-A2 complexes that display the specific hTERT-derived peptide.

These antibodies have been used to directly visualize, by flow cytometry, the specific HLA-A2/hTERT epitopes on antigen-presenting cells as well as on the surface of tumor cells.

Results

Recombinant Single-Chain MHC-Peptide Complexes with Two hTERT-Derived HLA-A2-Restricted Peptides Two major T-cell epitopes were identified in hTERT that were recognized by HLA-A2-restricted CTLs derived from different patients (Vonderheide, et al. (1999) *Immunity* 10:673-9; Minev, et al. (2000) *Proc Natl Acad Sci USA* 97:4796-801): peptide 540 (ILAKFLHWL; SEQ ID NO:5) (T540) and peptide 865 (RLVDDFLLV; SEQ ID NO:6) (T865). Recombinant MHC-peptide complexes that present the two hTERT-derived epitopes were generated by using a single-chain MHC (scMHC) construct that was described previously (Denkberg and Reiter (2000) *Eur. J Immunol.* 30:3522-32; Denkberg and Reiter (2001) *J Immunol* 167, 270-6). In this construct, the extracellular domains of HLA-A2 are connected into a single-chain molecule with β-2 microglobulin using a 15-amino acid flexible linker. The scMHC-peptide complexes were produced by in vitro refolding of inclusion bodies from bacterial cultures transformed with the scMHC construct. Refolding was performed in the presence of the two hTERT-derived peptides followed by a purification protocol employing ion-exchange chromatography. The refolded hTERT-derived peptide-MHC complexes were very pure, homogenous and monomeric, as shown by analysis on SDS-PAGE and size-exclusion chromatography. Recombinant scMHC-peptide complexes generated by this strategy have been previously characterized in detail for their biochemical, biophysical, and biological properties and were found to be correctly folded and functional (Denkberg and Reiter (2000) *Eur. J Immunol.* 30:3522-32; Denkberg and Reiter (2001) *J Immunol* 167, 270-6).

To clearly demonstrate that the scMHC complex is folded correctly and contains peptide, we performed mass spectrometry analysis. The MHC-peptide complexes were deposited on a metal target as co-crystals with α-Xyano-4-hydroxycinnamic acid (for the peptide identification) and separately as co-crystals with sinapinic acid (for the protein identification). The mass spectrometry analysis was done using Matrix-assisted laser-desorption time-of-flight (MALDI-TOF) in the positive ion mode. The peptide was easily detected, with the expected mass of 1140 dalton corresponding to the mass of the T540 peptide used for the refolding of the scMHC-peptide complex. This was the only peptide detected indicating that the refolded complex is a homogenous population of molecules containing a single specific peptide. The profile of the scMHC protein revealed a single peak with a mass of 44.5 kDa corresponding to the expected molecular weight of the scMHC protein. As shown above for the peptide, this was the only identified protein peak in the analyzed spectrum indicating that the protein consists of a very homogenous population of folded complexes.

Selection of Recombinant Antibodies with TCR-Like Specificity to HLA-A2-Restricted T-Cell Epitopes of hTERT To enable efficient selection, scMHC-peptide complexes were biotinylated using a BirA sequence tag that was engineered at the C-terminus of the HLA-A2 gene for site-specific biotinylation as previously described (Altman et al. (1996) *Science* 274:94-96; Denkberg and Reiter (2000) *Eur. J Immunol.* 30:3522-32). The phage display large repertoire of 3.7× $10^{10}$ human recombinant Fab fragments (de Haard et al. (1999) *J Biol Chem.* 274:18218-30), was incubated first with streptavidin-coated beads to avoid the selection of anti-streptavidin antibodies. A magnetic field was applied to precipitate the beads, and the supernatant containing the library depleted of streptavidin binders was used for the subsequent panning in solution on soluble recombinant MHC-peptide complexes containing the two hTERT-derived T cell epitopes. After incubation of the library with soluble complexes, binding phages were collected using streptavidin-coated magnetic beads followed by elution with triethylamine. A 600 to-1200-fold enrichment in phage titer was observed after three rounds of panning using the two different hTERT-derived peptide-MHC complexes (FIG. 34A). An ELISA with phage particles was performed on biotinylated recombinant scMHC-peptide complexes immobilized on streptavidin-coated immunoplates to determine antibody specificity. The fine specificity of the selected phage antibodies was determined by a differential ELISA on wells coated with scMHC HLA-A2 complexes containing either the specific hTERT-derived peptide, or control complexes containing other HLA-A2-restricted peptides. Phage clones analyzed after the third round of selection exhibited two types of binding pattern toward the MHC-peptide complex: one class of antibodies were pan-MHC binders which can not differentiate between the various MHC-peptide complexes; the second type were antibodies which bound the MHC-peptide complex in a peptide specific manner. The ELISA screen revealed that 62-64% of randomly selected clones from the third round of panning appeared to be binding to the HLA-A2/peptide complex. Twenty percent (for the T540 epitope) and 40% (for the T865) bound to 4-5 out of 5 different peptide/MHC complexes tested. However, a surprisingly high percentage of antibodies though were fully specific for the peptide/MHC used in selection when tested as phage antibodies in ELISA on different peptide/MHC complexes. As shown in FIG. 34A, 22% and 44% of the clones directed toward the T865 and T540 epitopes, respectively, exhibited antigen-specific, MHC-restricted binding characteristics of T cells. Thus, they bound only to the MHC peptide complex containing the specific T540 or T865 hTERT-derived peptides and did not bind to control complexes containing other HLA-A2-restricted peptides. These apparent MHC/peptide-specific positive clones remained specific in a secondary screening on more complexes (see materials and methods for list of HLA-A2 restricted peptides tested).

We examined the diversity pattern of these 21 respectively 41 peptide-specific clones by DNA fingerprint analysis and found 5-6 different restriction patterns (from round two or three) for each hTERT-derived complex, indicating the selection of several different antibodies with TCR-like specificity. DNA sequencing analysis confirmed these observations.

FIGS. 34A-34C shows a representative analysis of 5 TCR-like Fab clones of each of the two selections. The 5 different T540-specific clones tested reacted only with scMHC-T540 complexes and not with MHC-peptide complexes displaying the hTERT-derived T865 epitope or two melanoma gp100-derived epitopes, G9-209 and G9-280 (FIG. 34B). Similar results were observed in phage ELISA assays that determined the specificity of 6 phage clones isolated against the hTERT-derived T865 epitope (FIG. 34C).

Characterization of Recombinant Soluble Fab Antibodies with TCR-Like Specificity We produced soluble Fab fragments from the phage clones (analyzed above, FIGS. 34B and 34C) that exhibited the specific binding pattern to the different hTERT-derived HLA-A2-peptide complexes in *E. coli* BL21 cells.

These were purified by metal affinity chromatography from the periplasm by use of the hexahistidine tag fused to the CH1 domain of the Fabs. SDS-PAGE analysis of the affinity-purified material revealed homogenous, very pure Fabs antibodies with the expected molecular weight. Approximately 0.5-2 mg of pure material could be obtained from 1 liter of bacterial culture.

Figure 35A:
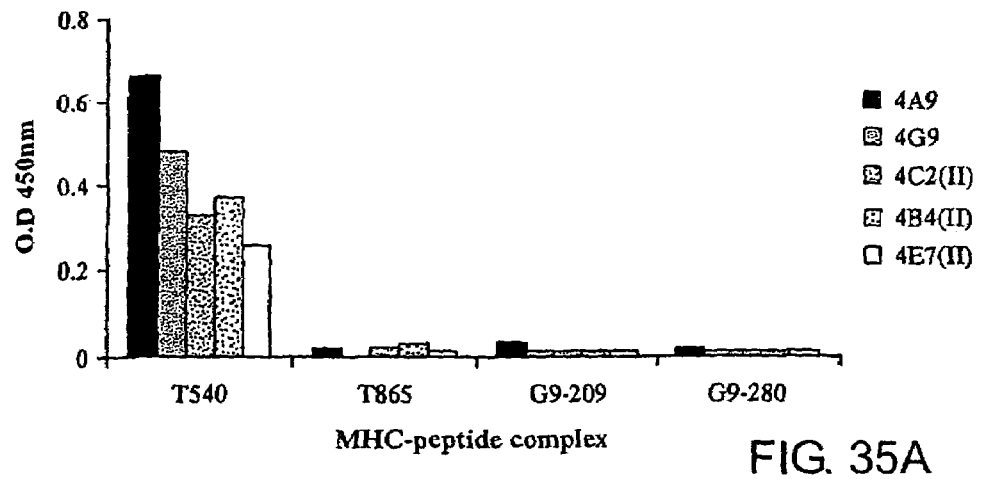
FIGS. 35A-35B. Binding of soluble purified Fab antibodies with TCR-like specificity in ELISA (A+B) Binding of soluble Fab's to immobilized MHC-peptide complexes containing various HLA-A2-restricted peptides. In (A) Fab clones selected against scHLA-A2/T540 complexes; in (B) Fab clones selected against scHLA-A2/T865 complexes.
Figure 35B:
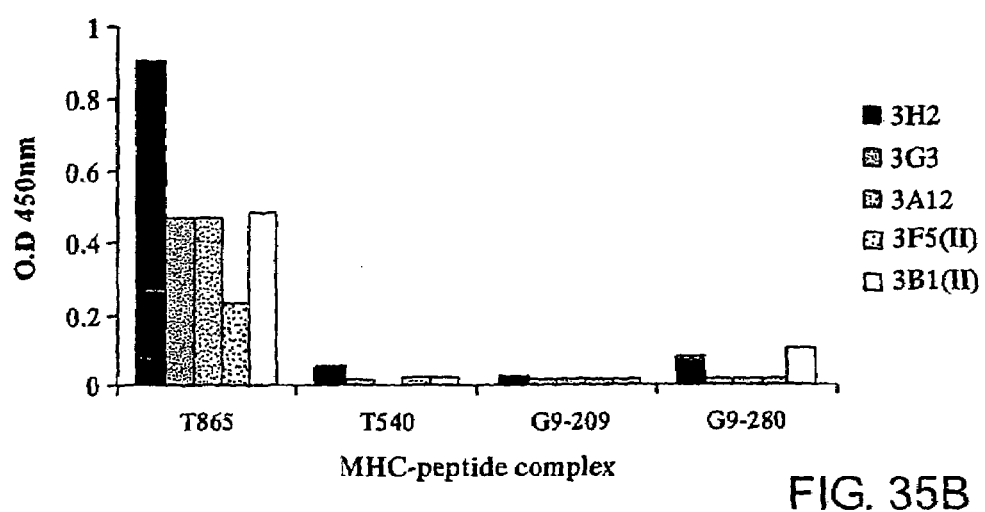

We determined the fine specificity of the soluble molecules by ELISA on biotinylated MHC-peptide complexes that were immobilized to BSA-streptavidin-coated wells. The BSA-streptavidin-biotin spacer enables the correct folding of the complexes, which can be distorted by direct binding to plastic. To determine the correct folding of the bound complexes and their stability during the binding assays, we monitored their ability to react with the conformational specific monoclonal antibody w6/32, which recognizes HLA complexes only when folded correctly and when containing peptide. FIG. 35A shows a representative analysis of five soluble Fab antibodies directed to HLA-A2/T540 complexes. All five antibodies react specifically with the T540-containing HLA-A2 complexes but not with control complexes containing the T865 hTERT-derived MHC-peptide complex, nor with HLA-A2 complexes containing the two melanoma gp100-derived epitopes, G9-209 and G9-280. We tested the fine specificity of these antibodies on five other MHC-peptide complexes displaying various HLA-A2-restricted peptides with similar results (see materials and methods for list of HLA-A2-restricted peptides tested). Similarly, soluble purified Fab fragment antibodies from the antibody clones isolated against the T865 epitope bound to the specific HLA-A2/T865 complexes, but not to control T540 hTERT-derived complexes nor to the melanoma gp100-derived HLA-A2/G9-209 and HLA-A2/G9-280 complexes (FIG. 35B). Thus, these peptide-specific and MHC-restricted Fab fragments exhibit the binding characteristics and fine specificity of a TCR-like molecule. The Fab antibodies did not recognize the peptide alone when immobilized on the plate neither streptavidin or other protein antigens (such as: BSA. IgG, RNAse, Chymotrypsin).

Figure 36B:
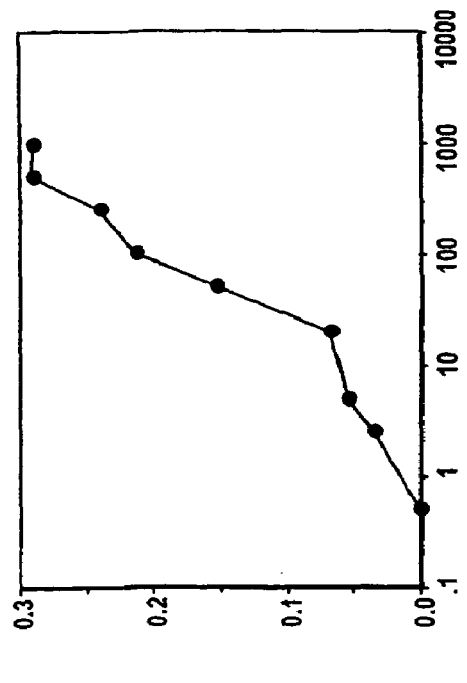
FIGS. 36A-36D. Binding characteristics of two recombinant TCR-like Fab antibodies. (A+B) Titration ELISA of purified soluble Fab antibodies 4A9 (A) and 3H2 (B) directed to scHLA-A2/T540 and scHLA-A2/T865, respectively. Wells were coated with the corresponding MHC-peptide complexes as described M&M. (C+D) Competitive binding analysis of the ability of purified Fab 4G9 (C) or 3G3 (D) to inhibit the binding of $^{125}$I-labeled Fab to the corresponding HLA-A2-peptide complex. The apparent binding affinity of the recombinant Fab was determined as the concentration of competitor (soluble purified Fab) required for 50% inhibition of the binding of the $^{125}$I-labeled tracer.
Figure 36D:
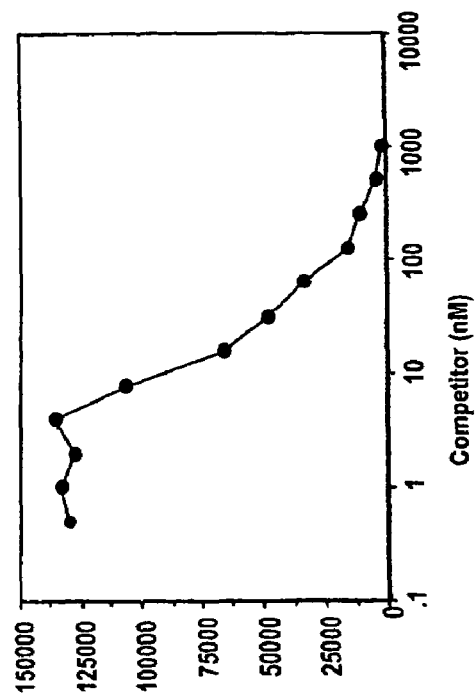
Figure 36A:
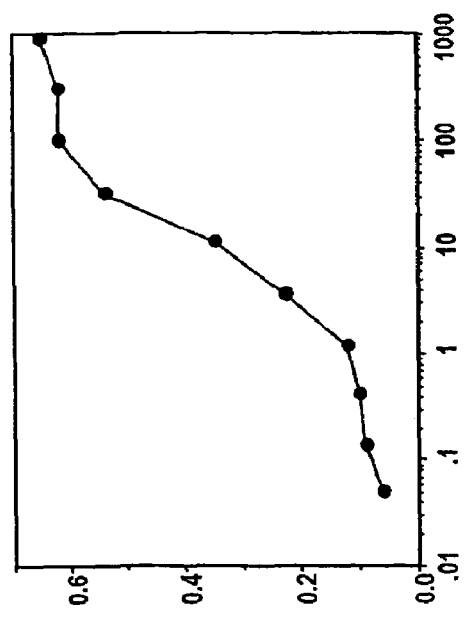

Next, we tested the affinity binding properties of two of the TCR-like soluble Fabs, using a saturation ELISA assay in which biotinylated complexes were bound to streptavidin-coated plates and to which increasing amounts of Fab antibody were added. As shown in FIGS. 36A and 36B, the binding of two specific Fabs (4A9 and 3H2) was dose-dependent and saturable. Extrapolating the 50% binding signal of either antibody revealed that their affinity is in the nanomolar range.

Figure 36C:
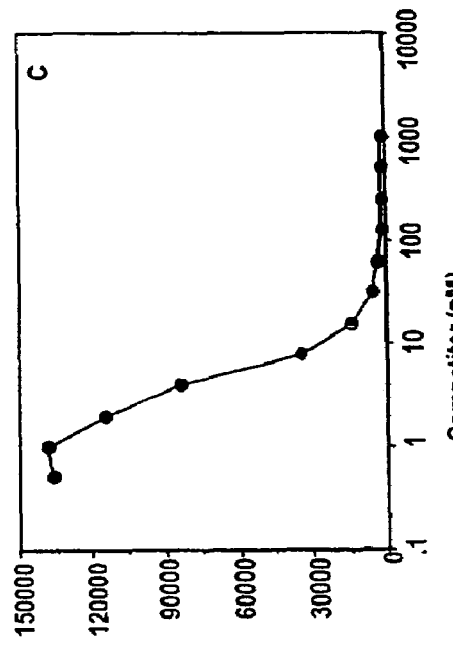

Finally, we determined the apparent binding affinity of the TCR-like Fab fragments to their cognate MHC-peptide complex by a competition binding assay in which the binding of 125I-labeled Fab was competed with increasing concentrations of unlabeled Fab fragment. These binding studies (FIGS. 36C and 36D) revealed an apparent binding affinity of approximately 5 nM for the 4A9 antibody specific for the T540 hTERT epitope and 10-15 nM for the 3G3 antibody specific for the T865 epitope.

Binding of Fab Fragments to APCs Displaying the hTERT-Derived Epitopes

To demonstrate that the isolated Fab fragments can bind the specific MHC-peptide complex not only in the recombinant soluble form but also in the native form as expressed on the cell surface, we used murine TAP2-deficient RMA-S cells transfected with the human HLA-A2 gene in a single-chain format38 (HLA-A2.1/Db-β2m single chain) (RMA-S-HHD cells). The hTERT-derived and control peptides were loaded on RMA-S-HHD cells and the ability of the selected Fab antibodies to bind to peptide-loaded cells was monitored by FACS. Peptide-induced MHC stabilization of the TAP2 mutant RMA-S-HHD cells was demonstrated by the reactivity of MAbs w6/32 (HLA conformation-dependent) and BB7.2 (HLA-A2-specific) with peptide-loaded but not unloaded cells. Fabs 4A9 and 4G9, which recognize the T540-containing HLA-A2 complexes, reacted only with T540-loaded RMA-S-HHD cells but not with cells loaded with the gp100-derived G9-209 peptide or the gp100-derived G9-280 peptide, respectively. Similarly the T865-HLA-A2-specific Fab antibodies 3G3 and 3H2 recognized only T865-loaded RMA-S-HHD cells and did not recognize cells loaded with the gp100-derived peptides at all. Similar results were observed in FACS analysis using 4 other HLA-A2 restricted peptides.

We have also used the TAP+ EBV-transformed B-lymphoblast HLA-A2+ JY cells as APCs. They have normal TAP and consequently peptide loading is facilitated by the exchange of endogenously derived peptides with HLA-A2-restricted peptides supplied externally by incubation of the cells with the desired peptides. We incubated these cells first with the T540, T865 telomerase-derived, and control HLA-A2-restricted peptides, then washed the cells, followed by incubation with Fab antibodies 4A9 and 3H2, respectively. These Fab fragments recognize only JY cells incubated with the specific telomerase peptide to which they were selected but not control HLA-A2-restricted peptides including the other telomerase epitope. We also tested the cross-reactivity of Fabs 4A9 and 3H2 on JY cells loaded with T540 and T865, respectively. JY cells loaded with T540 were only recognized by Fab 4A9 but not by Fab 3H2 nor by control Fabs recognizing a melanoma-derived gp100 epitope. Similarly, T865-loaded JY cells were recognized by Fab 3H2 specific for T865 in complex with HLA-A2 but not by Fab 4A9 nor by other gp100-specific Fabs. As control we used peptide-loaded HLA-A2−/HLA-A1+ APD B cells. No binding of the Fab antibodies to these cells was detected. These results demonstrate that the Fab antibodies exhibit a TCR-like fine specificity and can recognize the corresponding native HLA-A2 complexes in situ on the surface of cells.

Binding of TCR-Like Fab Antibody to Telomerase-Expressing Tumor Cells

Figure 37A:
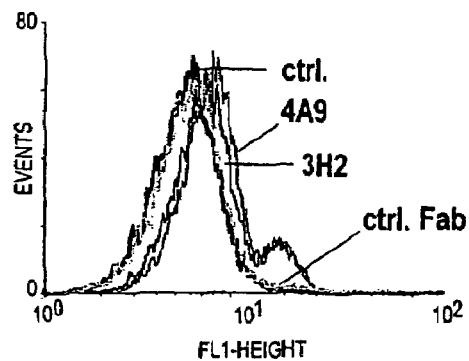
FIGS. 37A-37F. Detection of HLA-A2/Telomerase-derived peptide complexes on tumor cells. HLA-A2 positive FM3D melanoma, LnCap prostate carcinoma, HeLa epithelial carcinoma cells or hTERT-transfected human foreskin fibroblasts and control non-transfected cells ($10^6$) expressing telomerase were incubated with Fab antibodies 4A9 and 3H2 specific for the HLA-A2/T540 and HLA-A2/T865 complexes, respectively. Binding was detected using FITC-labeled anti human Fab. The HLA-A2 negative but hTERT-positive prostate carcinoma PC3 cells are used as control. FM3D cells stained with 4A9, 3H2, and control Fab directed against a mucin peptide in complex with HLA-A2. Cells stained with secondary FITC-labeled anti-human Fab are in black throughout. LnCap cells stained with 4A9, or 3H2; HeLa cells stained with 3H2, or control Fab directed to a melanoma gp100-derived peptide in complex with HLA-A2; PC3 cells stained with 4A9, or 3H2; HTERT-transfected human fibroblasts stained with 4A9, 3H2, or a control melanoma specific Fab; Control non-transfected fibroblasts stained with 4A9, 3H2, or control Fab.
Figure 37B:
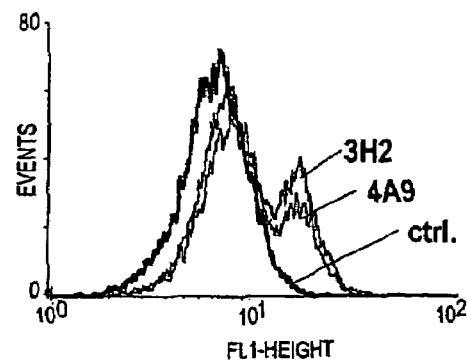
Figure 37C:
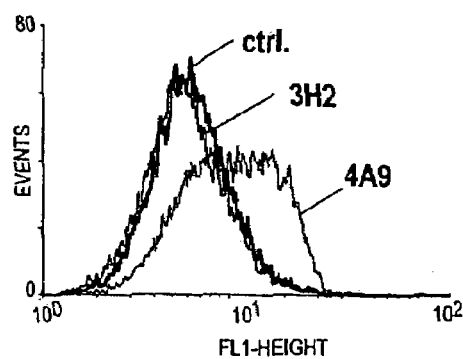
Figure 37D:
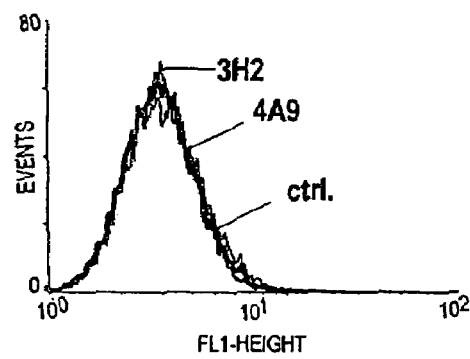

To confirm that the telomerase-specific TCR-like Fab antibodies can bind endogenously derived MHC-peptide complexes on the surface of tumor cells, we performed flow cytometry analysis on various tumor cells that express hTERT and HLA-A2. These cells represent the normal situation in which MHC-peptide complexes are expected to be present on tumor cells at a much lower density on the cell surface compared with the peptide-loaded APCs. The T540-specific Fab antibody 4A9 and T865-specific Fab 3H2 reacted with the HLA-A2+ FM3D melanoma, LnCap prostate carcinoma, and HeLa epithelial carcinoma tumor cells (FIGS. 37A-37C) but not with the HLA-A2− prostate carcinoma PC3 cells that express hTERT (FIG. 37D). Telomerase activity in these cells was measured by a telomerase repeat amplification protocol (TRAP) using total cellular extracts, buffer control, and of telomerase-positive cells. The results were obtained using 100 or 500 ng of each extract with and without heat inactivation (15 min at 85° C.). A 36-bp internal control for amplification efficiency and quantitative analysis was run for each reaction. The reaction products were separated on 10% nondenaturing polyacrylamide gel.

Figure 37E:
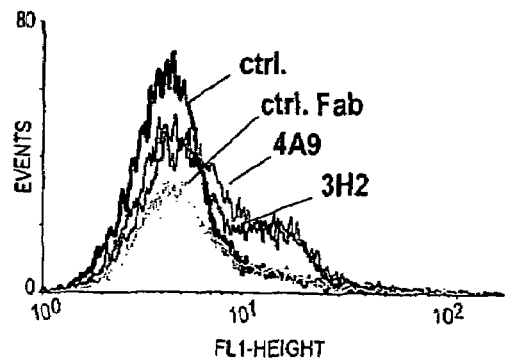
Figure 37F:
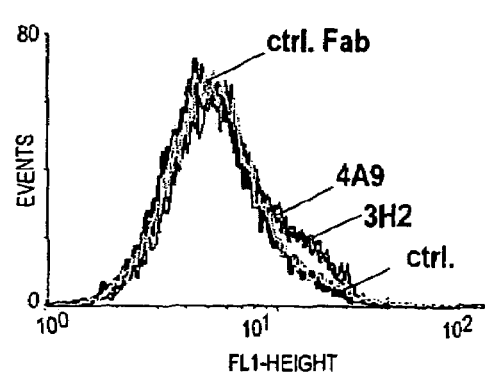

FM3D, LnCap, Hela, and PC3 cells exhibit moderate to high telomerase activity. In these experiments we observed a moderate shift in fluorescence intensity in most of the cell population. However, a sub-population (20-30%) of the cells exhibited a substantial shift in staining intensity, indicating increased expression of telomerase T540 and T865-specific MHC-peptide complexes. These observations may reflect the antigenic variations in expression levels of MHC-peptide complexes expected to occur on the surface of tumor cells. Control HLA-A2+ cells that do not express hTERT were not stained by the antibodies. In addition, we tested the reactivity of Fabs 4A9 and 3H2 with HLA-A2 positive human foreskin fibroblasts that were transfected with hTERT and control non-transfected cells (FIGS. 37E and 37F). The telomerase-specific Fabs reacted only with the transfected cells but not with the control normal fibroblasts. TRAP activity assays revealed high telomerase activity in the transfected but not in control cells. These results therefore demonstrate the ability of these high-affinity TCR-like antibodies to detect MHC-peptide complexes on the surface of tumor cells. This occurs despite the fact that the Fab antibodies are monovalent. Thus, these TCR-like antibodies can bind to cells that express the specific MHC-peptide complex at a density most likely to be found on tumor cells, antigen-presenting cells such as dendritic cells, and other cells involved in tumor-antigen presentation to the immune system.

Discussion

This study demonstrates our ability to select from a large non-immune repertoire of human Fab fragments displayed on phage a panel of antibodies directed against two HLA-A2-restricted T cell epitopes of the most widely expressed tumor-associated antigen identified so far, the human telomerase reverse transcriptase.

These antibodies can bind with high affinity in an antigen-specific, MHC-restricted manner, soluble HLA-A2 molecules complexed with the cognate peptides.

Moreover, they can detect and visualize peptide/MHC complexes on the surface of cells. Hence, these are recombinant antibodies with the T-cell antigen receptor-like specificity of T cells. In contrast to the inherently low affinity of TCRs to MHC-peptide complexes, these molecules display the high affinity binding characteristics of antibodies, yet they retain TCR-like fine specificity.

Unlike recombinant TCRs, these recombinant antibodies recognize the corresponding native MHC-peptide complexes on cells.

We have selected the antibodies against one of the most interesting TAAs isolated so far, the human telomerase catalytic subunit. It has been recently shown that a CTL repertoire for hTERT is preserved in normal individuals as well as, most importantly, in cancer patients (Vonderheide, et al. (1999) *Immunity* 10:673-9; Minev, et al. (2000) *Proc Natl Acad Sci USA* 97:4796-801; Counter, et al. (1995) *Blood* 85:2315-20; Arai, et al. (2001) *Blood* 97:2903-7). Two observations may contribute to the suggested importance of hTERT as a TAA; (1) telomerase is expressed and active in more than 85% of human cancers but not in most normal human somatic cells (McEachern, et al. (2000) *Annu Rev Genet* 34:331-58; Nakamura and Cech (1998) *Cell* 92:587-90; Shay, et al. (2001) *Hum Mol Genet* 10:677-85; Kim, et al. (1994) *Science* 266:2011-5); and (2) peptides derived from the telomerase catalytic subunit can be naturally processed by tumor cells, presented in an HLA-A2-restricted fashion, and then serve as a target for antigen-specific CTLs (Vonderheide, et al. (1999) *Immunity* 10:673-9; Minev, et al. (2000) *Proc Natl Acad Sci USA* 97:4796-801; Counter, et al. (1995) *Blood* 85:2315-20; Arai, et al. (2001) *Blood* 97:2903-7). Moreover, the finding that CTLs specific for telomerase-derived epitopes isolated from a prostate cancer patient mediate efficient lysis of a variety of HLA-A2+ cancer cells such as prostate, breast, colon, lung, and melanoma is unprecedented (Vonderheide, et al. (1999) *Immunity* 10:673-9; Minev, et al. (2000) *Proc Natl Acad Sci USA* 97:4796-801). Thus, we think that these cancer cells are equally effective in processing and presenting the same endogenous hTERT peptides. Therefore, similar hTERT peptides are expressed and complexed with MHC class I molecules on a variety of cancer cells of different histological origins and types. This suggests that hTERT represents the most widely expressed TAA described so far and renders telomerase-expressing tumor cells susceptible to destruction by CTL. Furthermore, this underscores the potential advantages that hTERT may have in controlling primary tumors and metastases in a large variety of cancer types in humans. Thus, hTERT-derived MHC-peptide complexes may turn out to be a very attractive target for cancer immunotherapy.

Our study demonstrates the power of the phage display approach for selecting antibodies with unusually and unique fine specificity. Until now antibodies with TCR-like specificity have been generated against murine MHC-peptide complexes employing various strategies of immunization (Andersen et al. (1996) *Proc. Natl. Acad. Sci. U.S.A.* 93:1820-24; Porgador (1997) *Immunity* 6:715-26; Day (1997) *Proc Natl Acad Sci USA* 94:8064-9; Zhong (1997) *Proc Natl Acad Sci USA* 1997 94, 13856-61; Dadaglio (1997) *Immunity* 6, 727-38; Aharoni (1991) *Nature*. 351:147-50; Krogsgaard et al. (2000) *J Exp Med.* 191, 1395-412; Chames and Hoogenboom (2000) *Proc. Natl. Acad. Sci. U.S.A.* 97:7969-74). Recently using the same phage-displayed Fab library, a recombinant Fab antibody was isolated that recognizes the melanoma antigen MAGE-A1 in complex with the human HLA-A1 MHC molecule. The affinity of this antibody was quite low (250 nM); therefore, it could be used to detect HLA-A1-MAGE-A1 complexes only when displayed in multiple copies on a phage (Chames and Hoogenboom (2000) *Proc. Natl. Acad. Sci. U.S.A.* 97:7969-74). The fact that high-affinity antibodies with such unique, -fine specificity targeting a rather difficult antigen were readily obtained in this study, and that they were in some cases with low nanomolar affinity, underscores the power of the display technology for this application, as well as add proof to the quality of the human non-immune antibody library used in the selections. The observation that 20-40% of the MHC-peptide binding antibodies had the fine specificity of a TCR-like molecule is nevertheless surprising, especially since they were selected from a non-immune repertoire considered not to be biased towards such specificity. More recently we have been able to isolate recombinant Fab antibodies against a large variety of MHC-peptide complexes containing other cancer-associated or viral HLA-A2-restricted peptides, indicating that this behavior is not telomerase peptides related. The unexpected high frequency of these antibodies and our ability to isolate several different antibodies directed to either complex is even more surprising in view of previous reports, in which the use of immunized or naive phage libraries resulted in only a single antibody clone (Andersen et al. (1996) *Proc. Natl. Acad. Sci. U.S.A.* 93:1820-24; Porgador (1997) *Immunity* 6:715-26; Chames and Hoogenboom (2000) *Proc. Natl. Acad. Sci. U.S.A.* 97:7969-74).

It would have been possible that one particular antibody family or antibody V-gene segment would have an intrinsic propensity to bind HLA-A2 molecules, and that the high frequency could be explained by a high abundance of such antibodies in the non-immune library. However, the sequences of the selected clones are derived from many different antibody families and germline segments, without any biases visible in the CDRs either. The high frequency and high affinities for some of the antibodies isolated here, suggest that these molecules may well be present at a high frequency in the antibody repertoires from the B-cell donors of the phage library, but a role for such antibodies remains unclear.

Whatever eventually the reason for this high frequency of antibodies to MHC-peptides may be, it appears that this phage-based approach can be successfully applied to isolate recombinant antibodies with TCR-like specificity to a large variety of MHC-peptide complexes. Thus, it is possible to dissect the role of antigens in various pathological conditions such as cancer, viral infections and autoimmune disease, not only at the level of the T-cell using MHC-tetramers, but also at the level of the APC and diseased cell, using antibodies of the type described here.

The state and quality of the antigen used in the selection process was significant. In particular with a trimolecular complex as an HLA-peptide complex, it is important to define those recombinant forms that do exhibit the 'natural' conformation. We found that in vitro refolding from *E. coli* inclusion bodies, of a single-chain MHC molecule complexed with various peptides yielded large quantities of correctly folded protein and that these refolded scMHC HLA-A2-peptide complexes are indeed functional, as demonstrated by their ability to stimulate T-cell activation, and can be used in the form of scMHC-peptide tetramers to phenotypically stain CTL clones specific for melanoma peptides (Denkberg and Reiter (2000) *Eur. J Immunol.* 30:3522-32; Denkberg and Reiter (2001) *J Immunol* 167, 270-6).

Thus, these advantages may play a critical role in our ability to select these high-affinity TCR-like antibodies even though such peptide-specific binders are thought to be quite rare in even the most sizable library.

Recombinant antibodies with TCR-like specificity, such as we have selected and characterized herein, also represent an innovative and valuable tool in molecular immunology. These antibodies may now be used to detect and visualize the presence of specific MHC-restricted T-cell epitopes by standard methods of flow cytometry and immuno-histochemistry. As such, they are useful for the study and analysis of antigen presentation on tumor cells by determining the expression of specific tumor-related MHC-peptide complexes on the surface of tumor cells, metastases, antigen presenting cells, and lymphoid cells. These antibodies can be used to analyze immunotherapy-based approaches by determining the alterations in MHC-peptide complex expression on antigen-presenting cells before, during, and after vaccination protocols with peptides or with APCs loaded with tumor cell extracts or dendritic-tumor cell hybrid vaccinations (Offringa and Melief (2000) *Curr Opin Immunol* 12:576-82; Esche (1999) *Curr Opin Mol Ther* 1:72-81; Kugler et al. (2000) *Nat. Med.* 6:332-36). For immunotherapeutic applications, this approach presents new opportunities for using these specific molecules, which recognize very specific and unique human tumor antigens as candidates to serve as targeting moieties for antibody-based immunotherapies. Such approaches could include recombinant immunotoxins (Pastan (1997) *Biochim Biophys Acta.* 1333, C1-6), fusions with cytokine molecules (Lode and Reisfeld (2000) *Immunol Res.* 21:279-88); bispecific antibody therapy (Withoff (2001) *Curr Opin Mol Ther.* 3:53-62) or immuno-gene therapy (Willemsen et al. (2000) *Gene Ther.* 7:1369). This is particularly important for the molecules described herein because they target T-cell epitopes of the hTERT, which, as noted above, represents a very widely expressed TAA displayed on cancer cell types of widely varying cellular origins.

These antibodies also represent a valuable tool for structural and functional studies of TCR-peptide-MHC interactions. As previously shown for a murine system, TCR-like antibodies were used to define fine specificities of TCR interactions (Stryhn et al. (1996) *Proc. Natl. Acad. Sci. U.S.A.* 93:10338-42). A striking similarity between the specificity of the T-cells and that of the murine TCR-like antibody was found and most of the peptide residues, which could be recognized by the T-cells, could also be recognized by the antibody.

Here we have demonstrated binding of some of our antibodies to telomerase-expressing tumor cells, thus showing for the first time the feasibility of detecting and visualizing specific MHC-peptide complexes on the surface of tumor cells with a soluble phage-library-derived antibody. The antibodies isolated in this study, which exhibit the specificity of hTERT-restricted T cells, can be used for the design of new antibody-based targeting molecules for immunotherapy because they have the unique antigen-specific, MHC-restricted specificity of T cells, combined with the high affinity characteristics of antibodies. This is in contrast to the inherently low affinity of TCR to MHC-peptide complexes.

The density (and turnover rate) of these specific epitopes on the target cell surface, and the specificity of the antibody may impact immunotherapy and research applications. With regard to surface density, we have previously shown in a murine model that, to achieve efficient killing with a TCR-like immunotoxin molecule, a density of several thousand specific MHC-peptide complexes is required for selective elimination of APCs (Reiter and Pastan (1997) *Proc. Natl. Acad. Sci. U.S.A.* 94:4631-36).

It remains to be determined what the density of the telomerase complexes on the cancer cells tested is. Clear shifts in FACS analysis indicate that the density of TAA of the telomerase complex on cancer cells is higher than previously noted. The other important issue to consider is the fine-specificity of the antibody. The antibodies characterized in this study were specific for their particular peptide in the HLA-A2 context, in two tests, ELISA and flow cytometry, with a panel of less then 10 other unrelated peptides tested as controls. It is clear from structural studies with MHC-peptide specific antibodies, that related peptides with one or a few mutations in the peptide may also be recognized. It therefore remains to be seen that the specificity of the antibodies will be in the context of a true natural repertoire of peptides displayed in the MHC. New data on the use of such antibodies for retargeting T-cell to tumor cells are highly encouraging in this respect. A recent study with Fab G8, an antibody that targets the HLA-A1 complexed to MAGE-A1 (Chames and Hoogenboom (2000) *Proc. Natl. Acad. Sci. U.S.A.* 97:7969-74), shows that expression of the Fab genes on the surface of transfected primary human T lymphocytes retargets these cells specifically to MAGE-A 1 expressing tumor cells, and in a manner indistinguishable from a T-cell receptor with similar specificity (Willemsen et al. (2000) *Gene Ther.* 7:1369).

To improve the targeting capabilities of these TCR-like antibody molecules two antibody engineering approaches can be employed: (1) increasing the affinity of the parental antibody by affinity maturation strategies without alteration of its TCR-like fine specificity (Chowdhury and Pastan (1999) *Nat Biotechnol.* 17:568-72), and (2) increasing the avidity of these recombinant monovalent molecules by rendering them bi or multi-valent. The combination of these affinity maturation strategies and avidity engineering may well result in second-generation, improved antibodies that can recognize levels of MHC-peptide complexes with sufficient sensitivity for their eventual immunotherapeutic use.

EXAMPLE 4

MUC1-HLA-A2 Antibodies

In this study we attempted to isolate human recombinant antibodies directed toward a T-cell epitope derived from the Mucin 1 antigen.

Mucin 1 (MUC1) is an epithelial cell-associated mucin that is developmentally regulated and aberrantly expressed by carcinomas, which makes it an important marker in malignancy (Mukherjee et al (2000) *J Immunol.* 165:3451-3460). This molecule exists as a large extended rod protruding from the apical cell membrane into the lumen of the ducts. MUC1 has an unusual structure, consisting mainly of a 20-amino acid sequence repeated in tandem on an average of 30-90 times. The tandem repeats (TRs) serve as the scaffold for O-linked oligosaccharides that cover the polypeptide core (Gendler et al (1995) *Annu. Rev. Physiol* 57:607-634; Spicer et al (1991) *J Biol. Chem.* 266:15099-15109).

In cancer, there are differences in expression that distinguish this protein as tumor specific. There is a large increase in the amount of mucin expressed on cells and in the circulation. Its distribution is no longer restricted to the apical surface of ducts and glands, but it is found throughout the tumor mass and on the surface of tumor cells. Importantly, the glycosylation is altered; oligosaccharide structures are shorter and fewer in number, revealing immunodominant peptide sequences in every TR that on normal surfaces would be concealed by glycosylation. Underglycosylation of MUC1 reveals peptide epitopes presented in the context of MHC molecules and recognized by CTLs that can kill tumor cells expressing this form of MUC1 (Barnd et al (1989) *Proc. Natl. Acad. Sci.* 86:7159-7163).

The recent description of MUC1 as a target for CTLs has raised interest in using this protein as a target for immunotherapy. It is expressed by most adenocarcinomas of the breast, lung, stomach, pancreas, colon, prostate, ovary, endometrium, and cervix, which makes MUC1 an attractive therapeutic target. In 1999, cancers that expressed MUC1 accounted for about 72% of new cases and for 66% of the deaths (Greenlee et al (2000) *CA Cancer J Clin.* 50:7-33).

However, expression of the underglycosylated MUC1 is not sufficient to stimulate CTL killing, as 90% of existing carcinomas express MUC1 and these tumors progress.

Recently, Carmon et al. (Carmon et al (2000) *Int. J Cancer* 85:391-397) characterized three new HLA-A2.1-restricted MUC1-derived CTL epitopes. These peptides, which are not deduced from the extracellular Tandem Repeat Array (TRA), were shown to be processed and presented by a breast-tumor cell line. Moreover, CTL induced against these peptides lysed target cells pulsed with breast-carcinoma-derived peptide extracts more efficiently than target cells pulsed with normal-breast-derived peptides. One of these MUC1 epitopes, was the D6 peptide (LLLTVLTVV; SEQ ID NO:4), which exhibited high MHC-binding affinity, positively correlated with preferential immunogenic properties in CTL assays.

Thus, there is a need to develop molecules that may specifically recognize tumor cells presenting MUC1 derived peptides; such molecules may serve as a targeting moiety to direct drugs or toxins to tumor cells. These molecules can also serve as a tool to study the presentation of MUC1 epitopes on the surface of tumor cells, antigen-presenting cells and lymphoid organs.

In the present work, we have isolated a panel of human recombinant antibodies with antigen-specific, MHC-restricted specificity of T cells binding with high affinity HLA-A2 complexes that display the specific Mucin-1 D6 peptide.

These antibodies have been used to directly visualize, by flow cytometry, the specific HLA-A2/MUC1-D6 epitope on antigen-presenting cells as well as on the surface of tumor cells.

Recombinant Single-Chain MHC-Peptide Complexes with Mucin-Derived HLA-A2-Restricted Peptide One of the potent T-cell epitope identified in the MUC1 antigen that was recognized by HLA-A2-restricted CTLs derived from HLA-A2 transgenic mice is the peptide D6 (LLLTVLTVV; SEQ ID NO:4) (Carmon et al (2000) Int. J Cancer 85:391-397). Recombinant MHC-peptide complexes that present the MUC1-derived epitope were generated by using a single-chain MHC (scMHC) construct that was described previously (Denkberg et al (2000) Eur. J Immunol. 30:3522-3532) (Denkberg et al (2001) J Immunol. 167:270-276). In this construct, the extracellular domains of HLA-A2 are connected into a single-chain molecule with β-2 microglobulin using a 15-amino acid flexible linker. The scMHC-peptide complexes were produced by in vitro refolding of inclusion bodies from bacterial cultures transformed with the scMHC construct. Refolding was performed in the presence of the MUC1-derived peptide followed by a purification protocol employing ion-exchange chromatography. The refolded scHLA-A2/D6 complexes were very pure, homogenous and monomeric, as shown by analysis on SDS-PAGE and size-exclusion chromatography. Recombinant scMHC-peptide complexes generated by this strategy have been previously characterized in detail for their biochemical, biophysical, and biological properties and were found to be correctly folded and functional (Denkberg et al (2000) Eur. J Immunol. 30:3522-3532; Denkberg et al (2001) J Immunol. 167:270-276).

Selection of Recombinant Antibodies with TCR-Like Specificity to HLA-A2-Restricted T-Cell Epitope of MUC1

Figures 38A, 38B:
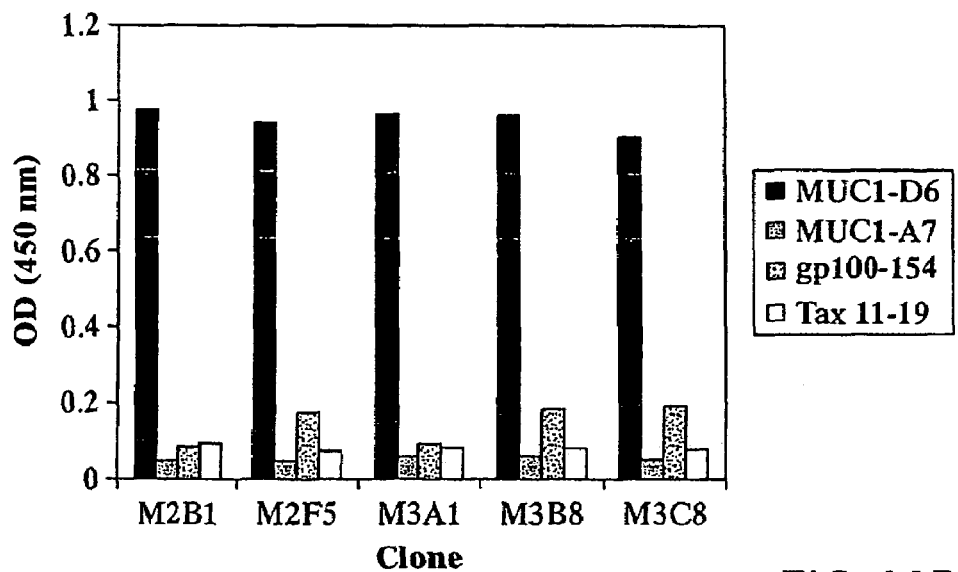
FIGS. 38A and 38B. Frequency (A) and specificity (B) of recombinant Fab antibodies selected on HLA-A2/MUC1-D6 complexes. (A) Summary of panning against MUC1-D6 T cell epitope in complex with scHLA-A2. ELISA with phage particles was performed on immobilized scHLA-A2/peptide complexes as described in Materials and Methods. (B) Phage ELISA of clones selected against scHLA-A2/MUC1-D6 complex. (clones M2B1, M2F5 are from the second round of panning and clones M3A1, M3B8, M3C8 are from the third round).
Figure 39:
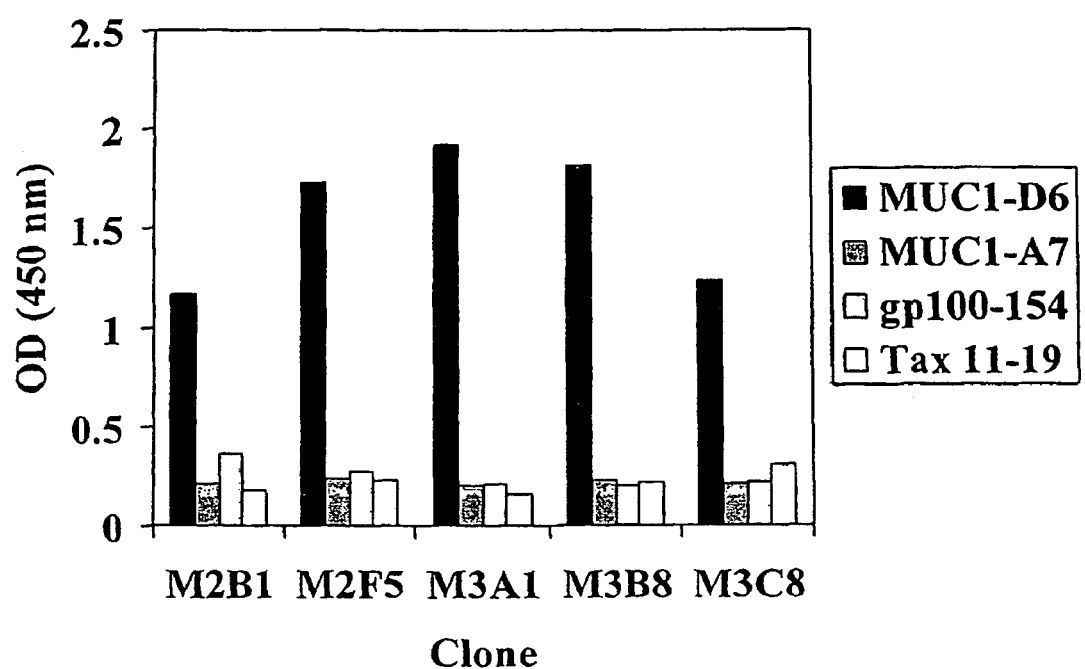
FIG. 39. Binding of soluble purified Fab antibodies with TCR-like specificity to immobilized MHC/MUC2-D6 complexes in ELISA.

To enable efficient selection, scMHC-peptide complexes were biotinylated using a BirA sequence tag that was engineered at the C-terminus of the HLA-A2 gene for site-specific biotinylation as previously described (Altman et al (1996) Science 274:94-96; Denkberg et al (2000) Eur. J Immunol. 30:3522-3532). The phage display large repertoire of 3.7× $10^{10}$ human recombinant Fab fragments (de Haard et al (1999) J Biol. Chem. 274:18218-18230), was incubated first with streptavidin-coated beads to avoid the selection of anti-streptavidin antibodies. A magnetic field was applied to precipitate the beads, and the supernatant containing the library depleted of streptavidin binders was used for the subsequent panning in solution on soluble recombinant MHC-peptide complexes containing the MUC1-derived T cell epitope. After incubation of the library with soluble complexes, binding phages were collected using streptavidin-coated magnetic beads followed by elution with triethylamine. A 580-fold enrichment in phage titer was observed after three rounds of panning using the MUC1-derived D6 peptide-MHC complexes (FIG. 38A). The fine specificity of the selected phage antibodies was determined by a differential ELISA on streptavidin-coated wells incubated with biotinylated scMHC HLA-A2 complexes containing either the specific MUC1-derived D6 peptide, or control complexes containing other HLA-A2-restricted peptides. Phage clones analyzed after the third round of selection exhibited two types of binding pattern toward the MHC-peptide complex: one class of antibodies were pan-MHC binders which cannot differentiate between the various MHC-peptide complexes; the second type were antibodies which bound the MHC-peptide complex in a peptide specific manner. The ELISA screen revealed that 84% of randomly selected clones from the third round of panning appeared to be binding to the HLA-A2/peptide complex.

However, a surprisingly high percentage of antibodies though were fully specific for the peptide/MHC used in selection (i.e., the scHLA-A2/D6 complex) when tested as phage antibodies in ELISA on different peptide/MHC complexes. As shown in FIG. 43A, 80% of the clones exhibited antigen-specific, MHC-restricted binding characteristics of T cells. Thus, they bound only to the MHC peptide complex containing the specific D6 MUC1-derived peptide and did not bind to control complexes containing other HLA-A2-restricted peptides. These apparent MHC/peptide-specific positive clones remained specific in a secondary screening on more complexes. FIG. 38B shows a representative analysis of 5 TCR-like Fab clones. Clones M2B1 and M2F2 are from the second round of panning and clones M3A1 and M3B8 are from the third round. The different MUC1-D6 specific clones tested, reacted only with scMHC-MUC1-D6 complexes and not with MHC-peptide complexes displaying the MUC1-derived A7 epitope, the melanoma gp100-derived epitope, G9-154 and the viral $TAX_{11-19}$ epitope (FIG. 38B).

We examined the diversity pattern of 26 peptide-specific clones (from round two or three) by DNA fingerprint analysis and found 16 different restriction patterns indicating the selection of several different antibodies with TCR-like specificity. DNA sequencing analysis confirmed these observations.

Characterization of Recombinant Soluble Fab Antibodies with TCR-Like Specificity We produced, in E. coli BL21 cells, soluble Fab fragments from the phage clones (analyzed above) that exhibited the specific binding pattern to the MUC1-derived HLA-A2-peptide complexes.

These were purified by metal affinity chromatography from the periplasm by use of the hexahistidine tag fused to the CH1 domain of the Fabs. SDS-PAGE analysis of the affinity-purified material revealed homogenous, very pure Fabs antibodies with the expected molecular weight. Approximately 0.5-2 mg of pure material could be obtained from 1 liter of bacterial culture.

We determined the fine specificity of the soluble molecules by ELISA on biotinylated MHC-peptide complexes that were immobilized to BSA-streptavidin-coated wells. The BSA-streptavidin-biotin spacer enables the correct folding of the complexes, which can be distorted by direct binding to plastic. To determine the correct folding of the bound complexes and their stability during the binding assays, we monitored their ability to react with the conformational specific monoclonal antibody w6/32, which recognizes HLA complexes only when folded correctly and when containing peptide. FIG. 44B shows a representative analysis of five soluble Fab antibodies directed to HLA-A2/MUC1-D6 complexes. All five antibodies react specifically with the D6-containing HLA-A2 complexes but not with control complexes containing the A7 MUC1-derived MHC-peptide complex, nor with HLA-A2 complexes containing the melanoma gp100-derived epitope, G9-154 or the viral $TAX_{11-19}$ epitope. We tested the fine specificity of these antibodies on five other MHC-peptide complexes displaying various HLA-A2-restricted peptides with similar results. Thus, these peptide-specific and MHC-restricted Fab fragments exhibit the binding characteristics and fine specificity of a TCR-like molecule. The Fab antibodies did not recognize the peptide alone when immobilized on the plate neither streptavidin or other protein antigens (such as: BSA. IgG, RNAse, Chymotrypsin).

Figure 40A:
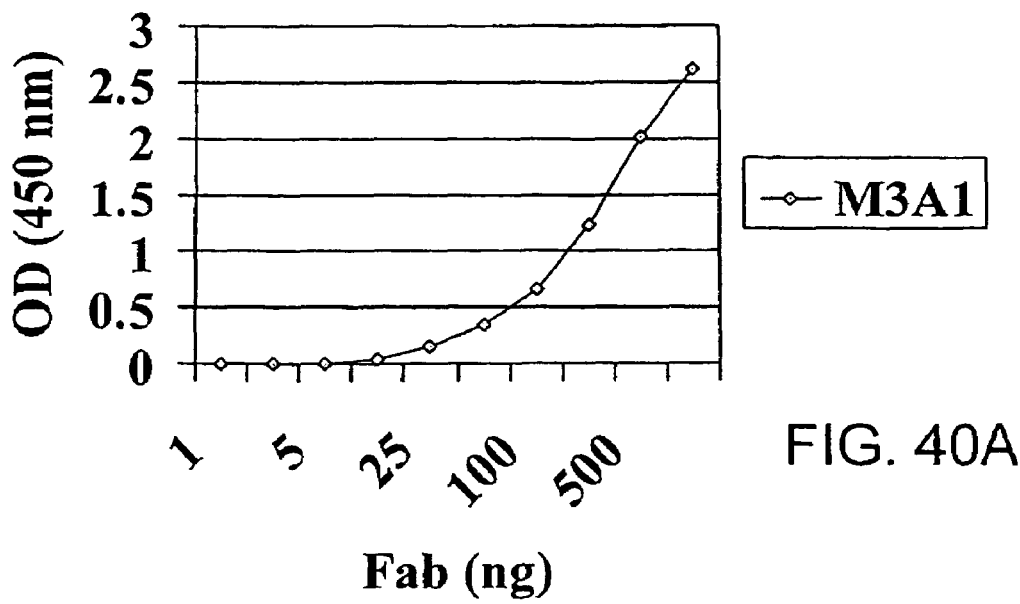
FIGS. 40A and 40B. Binding characteristics of two recombinant TCR-like Fab antibodies (A+B) Titration ELISA of purified soluble Fab antibodies M3A1 (A) and M3B8 (B) directed to scHLA-A2/MUC1-D6. Wells were coated with the corresponding MHC-peptide complexes as described M&M.
Figure 40B:
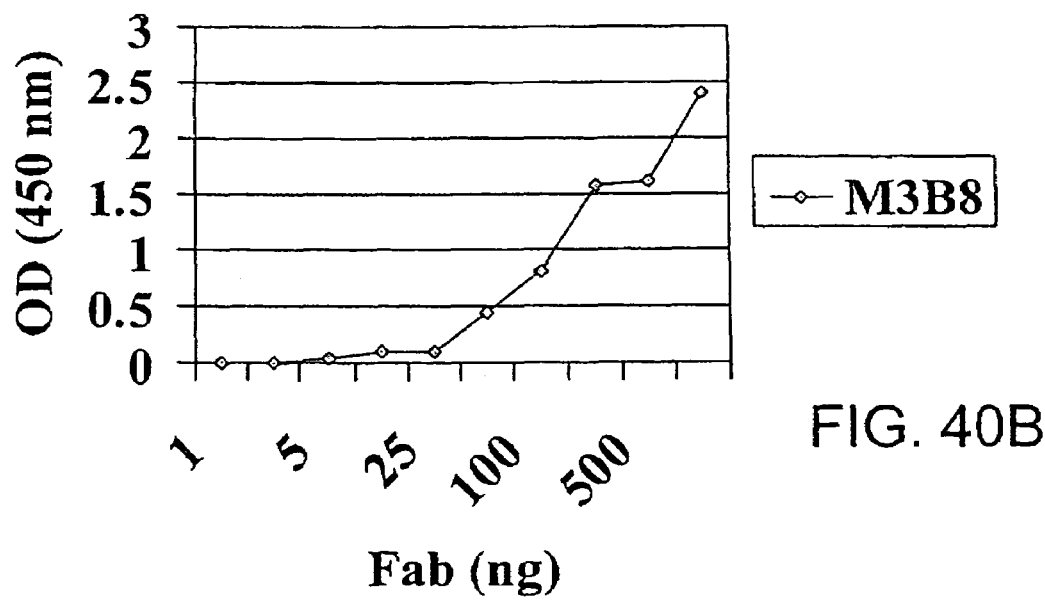

Next, we tested the affinity binding properties of two of the TCR-like soluble Fabs, using a saturation ELISA assay in which biotinylated complexes were bound to streptavidin-coated plates and to which increasing amounts of Fab antibody were added. As shown in FIGS. 40A and 40B, the binding of two specific Fabs (M3A1 and M3B8) was dose-dependent and saturable. Extrapolating the 50% binding signal of either antibody revealed that their affinity is in the nanomolar range.

Finally, we determined the apparent binding affinity of the TCR-like Fab fragments to their cognate MHC-peptide complex by a competition binding assay in which the binding of $^{125}$I-labeled Fab was competed with increasing concentrations of unlabeled Fab fragment. These binding studies revealed an apparent binding affinity of approximately 10-15 nM for the M3A1 antibody and the M3B8 antibody specific for the MUC1-D6 epitope.

Binding of Fab Fragments to APCs Displaying the MUC1-Derived Epitope

To demonstrate that the isolated Fab fragments can bind the specific MHC-peptide complex not only in the recombinant soluble form but also in the native form as expressed on the cell surface, we used murine TAP2-deficient RMA-S cells transfected with the human HLA-A2 gene in a single-chain format (HLA-A2.1/Db-β2m single chain) (RMA-S-HHD cells). The MUC1-derived D6 and control peptides were loaded on RMA-S-HHD cells and the ability of the selected Fab antibodies to bind to peptide-loaded cells was monitored by FACS. Peptide-induced MHC stabilization of the TAP2 mutant RMA-S-HHD cells was demonstrated by the reactivity of MAbs w6/32 (HLA conformation-dependent) and BB7.2 (HLA-A2-specific) with peptide-loaded but not unloaded cells. Fabs M3A1 and M3B8, reacted only with D6-loaded RMA-S-HHD cells but not with cells loaded with the gp100-derived G9-154 peptide. Similar results were observed in FACS analysis using 4 other HLA-A2 restricted peptides.

We have also used the TAP+ EBV-transformed B-lymphoblast HLA-A2+ JY cells as APCs. They have normal TAP and consequently peptide loading is facilitated by the exchange of endogenously derived peptides with HLA-A2-restricted peptides supplied externally by incubation of the cells with the desired peptides. We incubated these cells first with the D6 MUC1-derived, and control HLA-A2-restricted peptides, then washed the cells, followed by incubation with Fab antibodies M3A1 and M3B8. These Fab fragments recognize only JY cells incubated with the specific Mucin1 peptide to which they were selected but not control HLA-A2-restricted peptides including the other MUC1 epitope. As control we used peptide-loaded HLA-A2−/HLA-A1+ APD B cells. No binding of the Fab antibodies to these cells was observed.

Binding of TCR-Like Fab Antibody to MUC1-Expressing Tumor Cells

To confirm that the MUC1-specific TCR-like Fab antibodies can bind endogenously derived MHC-peptide complexes on the surface of tumor cells, we performed flow cytometry analysis on various tumor cells that express MUC1 and HLA-A2.

Figure 41A:
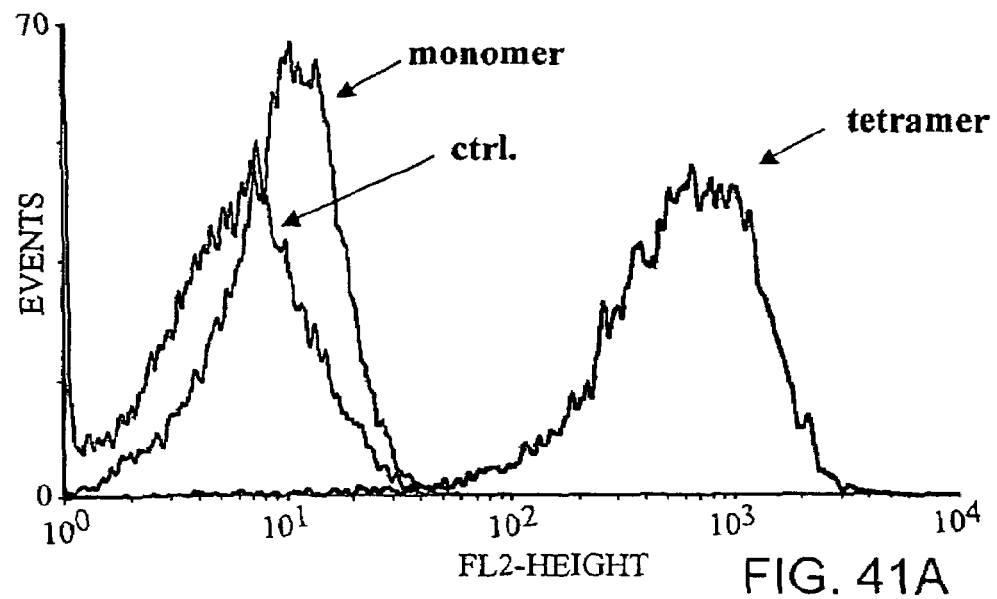
FIGS. 41A and 41B. Detection of MHC-peptide complexes on the surface of tumor cells. (A) MDA-MB-231 cells were loaded with MUC1-D6 peptide. Peptide loaded cells were then incubated with the HLA-A2/MUC1-D6-specific refolded M3A1-tetramer or with the monomer. High mean fluorescence intensity of tetramer stained cells relative to monomer-stained cells is shown. Control unloaded cells, stained with the M3A1 tetramer are also shown. (B) MDA-MB-231 cells were loaded with different concentration of MUC1-D6 peptide: 30 μM, 10 μM, 5 μM, and 1 μM. Peptide loaded cells were then incubated with the HLA-A2/MUC1-D6-specific refolded M3A1-tetramer. The relation between the intensity of the staining and the peptide concentration is shown. Control unloaded cells stained with the M3A1 tetramer are also shown (0 μM).
Figure 41B:
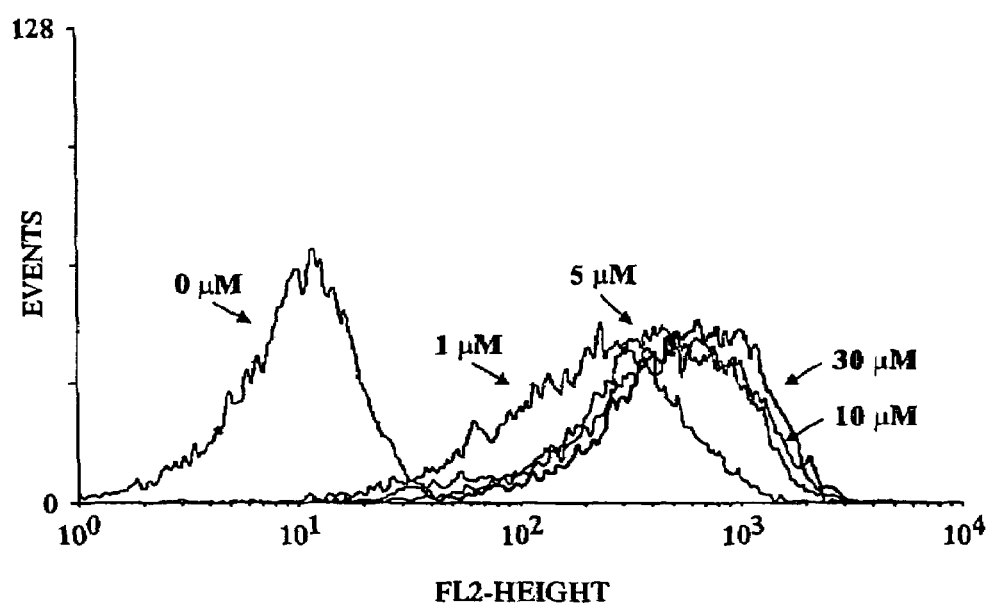

Since the density of a particular peptide-HLA complex on these tumor cells is expected to be lower compared to peptide-pulsed APCs we increased the avidity of Fab M3A1 by making Fab tetramers which are directly tagged with a fluorescent probe. This approach was used previously to increase the binding avidity of peptide-MHC complexes to the TCR or to increase sensitivity of recombinant antibody molecules (Cloutier et al (2000) *Mol. Immunol.* 37:1067-1077). Another advantage in using fluorescent labeled tetramers lies in the fact that only a single staining step is required while monomeric unlabeled Fab's require a fluorescent labeled secondary antibody. We thus used our Fab tetramers, which were generated with fluorescent-labelled streptavidin, to measure the expression of MUC1-derived D6 peptide-MHC complexes on the surface of MUC1 expressing tumor cells. The intensity of binding measured by flow cytometry with peptide loaded JY cells was dramatically increased by two logs compared to the staining intensity with the M3A1 Fab monomer. Next, we tested the ability of the Fab M3A1 tetramer to stain breast cancer HLA-A2+ tumor cells pulsed with the Muc1-derived D6 peptide. As shown in FIG. 41A, significant staining of peptide-pulsed MDA-MB-231 cells was observed with the tetramer while a lower degree of staining was observed when cells were stained using the Fab monomer. Titration of peptide-pulsed MDA-MB-231 cells with different concentrations of the MUC1-derived D6 peptide demonstrated that staining intensity was dependent on the concentration of peptide used for pulsing and that pulsing with a concentration as low as 10-15 nM was sufficient to detect binding using the Fab M3A1 tetramer (FIG. 41B). Similar experiments were performed on MUC1-expressing MCF7 breast carcinoma cells, however the staining intensity with these cells was lower compared to MDA-MB-231 cells. This may be explained by the expression level of HLA-A2 molecules on the surface of these cells. MDA-MB-231 cells express significantly higher levels of HLA-A2 compared to MCF7 cells as monitored by the anti-HLA-A2 antibody BB7.2.

Figure 42:
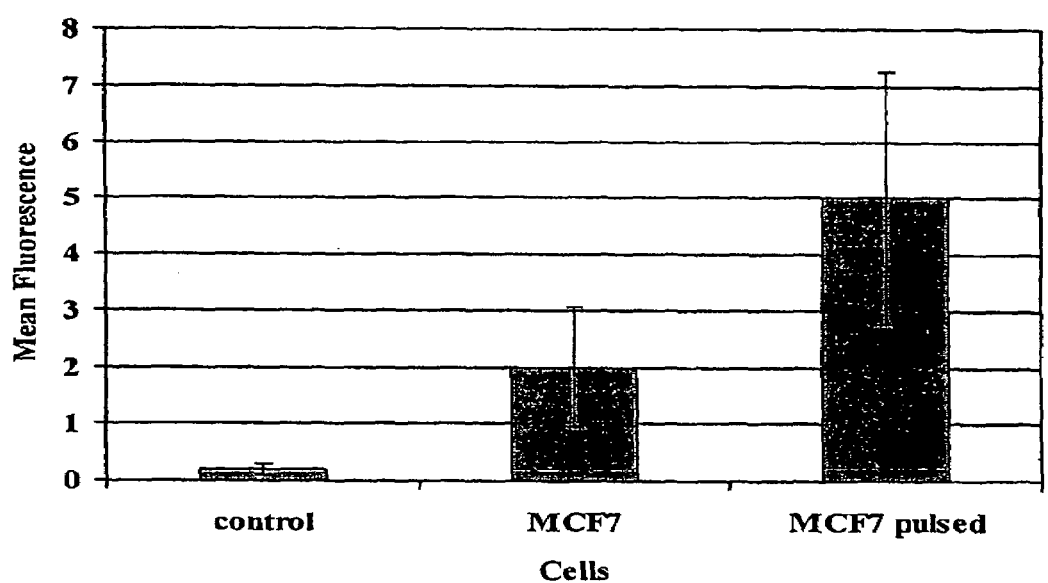
FIG. 42. Detection of HLA-A2/MUC1-derived peptide complexes on tumor cells. MCF7 cells were stained with the specific-D6 M3A1-tetramer with or without peptide pulsing. Controls are MCF7 cells pulsed with HLA-A2-restricted melanoma specific gp100-derived peptide. Shown are mean fluorescence results of 5 representative experiments.

We also detected the natural occurrence of HLA-A2/Mucin1-D6 complexes on MCF7 cells without prior peptide pulsing, using the Fab M3A1 tetramer. These cells represent the normal situation in which MHC-peptide complexes are expected to be present on tumor cells at a much lower density on the cell surface compared with the peptide-loaded APCs or peptide-pulsed tumor cells. As control, we used MCF7 cells pulsed with the MUC1/D6 peptide (positive control) and other HLA-A2 restricted peptides (negative control) at a concentration of 10 μM. The MUC1/D6-specific Fab M3A1 tetramer reacted specifically and yielded a significant intensity of staining compared to controls with the D6-pulsed and native MCF7 cells (FIG. 42), but not with the cells pulsed with non-specific peptide. MUC1 expression in these cells was visualized by staining with an anti-Mucin1 antibody. These results demonstrate the ability of these high-affinity TCR-like antibodies to detect MHC-peptide complexes on the surface of tumor cells.

Thus, these TCR-like antibodies can bind to cells that express the specific MHC-peptide complex at a density most likely to be found on tumor cells, antigen-presenting cells such as dendritic cells, and other cells involved in tumor-antigen presentation to the immune system.

TAX

Using the methods described above, antibodies against the TAX-MHC complex were isolated. Three exemplary antibodies are T3E3, T3F1, and T3F2.

Other embodiments are within the claims and in the summary.

What is claimed is:

1. A protein comprising an immunoglobulin heavy chain variable (VH) domain and an immunoglobulin light chain variable (VL) domain, wherein the protein binds a complex comprising a major histocompatibility complex (MHC) which comprises HLA-A*0201 and a hTERT-derived peptide T540 (ILAKFLHWL; SEQ ID NO:5), does not substantially bind the MHC in the absence of the bound peptide, and does not substantially bind the peptide in the absence of the MHC, and comprises all the six CDRs of the variable region of the light chain and of the heavy chain, respectively, 4A9 (SEQ ID NOs:84 and 86), or 4G9 (SEQ ID NOs:96 and 98), or 4C2 (SEQ ID NOs:92 and 94), or 4B4 (SEQ ID NOs:88 and 90).

2. A protein comprising an immunoglobulin heavy chain variable (VH) domain and an immunoglobulin light chain variable (VL) domain, wherein the protein binds a complex comprising a major histocompatibility complex (MHC) which comprises HLA-A*0201 and a hTERT-derived peptide T865 (RLVDDFLLV; SEQ ID NO:6), does not substantially bind the MHC in the absence of the bound peptide, and does not substantially bind the peptide in the absence of the MHC, and comprises all the six CDRs of the variable region of the light chain and of the heavy chain, respectively, 3H2 (SEQ ID NOs:116 and 118), or 3G3 (SEQ ID NOs:112 and 114), or 3A12 (SEQ ID NOs:100 and 102), or 3F5 (SEQ ID NOs:108 and 110), or 3B1 (SEQ ID NOs:104 and 106).

* * * * *

SEQUENCE LISTING

```
<160> NUMBER OF SEQ ID NOS: 121

<210> SEQ ID NO 1
<211> LENGTH: 9
<212> TYPE: PRT
<213> ORGANISM: Homo sapiens

<400> SEQUENCE: 1

Ile Met Asp Gln Val Pro Phe Ser Val
 1               5

<210> SEQ ID NO 2
<211> LENGTH: 9
<212> TYPE: PRT
<213> ORGANISM: Homo sapiens

<400> SEQUENCE: 2

Tyr Leu Glu Pro Gly Pro Val Thr Val
 1               5

<210> SEQ ID NO 3
<211> LENGTH: 9
<212> TYPE: PRT
<213> ORGANISM: Homo sapiens

<400> SEQUENCE: 3

Lys Thr Trp Gly Gln Tyr Trp Gln Val
 1               5

<210> SEQ ID NO 4
<211> LENGTH: 9
<212> TYPE: PRT
<213> ORGANISM: Homo sapiens

<400> SEQUENCE: 4

Leu Leu Leu Thr Val Leu Thr Val Val
 1               5

<210> SEQ ID NO 5
<211> LENGTH: 9
<212> TYPE: PRT
<213> ORGANISM: Homo sapiens

<400> SEQUENCE: 5

Ile Leu Ala Lys Phe Leu His Trp Leu
 1               5

<210> SEQ ID NO 6
<211> LENGTH: 9
<212> TYPE: PRT
<213> ORGANISM: Homo sapiens

<400> SEQUENCE: 6

Arg Leu Val Asp Asp Phe Leu Leu Val
 1               5
```

<210> SEQ ID NO 7
<211> LENGTH: 324
<212> TYPE: DNA
<213> ORGANISM: Homo sapiens

<400> SEQUENCE: 7

```
gacatccagt tgacccagtc tccatcctcc ctgtctgcat ctgtaggaga cagagtcacc    60
atcacttgcc gggcaagtca gagcattagc acctatttaa attggtatca acacagacca   120
gggaaagccc ctaagctcct gatctattct gcatccagtt tgcagagtgg ggtcccatca   180
aggttcagtg gcagtgggtc tgggacagat ttcactctca ccatcagcag tctccaacct   240
gaagattttg caacctacta ctgtcagcag agtgacatta tccctctcac tttcggcgga   300
gggaccaagg tggagatcaa ccga                                          324
```

<210> SEQ ID NO 8
<211> LENGTH: 108
<212> TYPE: PRT
<213> ORGANISM: Homo sapiens

<400> SEQUENCE: 8

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Thr Tyr
            20                  25                  30

Leu Asn Trp Tyr Gln His Arg Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Ile Pro Leu
                85                  90                  95

Thr Phe Gly Gly Gly Thr Lys Val Glu Ile Asn Arg
            100                 105
```

<210> SEQ ID NO 9
<211> LENGTH: 369
<212> TYPE: DNA
<213> ORGANISM: Homo sapiens

<400> SEQUENCE: 9

```
caggtacagc tgcagcagtc aggtccagga ctggtgaagc cctcgcagac cctctcactc    60
acctgcgcca tctccgggga cagtatctct agtaacagtg ttgtttggaa ctggatcagg   120
cagtccccat cgagaggcct tgagtggctg gaaggacat actataggtc caagtggtat    180
aatgattatg cagtatctgt gaaaagtcga ataaccatca cccgacac atccaagaac    240
cagttctccc tgcaactgaa ctctgtgact cccgacgaca cggctctcta ttactgtgca   300
agagcatcat ttgggaccag cggcaaattc gacgactggg gccagggaac cctggtcacc   360
gtctcaagc                                                           369
```

<210> SEQ ID NO 10
<211> LENGTH: 123
<212> TYPE: PRT
<213> ORGANISM: Homo sapiens

<400> SEQUENCE: 10

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Ile Ser Ser Asn
            20                  25                  30

Ser Val Val Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Asp Thr Ala Leu
                85                  90                  95

Tyr Tyr Cys Ala Arg Ala Ser Phe Gly Thr Ser Gly Lys Phe Asp Asp
            100                 105                 110

Trp Gly Gln Gly Thr Leu Val Thr Val Ser Ser
        115                 120

<210> SEQ ID NO 11
<211> LENGTH: 330
<212> TYPE: DNA
<213> ORGANISM: Homo sapiens

<400> SEQUENCE: 11
cagtctgtcg tgacgcagcc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tatggtaaca gcaatcggcc ctcaggggtc     180
cctgaccgat tctctggctc caagtctggc acctcagcct ccctggccat cactgggctc     240
caggctgagg atgaggctga ttattactgc cagtcctatg acagcagcct gagtgcccta     300
ttcggcggag ggaccaagct gaccgtccta                                     330

<210> SEQ ID NO 12
<211> LENGTH: 110
<212> TYPE: PRT
<213> ORGANISM: Homo sapiens

<400> SEQUENCE: 12

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Leu Phe Gly Gly Gly Thr Lys Leu Thr Val Leu
            100                 105                 110

<210> SEQ ID NO 13
<211> LENGTH: 381
<212> TYPE: DNA
<213> ORGANISM: Homo sapiens

<400> SEQUENCE: 13

```
caggtacagc tgcagcagtc aggcccagga ctggtgaagc cttcggagac cctgtccctc    60
acttgcactg tctctggtgg ctccatcaga aattactact ggagctggat ccggcagccc   120
ccagggaagg gactggagtg gattgggtat atgtattaca gtgggggagc caattacaac   180
ccctccctca acagtcgagt caccatatca ctagacacgt ccaagaacca gttctccctg   240
aaactgacct ctgtgaccgc tgcggacacg gccgtgtatt attgtgcgag aattcccaac   300
tactatgata agagtggtta ttatcccggt tactggtact cgatctctg gggccgtgga   360
accctggtca ccgtctcaag c                                             381
```

<210> SEQ ID NO 14
<211> LENGTH: 127
<212> TYPE: PRT
<213> ORGANISM: Homo sapiens

<400> SEQUENCE: 14

```
Gln Val Gln Leu Gln Gln Ser Gly Pro Gly Leu Val Lys Pro Ser Glu
  1               5                  10                  15

Thr Leu Ser Leu Thr Cys Thr Val Ser Gly Gly Ser Ile Arg Asn Tyr
             20                  25                  30

Tyr Trp Ser Trp Ile Arg Gln Pro Pro Gly Lys Gly Leu Glu Trp Ile
         35                  40                  45

Gly Tyr Met Tyr Tyr Ser Gly Gly Ala Asn Tyr Asn Pro Ser Leu Asn
     50                  55                  60

Ser Arg Val Thr Ile Ser Leu Asp Thr Ser Lys Asn Gln Phe Ser Leu
 65                  70                  75                  80

Lys Leu Thr Ser Val Thr Ala Ala Asp Thr Ala Val Tyr Tyr Cys Ala
                 85                  90                  95

Arg Ile Pro Asn Tyr Tyr Asp Arg Ser Gly Tyr Tyr Pro Gly Tyr Trp
            100                 105                 110

Tyr Phe Asp Leu Trp Gly Arg Gly Thr Leu Val Thr Val Ser Ser
        115                 120                 125
```

<210> SEQ ID NO 15
<211> LENGTH: 339
<212> TYPE: DNA
<213> ORGANISM: Homo sapiens

<400> SEQUENCE: 15

```
gatgttgtga tgactcagtc tccactctcc ctgcccgtca cccctggaga gccggcctcc    60
atctcctgca ggtctagtca gagcctcctg cacagtaatg gatacaagta tgtgaattgg   120
tacctgcaga agccggggca gtctccacag ctcctgatct atttcggttc ttatcgggcc   180
tccggggtcc ctgacaggtt cagtggcagt ggatcaggca cagattttac actgaaaatc   240
agcagagtgg aggctgagga tgttgggatt tattactgca tgcaagctac acactggccg   300
tacactttg gccaggggac caggctggag atcaaacga                          339
```

<210> SEQ ID NO 16
<211> LENGTH: 113
<212> TYPE: PRT
<213> ORGANISM: Homo sapiens

<400> SEQUENCE: 16

```
Asp Val Val Met Thr Gln Ser Pro Leu Ser Leu Pro Val Thr Pro Gly
  1               5                  10                  15
```

Glu Pro Ala Ser Ile Ser Cys Arg Ser Ser Gln Ser Leu Leu His Ser
            20                  25                  30

Asn Gly Tyr Lys Tyr Val Asn Trp Tyr Leu Gln Lys Pro Gly Gln Ser
        35                  40                  45

Pro Gln Leu Leu Ile Tyr Phe Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Thr His Trp Pro Tyr Thr Phe Gly Gln Gly Thr Arg Leu Glu Ile Lys
                100                 105                 110

Arg

<210> SEQ ID NO 17
<211> LENGTH: 360
<212> TYPE: DNA
<213> ORGANISM: Homo sapiens

<400> SEQUENCE: 17
caggtgcagc tggtgcagtc tggggagggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagattac     300
tacggtgact acgctttgct tgactactgg ggccagggca ccctggtcac cgtctcaagc     360

<210> SEQ ID NO 18
<211> LENGTH: 120
<212> TYPE: PRT
<213> ORGANISM: Homo sapiens

<400> SEQUENCE: 18

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Gly Asp Tyr Ala Leu Leu Asp Tyr Trp Gly Gln
                100                 105                 110

Gly Thr Leu Val Thr Val Ser Ser
        115                 120

<210> SEQ ID NO 19
<211> LENGTH: 324
<212> TYPE: DNA
<213> ORGANISM: Homo sapiens

<400> SEQUENCE: 19

```
gacatccagt tgacccagtc tccatcctcc ctgtctgcat ctgtaggaga cagagtcacc    60
atcacttgcc gggcaagtca gagcattagc acctatttaa attggtatca acacagacca   120
gggaaagccc ctaagctcct gatctattct gcatccagtt tgcagagtgg ggtcccatca   180
aggttcagtg gcagtgggtc tgggacagat ttcactctca ccatcagcag tctccaacct   240
gaagattttg caacctacta ctgtcagcag agtgacatta tccctctcac tttcggcgga   300
gggaccaagg tggagatcaa ccga                                          324
```

<210> SEQ ID NO 20
<211> LENGTH: 108
<212> TYPE: PRT
<213> ORGANISM: Homo sapiens

<400> SEQUENCE: 20

```
Asp Ile Gln Leu Thr Gln Ser Pro Ser Ser Leu Ser Ala Ser Val Gly
 1               5                  10                  15
Asp Arg Val Thr Ile Thr Cys Arg Ala Ser Gln Ser Ile Ser Thr Tyr
            20                  25                  30
Leu Asn Trp Tyr Gln His Arg Pro Gly Lys Ala Pro Lys Leu Leu Ile
        35                  40                  45
Tyr Ser Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Asp Ile Ile Pro Leu
                85                  90                  95
Thr Phe Gly Gly Gly Thr Lys Val Glu Ile Asn Arg
            100                 105
```

<210> SEQ ID NO 21
<211> LENGTH: 369
<212> TYPE: DNA
<213> ORGANISM: Homo sapiens

<400> SEQUENCE: 21

```
caggtacagc tgcagcagtc aggtccagga ctggtgaagc cctcgcagac cctctcactc    60
acctgcgcca tctccgggga cagtatctct agtaacagtg ttgtttggaa ctggatcagg   120
cagtccccat cgagaggcct tgagtggctg gaaggacat actataggtc caagtggtat    180
aatgattatg cagtatctgt gaaaagtcga ataaccatca cccagacac atccaagaac    240
cagttctccc tgcaactgaa ctctgtgact cccgacgaca cggctctcta ttactgtgca   300
agagcatcat ttgggaccag cggcaaattc gacgactggg gccagggaac cctggtcacc   360
gtctcaagc                                                          369
```

<210> SEQ ID NO 22
<211> LENGTH: 123
<212> TYPE: PRT
<213> ORGANISM: Homo sapiens

<400> SEQUENCE: 22

```
Gln Val Gln Leu Gln Gln Ser Gly Pro Gly Leu Val Lys Pro Ser Gln
 1               5                  10                  15
Thr Leu Ser Leu Thr Cys Ala Ile Ser Gly Asp Ser Ile Ser Ser Asn
            20                  25                  30
```

Ser Val Val Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Asp Thr Ala Leu
                85                  90                  95

Tyr Tyr Cys Ala Arg Ala Ser Phe Gly Thr Ser Gly Lys Phe Asp Asp
            100                 105                 110

Trp Gly Gln Gly Thr Leu Val Thr Val Ser Ser
        115                 120

<210> SEQ ID NO 23
<211> LENGTH: 327
<212> TYPE: DNA
<213> ORGANISM: Homo sapiens

<400> SEQUENCE: 23
gaaacgacac tcacgcagtc tccaggcacc ctgtctttgt ctccaggaga gagagccacc      60
ctctcctgca gggccagtcg gtatattaac gccaacttct tagcctggta ccagcagaaa     120
cctggccagg ctcccaggct cctcatctat gatgcatcca cccggccac tggcatccca      180 gacaggttca gtggcagtgg gtctgggaca gacttcactc tcaccatcag caggctggag     240
cctgaagatt ttgcagtgta ttactgtcag cagtatggta gctcacctcg acgttcggc      300 caggggacca aggtggaaat caaacga                                          327

<210> SEQ ID NO 24
<211> LENGTH: 109
<212> TYPE: PRT
<213> ORGANISM: Homo sapiens

<400> SEQUENCE: 24

Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Arg Tyr Ile Asn Ala Asn
            20                  25                  30

Phe Leu Ala Trp Tyr Gln Gln Lys Pro Gly Gln Ala Pro Arg Leu Leu
        35                  40                  45

Ile Tyr Asp Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys Arg
            100                 105

<210> SEQ ID NO 25
<211> LENGTH: 366
<212> TYPE: DNA
<213> ORGANISM: Homo sapiens

<400> SEQUENCE: 25
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120

```
cctggacaag ggcttgagtg gatgggaggg atcatccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagattcc    300
agcagtggct ggctctatga tgcttttgat atctggggcc aagggacaat ggtcaccgtc    360
tcaagc                                                              366
```

```
<210> SEQ ID NO 26
<211> LENGTH: 122
<212> TYPE: PRT
<213> ORGANISM: Homo sapiens

<400> SEQUENCE: 26
```

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Gly Trp Leu Tyr Asp Ala Phe Asp Ile Trp
            100                 105                 110

Gly Gln Gly Thr Met Val Thr Val Ser Ser
        115                 120

```
<210> SEQ ID NO 27
<211> LENGTH: 327
<212> TYPE: DNA
<213> ORGANISM: Homo sapiens

<400> SEQUENCE: 27
```

```
gaaattgtgc tgactcagtc tccagacacc ctgtctttgt ctccagggga aagagccacc    60
ctctcctgca gggccagtca gagtgttagc cacagctact tagcctggta ccagcagaaa    120
cctggccagg ctcccaggct cctcatttat gatacatcca gcagggccac tgacatccca    180
gacaggttca gtggcagtgg gtctgggaca gacttcactc tcaccatcag cagattggag    240
cctgaagatt ctgcagtgta ttactgtcag cagtatgtta gctcacctct cacttttggc    300
caggggacca gctggagat caaacga                                        327
```

```
<210> SEQ ID NO 28
<211> LENGTH: 109
<212> TYPE: PRT
<213> ORGANISM: Homo sapiens

<400> SEQUENCE: 28
```

Glu Ile Val Leu Thr Gln Ser Pro Asp Thr Leu Ser Leu Ser Pro Gly
 1               5                  10                  15

Glu Arg Ala Thr Leu Ser Cys Arg Ala Ser Gln Ser Val Ser His Ser
            20                  25                  30

Tyr Leu Ala Trp Tyr Gln Gln Lys Pro Gly Gln Ala Pro Arg Leu Leu
        35                  40                  45

```
Ile Tyr Asp Thr Ser Ser Arg Ala Thr Asp Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Ser Ala Val Tyr Tyr Cys Gln Gln Tyr Val Ser Ser Pro
                 85                  90                  95
Leu Thr Phe Gly Gln Gly Thr Lys Leu Glu Ile Lys Arg
            100                 105
```

<210> SEQ ID NO 29
<211> LENGTH: 366
<212> TYPE: DNA
<213> ORGANISM: Homo sapiens

<400> SEQUENCE: 29

```
caggtccagc tggtacagtc tgggggaggc gtggtccagc ctgggaggtc cctgagactc      60
tcctgtgcag cctctggatt caccttcagt acctatggct tgcactgggt ccgccaggct     120
ccaggcaagg ggctggagtg ggtggcattt atatcatatg atggaagtaa taaatactac     180
gcagactccg tgaagggccg attcaccatc tccagagaca attccaagaa cacgctgtat     240
ctgcaaatga acggcctgag agccgaggac acggccgtat attactgtgc gaagactgtg     300
ggtgtcacgt ttgtctcgga tgcttttgat atatggggcc aagggacaat ggtcaccgtc     360
tcaagc                                                                366
```

<210> SEQ ID NO 30
<211> LENGTH: 122
<212> TYPE: PRT
<213> ORGANISM: Homo sapiens

<400> SEQUENCE: 30

```
Gln Val Gln Leu Val Gln Ser Gly Gly Gly Val Val Gln Pro Gly Arg
  1               5                  10                  15
Ser Leu Arg Leu Ser Cys Ala Ala Ser Gly Phe Thr Phe Ser Thr Tyr
                 20                  25                  30
Gly Leu His Trp Val Arg Gln Ala Pro Gly Lys Gly Leu Glu Trp Val
             35                  40                  45
Ala Phe Ile Ser Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Gly Leu Arg Ala Glu Asp Thr Ala Val Tyr Tyr Cys
                 85                  90                  95
Ala Lys Thr Val Gly Val Thr Phe Val Ser Asp Ala Phe Asp Ile Trp
            100                 105                 110
Gly Gln Gly Thr Met Val Thr Val Ser Ser
            115                 120
```

<210> SEQ ID NO 31
<211> LENGTH: 327
<212> TYPE: DNA
<213> ORGANISM: Homo sapiens

<400> SEQUENCE: 31

```
gatgttgtga tgactcagtc tccaggcacc ctgtctgtgt ctccggggga tagcgccacc      60
ctctcctgct gggccagtca gagtcttagt gacagctacg tgtcctggta ccaacagaag     120
cctggccagg ctcccaggct cctaatacat agcgcgtcca tcagggcccc tggcatcccg     180
```

```
gacaggttca gtggcagtgt gtctggcacg gagttcactc tgaccatcag cggactggag    240
cctgaagatt ttgcagtgta ttcctgtcac cagtatggtt tcttaccttg gacgttcggc    300
caagggacca aggtggagat cagacga                                        327
```

<210> SEQ ID NO 32
<211> LENGTH: 109
<212> TYPE: PRT
<213> ORGANISM: Homo sapiens

<400> SEQUENCE: 32

```
Asp Val Val Met Thr Gln Ser Pro Gly Thr Leu Ser Val Ser Pro Gly
  1               5                  10                  15

Asp Ser Ala Thr Leu Ser Cys Trp Ala Ser Gln Ser Leu Ser Asp Ser
             20                  25                  30

Tyr Val Ser Trp Tyr Gln Gln Lys Pro Gly Gln Ala Pro Arg Leu Leu
         35                  40                  45

Ile His Ser Ala Ser Ile Arg Ala Pro Gly Ile Pro Asp Arg Phe Ser
     50                  55                  60

Gly Ser Val Ser Gly Thr Glu Phe Thr Leu Thr Ile Ser Gly Leu Glu
 65                  70                  75                  80

Pro Glu Asp Phe Ala Val Tyr Ser Cys His Gln Tyr Gly Phe Leu Pro
                 85                  90                  95

Trp Thr Phe Gly Gln Gly Thr Lys Val Glu Ile Arg Arg
            100                 105
```

<210> SEQ ID NO 33
<211> LENGTH: 360
<212> TYPE: DNA
<213> ORGANISM: Homo sapiens

<400> SEQUENCE: 33

```
caggtccagc tggtacagtc tggggctgag gtgaagaagc ctggggcctc agtgaaggtc     60
tcctgcaagg cttctggtta cacctttacc aggtatggta tcagctgggt gcgacaggcc    120
cctggacaag gcttgagtg atgggatgg atcagctctt ccaatggtta cacaaagtat    180
gcacagaatc tccagggcag actcaccctg accacagaca catccacggg cacagcctac    240
atggaactga ggagcctgag atctgaggac acggcccttt attactgtgc gagatatgat    300
attagtggcc tagatggttt tgatatttgg ggccaaggga caatggtcac cgtctcaagc    360
```

<210> SEQ ID NO 34
<211> LENGTH: 120
<212> TYPE: PRT
<213> ORGANISM: Homo sapiens

<400> SEQUENCE: 34

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Arg Tyr
             20                  25                  30

Gly Ile Ser Trp Val Arg Gln Ala Pro Gly Gln Gly Leu Glu Trp Met
         35                  40                  45

Gly Trp Ile Ser Ser Ser Asn Gly Tyr Thr Lys Tyr Ala Gln Asn Leu
     50                  55                  60

Gln Gly Arg Leu Thr Leu Thr Thr Asp Thr Ser Thr Gly Thr Ala Tyr
 65                  70                  75                  80
```

```
Met Glu Leu Arg Ser Leu Arg Ser Glu Asp Thr Ala Leu Tyr Tyr Cys
             85                  90                  95

Ala Arg Tyr Asp Ile Ser Gly Leu Asp Gly Phe Asp Ile Trp Gly Gln
            100                 105                 110

Gly Thr Met Val Thr Val Ser Ser
        115                 120

<210> SEQ ID NO 35
<211> LENGTH: 324
<212> TYPE: DNA
<213> ORGANISM: Homo sapiens

<400> SEQUENCE: 35
gaaacgacac tcacgcagtc tccaggcacc ctgtctttgt ctccagggga aagagccacc     60
ctctcctgca gggccagtca gagtgttagc agcaactact tagcctggta ccagcagaaa   120
cctggccagg ctcccaggct cctcatctat gctgcttcca gcagggccac tggcatccca   180
gacaggttca gtggcagtgg gtctgggaca gacttcactc tcaccatcag cagactggag   240
cctgaagatt ttgcagtgta ttactgtcag cagtatggtt cctcacgcag ttttggccag   300
gggaccaagc tggagatcaa acga                                          324

<210> SEQ ID NO 36
<211> LENGTH: 108
<212> TYPE: PRT
<213> ORGANISM: Homo sapiens

<400> SEQUENCE: 36

Glu Thr Thr Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Asn
             20                  25                  30

Tyr Leu Ala Trp Tyr Gln Gln Lys Pro Gly Gln Ala Pro Arg Leu Leu
         35                  40                  45

Ile Tyr Ala Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Arg
             85                  90                  95

Ser Phe Gly Gln Gly Thr Lys Leu Glu Ile Lys Arg
            100                 105

<210> SEQ ID NO 37
<211> LENGTH: 363
<212> TYPE: DNA
<213> ORGANISM: Homo sapiens

<400> SEQUENCE: 37
caggtgcagc tgcaggagtc tgggggaggc tggtcaagc ctgggggtc cctgagactc     60 tcctgtgcag cctctggatt caccttcagt agctatagca tgaactgggt ccgccaggct   120
ccagggaagg ggctggagtg ggtttcatac attagtagta gtggtagtac catatactac   180
gcagactctg tgaggggccg attcaccatc tccagagaca acgccaagaa cacgctgtat   240
ctccaaatga acagtctgag agccgaggac acagctgttt attactgtgt aagaggtgat   300
ccttacttct actactacgg tatggacatc tggggccaag gaccacggt caccgtctca   360 agc                                                                 363
```

<210> SEQ ID NO 38
<211> LENGTH: 121
<212> TYPE: PRT
<213> ORGANISM: Homo sapiens

<400> SEQUENCE: 38

Gln Val Gln Leu Gln Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Ser Met Asn Trp Val Arg Gln Ala Pro Gly Lys Gly Leu Glu Trp Val
        35                  40                  45
Ser Tyr Ile Ser Ser Ser Gly Ser Thr Ile Tyr Tyr Ala Asp Ser Val
    50                  55                  60
Arg Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Val Arg Gly Asp Pro Tyr Phe Tyr Tyr Tyr Gly Met Asp Ile Trp Gly
            100                 105                 110
Gln Gly Thr Thr Val Thr Val Ser Ser
        115                 120

<210> SEQ ID NO 39
<211> LENGTH: 327
<212> TYPE: DNA
<213> ORGANISM: Homo sapiens

<400> SEQUENCE: 39
gacatccagt tgacccagtc tccatcctcc ctgtctgctt ctgtaggaga cagagtcatc      60
atcacttgcc gggcaactca gagcattagc acccacttaa attggtatca gcagaagcca    120
gggaaagccc ctaagctcct gatctattct gcatccagtt acaaagtggg gtcccatct     180
aggttcagtg gcagtggatc tgggacagat ttcactctca ccatcagcag tctgcaacct    240
gaagattttg caacttacta ctgtcaacag agttacagtt ccccccccgat caccttcggc   300
caagggacac gactggagat taaacga                                        327

<210> SEQ ID NO 40
<211> LENGTH: 109
<212> TYPE: PRT
<213> ORGANISM: Homo sapiens

<400> SEQUENCE: 40

Asp Ile Gln Leu Thr Gln Ser Pro Ser Ser Leu Ser Ala Ser Val Gly
1               5                   10                  15
Asp Arg Val Ile Ile Thr Cys Arg Ala Thr Gln Ser Ile Ser Thr His
            20                  25                  30
Leu Asn Trp Tyr Gln Gln Lys Pro Gly Lys Ala Pro Lys Leu Leu Ile
        35                  40                  45
Tyr Ser Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Ser Pro Pro
                85                  90                  95

```
Ile Thr Phe Gly Gln Gly Thr Arg Leu Glu Ile Lys Arg
            100                 105
```

<210> SEQ ID NO 41
<211> LENGTH: 360
<212> TYPE: DNA
<213> ORGANISM: Homo sapiens

<400> SEQUENCE: 41

```
caggtgcagc tgcaggagtc cggcccagga ctggtgaagc cttcggagac cctgtccctc    60
acctgcactg tctctggtgg ctccatcagt agtaacatgt actactgggg ctgggtccgc   120
cagcccccag ggaaggggct ggagtggatt gggagtatcg attatagtgg gagcacctac   180
tacaatccgt ccctcaggag tcgagtcacc atgtccgtag acacgtccaa gaagcagttc   240
tccctgaaga tgacctctgt gaccgctgcg gacacggccg tgtattactg tgcgagagaa   300
tccgggtccc catactactt tgactactgg ggccagggca ccctggtcac cgtctcaagc   360
```

<210> SEQ ID NO 42
<211> LENGTH: 120
<212> TYPE: PRT
<213> ORGANISM: Homo sapiens

<400> SEQUENCE: 42

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Asn
             20                  25                  30

Met Tyr Tyr Trp Gly Trp Val Arg Gln Pro Pro Gly Lys Gly Leu Glu
         35                  40                  45

Trp Ile Gly Ser Ile Asp Tyr Ser Gly Ser Thr Tyr Tyr Asn Pro Ser
     50                  55                  60

Leu Arg Ser Arg Val Thr Met Ser Val Asp Thr Ser Lys Lys Gln Phe
 65                  70                  75                  80

Ser Leu Lys Met Thr Ser Val Thr Ala Ala Asp Thr Ala Val Tyr Tyr
                 85                  90                  95

Cys Ala Arg Glu Ser Gly Ser Pro Tyr Tyr Phe Asp Tyr Trp Gly Gln
            100                 105                 110

Gly Thr Leu Val Thr Val Ser Ser
            115                 120
```

<210> SEQ ID NO 43
<211> LENGTH: 330
<212> TYPE: DNA
<213> ORGANISM: Homo sapiens

<400> SEQUENCE: 43

```
cagtctgtgt tgacgcagcc gccctcagtg tctgcggccc caggacagac agtcaccatc    60
tcctgctctg gaagcagctc caacattggg aggaattatg tctcgtggtt ccaacaagtc   120
ccagggagag cccccaaact cctcatttat gacaataatc agcgaccgtc agggattcct   180
ggccgattct cagcctccaa gtctgacacc tcagccaccc tggacatcac cggactccag   240
agtggggacg aggccgttta ttactgcgga acatgggatt ccaccctgga cctttatgtc   300
ttcggcggtg ggaccatgt ccccgtccta                                      330
```

<210> SEQ ID NO 44
<211> LENGTH: 110
<212> TYPE: PRT

<213> ORGANISM: Homo sapiens

<400> SEQUENCE: 44

Gln Ser Val Leu Thr Gln Pro Pro Ser Val Ala Ala Pro Gly Gln
1               5                   10                  15

Thr Val Thr Ile Ser Cys Ser Gly Ser Ser Asn Ile Gly Arg Asn
            20                  25                  30

Tyr Val Ser Trp Phe Gln Gln Val Pro Gly Arg Ala Pro Lys Leu Leu
        35                  40                  45

Ile Tyr Asp Asn Asn Gln Arg Pro Ser Gly Ile Pro Gly Arg Phe Ser
50                  55                  60

Ala Ser Lys Ser Asp Thr Ser Ala Thr Leu Asp Ile Thr Gly Leu Gln
65                  70                  75                  80

Ser Gly Asp Glu Ala Val Tyr Tyr Cys Gly Thr Trp Asp Ser Thr Leu
                85                  90                  95

Asp Leu Tyr Val Phe Gly Gly Gly Thr His Val Pro Val Leu
            100                 105                 110

<210> SEQ ID NO 45
<211> LENGTH: 384
<212> TYPE: DNA
<213> ORGANISM: Homo sapiens

<400> SEQUENCE: 45
gaggtccagc tggtgcagtc tggggctgag gtgaagaagc ctggggcctc agtgaaggtt      60
tcctgcaagg catctggata caccttcacc agctactata tccactgggt gcgacaggcc    120
cctggacaag gtcttgagtg gatgggagca atcaacccga gtggtggtag cacaccctac    180
gcacagaagt tccagggcag agtcaccatg accaggaca cgtccacgag cacagtctac     240
atggagctga gcagcctgag atctgaggac acggccgtgt attactgtgc gagagatggg    300
acctatggtt cggggagtta ccctactac tactactacg gtatggacgt ctggggccaa     360
gggaccacgg tcaccgtctc aagc                                            384

<210> SEQ ID NO 46
<211> LENGTH: 128
<212> TYPE: PRT
<213> ORGANISM: Homo sapiens

<400> SEQUENCE: 46

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Ala Ile Asn Pro Ser Gly Gly Ser Thr Pro Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Thr Tyr Gly Ser Gly Ser Tyr Pro Tyr Tyr Tyr
            100                 105                 110

Tyr Gly Met Asp Val Trp Gly Gln Gly Thr Thr Val Thr Val Ser Ser
        115                 120                 125

<210> SEQ ID NO 47
<211> LENGTH: 336
<212> TYPE: DNA
<213> ORGANISM: Homo sapiens

<400> SEQUENCE: 47

```
aattttatgc tgactcagcc ccactctgtg tcggagtctc cgggaaagac ggtaaccatc        60
tcctgcaccg gcagcggtgg cagcattgac aacaattatg tccactggta ccaacagcgc       120 ccggcagtg cccccaccac tgtgatgttt gaagataacc aaagaccctc tggggtccct        180
gatcggttct ctggctccat tgacagctcc tccaactctg cctccctcgt catctctgga       240
ctgaagactg aggacgaggg tgactactac tgtcagtctt ctgatggaag taaagtggtc       300
ttcggcggag ggaccaagct gaccgtccta ggtcag                                 336
```

<210> SEQ ID NO 48
<211> LENGTH: 112
<212> TYPE: PRT
<213> ORGANISM: Homo sapiens

<400> SEQUENCE: 48

```
Asn Phe Met Leu Thr Gln Pro His Ser Val Ser Glu Ser Pro Gly Lys
 1               5                  10                  15

Thr Val Thr Ile Ser Cys Thr Gly Ser Gly Gly Ser Ile Asp Asn Asn
             20                  25                  30

Tyr Val His Trp Tyr Gln Gln Arg Pro Gly Ser Ala Pro Thr Thr Val
         35                  40                  45

Met Phe Glu Asp Asn Gln Arg Pro Ser Gly Val Pro Asp Arg Phe Ser
     50                  55                  60

Gly Ser Ile Asp Ser Ser Ser Asn Ser Ala Ser Leu Val Ile Ser Gly
 65                  70                  75                  80

Leu Lys Thr Glu Asp Glu Gly Asp Tyr Tyr Cys Gln Ser Ser Asp Gly
                 85                  90                  95

Ser Lys Val Val Phe Gly Gly Gly Thr Lys Leu Thr Val Leu Gly Gln
            100                 105                 110
```

<210> SEQ ID NO 49
<211> LENGTH: 372
<212> TYPE: DNA
<213> ORGANISM: Homo sapiens

<400> SEQUENCE: 49

```
gaggtccagc tggtgcagtc tgggggaggc gtggtccagc ctggagggtc cctgacactc        60
tcctgtgcag cctctggatt caccttcagt agctatggca tgcactgggt ccgccaggct       120
ccaggcaagg ggctggagtg ggtgtcagtt atatcatatg atggaagtaa taatactat        180 gcagactccg tgaagggccg attcaccatc tccagagaca attccaagaa cacgctgtat       240
ctgcaaatga acagcctgag aactgaggac acggctgtgt attactgtgc gaaaaccctg       300
tccgcggggg agtggattgg aggggagct tttgatatct ggggccatgg gacaatggtc       360
accgtctcaa gc                                                           372
```

<210> SEQ ID NO 50
<211> LENGTH: 124
<212> TYPE: PRT
<213> ORGANISM: Homo sapiens

<400> SEQUENCE: 50

```
Glu Val Gln Leu Val Gln Ser Gly Gly Gly Val Val Gln Pro Gly Arg
1               5                   10                  15

Ser Leu Thr Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ser Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Lys Thr Leu Ser Ala Gly Glu Trp Ile Gly Gly Gly Ala Phe Asp
                100                 105                 110

Ile Trp Gly His Gly Thr Met Val Thr Val Ser Ser
            115                 120
```

<210> SEQ ID NO 51
<211> LENGTH: 327
<212> TYPE: DNA
<213> ORGANISM: Homo sapiens

<400> SEQUENCE: 51

```
gaaacgacac tcacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagcatgata gctcaccacg gacgttcggc   300
caagggacca aggtggaaat caaacga                                      327
```

<210> SEQ ID NO 52
<211> LENGTH: 109
<212> TYPE: PRT
<213> ORGANISM: Homo sapiens

<400> SEQUENCE: 52

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asp Ser Ser Pro
                85                  90                  95

Arg Thr Phe Gly Gln Gly Thr Lys Val Glu Ile Lys Arg
                100                 105
```

<210> SEQ ID NO 53
<211> LENGTH: 363
<212> TYPE: DNA
<213> ORGANISM: Homo sapiens

<400> SEQUENCE: 53

```
caggtccagc tggtgcagtc tggggggaggc gtggtccagc ctggagggtc cctgagactc      60
tcctgtgcag cctctggatt caccttcagt agttatggca tgcactgggt ccgccaggct     120
ccaggcaagg ggctggagtg ggtggcattt atatcatatg atggaagtga taagaacttt     180
gcagactccg tgaagggccg attcaccatc tccagagaca attccaagaa cactctatat     240
ctgcaaatga acagcctgag agctgaggac acggctgtgt attactgtgc gaaagattcc     300
tactatgata atagtgcttt tcaggcagac tggggccagg gcaccctggt caccgtctca     360
agc                                                                   363
```

<210> SEQ ID NO 54
<211> LENGTH: 121
<212> TYPE: PRT
<213> ORGANISM: Homo sapiens

<400> SEQUENCE: 54

```
Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Ser Tyr Asp Gly Ser Asp Lys Asn Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Tyr Tyr Asp Asn Ser Ala Phe Gln Ala Asp Trp Gly
            100                 105                 110

Gln Gly Thr Leu Val Thr Val Ser Ser
        115                 120
```

<210> SEQ ID NO 55
<211> LENGTH: 330
<212> TYPE: DNA
<213> ORGANISM: Homo sapiens

<400> SEQUENCE: 55

```
aattttatgc tgactcagcc ccactctgtg tcggagtctc cgggaaagac ggtaaccatc      60
tcctgcaccg gcagcggtgg cagcattgac aacaattatg tccactggta ccaacagcgc     120
ccgggcagtg cccccaccac tgtgatgttt gaagataacc aaagaccctc tggggtccct     180
gatcggttct ctggctccat tgacagctcc tccaactctg cctccctcgt catctctgga     240
ctgaagactg aggacgaggg tgactactac tgtcagtctt ctgatggaag taaagtggtc     300
ttcggcggag ggaccaagct gaccgtccta                                       330
```

<210> SEQ ID NO 56
<211> LENGTH: 110
<212> TYPE: PRT
<213> ORGANISM: Homo sapiens

<400> SEQUENCE: 56

```
Asn Phe Met Leu Thr Gln Pro His Ser Val Ser Glu Ser Pro Gly Lys
 1               5                  10                  15
```

Thr Val Thr Ile Ser Cys Thr Gly Gly Ser Ile Asp Asn Asn
            20                  25                  30

Tyr Val His Trp Tyr Gln Gln Arg Pro Gly Ser Ala Pro Thr Thr Val
                35                  40                  45

Met Phe Glu Asp Asn Gln Arg Pro Ser Gly Val Pro Asp Arg Phe Ser
    50                  55                  60

Gly Ser Ile Asp Ser Ser Asn Ser Ala Ser Leu Val Ile Ser Gly
65                  70                  75                  80

Leu Lys Thr Glu Asp Glu Gly Asp Tyr Tyr Cys Gln Ser Ser Asp Gly
                85                  90                  95

Ser Lys Val Val Phe Gly Gly Thr Lys Leu Thr Val Leu
                100                 105                 110

<210> SEQ ID NO 57
<211> LENGTH: 372
<212> TYPE: DNA
<213> ORGANISM: Homo sapiens

<400> SEQUENCE: 57
gaggtccagc tggtgcagtc tgggggaggc gtggtccagc ctgggaggtc cctgacactc    60
tcctgtgcag cctctggatt caccttcagt agctatggca tgcactgggt ccgccaggct   120
ccaggcaagg ggctggagtg ggtgtcagtt atatcatatg atggaagtaa taaatactat   180
gcagactccg tgaagggccg attcaccatc tccagagaca attccaagaa cacgctgtat   240
ctgcaaatga acagcctgag aactgaggac acggctgtgt attactgtgc gaaaaccctg   300
tccgcggggg agtggattgg agggggagct tttgatatct ggggccatgg gacaatggtc   360
accgtctcaa gc                                                       372

<210> SEQ ID NO 58
<211> LENGTH: 124
<212> TYPE: PRT
<213> ORGANISM: Homo sapiens

<400> SEQUENCE: 58

Glu Val Gln Leu Val Gln Ser Gly Gly Gly Val Val Gln Pro Gly Arg
1               5                   10                  15

Ser Leu Thr Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Lys Thr Leu Ser Ala Gly Glu Trp Ile Gly Gly Gly Ala Phe Asp
                100                 105                 110

Ile Trp Gly His Gly Thr Met Val Thr Val Ser Ser
        115                 120

<210> SEQ ID NO 59
<211> LENGTH: 327
<212> TYPE: DNA
<213> ORGANISM: Homo sapiens

<400> SEQUENCE: 59

```
gaaacgacac tcacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagcatgata gctcaccacg acgttcggc    300 caagggacca aggtggaaat caaacga                                      327
```

<210> SEQ ID NO 60
<211> LENGTH: 109
<212> TYPE: PRT
<213> ORGANISM: Homo sapiens

<400> SEQUENCE: 60

```
Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln His Asp Ser Ser Pro
                85                  90                  95

Arg Thr Phe Gly Gln Gly Thr Lys Val Glu Ile Lys Arg
            100                 105
```

<210> SEQ ID NO 61
<211> LENGTH: 363
<212> TYPE: DNA
<213> ORGANISM: Homo sapiens

<400> SEQUENCE: 61

```
caggtccagc tggtgcagtc tggggggaggc gtggtccagc ctgggaggtc cctgagactc    60
tcctgtgcag cctctggatt caccttcagt agttatggca tgcactgggt ccgccaggct   120
ccaggcaagg ggctggagtg ggtggcattt atatcatatg atggaagtga taagaacttt   180
gcagactccg tgaagggccg attcaccatc tccagagaca attccaagaa cactctatat   240
ctgcaaatga acagcctgag agctgaggac acggctgtgt attactgtgc gaaagattcc   300
tactatgata atagtgcttt tcaggcagac tggggccagg gcaccctggt caccgtctca   360
agc                                                                363
```

<210> SEQ ID NO 62
<211> LENGTH: 121
<212> TYPE: PRT
<213> ORGANISM: Homo sapiens

<400> SEQUENCE: 62

```
Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
```

-continued

```
                35                  40                  45
Ala Phe Ile Ser Tyr Asp Gly Ser Asp Lys Asn Phe Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Tyr Tyr Asp Asn Ser Ala Phe Gln Ala Asp Trp Gly
                100                 105                 110

Gln Gly Thr Leu Val Thr Val Ser Ser
            115                 120

<210> SEQ ID NO 63
<211> LENGTH: 327
<212> TYPE: DNA
<213> ORGANISM: Homo sapiens

<400> SEQUENCE: 63
gaaacgacac tcacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctcg aacgttcggc     300
caagggacca aggtggaaat caaacga                                         327

<210> SEQ ID NO 64
<211> LENGTH: 109
<212> TYPE: PRT
<213> ORGANISM: Homo sapiens

<400> SEQUENCE: 64

Glu Thr Thr Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Arg Thr Phe Gly Gln Gly Thr Lys Val Glu Ile Lys Arg
            100                 105

<210> SEQ ID NO 65
<211> LENGTH: 369
<212> TYPE: DNA
<213> ORGANISM: Homo sapiens

<400> SEQUENCE: 65
gaggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gccttgagtg gatgggaggg atcatcccta tctttggtac agcaaactac     180
```

```
gcacagaagt tccagggcag agtcacgatt accgcggacg aatccacgag cacagcctac      240
atggagctga gcagcctgag atctgaggac acggccgtgt attactgtgc gagaggtcca      300
gaatattgta ttaatggtgt atgctctctg gacgtctggg gccaagggac cacggtcacc      360
gtctcaagc                                                              369
```

<210> SEQ ID NO 66
<211> LENGTH: 123
<212> TYPE: PRT
<213> ORGANISM: Homo sapiens

<400> SEQUENCE: 66

```
Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Glu Tyr Cys Ile Asn Gly Val Cys Ser Leu Asp Val
            100                 105                 110

Trp Gly Gln Gly Thr Thr Val Thr Val Ser Ser
        115                 120
```

<210> SEQ ID NO 67
<211> LENGTH: 324
<212> TYPE: DNA
<213> ORGANISM: Homo sapiens

<400> SEQUENCE: 67

```
gaaattgtga tgacacagtc tccagccacc ctgtctttgt ctccagggga aagagccacc       60
ctctcctgca gggccagtca gagtgttagc agctacttag cctggtacca acagaaacct      120
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg cagtgtatta ctgtcaccaa tatggtagct cacctcaaac gttcggccaa      300
gggaccaagg tggaaatcaa acga                                              324
```

<210> SEQ ID NO 68
<211> LENGTH: 108
<212> TYPE: PRT
<213> ORGANISM: Homo sapiens

<400> SEQUENCE: 68

```
Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
```

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Tyr Gly Ser Ser Pro Gln
                85                  90                  95

Thr Phe Gly Gln Gly Thr Lys Val Glu Ile Lys Arg
            100                 105

<210> SEQ ID NO 69
<211> LENGTH: 363
<212> TYPE: DNA
<213> ORGANISM: Homo sapiens

<400> SEQUENCE: 69
gaggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc ggtccactac     300
ggtgactacg tttttctcctc tatggacgtc tggggccaag ggaccacggt caccgtctca     360
agc                                                                    363

<210> SEQ ID NO 70
<211> LENGTH: 121
<212> TYPE: PRT
<213> ORGANISM: Homo sapiens

<400> SEQUENCE: 70

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Val His Tyr Gly Asp Tyr Val Phe Ser Ser Met Asp Val Trp Gly
                100                 105                 110

Gln Gly Thr Thr Val Thr Val Ser Ser
            115                 120

<210> SEQ ID NO 71
<211> LENGTH: 330
<212> TYPE: DNA
<213> ORGANISM: Homo sapiens

<400> SEQUENCE: 71
gaaattgtgc tgactcagtc tccagccacc ctgtctttgt ctccagggga aagagccacc      60
ctctcctgca gggccagtca gagtgttggc agctacttag cctggtacca acagaagcct     120
ggctaggctc ccagactcct catctatgat gcatcccaca gggccactgg catcccagcc     180

```
aggttcagtg gcagtgggtc tgggacagac ttcactctca ccatcagcag cctagagcct    240
gaagattttg cagtttatta ctgtcagcag cgtagcaact ggcctccgat gtacactttt    300
ggccagggga ccaagctgga gatcaaacga                                     330
```

<210> SEQ ID NO 72
<211> LENGTH: 109
<212> TYPE: PRT
<213> ORGANISM: Homo sapiens

<400> SEQUENCE: 72

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Gly Ser Tyr
            20                  25                  30

Leu Ala Trp Tyr Gln Gln Lys Pro Gly Ala Pro Arg Leu Leu Ile Tyr
        35                  40                  45

Asp Ala Ser His Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Asn Trp Pro Pro Met
                85                  90                  95

Tyr Thr Phe Gly Gln Gly Thr Lys Leu Glu Ile Lys Arg
            100                 105
```

<210> SEQ ID NO 73
<211> LENGTH: 366
<212> TYPE: DNA
<213> ORGANISM: Homo sapiens

<400> SEQUENCE: 73

```
gaggtccagc tggtgcagtc tggggctgag gtgaagaagc ctgggtcctc ggtgaaggtc     60
tcctgcaagg cttctggagg caccttcagc agctatacta tcagctgggt gcgacaggcc    120
cctggacaag gcttgagtg gatgggaggg atcatcccta tctttggtac agcaaactac    180
gcacagaagt tccagggcag agtcacgatt accgcggaca aatccacgag cacagcctac    240
atggagctga gcagcctgag atctgaggac acggccgtgt attactgtgc gggggatacg    300
gatagtagtg gttattacgg cgcggttgac tactggggcc agggcaccct ggtcaccgtc    360
tcaagc                                                              366
```

<210> SEQ ID NO 74
<211> LENGTH: 122
<212> TYPE: PRT
<213> ORGANISM: Homo sapiens

<400> SEQUENCE: 74

```
Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Gly Asp Thr Asp Ser Ser Gly Tyr Tyr Gly Ala Val Asp Tyr Trp
            100                 105                 110

Gly Gln Gly Thr Leu Val Thr Val Ser Ser
        115                 120

<210> SEQ ID NO 75
<211> LENGTH: 330
<212> TYPE: DNA
<213> ORGANISM: Homo sapiens

<400> SEQUENCE: 75
gaaattgtgc tgactcagtc tccagccacc ctgtctttgt ctccagggga aagagccacc      60
ctctcctgca gggccagtca gagtgttggc agctacttag cctggtacca acagaagcct     120
ggctaggctc ccagactcct catctatgat gcatcccaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccgat gtacactttt     300
ggccagggga ccaagctgga gatcaaacga                                       330

<210> SEQ ID NO 76
<211> LENGTH: 109
<212> TYPE: PRT
<213> ORGANISM: Homo sapiens

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Lys Pro Gly Ala Pro Arg Leu Leu Ile Tyr
        35                  40                  45

Asp Ala Ser His Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Asn Trp Pro Pro Met
                85                  90                  95

Tyr Thr Phe Gly Gln Gly Thr Lys Leu Glu Ile Lys Arg
            100                 105

<210> SEQ ID NO 77
<211> LENGTH: 366
<212> TYPE: DNA
<213> ORGANISM: Homo sapiens

<400> SEQUENCE: 77
gaggtccagc tggtgcagtc tggggctgag gtgaagaagc ctgggtcctc ggtgaaggtc      60
tcctgcaagg cttctggagg caccttcagc agctatacta tcagctgggt gcgacaggcc     120
cctggacaag gcttgagtg gatgggaggg atcatcccta tctttggtac agcaaactac     180
gcacagaagt tccagggcag agtcacgatt accgcggaca atccacgag cacagcctac      240 atggagctga gcagcctgag atctgaggac acggccgtgt attactgtgc gggggatacg     300
gatagtagtg gttattacgg cgcggttgac tactgggggcc agggcaccct ggtcaccgtc     360
tcaagc                                                                366

<210> SEQ ID NO 78
<211> LENGTH: 122
<212> TYPE: PRT
<213> ORGANISM: Homo sapiens

<400> SEQUENCE: 78

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Asp Thr Asp Ser Ser Gly Tyr Tyr Gly Ala Val Asp Tyr Trp
            100                 105                 110

Gly Gln Gly Thr Leu Val Thr Val Ser Ser
        115                 120

<210> SEQ ID NO 79
<211> LENGTH: 339
<212> TYPE: DNA
<213> ORGANISM: Homo sapiens

<400> SEQUENCE: 79
gaaattgtgc tgactcagtc tccactctcc ctgcccgtca cccctggaga gccggcctcc        60
atctcctgca ggtctagtca gagcctcctg catagtaatg gatacaacta tttggattgg       120
tacctgcaga agccagggca gtctccacag ctcctgatct atttgggttc taatcgggcc       180
tccggggtcc ctgacaggtt cagtggcagt ggatcaggca cagattttac actgaaaatc       240
agcagagtgg aggctgagga tgttggggtt tattactgca tgcaagctct acaaactcct       300
cggacgttcg gccaagggac caaggtggaa atcaaacga                              339

<210> SEQ ID NO 80
<211> LENGTH: 113
<212> TYPE: PRT
<213> ORGANISM: Homo sapiens

<400> SEQUENCE: 80

Glu Ile Val Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

-continued

```
Leu Gln Thr Pro Arg Thr Phe Gly Gln Gly Thr Lys Val Glu Ile Lys
            100                 105                 110
Arg
```

<210> SEQ ID NO 81
<211> LENGTH: 372
<212> TYPE: DNA
<213> ORGANISM: Homo sapiens

<400> SEQUENCE: 81

```
caggtgcagc tggtgcaatc tggggaggc gtggtccagc ctgggaggtc cctgagactc      60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gagagacttt    300
gactacggtg actcatacta ctactacggt atggacgtct ggggccaagg gaccacggtc    360
accgtctcaa gc                                                         372
```

<210> SEQ ID NO 82
<211> LENGTH: 124
<212> TYPE: PRT
<213> ORGANISM: Homo sapiens

<400> SEQUENCE: 82

```
Gln Val Gln Leu Val Gln Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Phe Asp Tyr Gly Asp Ser Tyr Tyr Tyr Gly Met Asp
            100                 105                 110
Val Trp Gly Gln Gly Thr Thr Val Thr Val Ser Ser
        115                 120
```

<210> SEQ ID NO 83
<211> LENGTH: 324
<212> TYPE: DNA
<213> ORGANISM: Homo sapiens

<400> SEQUENCE: 83

```
gacatccaga tgacccagtc tccttccatc ctgtctgcat ctgtaggaga cagagtcacc      60
atcacttgcc gggccagtca gagatttggt gattacttgg cctggtatca gcagaagcca    120
gggcaagccc ctaagctcct gatctatggt gcatccactt tgcagagtgg ggtcccatca    180
aggttcagcg gcagtggctc tgggacagag ttcactctca ccatcagcgg cctgcagcct    240
gaagattttg caacttacta ttgtcagcag gctaacagtt tccccatcac cttcggcaaa    300
gggacacggc tggacatcag acga                                            324
```

<210> SEQ ID NO 84
<211> LENGTH: 108
<212> TYPE: PRT
<213> ORGANISM: Homo sapiens

<400> SEQUENCE: 84

Asp Ile Gln Met Thr Gln Ser Pro Ser Ile Leu Ser Ala Ser Val Gly
1               5                   10                  15

Asp Arg Val Thr Ile Thr Cys Arg Ala Ser Gln Arg Phe Gly Asp Tyr
            20                  25                  30

Leu Ala Trp Tyr Gln Gln Lys Pro Gly Gln Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Lys Gly Thr Arg Leu Asp Ile Arg Arg
            100                 105

<210> SEQ ID NO 85
<211> LENGTH: 357
<212> TYPE: DNA
<213> ORGANISM: Homo sapiens

<400> SEQUENCE: 85
caggtccagc tggtgcagtc tggggctgag gtgaagaagc ctgggtcctc agtgaaggtc      60
tcctgcaagg cttctggagg caccttcagc agctatgcta tcagctgggt gcgacaggcc     120
cctggacaag gcttgagtg gatgggatgg atcaacgttg caatggtaa cgcaatatat       180 tcacagaagt tccagggcag agtcaccatt accagggaca catccgcgac cacagcctac     240
atggaactga gcagcctgag atctgaagac acggctgtgt attactgtgc gagagacggg     300
gagagagcct gggaccttga ctactggggc cagggaaccc tggtcaccgt ctcaagc       357

<210> SEQ ID NO 86
<211> LENGTH: 119
<212> TYPE: PRT
<213> ORGANISM: Homo sapiens

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Asn Val Gly Asn Gly Asn Ala Ile Tyr Ser Gln Lys Phe
    50                  55                  60

Gln Gly Arg Val Thr Ile Thr Arg Asp Thr Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Glu Arg Ala Trp Asp Leu Asp Tyr Trp Gly Gln Gly
            100                 105                 110

Thr Leu Val Thr Val Ser Ser
        115

<210> SEQ ID NO 87
<211> LENGTH: 330
<212> TYPE: DNA
<213> ORGANISM: Homo sapiens

<400> SEQUENCE: 87
aattttatgc tgactcagcc ccactctgtg tcggagtctc cggggaagac cgtaaccatc     60
tcctgcaccg gcagcggtgg cagcattgcc accaactatg tgcagtggta ccagcagcgc    120
ccgggcagtg cccccgccac tgtgatctat gaggatgacc aaagaccctc tggggtccct    180
gatcggttct ctggctccat cgacagctcc tccaactctg cctccctcac catctctgga    240
ctgaagactg aggacgaggc tgactactac tgtcagtctt atgatagcag caatcaggta    300
ttcggcggag ggaccaagct gaccgtccta                                     330

<210> SEQ ID NO 88
<211> LENGTH: 110
<212> TYPE: PRT
<213> ORGANISM: Homo sapiens

<400> SEQUENCE: 88

Asn Phe Met Leu Thr Gln Pro His Ser Val Ser Glu Ser Pro Gly Lys
 1               5                  10                  15

Thr Val Thr Ile Ser Cys Thr Gly Ser Gly Gly Ser Ile Ala Thr Asn
            20                  25                  30

Tyr Val Gln Trp Tyr Gln Gln Arg Pro Gly Ser Ala Pro Ala Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Gln Val Phe Gly Gly Gly Thr Lys Leu Thr Val Leu
            100                 105                 110

<210> SEQ ID NO 89
<211> LENGTH: 354
<212> TYPE: DNA
<213> ORGANISM: Homo sapiens

<400> SEQUENCE: 89
caggtgcagc tacagcagtg gggcgcagga ctgttgaagc cttcggagac cctgtccctc     60
acctgcgctg tctatggtgg gtccttcagt ggttactact ggagctggat ccgccagccc    120
ccagggaagg ggctggagtg gattggggaa atcaatcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtgcgag gatggtacgt    300
tactactacg gtatggacgt ctggggccaa gggaccacgg tcaccgtctc aagc          354

<210> SEQ ID NO 90
<211> LENGTH: 118
<212> TYPE: PRT
<213> ORGANISM: Homo sapiens

<400> SEQUENCE: 90

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                 85                  90                  95

Arg Met Val Arg Tyr Tyr Gly Met Asp Val Trp Gly Gln Gly Thr
            100                 105                 110

Thr Val Thr Val Ser Ser
            115
```

<210> SEQ ID NO 91
<211> LENGTH: 327
<212> TYPE: DNA
<213> ORGANISM: Homo sapiens

<400> SEQUENCE: 91

```
tcctatgtgc tgactcagcc accctcagtg tcagaggccc caggaaagac ggccaggatt    60
acctgtgagg gcatcacgat tggaaggaag agtgtgcatt ggtaccagca gaagccaggc   120
caggcccctg tgttggtcgt ctatgatgat actgtccggc cctcaggggt ccctgagcga   180
ttctctggct ccaactctgg gaacacggcc accctgatca tcagcggagt cgaagccggg   240
gatgaggccg actattactg ccaggtgtgg gatagtagca ctgatcccca gtggtcttc    300 ggcggaggga ccaaggtgac cgtcctg                                       327
```

<210> SEQ ID NO 92
<211> LENGTH: 109
<212> TYPE: PRT
<213> ORGANISM: Homo sapiens

<400> SEQUENCE: 92

```
Ser Tyr Val Leu Thr Gln Pro Pro Ser Val Ser Glu Ala Pro Gly Lys
 1               5                  10                  15

Thr Ala Arg Ile Thr Cys Glu Gly Ile Thr Ile Gly Arg Lys Ser Val
             20                  25                  30

His Trp Tyr Gln Gln Lys Pro Gly Gln Ala Pro Val Leu Val Val Tyr
         35                  40                  45

Asp Asp Thr Val Arg Pro Ser Gly Val Pro Glu Arg Phe Ser Gly Ser
     50                  55                  60

Asn Ser Gly Asn Thr Ala Thr Leu Ile Ile Ser Gly Val Glu Ala Gly
65                  70                  75                  80

Asp Glu Ala Asp Tyr Tyr Cys Gln Val Trp Asp Ser Ser Thr Asp Pro
                 85                  90                  95

Gln Val Val Phe Gly Gly Gly Thr Lys Val Thr Val Leu
            100                 105
```

<210> SEQ ID NO 93
<211> LENGTH: 354
<212> TYPE: DNA
<213> ORGANISM: Homo sapiens

<400> SEQUENCE: 93

```
caggtacagc tgcagcagtc aggtccagga ctggtgaagc cctcgcagac cctctcactc      60
acctgtgcca tctccgggga cagtgtctct agcaagaatt cttcttggaa ctggatcagg     120
cagtccccat cgagaggcct gagtggctg gggaggacat actacaggtc caagtggtat      180
tatgattatg cagtctctgt gaaaggtcga ataaccttca ccccagacac atccaagaac     240
caggtctccc tgcacctgaa cgctgtgact cccgaggaca cggctatgta ttactgtgta     300
agggggcagta ttttgatgt gtggggccaa gggacaatgg tcaccgtctc aagc           354
```

<210> SEQ ID NO 94
<211> LENGTH: 118
<212> TYPE: PRT
<213> ORGANISM: Homo sapiens

<400> SEQUENCE: 94

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Lys
             20                  25                  30

Asn Ser Ser Trp Asn Trp Ile Arg Gln Ser Pro Ser Arg Gly Leu Glu
         35                  40                  45

Trp Leu Gly Arg Thr Tyr Tyr Arg Ser Lys Trp Tyr Tyr Asp Tyr Ala
     50                  55                  60

Val Ser Val Lys Gly Arg Ile Thr Phe Thr Pro Asp Thr Ser Lys Asn
 65                  70                  75                  80

Gln Val Ser Leu His Leu Asn Ala Val Thr Pro Glu Asp Thr Ala Met
                 85                  90                  95

Tyr Tyr Cys Val Arg Gly Ser Ile Phe Asp Val Trp Gly Gln Gly Thr
            100                 105                 110

Met Val Thr Val Ser Ser
        115
```

<210> SEQ ID NO 95
<211> LENGTH: 324
<212> TYPE: DNA
<213> ORGANISM: Homo sapiens

<400> SEQUENCE: 95

```
gacatccaga tgacccagtc tccttccatc ctgtctgcat ctgtaggaga cagagtcacc      60
atcacttgcc gggccagtca gagatttggt gattacttgg cctggtatca gcagaagcca     120
gggcaagccc ctaagctcct gatctatggt gcatccactt tgcagagtgg ggtcccatca     180
aggttcagcg gcagtggctc tgggacagag ttcactctca ccatcagcgg cctgcagcct     240
gaagattttg caacttacta ttgtcagcag gctaacagtt tccccatcac cttcggcaaa     300
gggacacggc tggacatcag acga                                             324
```

<210> SEQ ID NO 96
<211> LENGTH: 108
<212> TYPE: PRT
<213> ORGANISM: Homo sapiens

<400> SEQUENCE: 96

```
Asp Ile Gln Met Thr Gln Ser Pro Ser Ile Leu Ser Ala Ser Val Gly
  1               5                  10                  15

Asp Arg Val Thr Ile Thr Cys Arg Ala Ser Gln Arg Phe Gly Asp Tyr
```

```
                    20                  25                  30
Leu Ala Trp Tyr Gln Gln Lys Pro Gly Gln Ala Pro Lys Leu Leu Ile
            35                  40                  45

Tyr Gly Ala Ser Thr Leu Gln Ser Gly Val Pro Ser Arg Phe Ser Gly
 50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Lys Gly Thr Arg Leu Asp Ile Arg Arg
            100                 105

<210> SEQ ID NO 97
<211> LENGTH: 357
<212> TYPE: DNA
<213> ORGANISM: Homo sapiens

<400> SEQUENCE: 97
caggtccagc tggtgcagtc tggggctgag gtgaagaagc ctgggtcctc agtgaaggtc      60
tcctgcaagg cttctggagg caccttcagc agctatgcta tcagctgggt gcgacaggcc     120
cctggacaag gcttgagtg gatgggatgg atcaacgttg gcaatggtaa cgcaatatat      180
tcacagaagt tccagggcag agtcaccatt accaggaca catccgcgac acagcctac      240 atggaactga gcagcctgag atctgaagac acggctgtgt attactgtgc gagagacggg     300
gagagagcct ggaccttga ctactggggc cagggaaccc tggtcaccgt ctcaagc        357

<210> SEQ ID NO 98
<211> LENGTH: 119
<212> TYPE: PRT
<213> ORGANISM: Homo sapiens

<400> SEQUENCE: 98

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Asn Val Gly Asn Gly Asn Ala Ile Tyr Ser Gln Lys Phe
    50                  55                  60

Gln Gly Arg Val Thr Ile Thr Arg Asp Thr Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Glu Arg Ala Trp Asp Leu Asp Tyr Trp Gly Gln Gly
            100                 105                 110

Thr Leu Val Thr Val Ser Ser
        115

<210> SEQ ID NO 99
<211> LENGTH: 324
<212> TYPE: DNA
<213> ORGANISM: Homo sapiens

<400> SEQUENCE: 99
gaaacgacac tcacgcagtc tccaggcacc ctgtctttgt ctccagggga aagagccacc      60
```

```
ctctcctgca gggccagtca gagtgttagc agcaggtact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaaacac ttttggccag    300
gggaccaagc tggagatcaa acga                                           324
```

<210> SEQ ID NO 100
<211> LENGTH: 108
<212> TYPE: PRT
<213> ORGANISM: Homo sapiens

<400> SEQUENCE: 100

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Asn
                85                  90                  95

Thr Phe Gly Gln Gly Thr Lys Leu Glu Ile Lys Arg
            100                 105

<210> SEQ ID NO 101
<211> LENGTH: 369
<212> TYPE: DNA
<213> ORGANISM: Homo sapiens

<400> SEQUENCE: 101

```
caggtgcagc tgcaggagtc gggcccagga ctggtgaagc cttcggagac cctgtccctc     60
acctgcactg tctctggtgg ctccatcagc agtagtagtt actactgggg ctggatccgc    120
cagcccccag gaaggggct ggagtggatt gggagtatct attatagtgg gagcacctac    180
tacaacccgt ccctcaagag tcgagtcacc atatccgtag acacgtccaa gaaccagttc    240
tccctgaagc tgagctctgt gaccgccgca gacacggctg tgtattactg tgcgagatcc    300
aggagtggga gctacctcaa tgatgctttt gatatctggg gccaagggac aatggtcacc    360
gtctcaagc                                                             369
```

<210> SEQ ID NO 102
<211> LENGTH: 123
<212> TYPE: PRT
<213> ORGANISM: Homo sapiens

<400> SEQUENCE: 102

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser

-continued

```
              50                  55                  60
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ser Arg Ser Gly Ser Tyr Leu Asn Asp Ala Phe Asp Ile
            100                 105                 110

Trp Gly Gln Gly Thr Met Val Thr Val Ser Ser
            115                 120
```

<210> SEQ ID NO 103
<211> LENGTH: 327
<212> TYPE: DNA
<213> ORGANISM: Homo sapiens

<400> SEQUENCE: 103

```
gaaacgacac tcacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcatcggg gacgttcggc     300
caagggacca aggtggaaat caaacga                                         327
```

<210> SEQ ID NO 104
<211> LENGTH: 109
<212> TYPE: PRT
<213> ORGANISM: Homo sapiens

<400> SEQUENCE: 104

```
Glu Thr Thr Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Ser
                 85                  90                  95

Gly Thr Phe Gly Gln Gly Thr Lys Val Glu Ile Lys Arg
            100                 105
```

<210> SEQ ID NO 105
<211> LENGTH: 363
<212> TYPE: DNA
<213> ORGANISM: Homo sapiens

<400> SEQUENCE: 105

```
caggtacagc tgcagcagtc aggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaagg atcatcccta tccttggtat agcaaactac     180
gcacagaagt tccagggcag agtcacgatt accgcggaca atccacgag cacagcctac     240
```

```
atggagctga gcagcctgag atctgaggac acggccgtgt attactgtgc gagaggtttc    300
cgtccgtact actactacgg tatggacgtc tggggccaag gaccacggt caccgtctca    360 agc                                                                  363
```

<210> SEQ ID NO 106
<211> LENGTH: 121
<212> TYPE: PRT
<213> ORGANISM: Homo sapiens

<400> SEQUENCE: 106

```
Gln Val Gln Leu Gln Gln Ser Gly Ala Glu Val Lys Lys Pro Gly Ser
 1               5                  10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Ile Leu Gly Ile Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Phe Arg Pro Tyr Tyr Tyr Gly Met Asp Val Trp Gly
               100                 105                 110
Gln Gly Thr Thr Val Thr Val Ser Ser
           115                 120
```

<210> SEQ ID NO 107
<211> LENGTH: 330
<212> TYPE: DNA
<213> ORGANISM: Homo sapiens

<400> SEQUENCE: 107

```
gaaacgacac tcacgcagtc tccaggcacc ctgtctttgt ctccagggga aagagccacc    60
ctctcctgca gggccagtca gagtgttggc agcaacttag cctggtacca gcagagacct   120
ggccaggctc ccagcctcct catctatggt gcatccagca gggccactgg cgtcccagac   180
aggttcagtg gcagtgggtc tgggacagac ttcactctca ccatcagcag actggagcct   240
gaagattttg ctgtatatta ctgtcagcag tatggtgact cacctcgctt gtacactttt   300
ggccagggga ccaagctgga gatcaaacga                                     330
```

<210> SEQ ID NO 108
<211> LENGTH: 110
<212> TYPE: PRT
<213> ORGANISM: Homo sapiens

<400> SEQUENCE: 108

```
Glu Thr Thr Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Gly Ser Asn
            20                  25                  30
Leu Ala Trp Tyr Gln Gln Arg Pro Gly Gln Ala Pro Ser Leu Leu Ile
        35                  40                  45
Tyr Gly Ala Ser Ser Arg Ala Thr Gly Val Pro Asp Arg Phe Ser Gly
    50                  55                  60
Ser Gly Ser Gly Thr Asp Phe Thr Leu Thr Ile Ser Arg Leu Glu Pro
```

65 70 75 80
Glu Asp Phe Ala Val Tyr Tyr Cys Gln Gln Tyr Gly Asp Ser Pro Arg
                85                  90                  95

Leu Tyr Thr Phe Gly Gln Gly Thr Lys Leu Glu Ile Lys Arg
            100                 105                 110

<210> SEQ ID NO 109
<211> LENGTH: 375
<212> TYPE: DNA
<213> ORGANISM: Homo sapiens

<400> SEQUENCE: 109
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg gctggagtg gattggggaa atcaatcata gtggaagcac caactacaac      180
ccgtccctca gagtcgagt caccatatca gtagacacgt ccaagaacca gttctccctg      240
aagctgagct ctgtgaccgc cgcggacacg gctgtgtatt actgtgcgag agtggcttac     300
tatgatagta gtggttatta ccctatgat gcttttgata tctggggcca agggacaatg      360
gtcaccgtct caagc                                                     375

<210> SEQ ID NO 110
<211> LENGTH: 125
<212> TYPE: PRT
<213> ORGANISM: Homo sapiens

<400> SEQUENCE: 110

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Ala Tyr Tyr Asp Ser Ser Gly Tyr Tyr Pro Tyr Asp Ala Phe
            100                 105                 110

Asp Ile Trp Gly Gln Gly Thr Met Val Thr Val Ser Ser
        115                 120                 125

<210> SEQ ID NO 111
<211> LENGTH: 327
<212> TYPE: DNA
<213> ORGANISM: Homo sapiens

<400> SEQUENCE: 111
gaaacgacac tcacgcagtc tccaggcacc ctgtctctgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgta cactttttggc    300 cagggggacca agctggagat caaacga 327

<210> SEQ ID NO 112
<211> LENGTH: 109
<212> TYPE: PRT
<213> ORGANISM: Homo sapiens

<400> SEQUENCE: 112

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys Arg
            100                 105

<210> SEQ ID NO 113
<211> LENGTH: 369
<212> TYPE: DNA
<213> ORGANISM: Homo sapiens

<400> SEQUENCE: 113
caggtgcagc tggtgcaatc tggggggaggc gtggtccagc ctggggaggtc cctgagactc      60
tcctgtgcag cctctggatt caccttcagt agctatgcta tgcactgggt ccgccaggct      120
ccaggcaagg ggctggagtg ggtggcagtt atatcatatg atggaagtaa taaatactat      180
gcagactccg tgaagggccg attcaccatc tccagagaca attccaagaa cacgctgtat      240
ctgcaaatga acagcctgag agccgaggac acggccgtgt attactgtgc gagagaatta      300
cgattttttgg agtggtcctc cgatgctttt gatatctggg gccaagggac aatggtcacc      360
gtctcaagc                                                              369

<210> SEQ ID NO 114
<211> LENGTH: 123
<212> TYPE: PRT
<213> ORGANISM: Homo sapiens

<400> SEQUENCE: 114

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Phe Leu Glu Trp Ser Ser Asp Ala Phe Asp Ile
            100                 105                 110

Trp Gly Gln Gly Thr Met Val Thr Val Ser Ser
        115                 120

<210> SEQ ID NO 115
<211> LENGTH: 330
<212> TYPE: DNA
<213> ORGANISM: Homo sapiens

<400> SEQUENCE: 115
gaaacgacac tcacgcagtc tccaggcacc ctgtctttgt ctccagggga aagagccacc      60
ctctcctgca gggccagtca gagtgttagc agcagctatt tagcctggta ccagcagaaa     120
cctggccagg ctcccaggct cctcatctat ggtgcatcca ccagggccac tggcgtccca     180
gacaggttca gtggcagtgg gtctgggaca gacttcactc tcaccatcag cagactggag     240
cctgaagatt ttgcagttta ttactgtcaa cagtacggta cctcacttac gtggacgttc     300
ggccaaggga ccaaggtgga aatcaaacga                                      330

<210> SEQ ID NO 116
<211> LENGTH: 110
<212> TYPE: PRT
<213> ORGANISM: Homo sapiens

<400> SEQUENCE: 116

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Leu
                85                  90                  95

Thr Trp Thr Phe Gly Gln Gly Thr Lys Val Glu Ile Lys Arg
            100                 105                 110

<210> SEQ ID NO 117
<211> LENGTH: 375
<212> TYPE: DNA
<213> ORGANISM: Homo sapiens

<400> SEQUENCE: 117
caggtgcagc tgcaggagtc gggcccagga ctggtgaagc cttcggagac cctgtccctc      60
acctgcactg tctctggtgg ctccatcagc agtagtagtt actactgggc ctggatccgc     120
cagcccccag ggaaggggct ggagtggatt gggaaatca atcatagtgg aagcaccaac     180
tacaacccgt ccctcaagag tcgagtcacc atatcagtag acacgtccaa gaaccagttc     240
tccctgaatc tgaactctgt gaccgccgca gacacggctg tgtattactg tgcgagagta     300
gtagcagcag ctggtcacta ctactactac tacatggacg tctgggcaa agggaccacg     360 gtcaccgtct caagc                                                      375

```
<210> SEQ ID NO 118
<211> LENGTH: 125
<212> TYPE: PRT
<213> ORGANISM: Homo sapiens

<400> SEQUENCE: 118

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Ser
             20                  25                  30

Ser Tyr Tyr Trp Ala Trp Ile Arg Gln Pro Pro Gly Lys Gly Leu Glu
         35                  40                  45

Trp Ile Gly Glu Ile Asn His Ser Gly Ser Thr Asn Tyr Asn Pro Ser
     50                  55                  60

Leu Lys Ser Arg Val Thr Ile Ser Val Asp Thr Ser Lys Asn Gln Phe
 65                  70                  75                  80

Ser Leu Asn Leu Asn Ser Val Thr Ala Ala Asp Thr Ala Val Tyr Tyr
                 85                  90                  95

Cys Ala Arg Val Val Ala Ala Ala Gly His Tyr Tyr Tyr Tyr Tyr Met
            100                 105                 110

Asp Val Trp Gly Lys Gly Thr Thr Val Thr Val Ser Ser
            115                 120                 125

<210> SEQ ID NO 119
<211> LENGTH: 23
<212> TYPE: DNA
<213> ORGANISM: Artificial Sequence
<220> FEATURE:
<223> OTHER INFORMATION: primer

<400> SEQUENCE: 119
agcggataac aatttcacac agg                                          23

<210> SEQ ID NO 120
<211> LENGTH: 24
<212> TYPE: DNA
<213> ORGANISM: Artificial Sequence
<220> FEATURE:
<223> OTHER INFORMATION: primer

<400> SEQUENCE: 120
tttgtcgtct ttccagacgt tagt                                         24

<210> SEQ ID NO 121
<211> LENGTH: 9
<212> TYPE: PRT
<213> ORGANISM: Homo sapiens

<400> SEQUENCE: 121

Leu Leu Phe Gly Tyr Pro Val Tyr Val
  1               5
```